(12) United States Patent
Kapeller-Libermann et al.

(10) Patent No.: US 7,001,753 B2
(45) Date of Patent: Feb. 21, 2006

(54) 59079 AND 12599, PROTEIN KINASE FAMILY MEMBERS AND USES THEREFOR

(75) Inventors: Rosana Kapeller-Libermann, Chestnut Hill, MA (US); Susan L. Acton, Lexington, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 499 days.

(21) Appl. No.: 10/077,130

(22) Filed: Feb. 15, 2002

(65) Prior Publication Data

US 2002/0168742 A1 Nov. 14, 2002

Related U.S. Application Data

(60) Provisional application No. 60/269,201, filed on Feb. 15, 2001.

(51) Int. Cl.
| | |
|---|---|
| C12N 9/20 | (2006.01) |
| C12N 15/00 | (2006.01) |
| C12N 1/20 | (2006.01) |
| C12Q 1/68 | (2006.01) |
| C07H 21/04 | (2006.01) |

(52) U.S. Cl. .................. 435/194; 435/252.3; 435/320.1; 435/6; 536/23.2

(58) Field of Classification Search .................. 435/194, 435/252.3, 320.1, 325, 6; 536/23.2, 23.1
See application file for complete search history.

(56) References Cited

U.S. PATENT DOCUMENTS

| 6,482,624 B1 | 11/2002 | Wei et al. | |
| 2003/0108533 A1 * | 6/2003 | Zeng et al. | ............... 424/93.21 |

FOREIGN PATENT DOCUMENTS

| WO | WO 00/63381 A1 | 10/2000 |
| WO | WO 01/55356 A2 | 8/2001 |
| WO | WO 02/33099 A2 | 4/2002 |
| WO | WO 02/40683 A2 | 5/2002 |

OTHER PUBLICATIONS

Nagase, Takahiro, et. al., "Prediction of the Coding Sequences of Unidentified Human Genes, XVIII. The Complete Sequences of 100 New cDNA Clones from Brain Which Code for Large Proteins in vitro", *DNA Research*, vol. 7, (2000), pp. 273–281.

Young, Paul, et. al., Obscurin, A Giant Sarcomeric Rho Guanine Nucleotide Exchange Factor Protein Involved in Sarcomere Assembly, vol. 154, No. 1, (Jul. 9, 2001), pp. 123–136.

Ohara, O., et. al., "Homo Sapiens mRNA for KIAA1639 Protein, Partial Cds," Feb. 22, 2001, (sequence) GenBank [online] Bethesda, MD, USA: National Center for Biotechnology Information [retrieved on Jul. 20, 2004]. Retrieved from the Internet: URL: http://www.ncbi.nlm.nih.gov/>. GenBank Accession No. AB046859.

Gautel, M.S., "Homo Sapiens mRNA for Obscurin (OBSCN gene)," Sep. 14, 2001, (sequence) GenBank [online] Bethesda, MD, USA: National Center for Biotechnology Information [retrieved on Jul. 20, 2004]. Retrieved from the Internet: URL: http://www.ncbi.nlm.nih.gov/>.GenBank Accession No. AJ002535.

* cited by examiner

*Primary Examiner*—Maryam Monshipouri
(74) *Attorney, Agent, or Firm*—Millennium Pharmaceuticals Inc.

(57) ABSTRACT

The invention provides isolated nucleic acids molecules, designated 59079 and 12599 nucleic acid molecules, which encode novel protein kinase family members. The invention also provides antisense nucleic acid molecules, recombinant expression vectors containing 59079 or 12599 nucleic acid molecules, host cells into which the expression vectors have been introduced, and nonhuman transgenic animals in which a 59079 or 12599 gene has been introduced or disrupted. The invention still further provides isolated 59079 and 12599 proteins, fusion proteins, antigenic peptides and anti-59079 and anti-12599 antibodies. Diagnostic and therapeutic methods utilizing compositions of the invention are also provided.

9 Claims, No Drawings

SEQUENCE LISTING

<160> NUMBER OF SEQ ID NOS: 9

<210> SEQ ID NO 1
<211> LENGTH: 8106
<212> TYPE: DNA
<213> ORGANISM: Homo sapiens -continued

```
<220> FEATURE:
<221> NAME/KEY: 5'UTR
<222> LOCATION: (1)...(71)
<221> NAME/KEY: CDS
<222> LOCATION: (72)...(7964)
<221> NAME/KEY: 3'UTR
<222> LOCATION: (7965)...(8106)

<400> SEQUENCE: 1
tgcacaccct ggagatcatc tccgtcaccc gggaggactc tggccagtat gcagcctata      60
tcagcaatgc c atg ggt gct gcc tac tcg tct gcc cgg ctg ctg gtt cga      110
            Met Gly Ala Ala Tyr Ser Ser Ala Arg Leu Leu Val Arg
              1               5                  10 ggc cct gat gag cca gaa gag aag cct gca tca gat gtg cat gag cag      158
Gly Pro Asp Glu Pro Glu Glu Lys Pro Ala Ser Asp Val His Glu Gln
     15                  20                  25 ctg gtg ccg ccc cga atg ctg gag agg ttc acc ccc aag aaa gtg aag      206
Leu Val Pro Pro Arg Met Leu Glu Arg Phe Thr Pro Lys Lys Val Lys
 30                  35                  40                  45 aaa ggc tcc agc atc acc ttc tct gtg aag gta gaa gga cgc ccg gtg      254
Lys Gly Ser Ser Ile Thr Phe Ser Val Lys Val Glu Gly Arg Pro Val
                 50                  55                  60 ccc acc gtg cac tgg ctc agg gag gag gct gag aga ggc gtg ctg tgg      302
Pro Thr Val His Trp Leu Arg Glu Glu Ala Glu Arg Gly Val Leu Trp
             65                  70                  75 att ggc cct gac aca ccg ggc tac acc gtg gcc agc tct gcg cag cag      350
Ile Gly Pro Asp Thr Pro Gly Tyr Thr Val Ala Ser Ser Ala Gln Gln
         80                  85                  90 cac agc ctg gtc ctg ctg gac gtg ggc cgg cag cac cag ggc acc tac      398
His Ser Leu Val Leu Leu Asp Val Gly Arg Gln His Gln Gly Thr Tyr
     95                 100                 105 aca tgc att gcc agc aac gct gcc ggc cag gcc ctc tgc tcc gcc agc      446
Thr Cys Ile Ala Ser Asn Ala Ala Gly Gln Ala Leu Cys Ser Ala Ser
110                 115                 120                 125 ctg cac gtc tcg ggc ctg cct aag gtg gag gag cag gag aaa gtg aag      494
Leu His Val Ser Gly Leu Pro Lys Val Glu Glu Gln Glu Lys Val Lys
                130                 135                 140 gaa gcg ctg att tcc act ttc ctg cag ggg acc aca caa gcc atc tca      542
Glu Ala Leu Ile Ser Thr Phe Leu Gln Gly Thr Thr Gln Ala Ile Ser
            145                 150                 155 gca cag ggg ttg gaa act gcg agt ttt gct gac ctt ggt ggg cag agg      590
Ala Gln Gly Leu Glu Thr Ala Ser Phe Ala Asp Leu Gly Gly Gln Arg
        160                 165                 170 aaa gaa gag cct ctg gct gcc aag gag gcc ctc ggc cac ctg tcc ctc      638
Lys Glu Glu Pro Leu Ala Ala Lys Glu Ala Leu Gly His Leu Ser Leu
    175                 180                 185 gct gag gtg ggc aca gag gag ttc ctg cag aaa ctg acc tcc cag atc      686
Ala Glu Val Gly Thr Glu Glu Phe Leu Gln Lys Leu Thr Ser Gln Ile
190                 195                 200                 205 act gag atg gta tcg gcc aag atc acg cag gcc aag ctg cag gtg ccc      734
Thr Glu Met Val Ser Ala Lys Ile Thr Gln Ala Lys Leu Gln Val Pro
                210                 215                 220 gga ggt gac agt gat gag gac tcc aag aca cca tct gca tcc ccc cgc      782
Gly Gly Asp Ser Asp Glu Asp Ser Lys Thr Pro Ser Ala Ser Pro Arg
            225                 230                 235 cat ggc cga tca cgg cca tcc tcc agc atc cag gag tct tcc tca gag      830
His Gly Arg Ser Arg Pro Ser Ser Ser Ile Gln Glu Ser Ser Ser Glu
        240                 245                 250 tca gag gac ggc gat gcc cga ggc gag atc ttt gac atc tac gtg gtc      878
Ser Glu Asp Gly Asp Ala Arg Gly Glu Ile Phe Asp Ile Tyr Val Val
    255                 260                 265
```

-continued

| | |
|---|---|
| acc gct gac tac ctg ccc cta ggg gct gag cag gat gcc atc acg ctg<br>Thr Ala Asp Tyr Leu Pro Leu Gly Ala Glu Gln Asp Ala Ile Thr Leu<br>270                       275                     280                     285 | 926 |
| cgg gaa ggc cag tat gtg gag gtc ctg gat gca gcc cac cca ctg cgc<br>Arg Glu Gly Gln Tyr Val Glu Val Leu Asp Ala Ala His Pro Leu Arg<br>290                     295                     300 | 974 |
| tgg ctt gtc cgc acc aag ccc acc aag tcc agc ccc tca cgg cag ggc<br>Trp Leu Val Arg Thr Lys Pro Thr Lys Ser Ser Pro Ser Arg Gln Gly<br>305                     310                     315 | 1022 |
| tgg gtg tca cca gcc tac ctg gac agg agg ctc aag ctg tca cct gag<br>Trp Val Ser Pro Ala Tyr Leu Asp Arg Arg Leu Lys Leu Ser Pro Glu<br>320                     325                     330 | 1070 |
| tgg ggg gcc gct gag gcc cct gag ttc cct ggg gag gct gtg tct gaa<br>Trp Gly Ala Ala Glu Ala Pro Glu Phe Pro Gly Glu Ala Val Ser Glu<br>335                     340                     345 | 1118 |
| gac gaa tac aag gca agg ctg agc tct gtg atc cag gag ctg ctg agt<br>Asp Glu Tyr Lys Ala Arg Leu Ser Ser Val Ile Gln Glu Leu Leu Ser<br>350                     355                     360                     365 | 1166 |
| tct gag cag gcc ttc gtg gag gag ctg cag ttc ctg cag agc cac cac<br>Ser Glu Gln Ala Phe Val Glu Glu Leu Gln Phe Leu Gln Ser His His<br>                     370                     375                     380 | 1214 |
| ctg cag cac ctg gag cgc tgc ccc cac gtg ccc ata gcc gtg gcc ggc<br>Leu Gln His Leu Glu Arg Cys Pro His Val Pro Ile Ala Val Ala Gly<br>385                     390                     395 | 1262 |
| cag aag gca gtc atc ttc cgc aat gtg cgg gac atc ggc cgc ttc cac<br>Gln Lys Ala Val Ile Phe Arg Asn Val Arg Asp Ile Gly Arg Phe His<br>                     400                     405                     410 | 1310 |
| agc agc ttc ctg cag gag ttg cag cag tgc gac acg gac gac gac gtg<br>Ser Ser Phe Leu Gln Glu Leu Gln Gln Cys Asp Thr Asp Asp Asp Val<br>415                     420                     425 | 1358 |
| gcc atg tgc ttc atc aag aac cag gcg gcc ttt gag cag tac ctg gag<br>Ala Met Cys Phe Ile Lys Asn Gln Ala Ala Phe Glu Gln Tyr Leu Glu<br>430                     435                     440                     445 | 1406 |
| ttc ctg gtg ggg cgt gtg cag gct gag tcg gtg gtc gtc agc acg gcc<br>Phe Leu Val Gly Arg Val Gln Ala Glu Ser Val Val Val Ser Thr Ala<br>                     450                     455                     460 | 1454 |
| atc cag gag ttc tac aag aaa tac gcg gag gag gcc ctg ttg gca ggg<br>Ile Gln Glu Phe Tyr Lys Lys Tyr Ala Glu Glu Ala Leu Leu Ala Gly<br>                     465                     470                     475 | 1502 |
| gac ccc tct cag ccc ccg cca cca cct ctg cag cac tac ctg gag cag<br>Asp Pro Ser Gln Pro Pro Pro Pro Pro Leu Gln His Tyr Leu Glu Gln<br>                     480                     485                     490 | 1550 |
| cca gtg gag cgg gtg cag cgc tac cag gcc ttg ctg aag gag ttg atc<br>Pro Val Glu Arg Val Gln Arg Tyr Gln Ala Leu Leu Lys Glu Leu Ile<br>495                     500                     505 | 1598 |
| cgc aac aag gcg cgg aac aga cag aac tgc gcg ctg ctg gag cag gcc<br>Arg Asn Lys Ala Arg Asn Arg Gln Asn Cys Ala Leu Leu Glu Gln Ala<br>510                     515                     520                     525 | 1646 |
| tat gcc gtg gtg tct gcc ctg cca cag cgc gct gag aac aag ctg cac<br>Tyr Ala Val Val Ser Ala Leu Pro Gln Arg Ala Glu Asn Lys Leu His<br>                     530                     535                     540 | 1694 |
| gtg tcc ctc atg gag aac tac cca ggc acc ctg gag gcc ctg ggc gag<br>Val Ser Leu Met Glu Asn Tyr Pro Gly Thr Leu Glu Ala Leu Gly Glu<br>545                     550                     555 | 1742 |
| ccc atc cgc cag ggc cac ttc atc gtg tgg gag ggt gca ccg ggg gcc<br>Pro Ile Arg Gln Gly His Phe Ile Val Trp Glu Gly Ala Pro Gly Ala<br>560                     565                     570 | 1790 |
| cgc atg ccc tgg aag ggc cac aac cgt cac gtg ttc ctc ttc cgc aac<br>Arg Met Pro Trp Lys Gly His Asn Arg His Val Phe Leu Phe Arg Asn | 1838 |

-continued

```
              575                 580                 585
cac ctg gta atc tgc aag ccc cgg cga gac tcc cgc acc gat acc gtc    1886
His Leu Val Ile Cys Lys Pro Arg Arg Asp Ser Arg Thr Asp Thr Val
590                 595                 600                 605 agc tac gtg ttc cgg aac atg atg aag ctg agc agc atc gac ctg aac    1934
Ser Tyr Val Phe Arg Asn Met Met Lys Leu Ser Ser Ile Asp Leu Asn
                610                 615                 620 gac cag gtg gag ggg gat gac cgc gcc ttc gag gtg tgg cag gag cgg    1982
Asp Gln Val Glu Gly Asp Asp Arg Ala Phe Glu Val Trp Gln Glu Arg
            625                 630                 635 gag gac tcg gtg cgc aag tac ctg ctg cag gca cgg aca gcc att atc    2030
Glu Asp Ser Val Arg Lys Tyr Leu Leu Gln Ala Arg Thr Ala Ile Ile
        640                 645                 650 aag agc tcg tgg gtg aag gag atc tgt ggc atc cag cag cgt ctg gcc    2078
Lys Ser Ser Trp Val Lys Glu Ile Cys Gly Ile Gln Gln Arg Leu Ala
655                 660                 665 ctg cct gtg tgg cgg ccc ccg gac ttt gaa gag gag ctg gcc gac tgc    2126
Leu Pro Val Trp Arg Pro Pro Asp Phe Glu Glu Glu Leu Ala Asp Cys
670                 675                 680                 685 aca gcc gag ctg ggt gag aca gtc aag ctg gcc tgc cgc gtg acg ggc    2174
Thr Ala Glu Leu Gly Glu Thr Val Lys Leu Ala Cys Arg Val Thr Gly
                690                 695                 700 aca ccc aag cct gtc atc agc tgg tac aaa gat ggg aaa gca gtg cag    2222
Thr Pro Lys Pro Val Ile Ser Trp Tyr Lys Asp Gly Lys Ala Val Gln
            705                 710                 715 gtg gac ccc cac cac atc ctc att gaa gac cct gat ggc tcg tgt gca    2270
Val Asp Pro His His Ile Leu Ile Glu Asp Pro Asp Gly Ser Cys Ala
        720                 725                 730 ctc atc ctg gac agc ctg acc ggt gtg gac tct ggc cag tac atg tgc    2318
Leu Ile Leu Asp Ser Leu Thr Gly Val Asp Ser Gly Gln Tyr Met Cys
735                 740                 745 ttc gcg gcc agc gcc gct ggc aac tgc agt acc ctg ggc aag atc ctg    2366
Phe Ala Ala Ser Ala Ala Gly Asn Cys Ser Thr Leu Gly Lys Ile Leu
750                 755                 760                 765 gtg caa gtc cca cca cgg ttc gtg aac aag gtc cgg gcc tca ccc ttt    2414
Val Gln Val Pro Pro Arg Phe Val Asn Lys Val Arg Ala Ser Pro Phe
                770                 775                 780 gtg gag gga gag gac gcc cag ttc acc tgc acc atc gaa ggc gcc ccg    2462
Val Glu Gly Glu Asp Ala Gln Phe Thr Cys Thr Ile Glu Gly Ala Pro
            785                 790                 795 tac ccg cag atc agg tgg tac aag gac ggg gcc ctg ctg acc act ggc    2510
Tyr Pro Gln Ile Arg Trp Tyr Lys Asp Gly Ala Leu Leu Thr Thr Gly
        800                 805                 810 aac aag ttc cag aca ctg agt gag cct cgc agc ggc ctg cta gtg ctg    2558
Asn Lys Phe Gln Thr Leu Ser Glu Pro Arg Ser Gly Leu Leu Val Leu
815                 820                 825 gtg atc cgg gcg gcc agc aag gag gac ctg ggg ctc tac gag tgt gag    2606
Val Ile Arg Ala Ala Ser Lys Glu Asp Leu Gly Leu Tyr Glu Cys Glu
830                 835                 840                 845 ctg gtg aac cgg ctg ggc tcc gcg cgg gct agt gcg gag ctg cgc att    2654
Leu Val Asn Arg Leu Gly Ser Ala Arg Ala Ser Ala Glu Leu Arg Ile
                850                 855                 860 cag agc ccc atg ctg cag gcc cag gag cag tgt cac agg gag cag ctc    2702
Gln Ser Pro Met Leu Gln Ala Gln Glu Gln Cys His Arg Glu Gln Leu
            865                 870                 875 gtg gct gca gtg gaa gac acc acc ctg gag cga gcg gac cag gag gtc    2750
Val Ala Ala Val Glu Asp Thr Thr Leu Glu Arg Ala Asp Gln Glu Val
        880                 885                 890 aca tct gtc ctg aag aga ctg ctg ggc ccc aag gcg cca ggc ccc tcc    2798
```

```
                                                                                    -continued Thr Ser Val Leu Lys Arg Leu Leu Gly Pro Lys Ala Pro Gly Pro Ser
    895                 900                 905 aca ggg gac ctc act ggc cct ggc ccc tgc ccc agg ggg gca ccc gca         2846
Thr Gly Asp Leu Thr Gly Pro Gly Pro Cys Pro Arg Gly Ala Pro Ala
910                 915                 920                 925 ctc cag gaa acc ggc tcc cag ccc cca gtc acc gga act tcg gag gca         2894
Leu Gln Glu Thr Gly Ser Gln Pro Pro Val Thr Gly Thr Ser Glu Ala
                930                 935                 940 cct gcc gtg ccc ccg agg gtg cca cag ccc ctc ctc cac gaa ggc cca         2942
Pro Ala Val Pro Pro Arg Val Pro Gln Pro Leu Leu His Glu Gly Pro
            945                 950                 955 gag cag gag ccg gag gcc att gcc aga gcc cag gaa tgg act gtg ccc         2990
Glu Gln Glu Pro Glu Ala Ile Ala Arg Ala Gln Glu Trp Thr Val Pro
        960                 965                 970 att cgg atg gag ggt gca gcc tgg ccc ggg gca ggc aca ggg gag ctg         3038
Ile Arg Met Glu Gly Ala Ala Trp Pro Gly Ala Gly Thr Gly Glu Leu
    975                 980                 985 ctc tgg gac gtc cac agc cac gtg gtc aga gag acc aca cag agg acc         3086
Leu Trp Asp Val His Ser His Val Val Arg Glu Thr Thr Gln Arg Thr
990                 995                 1000                1005 tac aca tac cag gcc atc gac acg cac acc gca cgg ccc cca tcc atg         3134
Tyr Thr Tyr Gln Ala Ile Asp Thr His Thr Ala Arg Pro Pro Ser Met
                1010                1015                1020 cag gta acc atc gag gat gtg cag gca cag aca ggc gga acg gcc caa         3182
Gln Val Thr Ile Glu Asp Val Gln Ala Gln Thr Gly Gly Thr Ala Gln
            1025                1030                1035 ttc gag gct atc att gag ggc gac cca cag ccc tcg gtg acc tgg tac         3230
Phe Glu Ala Ile Ile Glu Gly Asp Pro Gln Pro Ser Val Thr Trp Tyr
        1040                1045                1050 aag gac agc gtc cag ctg gtg gac agc acc cgg ctt agc cag cag caa         3278
Lys Asp Ser Val Gln Leu Val Asp Ser Thr Arg Leu Ser Gln Gln Gln
    1055                1060                1065 gaa ggc acc aca tac tcc ctg gtg ctg agg cat gtg gcc tcg aag gat         3326
Glu Gly Thr Thr Tyr Ser Leu Val Leu Arg His Val Ala Ser Lys Asp
1070                1075                1080                1085 gcc ggc gtt tac acc tgc ctg gcc caa aac act ggt ggc cag gtg ctc         3374
Ala Gly Val Tyr Thr Cys Leu Ala Gln Asn Thr Gly Gly Gln Val Leu
                1090                1095                1100 tgc aag gca gag ctg ctg gtg ctt ggg ggg gac aat gag ccg gac tca         3422
Cys Lys Ala Glu Leu Leu Val Leu Gly Gly Asp Asn Glu Pro Asp Ser
            1105                1110                1115 gag aag caa agc cac cgg agg aag ctg cac tcc ttc tat gag gtc aag         3470
Glu Lys Gln Ser His Arg Arg Lys Leu His Ser Phe Tyr Glu Val Lys
        1120                1125                1130 gag gag att gga agg ggc gtg ttt ggc ttc gta aaa aga gtg cag cac         3518
Glu Glu Ile Gly Arg Gly Val Phe Gly Phe Val Lys Arg Val Gln His
    1135                1140                1145 aaa gga aac aag atc ttg tgc gct gcc aag ttc atc ccc cta cgg agc         3566
Lys Gly Asn Lys Ile Leu Cys Ala Ala Lys Phe Ile Pro Leu Arg Ser
1150                1155                1160                1165 aga act cgg gcc cag gca tac agg gag cga gac atc ctg gcc gcg ctg         3614
Arg Thr Arg Ala Gln Ala Tyr Arg Glu Arg Asp Ile Leu Ala Ala Leu
                1170                1175                1180 agc cac ccg ctg gtc acg ggg ctg ctg gac cag ttt gag acc cgc aag         3662
Ser His Pro Leu Val Thr Gly Leu Leu Asp Gln Phe Glu Thr Arg Lys
            1185                1190                1195 acc ctc atc ctc atc ctg gag ctg tgc tca tcc gag gag ctg ctg gac         3710
Thr Leu Ile Leu Ile Leu Glu Leu Cys Ser Ser Glu Glu Leu Leu Asp
        1200                1205                1210
```

| | |
|---|---|
| cgc ctg tac agg aag ggc gtg gtg acg gag gcc gag gtc aag gtc tac<br>Arg Leu Tyr Arg Lys Gly Val Val Thr Glu Ala Glu Val Lys Val Tyr<br>    1215                      1220                  1225 | 3758 |
| atc cag cag ctg gtg gag ggg ctg cac tac ctg cac agc cat ggc gtt<br>Ile Gln Gln Leu Val Glu Gly Leu His Tyr Leu His Ser His Gly Val<br>1230                      1235                      1240                1245 | 3806 |
| ctc cac ctg gac ata aag ccc tct aac atc ctg atg gtg cat cct gcc<br>Leu His Leu Asp Ile Lys Pro Ser Asn Ile Leu Met Val His Pro Ala<br>                1250                      1255                      1260 | 3854 |
| cgg gaa gac att aaa atc tgc gac ttt ggc ttt gcc cag aac atc acc<br>Arg Glu Asp Ile Lys Ile Cys Asp Phe Gly Phe Ala Gln Asn Ile Thr<br>              1265                      1270                      1275 | 3902 |
| cca gca gag ctg cag ttc agc cag tac ggc tcc cct gag ttc gtc tcc<br>Pro Ala Glu Leu Gln Phe Ser Gln Tyr Gly Ser Pro Glu Phe Val Ser<br>                1280                      1285                      1290 | 3950 |
| ccc gag atc atc cag cag aac cct gtg agc gaa gcc tcc gac att tgg<br>Pro Glu Ile Ile Gln Gln Asn Pro Val Ser Glu Ala Ser Asp Ile Trp<br>    1295                      1300                      1305 | 3998 |
| gcc atg ggt gtc atc tcc tac ctc agc ctg acc tgc tca tcc cca ttt<br>Ala Met Gly Val Ile Ser Tyr Leu Ser Leu Thr Cys Ser Ser Pro Phe<br>1310                      1315                      1320                1325 | 4046 |
| gcc ggc gag agt gac cgt gcc acc ctc ctg aac gtc ctg gag ggg cgc<br>Ala Gly Glu Ser Asp Arg Ala Thr Leu Leu Asn Val Leu Glu Gly Arg<br>                1330                      1335                      1340 | 4094 |
| gtg tca tgg agc agc ccc atg gct gcc cac ctc agc gaa gac gcc aaa<br>Val Ser Trp Ser Ser Pro Met Ala Ala His Leu Ser Glu Asp Ala Lys<br>              1345                      1350                      1355 | 4142 |
| gac ttc atc aag gct acg ctg cag aga gcc cct cag gcc cgg cct agt<br>Asp Phe Ile Lys Ala Thr Leu Gln Arg Ala Pro Gln Ala Arg Pro Ser<br>        1360                      1365                      1370 | 4190 |
| gcg gcc cag tgc ctc tcc cac ccc tgg ttc ctg aaa tcc atg cct gcg<br>Ala Ala Gln Cys Leu Ser His Pro Trp Phe Leu Lys Ser Met Pro Ala<br>1375                      1380                      1385 | 4238 |
| gag gag gcc cac ttc atc aac acc aag cag ctc aag ttc ctc ctg gcc<br>Glu Glu Ala His Phe Ile Asn Thr Lys Gln Leu Lys Phe Leu Leu Ala<br>1390                      1395                      1400                1405 | 4286 |
| cga agt cgc tgg cag cgt tcc ctg atg agc tac aag tcc atc ctg gtg<br>Arg Ser Arg Trp Gln Arg Ser Leu Met Ser Tyr Lys Ser Ile Leu Val<br>                1410                      1415                      1420 | 4334 |
| atg cgc tcc atc cct gag ctg ctg cgg ggc cca ccc gac agc ccc tcc<br>Met Arg Ser Ile Pro Glu Leu Leu Arg Gly Pro Pro Asp Ser Pro Ser<br>            1425                      1430                      1435 | 4382 |
| ctc ggc gta gcc cgg cac ctc tgc agg gac act ggt ggc tcc tcc agt<br>Leu Gly Val Ala Arg His Leu Cys Arg Asp Thr Gly Gly Ser Ser Ser<br>        1440                      1445                      1450 | 4430 |
| tcc tcc tcc tct gac aac gag ctc gcc cca ttt gcc cgg gct aag<br>Ser Ser Ser Ser Ser Asp Asn Glu Leu Ala Pro Phe Ala Arg Ala Lys<br>1455                      1460                      1465 | 4478 |
| tca ctg cca ccc tcc ccg gtg aca cac tca cca ctg ctg cac ccc cgg<br>Ser Leu Pro Pro Ser Pro Val Thr His Ser Pro Leu Leu His Pro Arg<br>1470                      1475                      1480                1485 | 4526 |
| ggc ttc ctg cgg ccc tcg gcc agc ctg cct gag gaa gcc gag gcc agt<br>Gly Phe Leu Arg Pro Ser Ala Ser Leu Pro Glu Glu Ala Glu Ala Ser<br>                1490                      1495                      1500 | 4574 |
| gag cgc tcc acc gag gcc cca gct ccg cct gca tct ccc gag ggt gcc<br>Glu Arg Ser Thr Glu Ala Pro Ala Pro Pro Ala Ser Pro Glu Gly Ala<br>            1505                      1510                      1515 | 4622 |
| ggg cca ccg gcc gcc cag ggc tgc gtg ccc cgg cac agc gtc atc cgc<br>Gly Pro Pro Ala Ala Gln Gly Cys Val Pro Arg His Ser Val Ile Arg<br>        1520                      1525                      1530 | 4670 |

```
agc ctg ttc tac cac cag gcg ggt gag agc cct gag cac ggg gcc ctg    4718
Ser Leu Phe Tyr His Gln Ala Gly Glu Ser Pro Glu His Gly Ala Leu
    1535                1540                1545 gcc ccg ggg agc agg cgg cac ccg gcc cgg cgg cgg cac ctg ctg aag    4766
Ala Pro Gly Ser Arg Arg His Pro Ala Arg Arg Arg His Leu Leu Lys
1550                1555                1560                1565 ggc ggg tac att gcg ggg gcg ctg cca ggc ctg cgc gag cca ctg atg    4814
Gly Gly Tyr Ile Ala Gly Ala Leu Pro Gly Leu Arg Glu Pro Leu Met
            1570                1575                1580 gag cac cgc gtg ctg gag gag gag gcc gcc agg gag gag cag gcc acc    4862
Glu His Arg Val Leu Glu Glu Glu Ala Ala Arg Glu Glu Gln Ala Thr
        1585                1590                1595 ctc ctg gcc aaa gcc ccc tca ttc gag act gcc ctc cgg ctg cct gcc    4910
Leu Leu Ala Lys Ala Pro Ser Phe Glu Thr Ala Leu Arg Leu Pro Ala
    1600                1605                1610 tct ggc acc cac ttg gcc cct ggc cac agc cac tcc ctg gaa cat gac    4958
Ser Gly Thr His Leu Ala Pro Gly His Ser His Ser Leu Glu His Asp
1615                1620                1625 tct ccg agc acc ccc cgc ccc tcc tcg gag gcc tgc ggt gag gca cag    5006
Ser Pro Ser Thr Pro Arg Pro Ser Ser Glu Ala Cys Gly Glu Ala Gln
1630                1635                1640                1645 cga ctg cct tca gcc ccc tcc ggg ggg gcc cct atc agg gac atg ggg    5054
Arg Leu Pro Ser Ala Pro Ser Gly Gly Ala Pro Ile Arg Asp Met Gly
            1650                1655                1660 cac cct cag ggc tcc aag cag ctt cca tcc act ggt ggc cac cca ggc    5102
His Pro Gln Gly Ser Lys Gln Leu Pro Ser Thr Gly Gly His Pro Gly
        1665                1670                1675 act gct cag cca gag agg cca tcc ccg gac agc cct tgg ggg cag cca    5150
Thr Ala Gln Pro Glu Arg Pro Ser Pro Asp Ser Pro Trp Gly Gln Pro
    1680                1685                1690 gcc cct ttc tgc cac ccc aag cag ggt tct gcc ccc cag gag ggc tgc    5198
Ala Pro Phe Cys His Pro Lys Gln Gly Ser Ala Pro Gln Glu Gly Cys
1695                1700                1705 agc ccc cac cca gca gtt gcc cca tgc cct cct ggc tcc ttc cct cca    5246
Ser Pro His Pro Ala Val Ala Pro Cys Pro Pro Gly Ser Phe Pro Pro
1710                1715                1720                1725 gga tct tgc aaa gag gcc ccc tta gta ccc tca agc ccc ttc ttg gga    5294
Gly Ser Cys Lys Glu Ala Pro Leu Val Pro Ser Ser Pro Phe Leu Gly
            1730                1735                1740 cag ccc cag gca ccc cct gcc cct gcc aaa gca agc ccc cca ttg gac    5342
Gln Pro Gln Ala Pro Pro Ala Pro Ala Lys Ala Ser Pro Pro Leu Asp
        1745                1750                1755 tct aag atg ggg cct gga gac atc tct ctt cct ggg agg cca aaa ccc    5390
Ser Lys Met Gly Pro Gly Asp Ile Ser Leu Pro Gly Arg Pro Lys Pro
    1760                1765                1770 ggc ccc tgc agt tcc cca ggg tca gcc tcc cag gcg agc tct tcc caa    5438
Gly Pro Cys Ser Ser Pro Gly Ser Ala Ser Gln Ala Ser Ser Ser Gln
1775                1780                1785 gtg agc tcc ctc agg gtg ggc tcc tcc cag gtg ggc aca gag cct ggc    5486
Val Ser Ser Leu Arg Val Gly Ser Ser Gln Val Gly Thr Glu Pro Gly
1790                1795                1800                1805 ccc tcc ctg gat gcg gag ggc tgg acc cag gag gct gag gat ctg tcc    5534
Pro Ser Leu Asp Ala Glu Gly Trp Thr Gln Glu Ala Glu Asp Leu Ser
            1810                1815                1820 gac tcc aca ccc acc ttg cag cgg cct cag gaa cag gcg acc atg cgc    5582
Asp Ser Thr Pro Thr Leu Gln Arg Pro Gln Glu Gln Ala Thr Met Arg
        1825                1830                1835 aag ttc tcc ctg ggt ggt cgc ggg ggc tac gca ggc gtg gct ggc tat    5630
Lys Phe Ser Leu Gly Gly Arg Gly Gly Tyr Ala Gly Val Ala Gly Tyr
```

-continued

```
         1840                1845                1850
ggc acc ttt gcc ttt ggt gga gat gca ggg ggc atg ctg ggg cag ggg        5678
Gly Thr Phe Ala Phe Gly Gly Asp Ala Gly Gly Met Leu Gly Gln Gly
    1855                1860                1865 ccc atg tgg gcc agg ata gcc tgg gct gtg tcc cag tcg gag gag gag        5726
Pro Met Trp Ala Arg Ile Ala Trp Ala Val Ser Gln Ser Glu Glu Glu
1870                1875                1880                1885 gag cag gag gag gcc agg gct gag tcc cag tcg gag gag cag cag gag        5774
Glu Gln Glu Glu Ala Arg Ala Glu Ser Gln Ser Glu Glu Gln Gln Glu
            1890                1895                1900 gcc agg gct gag agc cca ctg ccc cag gtc agt gca agg cct gtg cct        5822
Ala Arg Ala Glu Ser Pro Leu Pro Gln Val Ser Ala Arg Pro Val Pro
        1905                1910                1915 gag gtc ggc agg gct ccc acc agg agc tct cca gag ccc acc cca tgg        5870
Glu Val Gly Arg Ala Pro Thr Arg Ser Ser Pro Glu Pro Thr Pro Trp
    1920                1925                1930 gag gac atc ggg cag gtc tcc ctg gtg cag atc cgg gac ctg tca ggt        5918
Glu Asp Ile Gly Gln Val Ser Leu Val Gln Ile Arg Asp Leu Ser Gly
    1935                1940                1945 gat gcg gag gcg gcc gac aca ata tcc ctg gac att tcc gag gtg gac        5966
Asp Ala Glu Ala Ala Asp Thr Ile Ser Leu Asp Ile Ser Glu Val Asp
1950                1955                1960                1965 ccc gcc tac ctc aac ctc tca gac ctg tac gat atc aag tac ctc cca        6014
Pro Ala Tyr Leu Asn Leu Ser Asp Leu Tyr Asp Ile Lys Tyr Leu Pro
            1970                1975                1980 ttc gag ttt atg atc ttc agg aaa gtc ccc aag tcc gct cag cca gag        6062
Phe Glu Phe Met Ile Phe Arg Lys Val Pro Lys Ser Ala Gln Pro Glu
        1985                1990                1995 ccg ccc tcc ccc atg gct gag gag gag ctg gcc gag ttc ccg gag ccc        6110
Pro Pro Ser Pro Met Ala Glu Glu Glu Leu Ala Glu Phe Pro Glu Pro
    2000                2005                2010 acg tgg ccc tgg cca ggt gaa ctg ggc ccc cac gca ggc ctg gag atc        6158
Thr Trp Pro Trp Pro Gly Glu Leu Gly Pro His Ala Gly Leu Glu Ile
    2015                2020                2025 aca gag gag tca gag gat gtg gac gcg ctg ctg gca gag gct gcc gtg        6206
Thr Glu Glu Ser Glu Asp Val Asp Ala Leu Leu Ala Glu Ala Ala Val
2030                2035                2040                2045 ggc agg aag cgc aag tgg tcc tcg ccg tca cgc agc ctc ttc cac ttc        6254
Gly Arg Lys Arg Lys Trp Ser Ser Pro Ser Arg Ser Leu Phe His Phe
            2050                2055                2060 cct ggg agg cac ctg ccg ctg gat gag cct gca gag ctg ggg ctg cgt        6302
Pro Gly Arg His Leu Pro Leu Asp Glu Pro Ala Glu Leu Gly Leu Arg
        2065                2070                2075 gag aga gtg aag gcc tcc gtg gag cac atc tcc cgg atc ctg aag ggc        6350
Glu Arg Val Lys Ala Ser Val Glu His Ile Ser Arg Ile Leu Lys Gly
    2080                2085                2090 agg ccg gaa ggt ctg gag aag gag ggg ccc ccc agg aag aag cca ggc        6398
Arg Pro Glu Gly Leu Glu Lys Glu Gly Pro Pro Arg Lys Lys Pro Gly
    2095                2100                2105 ctt gct tcc ttc cgg ctc tca ggt ctg aag agc tgg gac cga gcg ccg        6446
Leu Ala Ser Phe Arg Leu Ser Gly Leu Lys Ser Trp Asp Arg Ala Pro
2110                2115                2120                2125 aca ttc cta agg gag ctc tca gat gag act gtg gtc ctg ggc cag tca        6494
Thr Phe Leu Arg Glu Leu Ser Asp Glu Thr Val Val Leu Gly Gln Ser
            2130                2135                2140 gtg aca ctg gcc tgc cag gtg tca gcc cag cca gct gcc cag gcc acc        6542
Val Thr Leu Ala Cys Gln Val Ser Ala Gln Pro Ala Ala Gln Ala Thr
        2145                2150                2155 tgg agc aaa gac gga gcc ccc ctg gag agc agc agc cgt gtc ctc atc        6590
```

```
                                                       -continued

Trp Ser Lys Asp Gly Ala Pro Leu Glu Ser Ser Arg Val Leu Ile
        2160                2165                2170 tct gcc acc ctc aag aac ttc cag ctt ctg acc atc ctg gtg gtg gtg         6638
Ser Ala Thr Leu Lys Asn Phe Gln Leu Leu Thr Ile Leu Val Val Val
        2175                2180                2185 gct gag gac ctg ggt gtg tac acc tgc agc gtg agc aat gcg ctg ggg         6686
Ala Glu Asp Leu Gly Val Tyr Thr Cys Ser Val Ser Asn Ala Leu Gly
2190                2195                2200                2205 aca gtg acc acc acg ggc gtc ctc cgg aag gca gag cgc ccc tca tct         6734
Thr Val Thr Thr Thr Gly Val Leu Arg Lys Ala Glu Arg Pro Ser Ser
            2210                2215                2220 tcg cca tgc ccg gat atc ggg gag gtg tac gcg gat ggg gtg ctg ctg         6782
Ser Pro Cys Pro Asp Ile Gly Glu Val Tyr Ala Asp Gly Val Leu Leu
                2225                2230                2235 gtc tgg aag ccc gtg gaa tcc tac ggc cct gtg acc tac att gtg cag         6830
Val Trp Lys Pro Val Glu Ser Tyr Gly Pro Val Thr Tyr Ile Val Gln
            2240                2245                2250 tgc agc cta gaa ggc ggc agc tgg acc aca ctg gcc tcc gac atc ttt         6878
Cys Ser Leu Glu Gly Gly Ser Trp Thr Thr Leu Ala Ser Asp Ile Phe
        2255                2260                2265 gac tgc tgc tac ctg acc agc aag ctc tcc cgg ggt ggc acc tac acc         6926
Asp Cys Cys Tyr Leu Thr Ser Lys Leu Ser Arg Gly Gly Thr Tyr Thr
2270                2275                2280                2285 ttc cgc acg gca tgt gtc agc aag gca gga atg ggt ccc tac agc agc         6974
Phe Arg Thr Ala Cys Val Ser Lys Ala Gly Met Gly Pro Tyr Ser Ser
            2290                2295                2300 ccc tcg gag caa gtc ctc ctg gga ggg ccc agc cac ctg gcc tct gag         7022
Pro Ser Glu Gln Val Leu Leu Gly Gly Pro Ser His Leu Ala Ser Glu
                2305                2310                2315 gag gag agc cag ggg cgg tca gcc caa ccc ctg ccc agc aca aag acc         7070
Glu Glu Ser Gln Gly Arg Ser Ala Gln Pro Leu Pro Ser Thr Lys Thr
            2320                2325                2330 ttc gca ttc cag aca cag atc cag agg ggc cgc ttc agc gtg gtg cgg         7118
Phe Ala Phe Gln Thr Gln Ile Gln Arg Gly Arg Phe Ser Val Val Arg
        2335                2340                2345 caa tgc tgg gag aag gcc agc ggg cgg gcg ctg gcc gcc aag atc atc         7166
Gln Cys Trp Glu Lys Ala Ser Gly Arg Ala Leu Ala Ala Lys Ile Ile
2350                2355                2360                2365 ccc tac cac ccc aag gac aag aca gca gtg ctc gcc gaa tac gag gcc         7214
Pro Tyr His Pro Lys Asp Lys Thr Ala Val Leu Arg Glu Tyr Glu Ala
            2370                2375                2380 ctc aag ggc ctg cgc cac ccg cac ctg gcc cag ctg cac gca gcc tac         7262
Leu Lys Gly Leu Arg His Pro His Leu Ala Gln Leu His Ala Ala Tyr
                2385                2390                2395 ctc agc ccc cgg cac ctg gtg ctc atc ttg gag ctg tgc tct ggg ccc         7310
Leu Ser Pro Arg His Leu Val Leu Ile Leu Glu Leu Cys Ser Gly Pro
            2400                2405                2410 gag ctg ctc ccc tgc ctg gcc gag agg gcc tcc tac tca gaa tcc gag         7358
Glu Leu Leu Pro Cys Leu Ala Glu Arg Ala Ser Tyr Ser Glu Ser Glu
        2415                2420                2425 gtg aag gac tac ctg tgg cag atg ttg agt gcc acc cag tac ctg cac         7406
Val Lys Asp Tyr Leu Trp Gln Met Leu Ser Ala Thr Gln Tyr Leu His
2430                2435                2440                2445 aac cag cac atc ctg cac ctg gac ctg agg tcc gag aac atg atc atc         7454
Asn Gln His Ile Leu His Leu Asp Leu Arg Ser Glu Asn Met Ile Ile
            2450                2455                2460 acc gaa tac aac ctg ctc aag gtc gtg gac ctg ggc aat gca cag agc         7502
Thr Glu Tyr Asn Leu Leu Lys Val Val Asp Leu Gly Asn Ala Gln Ser
                2465                2470                2475
```

-continued

```
ctc agc cag gag aag gtg ctg ccc tca gac aag ttc aag gac tac cta    7550
Leu Ser Gln Glu Lys Val Leu Pro Ser Asp Lys Phe Lys Asp Tyr Leu
        2480                2485                2490 gag acc atg gct cca gag ctc ctg gag ggc cag ggg gct gtt cca cag    7598
Glu Thr Met Ala Pro Glu Leu Leu Glu Gly Gln Gly Ala Val Pro Gln
    2495                2500                2505 aca gac atc tgg gcc atc ggt gtg aca gcc ttc atc atg ctg agc gcc    7646
Thr Asp Ile Trp Ala Ile Gly Val Thr Ala Phe Ile Met Leu Ser Ala
2510                2515                2520                2525 gag tac ccg gtg agc agc gag ggt gca cgc gac ctg cag aga gga ctg    7694
Glu Tyr Pro Val Ser Ser Glu Gly Ala Arg Asp Leu Gln Arg Gly Leu
                2530                2535                2540 cgc aag ggg ctg gtc cgg ctg agc cgc tgc tac gcg ggg ctg tcc ggg    7742
Arg Lys Gly Leu Val Arg Leu Ser Arg Cys Tyr Ala Gly Leu Ser Gly
            2545                2550                2555 ggc gcc gtg gcc ttc ctg cgc agc act ctg tgc gcc cag ccc tgg ggc    7790
Gly Ala Val Ala Phe Leu Arg Ser Thr Leu Cys Ala Gln Pro Trp Gly
        2560                2565                2570 cgg ccc tgc gcg tcc agc tgc ctg cag tgc ccg tgg cta aca gag gag    7838
Arg Pro Cys Ala Ser Ser Cys Leu Gln Cys Pro Trp Leu Thr Glu Glu
    2575                2580                2585 ggc ccg gcc tgt tcg cgg ccc gcg ccc gtg acc ttc cct acc gcg cgg    7886
Gly Pro Ala Cys Ser Arg Pro Ala Pro Val Thr Phe Pro Thr Ala Arg
2590                2595                2600                2605 ctg cgc gtc ttc gtg cgc aat cgc gag aag aga cgc gcg ctg ctg tac    7934
Leu Arg Val Phe Val Arg Asn Arg Glu Lys Arg Arg Ala Leu Leu Tyr
                2610                2615                2620 aag agg cac aac ctg gcc cag gtg cgc tga gggtcgcccc ggccacaccc      7984
Lys Arg His Asn Leu Ala Gln Val Arg  *
            2625                2630 ttggtctccc cgctgggggt cgctgcagac gcgccaataa aaacgccag ccgggcgaga   8044 aaaaaaaaaa aaaaaaaaaa aaaaaaaaaa aaaaaaaag gcggccgcta aaaagtcta    8104 ga                                                                 8106

<210> SEQ ID NO 2
<211> LENGTH: 2630
<212> TYPE: PRT
<213> ORGANISM: Homo sapiens

<400> SEQUENCE: 2

Met Gly Ala Ala Tyr Ser Ser Ala Arg Leu Leu Val Arg Gly Pro Asp
 1               5                  10                  15

Glu Pro Glu Glu Lys Pro Ala Ser Asp Val His Glu Gln Leu Val Pro
            20                  25                  30

Pro Arg Met Leu Glu Arg Phe Thr Pro Lys Val Lys Lys Gly Ser
        35                  40                  45

Ser Ile Thr Phe Ser Val Lys Val Gly Arg Pro Val Pro Thr Val
    50                  55                  60

His Trp Leu Arg Glu Glu Ala Glu Arg Gly Val Leu Trp Ile Gly Pro
65                  70                  75                  80

Asp Thr Pro Gly Tyr Thr Val Ala Ser Ala Gln Gln His Ser Leu
                85                  90                  95

Val Leu Leu Asp Val Gly Arg Gln His Gln Gly Thr Tyr Thr Cys Ile
            100                 105                 110

Ala Ser Asn Ala Ala Gly Gln Ala Leu Cys Ser Ala Ser Leu His Val
        115                 120                 125

Ser Gly Leu Pro Lys Val Glu Glu Gln Glu Lys Val Lys Glu Ala Leu
```

```
         130                 135                 140
Ile Ser Thr Phe Leu Gln Gly Thr Thr Gln Ala Ile Ser Ala Gln Gly
145                 150                 155                 160

Leu Glu Thr Ala Ser Phe Ala Asp Leu Gly Gly Gln Arg Lys Glu Glu
                165                 170                 175

Pro Leu Ala Ala Lys Glu Ala Leu Gly His Leu Ser Leu Ala Glu Val
                180                 185                 190

Gly Thr Glu Glu Phe Leu Gln Lys Leu Thr Ser Gln Ile Thr Glu Met
                195                 200                 205

Val Ser Ala Lys Ile Thr Gln Ala Lys Leu Gln Val Pro Gly Gly Asp
210                 215                 220

Ser Asp Glu Asp Ser Lys Thr Pro Ser Ala Ser Pro Arg His Gly Arg
225                 230                 235                 240

Ser Arg Pro Ser Ser Ile Gln Glu Ser Ser Glu Ser Glu Asp
                245                 250                 255

Gly Asp Ala Arg Gly Glu Ile Phe Asp Ile Tyr Val Val Thr Ala Asp
                260                 265                 270

Tyr Leu Pro Leu Gly Ala Glu Gln Asp Ala Ile Thr Leu Arg Glu Gly
                275                 280                 285

Gln Tyr Val Glu Val Leu Asp Ala Ala His Pro Leu Arg Trp Leu Val
                290                 295                 300

Arg Thr Lys Pro Thr Lys Ser Ser Pro Ser Arg Gln Gly Trp Val Ser
305                 310                 315                 320

Pro Ala Tyr Leu Asp Arg Arg Leu Lys Leu Ser Pro Glu Trp Gly Ala
                325                 330                 335

Ala Glu Ala Pro Glu Phe Pro Gly Glu Ala Val Ser Glu Asp Glu Tyr
                340                 345                 350

Lys Ala Arg Leu Ser Ser Val Ile Gln Glu Leu Leu Ser Ser Glu Gln
                355                 360                 365

Ala Phe Val Glu Glu Leu Gln Phe Leu Gln Ser His His Leu Gln His
                370                 375                 380

Leu Glu Arg Cys Pro His Val Pro Ile Ala Val Ala Gly Gln Lys Ala
385                 390                 395                 400

Val Ile Phe Arg Asn Val Arg Asp Ile Gly Arg Phe His Ser Ser Phe
                405                 410                 415

Leu Gln Glu Leu Gln Gln Cys Asp Thr Asp Asp Val Ala Met Cys
                420                 425                 430

Phe Ile Lys Asn Gln Ala Ala Phe Glu Gln Tyr Leu Glu Phe Leu Val
                435                 440                 445

Gly Arg Val Gln Ala Glu Ser Val Val Ser Thr Ala Ile Gln Glu
450                 455                 460

Phe Tyr Lys Lys Tyr Ala Glu Glu Ala Leu Leu Ala Gly Asp Pro Ser
465                 470                 475                 480

Gln Pro Pro Pro Pro Leu Gln His Tyr Leu Glu Gln Pro Val Glu
                485                 490                 495

Arg Val Gln Arg Tyr Gln Ala Leu Leu Lys Glu Leu Ile Arg Asn Lys
                500                 505                 510

Ala Arg Asn Arg Gln Asn Cys Ala Leu Leu Glu Gln Ala Tyr Ala Val
                515                 520                 525

Val Ser Ala Leu Pro Gln Arg Ala Glu Asn Lys Leu His Val Ser Leu
530                 535                 540

Met Glu Asn Tyr Pro Gly Thr Leu Glu Ala Leu Gly Glu Pro Ile Arg
545                 550                 555                 560
```

-continued

```
Gln Gly His Phe Ile Val Trp Glu Gly Ala Pro Gly Ala Arg Met Pro
                565                 570                 575

Trp Lys Gly His Asn Arg His Val Phe Leu Phe Arg Asn His Leu Val
                580                 585                 590

Ile Cys Lys Pro Arg Arg Asp Ser Arg Thr Asp Thr Val Ser Tyr Val
                595                 600                 605

Phe Arg Asn Met Met Lys Leu Ser Ser Ile Asp Leu Asn Asp Gln Val
                610                 615                 620

Glu Gly Asp Asp Arg Ala Phe Glu Val Trp Gln Glu Arg Glu Asp Ser
625                 630                 635                 640

Val Arg Lys Tyr Leu Leu Gln Ala Arg Thr Ala Ile Ile Lys Ser Ser
                645                 650                 655

Trp Val Lys Glu Ile Cys Gly Ile Gln Gln Arg Leu Ala Leu Pro Val
                660                 665                 670

Trp Arg Pro Pro Asp Phe Glu Glu Leu Ala Asp Cys Thr Ala Glu
                675                 680                 685

Leu Gly Glu Thr Val Lys Leu Ala Cys Arg Val Thr Gly Thr Pro Lys
                690                 695                 700

Pro Val Ile Ser Trp Tyr Lys Asp Gly Lys Ala Val Gln Val Asp Pro
705                 710                 715                 720

His His Ile Leu Ile Glu Asp Pro Asp Gly Ser Cys Ala Leu Ile Leu
                725                 730                 735

Asp Ser Leu Thr Gly Val Asp Ser Gly Gln Tyr Met Cys Phe Ala Ala
                740                 745                 750

Ser Ala Ala Gly Asn Cys Ser Thr Leu Gly Lys Ile Leu Val Gln Val
                755                 760                 765

Pro Pro Arg Phe Val Asn Lys Val Arg Ala Ser Pro Phe Val Glu Gly
                770                 775                 780

Glu Asp Ala Gln Phe Thr Cys Thr Ile Glu Gly Ala Pro Tyr Pro Gln
785                 790                 795                 800

Ile Arg Trp Tyr Lys Asp Gly Ala Leu Leu Thr Thr Gly Asn Lys Phe
                805                 810                 815

Gln Thr Leu Ser Glu Pro Arg Ser Gly Leu Leu Val Leu Val Ile Arg
                820                 825                 830

Ala Ala Ser Lys Glu Asp Leu Gly Leu Tyr Glu Cys Glu Leu Val Asn
                835                 840                 845

Arg Leu Gly Ser Ala Arg Ala Ser Ala Glu Leu Arg Ile Gln Ser Pro
850                 855                 860

Met Leu Gln Ala Gln Glu Gln Cys His Arg Glu Gln Leu Val Ala Ala
865                 870                 875                 880

Val Glu Asp Thr Thr Leu Glu Arg Ala Asp Gln Glu Val Thr Ser Val
                885                 890                 895

Leu Lys Arg Leu Leu Gly Pro Lys Ala Pro Gly Pro Ser Thr Gly Asp
                900                 905                 910

Leu Thr Gly Pro Gly Pro Cys Pro Arg Gly Ala Pro Ala Leu Gln Glu
                915                 920                 925

Thr Gly Ser Gln Pro Pro Val Thr Gly Thr Ser Glu Ala Pro Ala Val
                930                 935                 940

Pro Pro Arg Val Pro Gln Pro Leu Leu His Glu Gly Pro Glu Gln Glu
945                 950                 955                 960

Pro Glu Ala Ile Ala Arg Ala Gln Glu Trp Thr Val Pro Ile Arg Met
                965                 970                 975
```

-continued

```
Glu Gly Ala Ala Trp Pro Gly Ala Gly Thr Gly Glu Leu Leu Trp Asp
            980                 985                 990

Val His Ser His Val Val Arg Glu Thr Thr Gln Arg Thr Tyr Thr Tyr
        995                 1000                1005

Gln Ala Ile Asp Thr His Thr Ala Arg Pro Pro Ser Met Gln Val Thr
    1010                1015                1020

Ile Glu Asp Val Gln Ala Gln Thr Gly Thr Ala Gln Phe Glu Ala
1025                1030                1035                1040

Ile Ile Glu Gly Asp Pro Gln Pro Ser Val Thr Trp Tyr Lys Asp Ser
                1045                1050                1055

Val Gln Leu Val Asp Ser Thr Arg Leu Ser Gln Gln Gln Glu Gly Thr
            1060                1065                1070

Thr Tyr Ser Leu Val Leu Arg His Val Ala Ser Lys Asp Ala Gly Val
        1075                1080                1085

Tyr Thr Cys Leu Ala Gln Asn Thr Gly Gly Gln Val Leu Cys Lys Ala
    1090                1095                1100

Glu Leu Leu Val Leu Gly Gly Asp Asn Glu Pro Asp Ser Glu Lys Gln
1105                1110                1115                1120

Ser His Arg Arg Lys Leu His Ser Phe Tyr Glu Val Lys Glu Glu Ile
                1125                1130                1135

Gly Arg Gly Val Phe Gly Phe Val Lys Arg Val Gln His Lys Gly Asn
            1140                1145                1150

Lys Ile Leu Cys Ala Ala Lys Phe Ile Pro Leu Arg Ser Arg Thr Arg
        1155                1160                1165

Ala Gln Ala Tyr Arg Glu Arg Asp Ile Leu Ala Ala Leu Ser His Pro
    1170                1175                1180

Leu Val Thr Gly Leu Leu Asp Gln Phe Glu Thr Arg Lys Thr Leu Ile
1185                1190                1195                1200

Leu Ile Leu Glu Leu Cys Ser Ser Glu Glu Leu Leu Asp Arg Leu Tyr
                1205                1210                1215

Arg Lys Gly Val Val Thr Glu Ala Glu Val Lys Val Tyr Ile Gln Gln
            1220                1225                1230

Leu Val Glu Gly Leu His Tyr Leu His Ser His Gly Val Leu His Leu
        1235                1240                1245

Asp Ile Lys Pro Ser Asn Ile Leu Met Val His Pro Ala Arg Glu Asp
    1250                1255                1260

Ile Lys Ile Cys Asp Phe Gly Phe Ala Gln Asn Ile Thr Pro Ala Glu
1265                1270                1275                1280

Leu Gln Phe Ser Gln Tyr Gly Ser Pro Glu Phe Val Ser Pro Glu Ile
                1285                1290                1295

Ile Gln Gln Asn Pro Val Ser Glu Ala Ser Asp Ile Trp Ala Met Gly
            1300                1305                1310

Val Ile Ser Tyr Leu Ser Leu Thr Cys Ser Ser Pro Phe Ala Gly Glu
        1315                1320                1325

Ser Asp Arg Ala Thr Leu Leu Asn Val Leu Glu Gly Arg Val Ser Trp
    1330                1335                1340

Ser Ser Pro Met Ala Ala His Leu Ser Glu Asp Ala Lys Asp Phe Ile
1345                1350                1355                1360

Lys Ala Thr Leu Gln Arg Ala Pro Gln Ala Arg Pro Ser Ala Ala Gln
                1365                1370                1375

Cys Leu Ser His Pro Trp Phe Leu Lys Ser Met Pro Ala Glu Glu Ala
            1380                1385                1390

His Phe Ile Asn Thr Lys Gln Leu Lys Phe Leu Leu Ala Arg Ser Arg
```

-continued

```
                1395                1400                1405
Trp Gln Arg Ser Leu Met Ser Tyr Lys Ser Ile Leu Val Met Arg Ser
        1410                1415                1420
Ile Pro Glu Leu Leu Arg Gly Pro Pro Asp Ser Pro Ser Leu Gly Val
1425                1430                1435                1440
Ala Arg His Leu Cys Arg Asp Thr Gly Gly Ser Ser Ser Ser Ser Ser
            1445                1450                1455
Ser Ser Asp Asn Glu Leu Ala Pro Phe Ala Arg Ala Lys Ser Leu Pro
        1460                1465                1470
Pro Ser Pro Val Thr His Ser Pro Leu Leu His Pro Arg Gly Phe Leu
    1475                1480                1485
Arg Pro Ser Ala Ser Leu Pro Glu Glu Ala Glu Ala Ser Glu Arg Ser
    1490                1495                1500
Thr Glu Ala Pro Ala Pro Pro Ala Ser Pro Glu Gly Ala Gly Pro Pro
1505                1510                1515                1520
Ala Ala Gln Gly Cys Val Pro Arg His Ser Val Ile Arg Ser Leu Phe
            1525                1530                1535
Tyr His Gln Ala Gly Glu Ser Pro Glu His Gly Ala Leu Ala Pro Gly
            1540                1545                1550
Ser Arg Arg His Pro Ala Arg Arg His Leu Leu Lys Gly Gly Tyr
            1555                1560                1565
Ile Ala Gly Ala Leu Pro Gly Leu Arg Glu Pro Leu Met Glu His Arg
        1570                1575                1580
Val Leu Glu Glu Ala Ala Arg Glu Glu Gln Ala Thr Leu Leu Ala
1585                1590                1595                1600
Lys Ala Pro Ser Phe Glu Thr Ala Leu Arg Leu Pro Ala Ser Gly Thr
            1605                1610                1615
His Leu Ala Pro Gly His Ser His Ser Leu Glu His Asp Ser Pro Ser
        1620                1625                1630
Thr Pro Arg Pro Ser Ser Glu Ala Cys Gly Glu Ala Gln Arg Leu Pro
        1635                1640                1645
Ser Ala Pro Ser Gly Gly Ala Pro Ile Arg Asp Met Gly His Pro Gln
    1650                1655                1660
Gly Ser Lys Gln Leu Pro Ser Thr Gly Gly His Pro Gly Thr Ala Gln
1665                1670                1675                1680
Pro Glu Arg Pro Ser Pro Asp Ser Pro Trp Gly Gln Pro Ala Pro Phe
            1685                1690                1695
Cys His Pro Lys Gln Gly Ser Ala Pro Gln Glu Gly Cys Ser Pro His
            1700                1705                1710
Pro Ala Val Ala Pro Cys Pro Pro Gly Ser Phe Pro Pro Gly Ser Cys
    1715                1720                1725
Lys Glu Ala Pro Leu Val Pro Ser Ser Pro Phe Leu Gly Gln Pro Gln
    1730                1735                1740
Ala Pro Pro Ala Pro Ala Lys Ala Ser Pro Pro Leu Asp Ser Lys Met
1745                1750                1755                1760
Gly Pro Gly Asp Ile Ser Leu Pro Gly Arg Pro Lys Pro Gly Pro Cys
            1765                1770                1775
Ser Ser Pro Gly Ser Ala Ser Gln Ala Ser Ser Gln Val Ser Ser
            1780                1785                1790
Leu Arg Val Gly Ser Ser Gln Val Gly Thr Glu Pro Gly Pro Ser Leu
        1795                1800                1805
Asp Ala Glu Gly Trp Thr Gln Glu Ala Glu Asp Leu Ser Asp Ser Thr
        1810                1815                1820
```

```
Pro Thr Leu Gln Arg Pro Gln Glu Gln Ala Thr Met Arg Lys Phe Ser
1825                1830                1835                1840

Leu Gly Gly Arg Gly Gly Tyr Ala Gly Val Ala Gly Tyr Gly Thr Phe
            1845                1850                1855

Ala Phe Gly Gly Asp Ala Gly Gly Met Leu Gly Gln Gly Pro Met Trp
            1860                1865                1870

Ala Arg Ile Ala Trp Ala Val Ser Gln Ser Glu Glu Glu Gln Glu
        1875                1880                1885

Glu Ala Arg Ala Glu Ser Gln Ser Glu Glu Gln Gln Glu Ala Arg Ala
        1890                1895                1900

Glu Ser Pro Leu Pro Gln Val Ser Ala Arg Pro Val Pro Glu Val Gly
1905                1910                1915                1920

Arg Ala Pro Thr Arg Ser Ser Pro Glu Pro Thr Pro Trp Glu Asp Ile
            1925                1930                1935

Gly Gln Val Ser Leu Val Gln Ile Arg Asp Leu Ser Gly Asp Ala Glu
            1940                1945                1950

Ala Ala Asp Thr Ile Ser Leu Asp Ile Ser Glu Val Asp Pro Ala Tyr
            1955                1960                1965

Leu Asn Leu Ser Asp Leu Tyr Asp Ile Lys Tyr Leu Pro Phe Glu Phe
1970                1975                1980

Met Ile Phe Arg Lys Val Pro Lys Ser Ala Gln Pro Glu Pro Pro Ser
1985                1990                1995                2000

Pro Met Ala Glu Glu Glu Leu Ala Glu Phe Pro Glu Pro Thr Trp Pro
            2005                2010                2015

Trp Pro Gly Glu Leu Gly Pro His Ala Gly Leu Glu Ile Thr Glu Glu
            2020                2025                2030

Ser Glu Asp Val Asp Ala Leu Leu Ala Glu Ala Ala Val Gly Arg Lys
            2035                2040                2045

Arg Lys Trp Ser Ser Pro Ser Arg Ser Leu Phe His Phe Pro Gly Arg
2050                2055                2060

His Leu Pro Leu Asp Glu Pro Ala Glu Leu Gly Leu Arg Glu Arg Val
2065                2070                2075                2080

Lys Ala Ser Val Glu His Ile Ser Arg Ile Leu Lys Gly Arg Pro Glu
            2085                2090                2095

Gly Leu Glu Lys Glu Gly Pro Pro Arg Lys Lys Pro Gly Leu Ala Ser
            2100                2105                2110

Phe Arg Leu Ser Gly Leu Lys Ser Trp Asp Arg Ala Pro Thr Phe Leu
            2115                2120                2125

Arg Glu Leu Ser Asp Glu Thr Val Val Leu Gly Gln Ser Val Thr Leu
2130                2135                2140

Ala Cys Gln Val Ser Ala Gln Pro Ala Ala Gln Ala Thr Trp Ser Lys
2145                2150                2155                2160

Asp Gly Ala Pro Leu Glu Ser Ser Arg Val Leu Ile Ser Ala Thr
            2165                2170                2175

Leu Lys Asn Phe Gln Leu Leu Thr Ile Leu Val Val Val Ala Glu Asp
            2180                2185                2190

Leu Gly Val Tyr Thr Cys Ser Val Ser Asn Ala Leu Gly Thr Val Thr
            2195                2200                2205

Thr Thr Gly Val Leu Arg Lys Ala Glu Arg Pro Ser Ser Ser Pro Cys
            2210                2215                2220

Pro Asp Ile Gly Glu Val Tyr Ala Asp Gly Val Leu Leu Val Trp Lys
2225                2230                2235                2240
```

```
Pro Val Glu Ser Tyr Gly Pro Val Thr Tyr Ile Val Gln Cys Ser Leu
            2245                2250                2255

Glu Gly Gly Ser Trp Thr Thr Leu Ala Ser Asp Ile Phe Asp Cys Cys
            2260                2265                2270

Tyr Leu Thr Ser Lys Leu Ser Arg Gly Gly Thr Tyr Thr Phe Arg Thr
            2275                2280                2285

Ala Cys Val Ser Lys Ala Gly Met Gly Pro Tyr Ser Ser Pro Ser Glu
            2290                2295                2300

Gln Val Leu Leu Gly Gly Pro Ser His Leu Ala Ser Glu Glu Glu Ser
2305                2310                2315                2320

Gln Gly Arg Ser Ala Gln Pro Leu Pro Ser Thr Lys Thr Phe Ala Phe
            2325                2330                2335

Gln Thr Gln Ile Gln Arg Gly Arg Phe Ser Val Val Arg Gln Cys Trp
            2340                2345                2350

Glu Lys Ala Ser Gly Arg Ala Leu Ala Ala Lys Ile Ile Pro Tyr His
            2355                2360                2365

Pro Lys Asp Lys Thr Ala Val Leu Arg Glu Tyr Glu Ala Leu Lys Gly
            2370                2375                2380

Leu Arg His Pro His Leu Ala Gln Leu His Ala Ala Tyr Leu Ser Pro
2385                2390                2395                2400

Arg His Leu Val Leu Ile Leu Glu Leu Cys Ser Gly Pro Glu Leu Leu
            2405                2410                2415

Pro Cys Leu Ala Glu Arg Ala Ser Tyr Ser Glu Ser Glu Val Lys Asp
            2420                2425                2430

Tyr Leu Trp Gln Met Leu Ser Ala Thr Gln Tyr Leu His Asn Gln His
            2435                2440                2445

Ile Leu His Leu Asp Leu Arg Ser Glu Asn Met Ile Ile Thr Glu Tyr
            2450                2455                2460

Asn Leu Leu Lys Val Val Asp Leu Gly Asn Ala Gln Ser Leu Ser Gln
2465                2470                2475                2480

Glu Lys Val Leu Pro Ser Asp Lys Phe Lys Asp Tyr Leu Glu Thr Met
            2485                2490                2495

Ala Pro Glu Leu Leu Glu Gly Gln Gly Ala Val Pro Gln Thr Asp Ile
            2500                2505                2510

Trp Ala Ile Gly Val Thr Ala Phe Ile Met Leu Ser Ala Glu Tyr Pro
            2515                2520                2525

Val Ser Ser Glu Gly Ala Arg Asp Leu Gln Arg Gly Leu Arg Lys Gly
            2530                2535                2540

Leu Val Arg Leu Ser Arg Cys Tyr Ala Gly Leu Ser Gly Gly Ala Val
2545                2550                2555                2560

Ala Phe Leu Arg Ser Thr Leu Cys Ala Gln Pro Trp Gly Arg Pro Cys
            2565                2570                2575

Ala Ser Ser Cys Leu Gln Cys Pro Trp Leu Thr Glu Glu Gly Pro Ala
            2580                2585                2590

Cys Ser Arg Pro Ala Pro Val Thr Phe Pro Thr Ala Arg Leu Arg Val
            2595                2600                2605

Phe Val Arg Asn Arg Glu Lys Arg Arg Ala Leu Leu Tyr Lys Arg His
            2610                2615                2620

Asn Leu Ala Gln Val Arg
2625                2630

<210> SEQ ID NO 3
<211> LENGTH: 7893
<212> TYPE: DNA
```

<213> ORGANISM: Homo sapiens

<400> SEQUENCE: 3

| | | | | | |
|---|---|---|---|---|---|
| atgggtgctg | cctactcgtc | tgcccggctg | ctggttcgag | ccctgatga | gccagaagag | 60 |
| aagcctgcat | cagatgtgca | tgagcagctg | gtgccgcccc | gaatgctgga | gaggttcacc | 120 |
| cccaagaaag | tgaagaaagg | ctccagcatc | accttctctg | tgaaggtaga | aggacgcccg | 180 |
| gtgcccaccg | tgcactggct | cagggaggag | gctgagagag | cgtgctgtg | gattggccct | 240 |
| gacacaccgg | gctacaccgt | ggccagctct | gcgcagcagc | acagcctggt | cctgctggac | 300 |
| gtgggccggc | agcaccaggg | cacctacaca | tgcattgcca | gcaacgctgc | cggccaggcc | 360 |
| ctctgctccg | ccagcctgca | cgtctcgggc | ctgcctaagg | tggaggagca | ggagaaagtg | 420 |
| aaggaagcgc | tgatttccac | tttcctgcag | gggaccacac | aagccatctc | agcacagggg | 480 |
| ttggaaactg | cgagttttgc | tgaccttggt | gggcagagga | agaagagcc | tctggctgcc | 540 |
| aaggaggccc | tcgccacct | gtccctcgct | gaggtgggca | cagaggagtt | cctgcagaaa | 600 |
| ctgacctccc | agatcactga | gatggtatcg | ccaagatca | cgcaggccaa | gctgcaggtg | 660 |
| cccggaggtg | acagtgatga | ggactccaag | acaccatctg | catcccccg | ccatggccga | 720 |
| tcacggccat | cctccagcat | ccaggagtct | tcctcagagt | cagaggacgg | cgatgcccga | 780 |
| ggcgagatct | ttgacatcta | cgtggtcacc | gctgactacc | tgcccctagg | ggctgagcag | 840 |
| gatgccatca | cgctgcggga | aggccagtat | gtggaggtcc | tggatgcagc | ccacccactg | 900 |
| cgctggcttg | tccgcaccaa | gcccaccaag | tccagcccct | cacggcaggg | ctgggtgtca | 960 |
| ccagcctacc | tggacaggag | gctcaagctg | tcacctgagt | gggggggccgc | tgaggcccct | 1020 |
| gagttccctg | gggaggctgt | gtctgaagac | gaatacaagg | caaggctgag | ctctgtgatc | 1080 |
| caggagctgc | tgagttctga | gcaggccttc | gtggaggagc | tgcagttcct | gcagagccac | 1140 |
| cacctgcagc | acctggagcg | ctgccccac | gtgcccatag | ccgtggccgg | ccagaaggca | 1200 |
| gtcatcttcc | gcaatgtgcg | ggacatcggc | cgcttccaca | gcagcttcct | gcaggagttg | 1260 |
| cagcagtgcg | cacggacga | cgacgtggcc | atgtgcttca | tcaagaacca | ggcggccttt | 1320 |
| gagcagtacc | tggagttcct | ggtggggcgt | gtgcaggctg | agtcggtggt | cgtcagcacg | 1380 |
| gccatccagg | agttctacaa | gaaatacgcg | gaggaggccc | tgttggcagg | gaccccctct | 1440 |
| cagccccgc | caccacctct | gcagcactac | ctggagcagc | cagtggagcg | ggtgcagcgc | 1500 |
| taccaggcct | tgctgaagga | gttgatccgc | aacaaggcgc | ggaacagaca | gaactgcgcg | 1560 |
| ctgctggagc | aggcctatgc | cgtggtgtct | gccctgccac | agcgcgctga | aacaagctg | 1620 |
| cacgtgtccc | tcatggagaa | ctacccaggc | accctggagg | ccctgggcga | gcccatccgc | 1680 |
| cagggccact | tcatcgtgtg | ggagggtgca | ccggggccc | gcatgccctg | gaagggccac | 1740 |
| aaccgtcacg | tgttcctctt | ccgcaaccac | ctggtaatct | gcaagccccg | gcgagactcc | 1800 |
| cgcaccgata | ccgtcagcta | cgtgttccgg | aacatgatga | agctgagcag | catcgacctg | 1860 |
| aacgaccagg | tggagggga | tgaccgcgcc | ttcgaggtgt | ggcaggagcg | ggaggactcg | 1920 |
| gtgcgcaagt | acctgctgca | ggcacggaca | gccattatca | gagctcgtg | ggtgaaggag | 1980 |
| atctgtggca | tccagcagcg | tctggccctg | cctgtgtggc | ggcccccgga | ctttgaagag | 2040 |
| gagctggccg | actgcacagc | cgagctgggt | gagacagtca | gctggcctg | ccgcgtgacg | 2100 |
| ggcacaccca | gcctgtcat | cagctggtac | aaagatggga | aagcagtgca | ggtggacccc | 2160 |
| caccacatcc | tcattgaaga | ccctgatggc | tcgtgtgcac | tcatcctgga | cagcctgacc | 2220 |
| ggtgtggact | ctggccagta | catgtgcttc | gcggccagcg | ccgctggcaa | ctgcagtacc | 2280 |

```
ctgggcaaga tcctggtgca agtcccacca cggttcgtga acaaggtccg ggcctcaccc    2340
tttgtggagg gagaggacgc ccagttcacc tgcaccatcg aaggcgcccc gtacccgcag    2400
atcaggtggt acaaggacgg ggccctgctg accactggca acaagttcca gacactgagt    2460
gagcctcgca gcggcctgct agtgctggtg atccggcgg ccagcaagga ggacctgggg    2520
ctctacgagt gtgagctggt gaaccggctg ggctccgcgc gggctagtgc ggagctgcgc    2580
attcagagcc ccatgctgca ggcccaggag cagtgtcaca gggagcagct cgtggctgca    2640
gtggaagaca ccaccctgga gcgagcggac caggaggtca catctgtcct gaagagactg    2700
ctgggcccca aggcgccagg cccctccaca ggggacctca ctggccctgg cccctgcccc    2760
aggggggcac ccgcactcca ggaaaccggc tcccagcccc cagtcaccgg aacttcggag    2820
gcacctgccg tgcccccgag ggtgccacag cccctcctcc acgaaggccc agagcaggag    2880
ccggaggcca ttgccagagc ccaggaatgg actgtgccca ttcggatgga gggtgcagcc    2940
tggcccgggg caggcacagg ggagctgctc tgggacgtcc acagccacgt ggtcagagag    3000
accacacaga ggacctacac ataccaggcc atcgacacgc acaccgcacg gcccccatcc    3060
atgcaggtaa ccatcgagga tgtgcaggca cagacaggcg gaacggccca attcgaggct    3120
atcattgagg gcgacccaca gccctcggtg acctggtaca aggacagcgt ccagctggtg    3180
gacagcaccc ggcttagcca gcagcaagaa ggcaccacat actccctggt gctgaggcat    3240
gtggcctcga aggatgccgg cgtttacacc tgcctggccc aaaacactgg tggccaggtg    3300
ctctgcaagg cagagctgct ggtgcttggg ggggacaatg agccggactc agagaagcaa    3360
agccaccgga ggaagctgca ctccttctat gaggtcaagg aggagattgg aagggcgtg    3420 tttggcttcg taaaagagt gcagcacaaa ggaaacaaga tcttgtgcgc tgccaagttc    3480 atcccctac ggagcagaac tcgggcccag gcatacaggg agcgagacat cctggccgcg    3540
ctgagccacc cgctggtcac ggggctgctg gaccagtttg agacccgcaa gaccctcatc    3600
ctcatcctgg agctgtgctc atccgaggag ctgctggacc gcctgtacag gaagggcgtg    3660
gtgacggagg ccgaggtcaa ggtctacatc agcagctgg tggaggggct gcactacctg    3720
cacagccatg gcgttctcca cctggacata aagccctcta acatcctgat ggtgcatcct    3780
gcccgggaag acattaaaat ctgcgacttt ggctttgccc agaacatcac cccagcagag    3840
ctgcagttca gccagtacgg ctcccctgag ttcgtctccc ccgagatcat ccagcagaac    3900
cctgtgagcg aagcctccga catttgggcc atgggtgtca tctcctacct cagcctgacc    3960
tgctcatccc catttgccgg cgagagtgac cgtgccaccc tcctgaacgt cctggagggg    4020
cgcgtgtcat ggagcagccc catggctgcc cacctcagcg aagacgccaa agacttcatc    4080
aaggctacgc tgcagagagc ccctcaggcc cggcctagtg cggcccagtg cctctcccac    4140
ccctggttcc tgaaatccat gctgcgggag gaggcccact tcatcaacac caagcagctc    4200
aagttcctcc tggcccgaag tcgctggcag cgttccctga tgagctacaa gtccatcctg    4260
gtgatgcgct ccatccctga gctgctgcgg ggcccaccg acagccctc cctcggcgta    4320 gcccggcacc tctgcaggga cactggtggc tcctccagtt cctcctcctc ctctgacaac    4380
gagctcgccc catttgcccg ggctaagtca ctgccaccct cccggtgac acactccacca    4440 ctgctgcacc cgggggctt cctgcggccc tcggccagct gcctgaggga gccgaggcc    4500 agtgagcgct ccaccgaggc cccagctccg cctgcatctc ccgagggtgc cgggccaccg    4560
gccgcccagg gctgcgtgcc ccggcacagc gtcatccgca gcctgttcta ccaccaggcg    4620
```

```
ggtgagagcc ctgagcacgg ggccctggcc ccggggagca ggcggcaccc ggcccggcgg    4680
cggcacctgc tgaagggcgg gtacattgcg ggggcgctgc caggcctgcg cgagccactg    4740
atggagcacc gcgtgctgga ggaggaggcc gccaggagg agcaggccac cctcctggcc      4800
aaagccccct cattcgagac tgccctccgg ctgcctgcct ctggcaccca cttggcccct    4860
ggccacagcc actccctgga acatgactct ccgagcaccc cccgcccctc ctcggaggcc    4920
tgcggtgagg cacagcgact gccttcagcc ccctccgggg gggcccctat cagggacatg    4980
gggcaccctc agggctccaa gcagcttcca tccactggtg gccacccagg cactgctcag    5040
ccagagaggc catccccgga cagcccttgg gggcagccag cccctttctg ccaccccaag    5100
cagggttctg ccccccagga gggctgcagc ccccacccag cagttgcccc atgccctcct    5160
ggctccttcc ctccaggatc ttgcaaagag ccccccttag taccctcaag ccccttcttg    5220
ggacagcccc aggcaccccc tgcccctgcc aaagcaagcc cccattgga ctctaagatg      5280 gggcctggag acatctctct tcctgggagg ccaaaacccg gccccctgcag ttccccaggg   5340 tcagcctccc aggcgagctc ttcccaagtg agctccctca gggtgggctc ctcccaggtg    5400
ggcacagagc ctgccccctc cctggatgcg gagggctgga cccaggaggc tgaggatctg    5460
tccgactcca cacccacctt gcagcggcct caggaacagg cgaccatgcg caagttctcc    5520
ctgggtggtc gcgggggcta cgcaggcgtg gctggctatg gcacctttgc ctttggtgga    5580
gatgcagggg gcatgctggg gcaggggccc atgtgggcca ggatagcctg ggctgtgtcc    5640
cagtcggagg aggaggagca ggaggaggcc agggctgagt cccagtcgga ggagcagcag    5700
gaggccaggg ctgagagccc actgccccag gtcagtgcaa ggcctgtgcc tgaggtcggc    5760
agggctccca ccaggagctc tccagagccc accccatggg aggacatcgg gcaggtctcc    5820
ctggtgcaga tccgggacct gtcaggtgat gcggaggcgg ccgacacaat atccctggac    5880
atttccgagg tggaccccgc ctacctcaac ctctcagacc tgtacgatat caagtacctc    5940
ccattcgagt ttatgatctt caggaaagtc cccaagtccg ctcagccaga gccgccctcc    6000
cccatggctg aggaggagct ggccgagttc ccggagccca gtggccctg gccaggtgaa    6060 ctgggccccc acgcaggcct ggagatcaca gaggagtcag aggatgtgga cgcgctgctg    6120
gcagaggctg ccgtgggcag gaagcgcaag tggtcctcgc cgtcacgcag cctcttccac    6180
ttccctggga ggcacctgcc gctggatgag cctgcagagc tggggctgcg tgagagagtg    6240
aaggcctccg tggagcacat ctcccggatc ctgaagggca ggccggaagg tctggagaag    6300
gaggggcccc ccaggaagaa gccaggcctt gcttccttcc ggctctcagg tctgaagagc    6360
tgggaccgag cgccgacatt cctaagggag ctctcagatg agactgtggt cctgggccag    6420
tcagtgacac tggcctgcca ggtgtcagcc agccagctg cccaggccac ctggagcaaa     6480 gacgcgagccc cctggagag cagcagccgt gtcctcatct ctgccaccct caagaacttc    6540
cagcttctga ccatcctggt ggtggtggct gaggacctgg gtgtgtacac ctgcagcgtg    6600
agcaatgcgc tgggacagt gaccaccacg ggcgtcctcc ggaaggcaga gcgcccctca     6660
tcttcgccat gccggatat cggggaggtg tacgcggatg ggtgctgct ggtctggaag      6720 cccgtggaat cctacggccc tgtgacctac attgtgcagt gcagcctaga aggcggcagc    6780
tggaccacac tggcctccga catctttgac tgctgctacc tgaccagcaa gctctcccgg    6840
ggtggcacct acaccttccg cacggcatgt gtcagcaagg caggaatggg tccctacagc    6900 agccctcgg agcaagtcct cctgggaggg cccagccacc tggcctctga ggaggagagc    6960
caggggcggt cagcccaacc cctgcccagc acaaagacct tcgcattcca gacacagatc    7020
```

-continued

```
cagaggggcc gcttcagcgt ggtgcggcaa tgctgggaga aggccagcgg gcgggcgctg    7080
gccgccaaga tcatcccta ccaccccaag acaagacag cagtgctgcg cgaatacgag      7140
gccctcaagg gcctgcgcca cccgcacctg gcccagctgc acgcagccta cctcagcccc    7200
cggcacctgg tgctcatctt ggagctgtgc tctgggcccg agctgctccc ctgcctggcc    7260
gagagggcct cctactcaga atccgaggtg aaggactacc tgtggcagat gttgagtgcc    7320
acccagtacc tgcacaacca gcacatcctg cacctggacc tgaggtccga aacatgatc    7380 atcaccgaat acaacctgct caaggtcgtg gacctgggca atgcacagag cctcagccag    7440
gagaaggtgc tgccctcaga caagttcaag gactacctag agaccatggc tccagagctc    7500
ctggagggcc aggggctgt tccacagaca gacatctggg ccatcggtgt gacagccttc     7560
atcatgctga gcgccgagta cccggtgagc agcgagggtg cacgcgacct gcagagagga    7620
ctgcgcaagg ggctggtccg gctgagccgc tgctacgcgg ggctgtccgg gggcgccgtg    7680
gccttcctgc gcagcactct gtgcgcccag ccctgggggcc ggccctgcgc gtccagctgc   7740
ctgcagtgcc cgtggctaac agaggagggc ccggcctgtt cgcggcccgc gcccgtgacc    7800
ttccctaccg cgcggctgcg cgtcttcgtg cgcaatcgcg agaagagacg cgcgctgctg    7860
tacaagaggc acaacctggc ccaggtgcgc tga                                 7893
```

<210> SEQ ID NO 4
<211> LENGTH: 24120
<212> TYPE: DNA
<213> ORGANISM: Homo sapiens
<220> FEATURE:
<221> NAME/KEY: 5'UTR
<222> LOCATION: (1)...(71)
<221> NAME/KEY: CDS
<222> LOCATION: (72)...(23978)
<221> NAME/KEY: 3'UTR
<222> LOCATION: (23979)...(24120)

<400> SEQUENCE: 4

```
tgcctaccag cagcccacac tccggccgct gcccagagcc cccatagaga gaggtccccg     60
ccgccaccgt c atg gat cag cca cag ttc agc ggg gcg ccc cgc ttt ctc    110
            Met Asp Gln Pro Gln Phe Ser Gly Ala Pro Arg Phe Leu
              1               5                   10 acc cgg ccc aag gcc ttc gtg gtg tcg gtg ggc aag gac gcc acc ctc    158
Thr Arg Pro Lys Ala Phe Val Val Ser Val Gly Lys Asp Ala Thr Leu
 15                  20                  25 agc tgc cag atc gtg ggt aat ccc acg cca cag gtg agc tgg gag aag    206
Ser Cys Gln Ile Val Gly Asn Pro Thr Pro Gln Val Ser Trp Glu Lys
 30                  35                  40                  45 gac cag cag ccg gtg acg gcc ggc gcg cgc ttc cgt ctg gcc cag gac    254
Asp Gln Gln Pro Val Thr Ala Gly Ala Arg Phe Arg Leu Ala Gln Asp
                 50                  55                  60 ggc gac ctc tac cgc ctc act atc ctg gac ctg gcg ctg ggc gac agt    302
Gly Asp Leu Tyr Arg Leu Thr Ile Leu Asp Leu Ala Leu Gly Asp Ser
             65                  70                  75 ggg caa tac gtg tgc cgc gcg cgc aat gcc ata ggc gag gcc ttc gct    350
Gly Gln Tyr Val Cys Arg Ala Arg Asn Ala Ile Gly Glu Ala Phe Ala
         80                  85                  90 gcc gtg ggc ctg cag gtg gac gcg gag gcc gcg tgc gcc gag cag gcg    398
Ala Val Gly Leu Gln Val Asp Ala Glu Ala Ala Cys Ala Glu Gln Ala
     95                 100                 105 ccg cac ttc ctg ctg cgg ccc acg tcc atc cgc gtg cgc gag ggc tca    446
Pro His Phe Leu Leu Arg Pro Thr Ser Ile Arg Val Arg Glu Gly Ser
110                 115                 120                 125
```

-continued

```
gag gcc acc ttc cgc tgc cgc gtg ggt ggc tcc ccg agg ccg gca gtg     494
Glu Ala Thr Phe Arg Cys Arg Val Gly Gly Ser Pro Arg Pro Ala Val
            130                 135                 140 agc tgg tcc aag gac ggg cgg cgc ctg ggt gag ccc gac ggc ccc cgc     542
Ser Trp Ser Lys Asp Gly Arg Arg Leu Gly Glu Pro Asp Gly Pro Arg
        145                 150                 155 gtg cgc gtg gag gag ctc ggc gag gca agt gcg ctg cgc att cgg gcg     590
Val Arg Val Glu Glu Leu Gly Glu Ala Ser Ala Leu Arg Ile Arg Ala
    160                 165                 170 gcg cgg ccg cgc gac ggc ggc act tac gag gtc cgc gcc gag aac ccg     638
Ala Arg Pro Arg Asp Gly Gly Thr Tyr Glu Val Arg Ala Glu Asn Pro
175                 180                 185 ctg ggc gct gcc agc gcc gcc gcg gcg cta gtg gtg gac tcg gac gcc     686
Leu Gly Ala Ala Ser Ala Ala Ala Ala Leu Val Val Asp Ser Asp Ala
190                 195                 200                 205 gcg gac acg gcc agc cgg ccc ggg acc tcc acg gcc gcg ctc ctg gcg     734
Ala Asp Thr Ala Ser Arg Pro Gly Thr Ser Thr Ala Ala Leu Leu Ala
                210                 215                 220 cac ctg cag cgg cgg cgc gag gct atg cgc gcc gag ggc gcc ccc gcc     782
His Leu Gln Arg Arg Arg Glu Ala Met Arg Ala Glu Gly Ala Pro Ala
            225                 230                 235 tca ccc ccc agc acc ggc acg cgc acc tgc acg gtg act gaa ggc aag     830
Ser Pro Pro Ser Thr Gly Thr Arg Thr Cys Thr Val Thr Glu Gly Lys
        240                 245                 250 cac gcg cgc ctc agc tgc tac gtg acc ggc gag ccc aag ccc gag acg     878
His Ala Arg Leu Ser Cys Tyr Val Thr Gly Glu Pro Lys Pro Glu Thr
    255                 260                 265 gtg tgg aag aag gac ggc cag ctg gtg acc gag ggc cgg cgc cac gtg     926
Val Trp Lys Lys Asp Gly Gln Leu Val Thr Glu Gly Arg Arg His Val
270                 275                 280                 285 gtg tac gag gac gcg cag gag aac ttc gtg ctc aag atc ctc ttc tgc     974
Val Tyr Glu Asp Ala Gln Glu Asn Phe Val Leu Lys Ile Leu Phe Cys
                290                 295                 300 aag cag tcg gac cgc ggc ctc tac acc tgc acg gcg tcc aac ctc gtg    1022
Lys Gln Ser Asp Arg Gly Leu Tyr Thr Cys Thr Ala Ser Asn Leu Val
            305                 310                 315 ggc cag acc tac agc tct gtg ctg gtc gta gtg cgc gag ccc gcg gtt    1070
Gly Gln Thr Tyr Ser Ser Val Leu Val Val Val Arg Glu Pro Ala Val
        320                 325                 330 ccc ttc aaa aag cgg ctg caa gat ctg gag gtg cgg gag aag gag tcg    1118
Pro Phe Lys Lys Arg Leu Gln Asp Leu Glu Val Arg Glu Lys Glu Ser
    335                 340                 345 gct acg ttc cta tgt gag gtg ccc cag ccg tcc act gag gcc gcg tgg    1166
Ala Thr Phe Leu Cys Glu Val Pro Gln Pro Ser Thr Glu Ala Ala Trp
350                 355                 360                 365 ttc aag gag gag acg cgg ttg tgg gcg agc gcc aag tac ggc atc gag    1214
Phe Lys Glu Glu Thr Arg Leu Trp Ala Ser Ala Lys Tyr Gly Ile Glu
                370                 375                 380 gag gag ggc acc gag cgc cgc ctg acc gtg cgc aat gtc tcg gcc gac    1262
Glu Glu Gly Thr Glu Arg Arg Leu Thr Val Arg Asn Val Ser Ala Asp
            385                 390                 395 gac gac gcg gtg tac atc tgc gag acg cca gag ggc agc cgc acg gtg    1310
Asp Asp Ala Val Tyr Ile Cys Glu Thr Pro Glu Gly Ser Arg Thr Val
        400                 405                 410 gcg gag ctc gca gtc caa gga aac ctc ctc cga aag ctc cct cgg aag    1358
Ala Glu Leu Ala Val Gln Gly Asn Leu Leu Arg Lys Leu Pro Arg Lys
    415                 420                 425 acg gcg gtg cgc gtg ggc gac acg gct atg ttt tgc gtg gag ctg gcg    1406
Thr Ala Val Arg Val Gly Asp Thr Ala Met Phe Cys Val Glu Leu Ala
```

```
                       430                 435                 440                 445
gtc ccg gtg ggc ccc gtc cac tgg ctg cgg aac cag gag gaa gtg gtg                              1454
Val Pro Val Gly Pro Val His Trp Leu Arg Asn Gln Glu Glu Val Val
                450                 455                 460 gcg ggg ggc cgc gtg gcc atc tcc gcg gag ggc acg cgc cac aca ctg                              1502
Ala Gly Gly Arg Val Ala Ile Ser Ala Glu Gly Thr Arg His Thr Leu
            465                 470                 475 acc atc tcc cag tgc tgc ctg gag gat gtg ggc cag gtg gcc ttt atg                              1550
Thr Ile Ser Gln Cys Cys Leu Glu Asp Val Gly Gln Val Ala Phe Met
        480                 485                 490 gct ggc gac tgc cag acg tcc acc cgg ttc tgc gtg tcg gcc ccc agg                              1598
Ala Gly Asp Cys Gln Thr Ser Thr Arg Phe Cys Val Ser Ala Pro Arg
    495                 500                 505 aag cct ccc ctg caa ccc cct gtg gat cct gtg gta aag gcc agg atg                              1646
Lys Pro Pro Leu Gln Pro Pro Val Asp Pro Val Val Lys Ala Arg Met
510                 515                 520                 525 gag agt tcc gtg att ctc agc tgg tcc cca cca ccc cat ggg gaa cgc                              1694
Glu Ser Ser Val Ile Leu Ser Trp Ser Pro Pro Pro His Gly Glu Arg
                530                 535                 540 cct gtc act atc gac ggc tac ctg gta gag aag aag aag ctt ggc acc                              1742
Pro Val Thr Ile Asp Gly Tyr Leu Val Glu Lys Lys Lys Leu Gly Thr
            545                 550                 555 tac acc tgg atc agg tgc cac gag gct gaa tgg gtg gct aca cct gag                              1790
Tyr Thr Trp Ile Arg Cys His Glu Ala Glu Trp Val Ala Thr Pro Glu
        560                 565                 570 ctg acc gtg gct gat gtg gcg gag gag ggg aac ttc cag ttc cga gtg                              1838
Leu Thr Val Ala Asp Val Ala Glu Glu Gly Asn Phe Gln Phe Arg Val
    575                 580                 585 tcc gct ctc aac agc ttt ggt cag agt ccc tac ctc gag ttc ccg ggg                              1886
Ser Ala Leu Asn Ser Phe Gly Gln Ser Pro Tyr Leu Glu Phe Pro Gly
590                 595                 600                 605 act gtc cac ctg gcc ccc aag ctg gcc gtg agg aca ccg ctg aag gcg                              1934
Thr Val His Leu Ala Pro Lys Leu Ala Val Arg Thr Pro Leu Lys Ala
                610                 615                 620 gtg cag gcg gta gag ggt ggc gag gtc act ttc tcc gtg gac ctc acg                              1982
Val Gln Ala Val Glu Gly Gly Glu Val Thr Phe Ser Val Asp Leu Thr
            625                 630                 635 gtg gcc tca gcg ggt gag tgg ttc ctg gat ggg cag gcc ctg aag gcc                              2030
Val Ala Ser Ala Gly Glu Trp Phe Leu Asp Gly Gln Ala Leu Lys Ala
        640                 645                 650 agc agt gtg tat gag atc cac tgt gat cgc acc cgg cac acg ctc acc                              2078
Ser Ser Val Tyr Glu Ile His Cys Asp Arg Thr Arg His Thr Leu Thr
    655                 660                 665 atc cgg gag gtg ccc gcc agc ctg cac ggg gcg cag ctg aag ttc gtg                              2126
Ile Arg Glu Val Pro Ala Ser Leu His Gly Ala Gln Leu Lys Phe Val
670                 675                 680                 685 gcc aac ggc att gag agc agc atc cgg atg gag gtc cgg gcg gcc cca                              2174
Ala Asn Gly Ile Glu Ser Ser Ile Arg Met Glu Val Arg Ala Ala Pro
                690                 695                 700 ggg ctg act gcc aac aag ccg cca gcc gca gct gcc cgg gag gtg ctg                              2222
Gly Leu Thr Ala Asn Lys Pro Pro Ala Ala Ala Ala Arg Glu Val Leu
            705                 710                 715 gct cgg ctg cac gag gag gcg cag ctg ctg gct gag ctg tca gat cag                              2270
Ala Arg Leu His Glu Glu Ala Gln Leu Leu Ala Glu Leu Ser Asp Gln
        720                 725                 730 gct gcg gct gtg acg tgg ctg aag gat ggt cgc aca ctg tcc cca ggc                              2318
Ala Ala Ala Val Thr Trp Leu Lys Asp Gly Arg Thr Leu Ser Pro Gly
    735                 740                 745 ccc aag tat gag gtg cag gca tcg gcc ggg cgg cgg gtg ctc ctt gtg                              2366
```

```
                                        -continued
Pro Lys Tyr Glu Val Gln Ala Ser Ala Gly Arg Arg Val Leu Leu Val
750                 755                 760                 765 cga gat gtg gcc cgg gac gat gca ggc ctc tac gag tgc gtc agc cgc      2414
Arg Asp Val Ala Arg Asp Asp Ala Gly Leu Tyr Glu Cys Val Ser Arg
                770                 775                 780 ggg ggc cgc atc gcc tac cag ctc tcc gtg caa ggc ctc gcg cgc ttt      2462
Gly Gly Arg Ile Ala Tyr Gln Leu Ser Val Gln Gly Leu Ala Arg Phe
            785                 790                 795 ctg cac aag gac atg gcg ggc agc tgt gtg gat gcc gtg gct ggg ggc      2510
Leu His Lys Asp Met Ala Gly Ser Cys Val Asp Ala Val Ala Gly Gly
        800                 805                 810 ccg gcg cag ttt gag tgt gag acc tcc gaa gcc cac gtc cac gtg cac      2558
Pro Ala Gln Phe Glu Cys Glu Thr Ser Glu Ala His Val His Val His
    815                 820                 825 tgg tac aag gat ggc atg gag ctg ggc cac tcc ggt gag cgc ttc ttg      2606
Trp Tyr Lys Asp Gly Met Glu Leu Gly His Ser Gly Glu Arg Phe Leu
830                 835                 840                 845 cag gag gat gtg ggg acg cgg cac cgg ctg gtg gca gcc aca gtc acc      2654
Gln Glu Asp Val Gly Thr Arg His Arg Leu Val Ala Ala Thr Val Thr
                850                 855                 860 agg cag gat gaa ggc acc tac tcc tgc cgc gtg ggc gag gac tct gtg      2702
Arg Gln Asp Glu Gly Thr Tyr Ser Cys Arg Val Gly Glu Asp Ser Val
            865                 870                 875 gac ttc cgg ctc cgc gtc tct gag ccc aag gtg gtg ttt gct aag gag      2750
Asp Phe Arg Leu Arg Val Ser Glu Pro Lys Val Val Phe Ala Lys Glu
        880                 885                 890 cag ctg gca cgc agg aag ctg cag gca gag gca gga gcc agt gcc aca      2798
Gln Leu Ala Arg Arg Lys Leu Gln Ala Glu Ala Gly Ala Ser Ala Thr
    895                 900                 905 ctg agc tgc gag gtg gcc cag gcc cag acg gag gtg acg tgg tac aag      2846
Leu Ser Cys Glu Val Ala Gln Ala Gln Thr Glu Val Thr Trp Tyr Lys
910                 915                 920                 925 gat ggg aag aag ctg agc tcc agc tcg aaa gtg tgc atg gag gcc aca      2894
Asp Gly Lys Lys Leu Ser Ser Ser Ser Lys Val Cys Met Glu Ala Thr
                930                 935                 940 ggc tgc acg cgc agg ctg gtt gtg cag cag gca ggc cag gcg gat gcc      2942
Gly Cys Thr Arg Arg Leu Val Val Gln Gln Ala Gly Gln Ala Asp Ala
            945                 950                 955 ggg gag tat agc tgc gag gct ggg ggc cag cgg ctc tcc ttc cat ctg      2990
Gly Glu Tyr Ser Cys Glu Ala Gly Gly Gln Arg Leu Ser Phe His Leu
        960                 965                 970 gat gtc aaa gag ccc aag gtg gtg ttt gcc aag gac cag gtg gca cac      3038
Asp Val Lys Glu Pro Lys Val Val Phe Ala Lys Asp Gln Val Ala His
    975                 980                 985 agt gag gtg cag gct gag gca ggg gcc aat gcc acg ctg agc tgc gag      3086
Ser Glu Val Gln Ala Glu Ala Gly Ala Asn Ala Thr Leu Ser Cys Glu
990                 995                 1000                1005 gtg gcc cag gcc cag gcg gag gtg atg tgg tac aaa gat ggg aag aag      3134
Val Ala Gln Ala Gln Ala Glu Val Met Trp Tyr Lys Asp Gly Lys Lys
                1010                1015                1020 ctg agc tcc agc ttg aaa gtg cat gta gag gcc aaa ggc tgc aga cgg      3182
Leu Ser Ser Ser Leu Lys Val His Val Glu Ala Lys Gly Cys Arg Arg
            1025                1030                1035 agg ctg gtg gtg cag cag gca ggc aag acg gat gcc ggg gac tac agc      3230
Arg Leu Val Val Gln Gln Ala Gly Lys Thr Asp Ala Gly Asp Tyr Ser
        1040                1045                1050 tgc gag gcc agg ggc cag agg gtc tcc ttc cgc ctg cac atc aca gag      3278
Cys Glu Ala Arg Gly Gln Arg Val Ser Phe Arg Leu His Ile Thr Glu
    1055                1060                1065
```

-continued

| | |
|---|---|
| ccc aag atg atg ttt gca aag gag cag tca gtg cat aat gag gtg cag<br>Pro Lys Met Met Phe Ala Lys Glu Gln Ser Val His Asn Glu Val Gln<br>1070                                        1075                              1080                             1085 | 3326 |
| gct gag gcg ggg gcc agt gcc atg ctg agc tgt gag gtg gcc cag gcc<br>Ala Glu Ala Gly Ala Ser Ala Met Leu Ser Cys Glu Val Ala Gln Ala<br>                   1090                              1095                              1100 | 3374 |
| cag acg gag gtg acg tgg tac aag gat ggg aag aag ctg agc tcc agc<br>Gln Thr Glu Val Thr Trp Tyr Lys Asp Gly Lys Lys Leu Ser Ser Ser<br>1105                                        1110                              1115 | 3422 |
| tca aaa gtg ggc atg gag gtc aaa ggg tgc aca cgg agg ctg gtg ctg<br>Ser Lys Val Gly Met Glu Val Lys Gly Cys Thr Arg Arg Leu Val Leu<br>                   1120                              1125                              1130 | 3470 |
| cca cag gcg ggc aaa gca gat gct ggg gag tac agc tgt gag gct ggg<br>Pro Gln Ala Gly Lys Ala Asp Ala Gly Glu Tyr Ser Cys Glu Ala Gly<br>1135                                        1140                              1145 | 3518 |
| ggc cag aga gtc tcc ttc cac ctg cac atc aca gag ccc aag ggg gtg<br>Gly Gln Arg Val Ser Phe His Leu His Ile Thr Glu Pro Lys Gly Val<br>1150                                        1155                              1160                             1165 | 3566 |
| ttt gcg aag gag cag tca gtg cat aat gag gtg cag gct gag gcg ggg<br>Phe Ala Lys Glu Gln Ser Val His Asn Glu Val Gln Ala Glu Ala Gly<br>                   1170                              1175                              1180 | 3614 |
| acc act gcc atg ctg agc tgt gag gtg gcc cag ccc cag acg gag gtg<br>Thr Thr Ala Met Leu Ser Cys Glu Val Ala Gln Pro Gln Thr Glu Val<br>1185                                        1190                              1195 | 3662 |
| acg tgg tac aag gac ggg aag aag ctg agc tcc agc tca aaa gta cgc<br>Thr Trp Tyr Lys Asp Gly Lys Lys Leu Ser Ser Ser Ser Lys Val Arg<br>                   1200                              1205                              1210 | 3710 |
| atg gag gtc aag ggc tgc aca cga agg ctg gta gtg cag cag gtg ggc<br>Met Glu Val Lys Gly Cys Thr Arg Arg Leu Val Val Gln Gln Val Gly<br>1215                                        1220                              1225 | 3758 |
| aaa gca gat gct ggg gag tac agc tgc gag gct ggg ggc cag aga gtc<br>Lys Ala Asp Ala Gly Glu Tyr Ser Cys Glu Ala Gly Gly Gln Arg Val<br>1230                                      1235                              1240                             1245 | 3806 |
| tcc ttt caa ctg cac atc aca gag ccc aag gca gtg ttt gcc aag gag<br>Ser Phe Gln Leu His Ile Thr Glu Pro Lys Ala Val Phe Ala Lys Glu<br>                   1250                              1255                              1260 | 3854 |
| cag ttg gtg cat aat gag gtg cgg act gag gca ggg gcc agt gcc aca<br>Gln Leu Val His Asn Glu Val Arg Thr Glu Ala Gly Ala Ser Ala Thr<br>1265                                        1270                              1275 | 3902 |
| ctg agc tgt gag gtg gcc cag gcc cag aca gag gtg acg tgg tac aag<br>Leu Ser Cys Glu Val Ala Gln Ala Gln Thr Glu Val Thr Trp Tyr Lys<br>                   1280                              1285                              1290 | 3950 |
| gat ggg aag aag ctg agc tcc agt tcg aaa gtg cgc ata gag gct gcg<br>Asp Gly Lys Lys Leu Ser Ser Ser Ser Lys Val Arg Ile Glu Ala Ala<br>1295                                        1300                              1305 | 3998 |
| ggc tgc atg cgg cag ctg gtg gtg cag cag gca ggc cag gca gat gct<br>Gly Cys Met Arg Gln Leu Val Val Gln Gln Ala Gly Gln Ala Asp Ala<br>1310                                        1315                              1320                             1325 | 4046 |
| ggg gag tac acc tgt gag gct ggg ggc cag cgg ctc tcc ttc cac ctg<br>Gly Glu Tyr Thr Cys Glu Ala Gly Gly Gln Arg Leu Ser Phe His Leu<br>                   1330                              1335                              1340 | 4094 |
| gat gtt tca gag ccc aag gcg gtg ttt gca aag gag cag ctg gca cac<br>Asp Val Ser Glu Pro Lys Ala Val Phe Ala Lys Glu Gln Leu Ala His<br>1345                                        1350                              1355 | 4142 |
| agg aag gtg cag gcc gag gcg ggg gcc att gcc acg ctg agc tgc gag<br>Arg Lys Val Gln Ala Glu Ala Gly Ala Ile Ala Thr Leu Ser Cys Glu<br>                   1360                              1365                              1370 | 4190 |
| gtg gcc cag gcc cag aca gag gtg acg tgg tac aag gac ggg aag aag<br>Val Ala Gln Ala Gln Thr Glu Val Thr Trp Tyr Lys Asp Gly Lys Lys<br>1375                                        1380                              1385 | 4238 |

```
ctg agc tcc agc tcg aaa gtt cga atg gag gct gtg ggc tgc aca cgg    4286
Leu Ser Ser Ser Ser Lys Val Arg Met Glu Ala Val Gly Cys Thr Arg
1390                1395                1400                1405 agg ctg gtg gtg cag cag gca tgc cag gcg gac acc ggg gag tat agc    4334
Arg Leu Val Val Gln Gln Ala Cys Gln Ala Asp Thr Gly Glu Tyr Ser
                1410                1415                1420 tgc gag gcc ggg ggc cag cgg ctc tcc ttc agc ctg gac gtg gca gag    4382
Cys Glu Ala Gly Gly Gln Arg Leu Ser Phe Ser Leu Asp Val Ala Glu
        1425                1430                1435 ccc aag gtg gtg ttt gcc aag gag cag cca gtg cac agg gag gtg cag    4430
Pro Lys Val Val Phe Ala Lys Glu Gln Pro Val His Arg Glu Val Gln
    1440                1445                1450 gcc cag gcg ggg gcc agc acc aca ctc agc tgc gag gtg gct cag gcc    4478
Ala Gln Ala Gly Ala Ser Thr Thr Leu Ser Cys Glu Val Ala Gln Ala
1455                1460                1465 cag acg gag gtg atg tgg tac aag gac ggg aag aag ctg agc ttc agc    4526
Gln Thr Glu Val Met Trp Tyr Lys Asp Gly Lys Lys Leu Ser Phe Ser
1470                1475                1480                1485 tcg aaa gtg cgc atg gag gct gtg ggc tgc aca cgg agg ctg gtg gtg    4574
Ser Lys Val Arg Met Glu Ala Val Gly Cys Thr Arg Arg Leu Val Val
                1490                1495                1500 cag cag gcg ggc cag gcg gac gcc ggg gag tac agc tgc gag gcg ggg    4622
Gln Gln Ala Gly Gln Ala Asp Ala Gly Glu Tyr Ser Cys Glu Ala Gly
        1505                1510                1515 agc cag cgg ctc tcc ttc cac ctg cac gtg gca gag ccc aag gcg gtg    4670
Ser Gln Arg Leu Ser Phe His Leu His Val Ala Glu Pro Lys Ala Val
    1520                1525                1530 ttt gcc aag gag cag cca gcg agc agg gag gtg cag gct gag gcg ggg    4718
Phe Ala Lys Glu Gln Pro Ala Ser Arg Glu Val Gln Ala Glu Ala Gly
1535                1540                1545 acc agt gcc acg ctg agc tgc gag gtg gcc cag gcc cag aca gag gtg    4766
Thr Ser Ala Thr Leu Ser Cys Glu Val Ala Gln Ala Gln Thr Glu Val
1550                1555                1560                1565 acg tgg tac aag gac ggg aag aaa ctg agc tcc agc tcg aaa gtg cga    4814
Thr Trp Tyr Lys Asp Gly Lys Lys Leu Ser Ser Ser Ser Lys Val Arg
                1570                1575                1580 atg gag gcc gtg ggc tgc aca cgg agg ctg gtg gtg cag gag gca ggc    4862
Met Glu Ala Val Gly Cys Thr Arg Arg Leu Val Val Gln Glu Ala Gly
        1585                1590                1595 cag gcg gac gcc ggg gag tac agc tgc aag gcc ggg gat cag cgg ctg    4910
Gln Ala Asp Ala Gly Glu Tyr Ser Cys Lys Ala Gly Asp Gln Arg Leu
    1600                1605                1610 tcc ttc cac ctg cac gtg gca gag ccc aag gtg gtg ttt gcc aag gag    4958
Ser Phe His Leu His Val Ala Glu Pro Lys Val Val Phe Ala Lys Glu
1615                1620                1625 cag cca gca cac agg gag gtg cag gct gag gcg ggg gcc agt gcc acg    5006
Gln Pro Ala His Arg Glu Val Gln Ala Glu Ala Gly Ala Ser Ala Thr
1630                1635                1640                1645 ctg agc tgc gag gtg gcc cag gcc cag aca gag gtg acg tgg tac aag    5054
Leu Ser Cys Glu Val Ala Gln Ala Gln Thr Glu Val Thr Trp Tyr Lys
                1650                1655                1660 gat ggg aag aag ctg agt tcc agc tcg aaa gtg cgc gtg gag gcc gtg    5102
Asp Gly Lys Lys Leu Ser Ser Ser Ser Lys Val Arg Val Glu Ala Val
        1665                1670                1675 ggc tgc aca cgg agg ctg gtg gtg cag gcg ggc cag gcg gat gct gca    5150
Gly Cys Thr Arg Arg Leu Val Val Gln Ala Gly Gln Ala Asp Ala Ala
    1680                1685                1690 ggg gag tac agc tgt gag gcg ggg ggc caa cgg ctg tcc ttc cgc ctg    5198
Gly Glu Tyr Ser Cys Glu Ala Gly Gly Gln Arg Leu Ser Phe Arg Leu
```

-continued

|     | 1695 |     |     |     | 1700 |     |     |     | 1705 |     |     |     |     |      |
|-----|------|-----|-----|-----|------|-----|-----|-----|------|-----|-----|-----|-----|------|
| cac | gtg  | gca | gag | ctg | gag  | ccc | caa | att | tca  | gag | aga | ccc | tgc cgc agg | 5246 |
| His | Val  | Ala | Glu | Leu | Glu  | Pro | Gln | Ile | Ser  | Glu | Arg | Pro | Cys Arg Arg |      |
| 1710|      |     |     |     | 1715 |     |     |     | 1720 |     |     |     | 1725 |      |

```
gag cct ctg gtg gtc aag gag cat gaa gac atc atc ctg acc gcc aca    5294
Glu Pro Leu Val Val Lys Glu His Glu Asp Ile Ile Leu Thr Ala Thr
            1730                1735                1740 ctg gcc aca ccc tct gcg gcc acg gtg acc tgg ctc aag gat ggt gtg    5342
Leu Ala Thr Pro Ser Ala Ala Thr Val Thr Trp Leu Lys Asp Gly Val
        1745                1750                1755 gag att cgc cgc agc aag cgg cat gag aca gcc agc cag ggg gac acc    5390
Glu Ile Arg Arg Ser Lys Arg His Glu Thr Ala Ser Gln Gly Asp Thr
    1760                1765                1770 cac acc ctg acc gtg cat ggc gcc cag gtt ctg gac agc gcc atc tac    5438
His Thr Leu Thr Val His Gly Ala Gln Val Leu Asp Ser Ala Ile Tyr
1775                1780                1785 agc tgc cgt gtg ggc gca gag ggg cag gac ttc cca gtg cag gtg gaa    5486
Ser Cys Arg Val Gly Ala Glu Gly Gln Asp Phe Pro Val Gln Val Glu
1790                1795                1800                1805 gag gtg gcc gcc aag ttc tgc cgg ctg ctg gag cct gtg tgc ggc gag    5534
Glu Val Ala Ala Lys Phe Cys Arg Leu Leu Glu Pro Val Cys Gly Glu
        1810                1815                1820 ctg ggt ggc acg gtg aca ctg gcc tgc gag cta agc cca gcg tgt gca    5582
Leu Gly Gly Thr Val Thr Leu Ala Cys Glu Leu Ser Pro Ala Cys Ala
    1825                1830                1835 gag gtg gtg tgg cgc tgc ggc aac acg cag cct cgg gtg ggc aag cgc    5630
Glu Val Val Trp Arg Cys Gly Asn Thr Gln Pro Arg Val Gly Lys Arg
        1840                1845                1850 ttc cag atg gtg gcc gag ggg ccc gtg cgc tca ctc act gtg ttg ggg    5678
Phe Gln Met Val Ala Glu Gly Pro Val Arg Ser Leu Thr Val Leu Gly
    1855                1860                1865 ctg cgc gca gag gac gca ggg gag tac gtg tgt gag agc cgt gat gac    5726
Leu Arg Ala Glu Asp Ala Gly Glu Tyr Val Cys Glu Ser Arg Asp Asp
1870                1875                1880                1885 cac acc agt gcg cag ctc acc gtc agt gtg ccc cga gtg gtg aag ttt    5774
His Thr Ser Ala Gln Leu Thr Val Ser Val Pro Arg Val Val Lys Phe
        1890                1895                1900 atg tct ggg ctg agc acc gtg gtc gca gag gag ggc ggc gag gcc acc    5822
Met Ser Gly Leu Ser Thr Val Val Ala Glu Glu Gly Gly Glu Ala Thr
        1905                1910                1915 ttc cag tgc gtg gtg tcc ccc agt gat gtg gca gtc gtg tgg ttc cgg    5870
Phe Gln Cys Val Val Ser Pro Ser Asp Val Ala Val Val Trp Phe Arg
        1920                1925                1930 gac ggt gcc ctg ctt cag ccc agc gag aag ttt gcc ata tca cag agt    5918
Asp Gly Ala Leu Leu Gln Pro Ser Glu Lys Phe Ala Ile Ser Gln Ser
    1935                1940                1945 ggc gcc agc cac agc ctg acc atc tca gac ctg gtg ctg gag gac gcg    5966
Gly Ala Ser His Ser Leu Thr Ile Ser Asp Leu Val Leu Glu Asp Ala
1950                1955                1960                1965 ggc cag atc acc gtg gag gct gag ggc gcc tca tcc tct gct gcc ctg    6014
Gly Gln Ile Thr Val Glu Ala Glu Gly Ala Ser Ser Ser Ala Ala Leu
        1970                1975                1980 agg gtc cga gag gcg cct gtg ctg ttc aaa aag aag ctg gag ccg cag    6062
Arg Val Arg Glu Ala Pro Val Leu Phe Lys Lys Lys Leu Glu Pro Gln
    1985                1990                1995 acg gtg gag gag cgg agc tcg gtg acc ctg gag gtg gag ctg acg cgg    6110
Thr Val Glu Glu Arg Ser Ser Val Thr Leu Glu Val Glu Leu Thr Arg
2000                2005                2010 ccg tgg ccg gag ctg agg tgg aca cgg aac gcg acg gcc ctg gcg ccg    6158
```

```
                Pro Trp Pro Glu Leu Arg Trp Thr Arg Asn Ala Thr Ala Leu Ala Pro
                    2015                2020                2025 gga aag aac gtg gag atc cac gcc gag ggc gcc cgc cac cgc ctg gtt        6206
Gly Lys Asn Val Glu Ile His Ala Glu Gly Ala Arg His Arg Leu Val
2030                2035                2040                2045 ctg cac aac gta ggt ttt gcc gac cgt ggc ttc ttt ggc tgc gag acg        6254
Leu His Asn Val Gly Phe Ala Asp Arg Gly Phe Phe Gly Cys Glu Thr
                2050                2055                2060 ccg gat gac aag aca cag gcc aaa ctc acc gtg gag atg cgc cag gta        6302
Pro Asp Asp Lys Thr Gln Ala Lys Leu Thr Val Glu Met Arg Gln Val
            2065                2070                2075 cgg ctc gta cgg ggc ctg cag gca gtg gag gca cgg gag cag ggc acg        6350
Arg Leu Val Arg Gly Leu Gln Ala Val Glu Ala Arg Glu Gln Gly Thr
        2080                2085                2090 gct acc atg gag gtg cag ctg tcg cat gcg gac gtg gat ggc agc tgg        6398
Ala Thr Met Glu Val Gln Leu Ser His Ala Asp Val Asp Gly Ser Trp
    2095                2100                2105 act cgt gac ggt ctg cgg ttc cag cag ggg ccc acg tgc cac ctg gct        6446
Thr Arg Asp Gly Leu Arg Phe Gln Gln Gly Pro Thr Cys His Leu Ala
2110                2115                2120                2125 gtg cgg ggc ccc atg cac acc ctc aca ctc tcg ggg ctg cgg cca gag        6494
Val Arg Gly Pro Met His Thr Leu Thr Leu Ser Gly Leu Arg Pro Glu
                2130                2135                2140 gat agt ggc ctt atg gtc ttc aag gcc gaa gga gtg cac acg tcg gcg        6542
Asp Ser Gly Leu Met Val Phe Lys Ala Glu Gly Val His Thr Ser Ala
            2145                2150                2155 cgg ctc gtg gtc acc gag ctt ccc gtg agc ttc agc cgc ccg ctg cag        6590
Arg Leu Val Val Thr Glu Leu Pro Val Ser Phe Ser Arg Pro Leu Gln
        2160                2165                2170 gac gtg gtg acc act gag aag gag aag gtt acc ctg gag tgc gag ctg        6638
Asp Val Val Thr Thr Glu Lys Glu Lys Val Thr Leu Glu Cys Glu Leu
    2175                2180                2185 tcg cgt cct aat gtg gat gtg cgc tgg ctg aag gac ggt gtg gag ctg        6686
Ser Arg Pro Asn Val Asp Val Arg Trp Leu Lys Asp Gly Val Glu Leu
2190                2195                2200                2205 cgg gca ggc aag acg atg gcc atc gca gcc cag ggc gcc tgc agg agc        6734
Arg Ala Gly Lys Thr Met Ala Ile Ala Ala Gln Gly Ala Cys Arg Ser
                2210                2215                2220 ctc acc att tac cgg tgc gag ttc gcg gat cag gga gtg tat gtg tgt        6782
Leu Thr Ile Tyr Arg Cys Glu Phe Ala Asp Gln Gly Val Tyr Val Cys
            2225                2230                2235 gat gcc cat gat gcc cag agc tct gcc tcc gtg aag gta caa gga agg        6830
Asp Ala His Asp Ala Gln Ser Ser Ala Ser Val Lys Val Gln Gly Arg
        2240                2245                2250 aca tac act ctc atc tac cgg aga gtc ctg gcg gaa gat gca gga gag        6878
Thr Tyr Thr Leu Ile Tyr Arg Arg Val Leu Ala Glu Asp Ala Gly Glu
    2255                2260                2265 atc caa ttt gta gcc gaa aat gca gaa tcg cga gcc cag ctc cga gtg        6926
Ile Gln Phe Val Ala Glu Asn Ala Glu Ser Arg Ala Gln Leu Arg Val
2270                2275                2280                2285 aag gag ctg cca gtg acc ctc gtg cgc ccg ctg cgg gac aag att gcc        6974
Lys Glu Leu Pro Val Thr Leu Val Arg Pro Leu Arg Asp Lys Ile Ala
                2290                2295                2300 atg gag aag cac cgc ggt gtg ctg gag tgt cag gtg tcc cgg gcc agc        7022
Met Glu Lys His Arg Gly Val Leu Glu Cys Gln Val Ser Arg Ala Ser
            2305                2310                2315 gcc cag gtg cgg tgg ttc aag ggc agt cag gag ctg cag ccc ggg ccc        7070
Ala Gln Val Arg Trp Phe Lys Gly Ser Gln Glu Leu Gln Pro Gly Pro
        2320                2325                2330
```

-continued

```
aag tac gag ctg gtc agt gat ggc ctc tac cgc aag ctg atc atc agt     7118
Lys Tyr Glu Leu Val Ser Asp Gly Leu Tyr Arg Lys Leu Ile Ile Ser
    2335            2340            2345 gat gtc cac gca gag gac gag gac acc tac acc tgt gac gcc ggt gat     7166
Asp Val His Ala Glu Asp Glu Asp Thr Tyr Thr Cys Asp Ala Gly Asp
2350            2355            2360            2365 gtc aag acc agt gca cag ttc ttc gtg gaa gag caa tcc atc acc att     7214
Val Lys Thr Ser Ala Gln Phe Phe Val Glu Glu Gln Ser Ile Thr Ile
        2370            2375            2380 gtg cgg ggt ctg cag gac gtg aca gtg atg gag ccc gct cct gcc tgg     7262
Val Arg Gly Leu Gln Asp Val Thr Val Met Glu Pro Ala Pro Ala Trp
    2385            2390            2395 ttt gag tgt gag acc tcc atc ccc tca gtg cgg cca cct aag tgg ctc     7310
Phe Glu Cys Glu Thr Ser Ile Pro Ser Val Arg Pro Pro Lys Trp Leu
    2400            2405            2410 ctg ggg aag acg gtg ttg cag gct ggg ggg aac gtg ggc ctg gag cag     7358
Leu Gly Lys Thr Val Leu Gln Ala Gly Gly Asn Val Gly Leu Glu Gln
    2415            2420            2425 gag ggc acg gtg cac cgg ctg atg ctg cgg cgg acc tgc tcc acc atg     7406
Glu Gly Thr Val His Arg Leu Met Leu Arg Arg Thr Cys Ser Thr Met
2430            2435            2440            2445 acc ggg ccc gtg cac ttc acc gtt ggc aag tcg cgc tcc tct gcc cgc     7454
Thr Gly Pro Val His Phe Thr Val Gly Lys Ser Arg Ser Ser Ala Arg
        2450            2455            2460 ctg gtg gtc tca gac atc ccc gta gtc ctc aca cgg ccg ttg gag ccc     7502
Leu Val Val Ser Asp Ile Pro Val Val Leu Thr Arg Pro Leu Glu Pro
    2465            2470            2475 aag aca ggg cgt gag ctg cag tca gtg gtc ctg tcc tgc gac ttc cgg     7550
Lys Thr Gly Arg Glu Leu Gln Ser Val Val Leu Ser Cys Asp Phe Arg
    2480            2485            2490 cca gcc ccc aag gct gtg cag tgg tac aag gat gac acg ccc ctg tct     7598
Pro Ala Pro Lys Ala Val Gln Trp Tyr Lys Asp Asp Thr Pro Leu Ser
    2495            2500            2505 ccc tct gag aag ttt aag atg agc ctg gag ggt cag atg gct gag ctg     7646
Pro Ser Glu Lys Phe Lys Met Ser Leu Glu Gly Gln Met Ala Glu Leu
2510            2515            2520            2525 cgc atc ctc cgg ctc atg cct gct gat gct ggt gtc tac cgg tgc cag     7694
Arg Ile Leu Arg Leu Met Pro Ala Asp Ala Gly Val Tyr Arg Cys Gln
        2530            2535            2540 gcg ggc agt gcc cac agc agc act gag gtc act gtg gaa gcg cgg gag     7742
Ala Gly Ser Ala His Ser Ser Thr Glu Val Thr Val Glu Ala Arg Glu
    2545            2550            2555 gtg aca gtg aca ggg ccg cta cag gat gca gag gcc acg gag gag ggc     7790
Val Thr Val Thr Gly Pro Leu Gln Asp Ala Glu Ala Thr Glu Glu Gly
    2560            2565            2570 tgg gcc agc ttc tcc tgt gag ctg tcc cac gag gat gag gag gtc gag     7838
Trp Ala Ser Phe Ser Cys Glu Leu Ser His Glu Asp Glu Glu Val Glu
    2575            2580            2585 tgg tcg ctc aac ggg atg ccc ctg tac aac gac agc ttc cat gag atc     7886
Trp Ser Leu Asn Gly Met Pro Leu Tyr Asn Asp Ser Phe His Glu Ile
2590            2595            2600            2605 tca cac aag ggc cgg cgc cac acg ctg gta ctg aag agc atc cag cgg     7934
Ser His Lys Gly Arg Arg His Thr Leu Val Leu Lys Ser Ile Gln Arg
        2610            2615            2620 gct gat gcg ggc ata gta cgc gcc tcc tcc ctg aag gtg tcg acc tct     7982
Ala Asp Ala Gly Ile Val Arg Ala Ser Ser Leu Lys Val Ser Thr Ser
    2625            2630            2635 gcc cgc ctg gag gtc cga gtg aag ccg gtg gtg ttc ctg aag gcg ctg     8030
Ala Arg Leu Glu Val Arg Val Lys Pro Val Val Phe Leu Lys Ala Leu
    2640            2645            2650
```

-continued

| | |
|---|---|
| gat gac ctg tcc gca gag gag cgc ggc acc ctg gcc ctg cag tgt gaa<br>Asp Asp Leu Ser Ala Glu Glu Arg Gly Thr Leu Ala Leu Gln Cys Glu<br>     2655                         2660                      2665 | 8078 |
| gtc tct gac ccc gag gcc cat gtg gtg tgg cgc aaa gat ggc gtg cag<br>Val Ser Asp Pro Glu Ala His Val Val Trp Arg Lys Asp Gly Val Gln<br>2670                    2675                      2680                      2685 | 8126 |
| ctg ggc ccc agt gac aag tat gac ttc ctg cac acg gcg ggc acg cgg<br>Leu Gly Pro Ser Asp Lys Tyr Asp Phe Leu His Thr Ala Gly Thr Arg<br>                  2690                      2695                      2700 | 8174 |
| ggg ctc gtg gtg cat gac gtg agc cct gaa gac gcc ggc ctg tac acc<br>Gly Leu Val Val His Asp Val Ser Pro Glu Asp Ala Gly Leu Tyr Thr<br>                2705                      2710                      2715 | 8222 |
| tgc cac gtg ggc tcc gag gag acc cgg gcc cgg gtc cgc gtg cac gat<br>Cys His Val Gly Ser Glu Glu Thr Arg Ala Arg Val Arg Val His Asp<br>              2720                      2725                      2730 | 8270 |
| ctg cac gtg ggc atc acc aag agg ctg aag aca atg gag gtg ctg gaa<br>Leu His Val Gly Ile Thr Lys Arg Leu Lys Thr Met Glu Val Leu Glu<br>                2735                      2740                      2745 | 8318 |
| ggg gaa agc tgc agc ttt gag tgc gtc ctg tcc cac gag agt gcc agc<br>Gly Glu Ser Cys Ser Phe Glu Cys Val Leu Ser His Glu Ser Ala Ser<br>2750                    2755                      2760                      2765 | 8366 |
| gac ccg gcc atg tgg aca gtc ggt ggg aag aca gtg ggc agc tcc agc<br>Asp Pro Ala Met Trp Thr Val Gly Gly Lys Thr Val Gly Ser Ser Ser<br>                  2770                      2775                      2780 | 8414 |
| cgc ttc cag gcc aca cgt cag ggc cga aaa tac atc ctg gtg gtc cgg<br>Arg Phe Gln Ala Thr Arg Gln Gly Arg Lys Tyr Ile Leu Val Val Arg<br>              2785                      2790                      2795 | 8462 |
| gag gct gca cca agt gat gcc ggg gag gtg gtc ttc tct gtg cgg ggc<br>Glu Ala Ala Pro Ser Asp Ala Gly Glu Val Val Phe Ser Val Arg Gly<br>                2800                      2805                      2810 | 8510 |
| ctc acc tcc aag gcc tca ctc att gtc aga gag agg ccg gcc gcc atc<br>Leu Thr Ser Lys Ala Ser Leu Ile Val Arg Glu Arg Pro Ala Ala Ile<br>            2815                      2820                      2825 | 8558 |
| atc aag ccc ctg gaa gac cag tgg gtg gcg cca ggg gag gac gtg gag<br>Ile Lys Pro Leu Glu Asp Gln Trp Val Ala Pro Gly Glu Asp Val Glu<br>2830                    2835                      2840                      2845 | 8606 |
| ctg cgc tgt gag ctg tca cgg gcg gga acg ccc gtg cac tgg ctg aag<br>Leu Arg Cys Glu Leu Ser Arg Ala Gly Thr Pro Val His Trp Leu Lys<br>                2850                      2855                      2860 | 8654 |
| gac agg aag gcc atc cgc aag agc cag aag tat gat gtg gtc tgc gag<br>Asp Arg Lys Ala Ile Arg Lys Ser Gln Lys Tyr Asp Val Val Cys Glu<br>            2865                      2870                      2875 | 8702 |
| ggc acg atg gcc atg ctg gtc atc cgc ggg gcc tcg ctc aag gac gcg<br>Gly Thr Met Ala Met Leu Val Ile Arg Gly Ala Ser Leu Lys Asp Ala<br>                2880                      2885                      2890 | 8750 |
| ggc gag tac acg tgt gag gtg gag gct tcc aag agc aca gcc agc ctc<br>Gly Glu Tyr Thr Cys Glu Val Glu Ala Ser Lys Ser Thr Ala Ser Leu<br>            2895                      2900                      2905 | 8798 |
| cat gtg gaa gaa aaa gca aac tgc ttc aca gag gag ctg acc aat ctg<br>His Val Glu Glu Lys Ala Asn Cys Phe Thr Glu Glu Leu Thr Asn Leu<br>2910                    2915                      2920                      2925 | 8846 |
| cag gtg gag gag aaa ggc aca gct gtg ttc acg tgc aag acg gag cac<br>Gln Val Glu Glu Lys Gly Thr Ala Val Phe Thr Cys Lys Thr Glu His<br>                2930                      2935                      2940 | 8894 |
| ccc gcg gcc aca gtg acc tgg cgc aag ggc ctc ttg gag cta cgg gcc<br>Pro Ala Ala Thr Val Thr Trp Arg Lys Gly Leu Leu Glu Leu Arg Ala<br>              2945                      2950                      2955 | 8942 |
| tca ggg aag cac cag ccc agc cag gag ggc ctg acc ctg cgg ctc acc<br>Ser Gly Lys His Gln Pro Ser Gln Glu Gly Leu Thr Leu Arg Leu Thr | 8990 |

-continued

```
             2960                2965                 2970
atc agt gcc ctg gag aag gca gac agc gac acc tat acc tgc gac att       9038
Ile Ser Ala Leu Glu Lys Ala Asp Ser Asp Thr Tyr Thr Cys Asp Ile
        2975                2980                2985 ggc cag gcc cag tcc cgg gcc cag ctc cta gtg caa ggc cgg aga gtg       9086
Gly Gln Ala Gln Ser Arg Ala Gln Leu Leu Val Gln Gly Arg Arg Val
2990                2995                3000                3005 cac atc atc gag gac ctg gag gat gtg gat gtg cag gag ggc tcc tcg       9134
His Ile Ile Glu Asp Leu Glu Asp Val Asp Val Gln Glu Gly Ser Ser
                3010                3015                3020 gcc acc ttc cgt tgc cgg atc tcc ccg gcc aac tac gag cct gtg cac       9182
Ala Thr Phe Arg Cys Arg Ile Ser Pro Ala Asn Tyr Glu Pro Val His
        3025                3030                3035 tgg ttc ctg gac aag aca ccc ctg cat gcc aac gag ctc aat gag atc       9230
Trp Phe Leu Asp Lys Thr Pro Leu His Ala Asn Glu Leu Asn Glu Ile
        3040                3045                3050 gat gcc cag ccc ggg ggc tac cac gtg ctg acc ctg cgg cag ctg gcg       9278
Asp Ala Gln Pro Gly Gly Tyr His Val Leu Thr Leu Arg Gln Leu Ala
        3055                3060                3065 ctc aag gac tcg ggc acc atc tac ttt gag gcg ggt gac cag cgg gcc       9326
Leu Lys Asp Ser Gly Thr Ile Tyr Phe Glu Ala Gly Asp Gln Arg Ala
3070                3075                3080                3085 tcg gcc gcc ctg cgg gtc act gag aag cca agc gtc ttc tcc cgg gag       9374
Ser Ala Ala Leu Arg Val Thr Glu Lys Pro Ser Val Phe Ser Arg Glu
        3090                3095                3100 ctc aca gat gcc acc atc aca gag ggt gag gac ttg acc ctg gtg tgc       9422
Leu Thr Asp Ala Thr Ile Thr Glu Gly Glu Asp Leu Thr Leu Val Cys
        3105                3110                3115 gag acc agc acc tgc gac att cct atg tgc tgg acc aag gat ggg aag       9470
Glu Thr Ser Thr Cys Asp Ile Pro Met Cys Trp Thr Lys Asp Gly Lys
        3120                3125                3130 acc ctg cgg ggg tct gcc cgg tgc cag ctg agc cat gag ggc cac cgg       9518
Thr Leu Arg Gly Ser Ala Arg Cys Gln Leu Ser His Glu Gly His Arg
        3135                3140                3145 gcc cag ctg ctc atc act ggg gcc acc ctg cag gac agt gga cgc tac       9566
Ala Gln Leu Leu Ile Thr Gly Ala Thr Leu Gln Asp Ser Gly Arg Tyr
3150                3155                3160                3165 aag tgt gag gct ggg ggc gcc tgc agc agc tcc att gtc agg gtg cat       9614
Lys Cys Glu Ala Gly Gly Ala Cys Ser Ser Ser Ile Val Arg Val His
        3170                3175                3180 gcg cgg cca gtg cgg ttc cag gag gcc ctg aag gac ctg gag gtg ctg       9662
Ala Arg Pro Val Arg Phe Gln Glu Ala Leu Lys Asp Leu Glu Val Leu
        3185                3190                3195 gag ggt ggt gct gcc aca ctg cgc tgt gtg ctg tca tct gtg gct gcg       9710
Glu Gly Gly Ala Ala Thr Leu Arg Cys Val Leu Ser Ser Val Ala Ala
        3200                3205                3210 ccc gtg aag tgg tgc tat gga aac aac gtc ctg agg cca ggt gac aaa       9758
Pro Val Lys Trp Cys Tyr Gly Asn Asn Val Leu Arg Pro Gly Asp Lys
        3215                3220                3225 tac agc cta cgc cag gag ggt gcc atg ctg gag ctg gtg gtc cgg aac       9806
Tyr Ser Leu Arg Gln Glu Gly Ala Met Leu Glu Leu Val Val Arg Asn
3230                3235                3240                3245 ctc cgg ccg cag gac agc ggg cgg tac tca tgc tcc ttc ggg gac cag       9854
Leu Arg Pro Gln Asp Ser Gly Arg Tyr Ser Cys Ser Phe Gly Asp Gln
        3250                3255                3260 act act tct gcc acc ctc aca gtg act gcc ctg cct gcc cag ttc atc       9902
Thr Thr Ser Ala Thr Leu Thr Val Thr Ala Leu Pro Ala Gln Phe Ile
        3265                3270                3275 ggg aaa ctg aga aac aag gag gcc aca gaa ggg gcc acg gcc acg ctg       9950
```

```
                Gly Lys Leu Arg Asn Lys Glu Ala Thr Glu Gly Ala Thr Ala Thr Leu
                        3280                3285                3290 cgg tgt gag ctg agc aag aca gcc cct gtg gag tgg aga aag ggg tcc          9998
Arg Cys Glu Leu Ser Lys Thr Ala Pro Val Glu Trp Arg Lys Gly Ser
        3295                3300                3305 gag acc ctc aga gat ggg gac aga tac tgt ctg agg cag gac ggg gcc          10046
Glu Thr Leu Arg Asp Gly Asp Arg Tyr Cys Leu Arg Gln Asp Gly Ala
3310                3315                3320                3325 atg tgt gag ctg cag atc cgt ggc ctg gcc atg gtg gat gcc gcg gag          10094
Met Cys Glu Leu Gln Ile Arg Gly Leu Ala Met Val Asp Ala Ala Glu
                3330                3335                3340 tac tcg tgt gtg tgt gga gag gag agg acc tca gcc tca ctc acc atc          10142
Tyr Ser Cys Val Cys Gly Glu Glu Arg Thr Ser Ala Ser Leu Thr Ile
        3345                3350                3355 agg ccc atg cct gcc cac ttc ata gga aga ctg aga cac caa gag agc          10190
Arg Pro Met Pro Ala His Phe Ile Gly Arg Leu Arg His Gln Glu Ser
                3360                3365                3370 ata gaa ggg gcc aca gcc acg ctg cgg tgt gag ctg agc aag gcg gcc          10238
Ile Glu Gly Ala Thr Ala Thr Leu Arg Cys Glu Leu Ser Lys Ala Ala
        3375                3380                3385 ccc gtg gag tgg agg aag ggg cgt gag agc ctc aga gat ggg gac aga          10286
Pro Val Glu Trp Arg Lys Gly Arg Glu Ser Leu Arg Asp Gly Asp Arg
3390                3395                3400                3405 cat agc ctg agg cag gac ggg gct gtg tgc gag ctg cag atc tgt ggc          10334
His Ser Leu Arg Gln Asp Gly Ala Val Cys Glu Leu Gln Ile Cys Gly
                3410                3415                3420 ctg gct gtg gca gat gct ggg gag tac tcc tgt gtg tgt ggg gag gag          10382
Leu Ala Val Ala Asp Ala Gly Glu Tyr Ser Cys Val Cys Gly Glu Glu
        3425                3430                3435 agg acc tct gcc act ctc acc gtg aag gcc ctg cca gcc aag ttc aca          10430
Arg Thr Ser Ala Thr Leu Thr Val Lys Ala Leu Pro Ala Lys Phe Thr
                3440                3445                3450 gag ggt ctg agg aat gaa gag gcc gtg gaa ggg gcc aca gcc atg ttg          10478
Glu Gly Leu Arg Asn Glu Glu Ala Val Glu Gly Ala Thr Ala Met Leu
        3455                3460                3465 tgg tgt gaa ctg agc aag gtg gcc cct gtg gag tgg agg aag ggg ccc          10526
Trp Cys Glu Leu Ser Lys Val Ala Pro Val Glu Trp Arg Lys Gly Pro
3470                3475                3480                3485 gag aac ctc aga gat ggg gac aga tac atc ctg agg cag gag ggg acc          10574
Glu Asn Leu Arg Asp Gly Asp Arg Tyr Ile Leu Arg Gln Glu Gly Thr
                3490                3495                3500 agg tgt gag ctg cag atc tgt ggc ctg gcc atg gcg gac gcc ggg gag          10622
Arg Cys Glu Leu Gln Ile Cys Gly Leu Ala Met Ala Asp Ala Gly Glu
        3505                3510                3515 tac ttg tgt gtg tgc ggg cag gag agg acc tca gcc acg ctc acc atc          10670
Tyr Leu Cys Val Cys Gly Gln Glu Arg Thr Ser Ala Thr Leu Thr Ile
                3520                3525                3530 agg gct ctg cct gcc agg ttc ata gaa gat gtg aaa aac cag gag gcc          10718
Arg Ala Leu Pro Ala Arg Phe Ile Glu Asp Val Lys Asn Gln Glu Ala
        3535                3540                3545 aga gaa ggg gcc acg gct gtg ctg cag tgt gag ctg aac agt gca gcc          10766
Arg Glu Gly Ala Thr Ala Val Leu Gln Cys Glu Leu Asn Ser Ala Ala
3550                3555                3560                3565 cct gtg gag tgg aga aag ggg tct gag acc ctc aga gat ggg gac aga          10814
Pro Val Glu Trp Arg Lys Gly Ser Glu Thr Leu Arg Asp Gly Asp Arg
        3570                3575                3580 tac agc ctg agg cag gac ggg act aaa tgt gag ctg cag att cgt ggc          10862
Tyr Ser Leu Arg Gln Asp Gly Thr Lys Cys Glu Leu Gln Ile Arg Gly
                3585                3590                3595
```

```
ctg gcc atg gca gac act ggg gag tac tcg tgc gtg tgc ggg cag gag    10910
Leu Ala Met Ala Asp Thr Gly Glu Tyr Ser Cys Val Cys Gly Gln Glu
        3600                3605                3610 agg acc tcg gct atg ctc acc gtc agg gct cta ccc atc aag ttc aca    10958
Arg Thr Ser Ala Met Leu Thr Val Arg Ala Leu Pro Ile Lys Phe Thr
    3615                3620                3625 gag ggt ctg agg aac gaa gag gcc aca gaa ggg gca aca gcc gtg ctg    11006
Glu Gly Leu Arg Asn Glu Glu Ala Thr Glu Gly Ala Thr Ala Val Leu
3630                3635                3640                3645 cgg tgt gag ctg agc aag atg gcc ccc gtg gag tgg tgg aag ggg cat    11054
Arg Cys Glu Leu Ser Lys Met Ala Pro Val Glu Trp Trp Lys Gly His
                3650                3655                3660 gag acc ctc aga gat gga gac aga cac agc ctg agg cag gac ggg gcc    11102
Glu Thr Leu Arg Asp Gly Asp Arg His Ser Leu Arg Gln Asp Gly Ala
            3665                3670                3675 agg tgt gag ctg cag atc cgc ggc ctc gtg gca gag gac gct ggg gag    11150
Arg Cys Glu Leu Gln Ile Arg Gly Leu Val Ala Glu Asp Ala Gly Glu
        3680                3685                3690 tac ctg tgc atg tgc ggg aag gag agg acc tca gcc atg ctc acc gtc    11198
Tyr Leu Cys Met Cys Gly Lys Glu Arg Thr Ser Ala Met Leu Thr Val
    3695                3700                3705 agg gcc atg cct tcc aag ttc ata gag ggt ctg agg aat gaa gag gcc    11246
Arg Ala Met Pro Ser Lys Phe Ile Glu Gly Leu Arg Asn Glu Glu Ala
3710                3715                3720                3725 aca gaa ggg gac acg gcc acg ctg tgg tgt gag ctg agc aag gcg gca    11294
Thr Glu Gly Asp Thr Ala Thr Leu Trp Cys Glu Leu Ser Lys Ala Ala
                3730                3735                3740 ccg gtg gag tgg agg aag ggg cat gag acc ctc aga gat ggg gac aga    11342
Pro Val Glu Trp Arg Lys Gly His Glu Thr Leu Arg Asp Gly Asp Arg
            3745                3750                3755 cac agc ctg agg cag gac ggg tcc agg tgt gag ctg cag atc cgt ggc    11390
His Ser Leu Arg Gln Asp Gly Ser Arg Cys Glu Leu Gln Ile Arg Gly
        3760                3765                3770 ctg gct gtg gtg gat gcc ggg gag tac tcg tgt gtg tgc ggg cag gag    11438
Leu Ala Val Val Asp Ala Gly Glu Tyr Ser Cys Val Cys Gly Gln Glu
    3775                3780                3785 agg acc tca gcc aca ctc act gtc agg gcc ctg cct gcc aga ttc ata    11486
Arg Thr Ser Ala Thr Leu Thr Val Arg Ala Leu Pro Ala Arg Phe Ile
3790                3795                3800                3805 gaa gat gtg aaa aac cag gag gcc aga gaa ggg gcc acg gcc gtg ctg    11534
Glu Asp Val Lys Asn Gln Glu Ala Arg Glu Gly Ala Thr Ala Val Leu
                3810                3815                3820 caa tgt gag ctg agc aag gcg gcc ccc gtg gag tgg agg aag ggg tct    11582
Gln Cys Glu Leu Ser Lys Ala Ala Pro Val Glu Trp Arg Lys Gly Ser
            3825                3830                3835 gag acc ctc aga ggt ggg gac aga tac agc ctg agg cag gat ggg acc    11630
Glu Thr Leu Arg Gly Gly Asp Arg Tyr Ser Leu Arg Gln Asp Gly Thr
        3840                3845                3850 aga tgt gag ctg cag att cat ggc ctg tct gtg gca gac act ggg gag    11678
Arg Cys Glu Leu Gln Ile His Gly Leu Ser Val Ala Asp Thr Gly Glu
    3855                3860                3865 tac tcg tgt gtg tgc ggg cag gag agg acc tcg gcc aca ctc acc gtc    11726
Tyr Ser Cys Val Cys Gly Gln Glu Arg Thr Ser Ala Thr Leu Thr Val
3870                3875                3880                3885 agg gcc cca cag cca gtg ttc cgg gag ccg ctg cag agt ctg cag gcg    11774
Arg Ala Pro Gln Pro Val Phe Arg Glu Pro Leu Gln Ser Leu Gln Ala
                3890                3895                3900 gag gag ggc tcc acg gcc acc ctg cag tgt gag ctg tct gag ccc act    11822
Glu Glu Gly Ser Thr Ala Thr Leu Gln Cys Glu Leu Ser Glu Pro Thr
            3905                3910                3915
```

```
                                                  -continued gct aca gtg gtc tgg agc aag ggt ggc ctg cag ctg cag gcc aat ggg      11870
Ala Thr Val Val Trp Ser Lys Gly Gly Leu Gln Leu Gln Ala Asn Gly
        3920                3925                3930 cgc cgg gag cca cgg ctt cag ggc tgc acc gcg gag ctg gtg tta cag      11918
Arg Arg Glu Pro Arg Leu Gln Gly Cys Thr Ala Glu Leu Val Leu Gln
3935                3940                3945 gac cta caa cgt gaa gac act ggc gaa tac act tgc acc tgt ggc tcc      11966
Asp Leu Gln Arg Glu Asp Thr Gly Glu Tyr Thr Cys Thr Cys Gly Ser
3950                3955                3960                3965 cag gcc acc agt gcc acc ctc act gtc aca gct gcg cct gtg cgg ttc      12014
Gln Ala Thr Ser Ala Thr Leu Thr Val Thr Ala Ala Pro Val Arg Phe
        3970                3975                3980 ctc cga gag ctg cag cac cag gag gtg gat gag gga ggc acc gca cac      12062
Leu Arg Glu Leu Gln His Gln Glu Val Asp Glu Gly Gly Thr Ala His
3985                3990                3995 tta tgc tgc gag ctg agc cgg gcg ggt gcg agc gtg gag tgg cgc aag      12110
Leu Cys Cys Glu Leu Ser Arg Ala Gly Ala Ser Val Glu Trp Arg Lys
        4000                4005                4010 ggc tcc cta cag ctc ttc cct tgt gcc aag tac cag atg gtg cag gat      12158
Gly Ser Leu Gln Leu Phe Pro Cys Ala Lys Tyr Gln Met Val Gln Asp
4015                4020                4025 ggt gca gct gca gag ctg ctg gta cgc gga gtg gag cag gag gat gcg      12206
Gly Ala Ala Ala Glu Leu Leu Val Arg Gly Val Glu Gln Glu Asp Ala
4030                4035                4040                4045 ggt gac tac acg tgt gac acg ggc cac acg cag agc atg gcc agc ctc      12254
Gly Asp Tyr Thr Cys Asp Thr Gly His Thr Gln Ser Met Ala Ser Leu
        4050                4055                4060 tct gtc cgt gtc ccc agg ccc aag ttc aag acc cgg ctt cag agt ctg      12302
Ser Val Arg Val Pro Arg Pro Lys Phe Lys Thr Arg Leu Gln Ser Leu
4065                4070                4075 gag cag gag aca ggt gac ata gcc cgg ctg tgc tgt cag ctg agt gat      12350
Glu Gln Glu Thr Gly Asp Ile Ala Arg Leu Cys Cys Gln Leu Ser Asp
        4080                4085                4090 gca gag tcg ggg gcc gtg gtg caa tgg ctc aag gag ggc gtg gag ctg      12398
Ala Glu Ser Gly Ala Val Val Gln Trp Leu Lys Glu Gly Val Glu Leu
4095                4100                4105 cat gcg ggc ccc aag tac gag atg cgg agc cag ggg gcc acg cgg gag      12446
His Ala Gly Pro Lys Tyr Glu Met Arg Ser Gln Gly Ala Thr Arg Glu
4110                4115                4120                4125 ctg ctg atc cac caa ctg gag gcc aag gac acg ggc gag tat gcc tgt      12494
Leu Leu Ile His Gln Leu Glu Ala Lys Asp Thr Gly Glu Tyr Ala Cys
        4130                4135                4140 gtg aca ggc ggc cag aaa acc gct gcc tcc ctc agg gtc aca gag cct      12542
Val Thr Gly Gly Gln Lys Thr Ala Ala Ser Leu Arg Val Thr Glu Pro
4145                4150                4155 gag gtg acc att gta cgg ggg ctg gtt gat gcg gag gtg acg gcc gat      12590
Glu Val Thr Ile Val Arg Gly Leu Val Asp Ala Glu Val Thr Ala Asp
        4160                4165                4170 gag gat gtt gag ttc agc tgt gag gtg tcc agg gct gga gcc aca ggc      12638
Glu Asp Val Glu Phe Ser Cys Glu Val Ser Arg Ala Gly Ala Thr Gly
4175                4180                4185 gtg cag tgg tgc cta cag ggc ctg cca ctg caa agc aat gag gtg aca      12686
Val Gln Trp Cys Leu Gln Gly Leu Pro Leu Gln Ser Asn Glu Val Thr
4190                4195                4200                4205 gag gtg gct gtg cgg gat ggc cgc atc cac acc ctg cgg ctg aag ggc      12734
Glu Val Ala Val Arg Asp Gly Arg Ile His Thr Leu Arg Leu Lys Gly
        4210                4215                4220 gtg acg ccc gag gac gct ggc act gtc tcc ttc cat ttg gga aac cat      12782
Val Thr Pro Glu Asp Ala Gly Thr Val Ser Phe His Leu Gly Asn His
```

```
                  4225            4230            4235
gct tcc tct gcc cag ctc acc gtc aga gct cct gag gtg acc atc ctg      12830
Ala Ser Ser Ala Gln Leu Thr Val Arg Ala Pro Glu Val Thr Ile Leu
         4240            4245            4250 gag ccc ctg cag gac gtg cag ctc agt gag ggc cag gat gcc agc ttc      12878
Glu Pro Leu Gln Asp Val Gln Leu Ser Glu Gly Gln Asp Ala Ser Phe
         4255            4260            4265 cag tgc cgg cta tcc aga gct tca ggc cag gag gcc cgc tgg gct tta      12926
Gln Cys Arg Leu Ser Arg Ala Ser Gly Gln Glu Ala Arg Trp Ala Leu
4270            4275            4280            4285 gga ggg gtg ccc ctg cag gcc aac gag atg aat gac atc act gtg gag      12974
Gly Gly Val Pro Leu Gln Ala Asn Glu Met Asn Asp Ile Thr Val Glu
             4290            4295            4300 cag ggc aca ctc cac ctg ctc acc ctg cac aag gtg acc ctt gag gat      13022
Gln Gly Thr Leu His Leu Leu Thr Leu His Lys Val Thr Leu Glu Asp
             4305            4310            4315 gct gga act gtc agt ttc cac gtg ggc acg tgt agc tct gag gcc cag      13070
Ala Gly Thr Val Ser Phe His Val Gly Thr Cys Ser Ser Glu Ala Gln
             4320            4325            4330 ctg aaa gtc aca gcc aag aac acg gtg gtg cgg ggg ctg gag aat gtg      13118
Leu Lys Val Thr Ala Lys Asn Thr Val Val Arg Gly Leu Glu Asn Val
         4335            4340            4345 gag gcg ctg gag ggc ggc gag gcg ctg ttc gag tgc cag ctg tcc cag      13166
Glu Ala Leu Glu Gly Gly Glu Ala Leu Phe Glu Cys Gln Leu Ser Gln
4350            4355            4360            4365 ccc gag gtg gcc gcc cac acc tgg ctg ctg gac gac gaa ccc gtg cgc      13214
Pro Glu Val Ala Ala His Thr Trp Leu Leu Asp Asp Glu Pro Val Arg
             4370            4375            4380 acc tcg gag aac gcc gag gtg gtc ttc ttc gag aac ggc ctg cgc cac      13262
Thr Ser Glu Asn Ala Glu Val Val Phe Phe Glu Asn Gly Leu Arg His
             4385            4390            4395 ctg ctg ctg ctc aaa aac ttg cgg cca caa gac agc tgc cgg gtg acc      13310
Leu Leu Leu Leu Lys Asn Leu Arg Pro Gln Asp Ser Cys Arg Val Thr
             4400            4405            4410 ttc ctg gct ggg gat atg gtg acg tcc gca ttc ctc acg gtc cga ggc      13358
Phe Leu Ala Gly Asp Met Val Thr Ser Ala Phe Leu Thr Val Arg Gly
             4415            4420            4425 tgg cgc ctg gag atc ctg gag cct ctg aaa aac gcg gcg gtc cgg gcc      13406
Trp Arg Leu Glu Ile Leu Glu Pro Leu Lys Asn Ala Ala Val Arg Ala
4430            4435            4440            4445 ggc gca cag gca cgc ttc acc tgc acg ctc agc gag gcg gtg ccc gtg      13454
Gly Ala Gln Ala Arg Phe Thr Cys Thr Leu Ser Glu Ala Val Pro Val
             4450            4455            4460 gga gag gcg tcc tgg tac atc aat ggc gcg gca gtg cag ccg gat gac      13502
Gly Glu Ala Ser Trp Tyr Ile Asn Gly Ala Ala Val Gln Pro Asp Asp
             4465            4470            4475 agc gac tgg act gtc acc gcc gac ggc agt cac caa gcc cta ctg ctg      13550
Ser Asp Trp Thr Val Thr Ala Asp Gly Ser His Gln Ala Leu Leu Leu
             4480            4485            4490 cgc agc gcc cag ccc cac cac gcc ggg gag gtc acc ttc gct tgc cgc      13598
Arg Ser Ala Gln Pro His His Ala Gly Glu Val Thr Phe Ala Cys Arg
             4495            4500            4505 gac gcc gtg gcc tct gca cgg ctc acc gtg ctg ggc ctc cct gat ccc      13646
Asp Ala Val Ala Ser Ala Arg Leu Thr Val Leu Gly Leu Pro Asp Pro
4510            4515            4520            4525 cca gag gat gct gag gtg gtg gct cac agc agc cac act gtg aca ctg      13694
Pro Glu Asp Ala Glu Val Val Ala His Ser Ser His Thr Val Thr Leu
             4530            4535            4540 tct tgg gca gct ccc atg agt gat gga ggc ggt ggt ctc tgt ggc tac      13742
```

```
                Ser Trp Ala Ala Pro Met Ser Asp Gly Gly Gly Leu Cys Gly Tyr
                              4545                4550                4555 cgc gtg gag gtg aag gag ggg gcc aca ggc cag tgg cgg ctg tgc cac            13790
Arg Val Glu Val Lys Glu Gly Ala Thr Gly Gln Trp Arg Leu Cys His
            4560                4565                4570 gag ctg gtg cct gga ccc gag tgt gtg gtg gat ggc ctg gcc ccc ggg            13838
Glu Leu Val Pro Gly Pro Glu Cys Val Val Asp Gly Leu Ala Pro Gly
    4575                4580                4585 gag acc tac cgc ttc cgt gtg gca gct gtg ggc cct gtg ggt gct ggg            13886
Glu Thr Tyr Arg Phe Arg Val Ala Ala Val Gly Pro Val Gly Ala Gly
4590                4595                4600                4605 gaa ccg gtt cac ctg ccc cag aca gtg cgg ctt gca gag cca ccg aag            13934
Glu Pro Val His Leu Pro Gln Thr Val Arg Leu Ala Glu Pro Pro Lys
                4610                4615                4620 cct gtg cct ccc cag ccc tca gcc cct gag agc cgg cag gtg gca gct            13982
Pro Val Pro Pro Gln Pro Ser Ala Pro Glu Ser Arg Gln Val Ala Ala
            4625                4630                4635 ggt gaa gat gtc tct ctg gag ctt gag gtg gtg gct gag gct ggt gag            14030
Gly Glu Asp Val Ser Leu Glu Leu Glu Val Val Ala Glu Ala Gly Glu
        4640                4645                4650 gtc atc tgg cac aag gga atg gag cgc atc cag ccc ggt ggg cgg ttc            14078
Val Ile Trp His Lys Gly Met Glu Arg Ile Gln Pro Gly Gly Arg Phe
    4655                4660                4665 gag gtg gtc tcc cag ggt cgg caa cag atg ctg gtg atc aag ggc ttc            14126
Glu Val Val Ser Gln Gly Arg Gln Gln Met Leu Val Ile Lys Gly Phe
4670                4675                4680                4685 acg gca gaa gac cag ggc gag tac cac tgt ggc ctg gct cag ggc tcc            14174
Thr Ala Glu Asp Gln Gly Glu Tyr His Cys Gly Leu Ala Gln Gly Ser
                4690                4695                4700 atc tgc cct gcg gct gcc acc ttc cag gtg gca ctg agc cca gcc tct            14222
Ile Cys Pro Ala Ala Ala Thr Phe Gln Val Ala Leu Ser Pro Ala Ser
            4705                4710                4715 gtg gat gag gcc cct cag ccc agc ttg ccc ccc gag gca gcc cag gag            14270
Val Asp Glu Ala Pro Gln Pro Ser Leu Pro Pro Glu Ala Ala Gln Glu
        4720                4725                4730 ggt gac ctg cac cta ctg tgg gag gcc ctg gct cgg aaa cgt cgc atg            14318
Gly Asp Leu His Leu Leu Trp Glu Ala Leu Ala Arg Lys Arg Arg Met
    4735                4740                4745 agc cgt gag ccc acg ctg gac tcc att agc gag ctg cca gag gag gac            14366
Ser Arg Glu Pro Thr Leu Asp Ser Ile Ser Glu Leu Pro Glu Glu Asp
4750                4755                4760                4765 ggc cgc tcg cag cgc ctg cca cag gag gca gag gag gtg gca cct gat            14414
Gly Arg Ser Gln Arg Leu Pro Gln Glu Ala Glu Glu Val Ala Pro Asp
                4770                4775                4780 ctc tct gaa ggc tac tcc acg gcc gat gag ctg gcc cgc act gga gat            14462
Leu Ser Glu Gly Tyr Ser Thr Ala Asp Glu Leu Ala Arg Thr Gly Asp
            4785                4790                4795 gct gac ctc tca cac acc agc tct gat gat gag tcc cgg gca ggc acc            14510
Ala Asp Leu Ser His Thr Ser Ser Asp Asp Glu Ser Arg Ala Gly Thr
        4800                4805                4810 cct tcc ctg gtc acc tac ctc aag aag gct ggg agg cca ggc acc tca            14558
Pro Ser Leu Val Thr Tyr Leu Lys Lys Ala Gly Arg Pro Gly Thr Ser
    4815                4820                4825 cca ctg gcc agc aag gtt ggg gcc cca gca gcc ccc tct gtg aag cca            14606
Pro Leu Ala Ser Lys Val Gly Ala Pro Ala Ala Pro Ser Val Lys Pro
4830                4835                4840                4845 cag cag cag cag gag cca ctg gct gct gtg cgc cca cca ctg gga gac            14654
Gln Gln Gln Gln Glu Pro Leu Ala Ala Val Arg Pro Pro Leu Gly Asp
                4850                4855                4860
```

```
ctg agc acc aaa gac ctg ggt gat ccc tca atg gac aag gca gct gtg      14702
Leu Ser Thr Lys Asp Leu Gly Asp Pro Ser Met Asp Lys Ala Ala Val
            4865                4870                4875 aag atc cag gct gcc ttt aag ggc tac aag gtc cgg aag gag atg aag      14750
Lys Ile Gln Ala Ala Phe Lys Gly Tyr Lys Val Arg Lys Glu Met Lys
        4880                4885                4890 cag cag gaa ggg ccc atg ttc tcc cac aca ttt ggg gac acc gag gca      14798
Gln Gln Glu Gly Pro Met Phe Ser His Thr Phe Gly Asp Thr Glu Ala
    4895                4900                4905 cag gtg ggg gat gcc ctg cgg ctg gag tgt gtc gtg gcc agc aag gca      14846
Gln Val Gly Asp Ala Leu Arg Leu Glu Cys Val Val Ala Ser Lys Ala
4910                4915                4920                4925 gat gtg cga gcc cgc tgg ctg aag gat ggt gtg gag ctg acc gat ggg      14894
Asp Val Arg Ala Arg Trp Leu Lys Asp Gly Val Glu Leu Thr Asp Gly
                4930                4935                4940 cgg cac cat cac atc gac cag ctt ggg gat ggc acc tgc tct ctg ctg      14942
Arg His His His Ile Asp Gln Leu Gly Asp Gly Thr Cys Ser Leu Leu
            4945                4950                4955 atc gct ggc ctg gac cgt gct gat gct ggc tgc tac acc tgt cag gtg      14990
Ile Ala Gly Leu Asp Arg Ala Asp Ala Gly Cys Tyr Thr Cys Gln Val
        4960                4965                4970 agc aac aag ttt ggc cag gtg acc cac agt gcc tgt gtg gtc agt         15038
Ser Asn Lys Phe Gly Gln Val Thr His Ser Ala Cys Val Val Val Ser
    4975                4980                4985 ggg tca gag agt gaa gcc gag agc tcc tct ggg ggt gag ctg gac gat     15086
Gly Ser Glu Ser Glu Ala Glu Ser Ser Ser Gly Gly Glu Leu Asp Asp
4990                4995                5000                5005 gcc ttc cgc cgg gct gcc cgt cgg ctg cac cgg ctc ttc cgc acc aaa     15134
Ala Phe Arg Arg Ala Ala Arg Arg Leu His Arg Leu Phe Arg Thr Lys
                5010                5015                5020 agt ccg gct gaa gtt tca gat gag gag ctc ttc ctg agt gca gac gag     15182
Ser Pro Ala Glu Val Ser Asp Glu Glu Leu Phe Leu Ser Ala Asp Glu
            5025                5030                5035 ggc cct gca gag cca gag gag ccc gcg gac tgg cag aca tac cgc gaa     15230
Gly Pro Ala Glu Pro Glu Glu Pro Ala Asp Trp Gln Thr Tyr Arg Glu
        5040                5045                5050 gat gag cat ttc atc tgc atc cgt ttt gag gcg ctc act gag gcc cgc     15278
Asp Glu His Phe Ile Cys Ile Arg Phe Glu Ala Leu Thr Glu Ala Arg
    5055                5060                5065 cag gcg gta act cgc ttc cag gag atg ttt gcc aca ctg ggc att ggg     15326
Gln Ala Val Thr Arg Phe Gln Glu Met Phe Ala Thr Leu Gly Ile Gly
5070                5075                5080                5085 gtg gag atc aag ctg gtg gaa cag ggg cct cgg agg gta gag atg tgc     15374
Val Glu Ile Lys Leu Val Glu Gln Gly Pro Arg Arg Val Glu Met Cys
                5090                5095                5100 atc agc aaa gag act cct gcc cct gtg gtg cct cca gag cca ttg ccc     15422
Ile Ser Lys Glu Thr Pro Ala Pro Val Val Pro Pro Glu Pro Leu Pro
            5105                5110                5115 agc cta ctg act tct gac gct gcc cca gtg ttc ctg act gag ttg cag     15470
Ser Leu Leu Thr Ser Asp Ala Ala Pro Val Phe Leu Thr Glu Leu Gln
        5120                5125                5130 aac caa gaa gtg cag gat ggg tat cct gtg agc ttt gac tgc gtg gtg     15518
Asn Gln Glu Val Gln Asp Gly Tyr Pro Val Ser Phe Asp Cys Val Val
    5135                5140                5145 aca ggt cag ccc atg ccc agt gtg cgc tgg ttc aag gat ggg aag ttg     15566
Thr Gly Gln Pro Met Pro Ser Val Arg Trp Phe Lys Asp Gly Lys Leu
5150                5155                5160                5165 ttg gag gag gat gat cac tac atg att aat gaa gac caa cag ggt ggc     15614
Leu Glu Glu Asp Asp His Tyr Met Ile Asn Glu Asp Gln Gln Gly Gly
                5170                5175                5180
```

```
cat cag ctc atc atc aca gcc gtg gtg cca gca gac atg ggc gtc tac    15662
His Gln Leu Ile Ile Thr Ala Val Val Pro Ala Asp Met Gly Val Tyr
         5185                5190                5195 cgc tgc ctg gcc gag aac agc atg ggt gtc tcc tcc acc aag gct gag    15710
Arg Cys Leu Ala Glu Asn Ser Met Gly Val Ser Ser Thr Lys Ala Glu
    5200                5205                5210 ctc cgt gtg gac ttg aca agc aca gac tat gac act gca gca gat gcc    15758
Leu Arg Val Asp Leu Thr Ser Thr Asp Tyr Asp Thr Ala Ala Asp Ala
        5215                5220                5225 acg gag tcc tca tcc tac ttc agt gcc caa ggc tac ctg tcc agc cgg    15806
Thr Glu Ser Ser Ser Tyr Phe Ser Ala Gln Gly Tyr Leu Ser Ser Arg
5230                5235                5240                5245 gag cag gag gga aca gag tcc acc act gat gag ggc cag ctg ccc cag    15854
Glu Gln Glu Gly Thr Glu Ser Thr Thr Asp Glu Gly Gln Leu Pro Gln
            5250                5255                5260 gtg gtg gag gag ctg aga gac ctc cag gtg gcc cct ggc aca cgc ctg    15902
Val Val Glu Glu Leu Arg Asp Leu Gln Val Ala Pro Gly Thr Arg Leu
        5265                5270                5275 gcc aag ttc cag ctc aag gtg aaa ggc tac cct gct ccc aga tta tac    15950
Ala Lys Phe Gln Leu Lys Val Lys Gly Tyr Pro Ala Pro Arg Leu Tyr
    5280                5285                5290 tgg ttc aaa gat ggc cag ccc ctg acc gca tct gcc cac atc cgc atg    15998
Trp Phe Lys Asp Gly Gln Pro Leu Thr Ala Ser Ala His Ile Arg Met
        5295                5300                5305 act ggc aag aag atc ctg cac acc ctg gag atc atc tcc gtc acc cgg    16046
Thr Gly Lys Lys Ile Leu His Thr Leu Glu Ile Ile Ser Val Thr Arg
5310                5315                5320                5325 gag gac tct ggc cag tat gca gcc tat atc agc aat gcc atg ggt gct    16094
Glu Asp Ser Gly Gln Tyr Ala Ala Tyr Ile Ser Asn Ala Met Gly Ala
            5330                5335                5340 gcc tac tcg tct gcc cgg ctg ctg gtt cga ggc cct gat gag cca gaa    16142
Ala Tyr Ser Ser Ala Arg Leu Leu Val Arg Gly Pro Asp Glu Pro Glu
        5345                5350                5355 gag aag cct gca tca gat gtg cat gag cag ctg gtg ccg ccc cga atg    16190
Glu Lys Pro Ala Ser Asp Val His Glu Gln Leu Val Pro Pro Arg Met
    5360                5365                5370 ctg gag agg ttc acc ccc aag aaa gtg aag aaa ggc tcc agc atc acc    16238
Leu Glu Arg Phe Thr Pro Lys Lys Val Lys Lys Gly Ser Ser Ile Thr
5375                5380                5385 ttc tct gtg aag gta gaa gga cgc ccg gtg ccc acc gtg cac tgg ctc    16286
Phe Ser Val Lys Val Glu Gly Arg Pro Val Pro Thr Val His Trp Leu
5390                5395                5400                5405 agg gag gag gct gag aga ggc gtg ctg tgg att ggc cct gac aca ccg    16334
Arg Glu Glu Ala Glu Arg Gly Val Leu Trp Ile Gly Pro Asp Thr Pro
            5410                5415                5420 ggc tac acc gtg gcc agc tct gcg cag cag cac agc ctg gtc ctg ctg    16382
Gly Tyr Thr Val Ala Ser Ser Ala Gln Gln His Ser Leu Val Leu Leu
        5425                5430                5435 gac gtg ggc cgg cag cac cag ggc acc tac aca tgc att gcc agc aac    16430
Asp Val Gly Arg Gln His Gln Gly Thr Tyr Thr Cys Ile Ala Ser Asn
    5440                5445                5450 gct gcc ggc cag gcc ctc tgc tcc gcc agc ctg cac gtc tcg ggc ctg    16478
Ala Ala Gly Gln Ala Leu Cys Ser Ala Ser Leu His Val Ser Gly Leu
5455                5460                5465 cct aag gtg gag gag cag gag aaa gtg aag gaa gcg ctg att tcc act    16526
Pro Lys Val Glu Glu Gln Glu Lys Val Lys Glu Ala Leu Ile Ser Thr
5470                5475                5480                5485 ttc ctg cag ggg acc aca caa gcc atc tca gca cag ggg ttg gaa act    16574
Phe Leu Gln Gly Thr Thr Gln Ala Ile Ser Ala Gln Gly Leu Glu Thr
```

-continued

| | |
|---|---|
| gcg agt ttt gct gac ctt ggt ggg cag agg aaa gaa gag cct ctg gct<br>Ala Ser Phe Ala Asp Leu Gly Gly Gln Arg Lys Glu Glu Pro Leu Ala<br>5505     5510     5515 | 16622 |
| gcc aag gag gcc ctc ggc cac ctg tcc ctc gct gag gtg ggc aca gag<br>Ala Lys Glu Ala Leu Gly His Leu Ser Leu Ala Glu Val Gly Thr Glu<br>5520     5525     5530 | 16670 |
| gag ttc ctg cag aaa ctg acc tcc cag atc act gag atg gta tcg gcc<br>Glu Phe Leu Gln Lys Leu Thr Ser Gln Ile Thr Glu Met Val Ser Ala<br>5535     5540     5545 | 16718 |
| aag atc acg cag gcc aag ctg cag gtg ccc gga ggt gac agt gat gag<br>Lys Ile Thr Gln Ala Lys Leu Gln Val Pro Gly Gly Asp Ser Asp Glu<br>5550     5555     5560     5565 | 16766 |
| gac tcc aag aca cca tct gca tcc ccc cgc cat ggc cga tca cgg cca<br>Asp Ser Lys Thr Pro Ser Ala Ser Pro Arg His Gly Arg Ser Arg Pro<br>5570     5575     5580 | 16814 |
| tcc tcc agc atc cag gag tct tcc tca gag tca gag gac ggc gat gcc<br>Ser Ser Ser Ile Gln Glu Ser Ser Ser Glu Ser Glu Asp Gly Asp Ala<br>5585     5590     5595 | 16862 |
| cga ggc gag atc ttt gac atc tac gtg gtc acc gct gac tac ctg ccc<br>Arg Gly Glu Ile Phe Asp Ile Tyr Val Val Thr Ala Asp Tyr Leu Pro<br>5600     5605     5610 | 16910 |
| cta ggg gct gag cag gat gcc atc acg ctg cgg gaa ggc cag tat gtg<br>Leu Gly Ala Glu Gln Asp Ala Ile Thr Leu Arg Glu Gly Gln Tyr Val<br>5615     5620     5625 | 16958 |
| gag gtc ctg gat gca gcc cac cca ctg cgc tgg ctt gtc cgc acc aag<br>Glu Val Leu Asp Ala Ala His Pro Leu Arg Trp Leu Val Arg Thr Lys<br>5630     5635     5640     5645 | 17006 |
| ccc acc aag tcc agc ccc tca cgg cag ggc tgg gtg tca cca gcc tac<br>Pro Thr Lys Ser Ser Pro Ser Arg Gln Gly Trp Val Ser Pro Ala Tyr<br>5650     5655     5660 | 17054 |
| ctg gac agg agg ctc aag ctg tca cct gag tgg ggg gcc gct gag gcc<br>Leu Asp Arg Arg Leu Lys Leu Ser Pro Glu Trp Gly Ala Ala Glu Ala<br>5665     5670     5675 | 17102 |
| cct gag ttc cct ggg gag gct gtg tct gaa gac gaa tac aag gca agg<br>Pro Glu Phe Pro Gly Glu Ala Val Ser Glu Asp Glu Tyr Lys Ala Arg<br>5680     5685     5690 | 17150 |
| ctg agc tct gtg atc cag gag ctg ctg agt tct gag cag gcc ttc gtg<br>Leu Ser Ser Val Ile Gln Glu Leu Leu Ser Ser Glu Gln Ala Phe Val<br>5695     5700     5705 | 17198 |
| gag gag ctg cag ttc ctg cag agc cac cac ctg cag cac ctg gag cgc<br>Glu Glu Leu Gln Phe Leu Gln Ser His His Leu Gln His Leu Glu Arg<br>5710     5715     5720     5725 | 17246 |
| tgc ccc cac gtg ccc ata gcc gtg gcc ggc cag aag gca gtc atc ttc<br>Cys Pro His Val Pro Ile Ala Val Ala Gly Gln Lys Ala Val Ile Phe<br>5730     5735     5740 | 17294 |
| cgc aat gtg cgg gac atc ggc cgc ttc cac agc agc ttc ctg cag gag<br>Arg Asn Val Arg Asp Ile Gly Arg Phe His Ser Ser Phe Leu Gln Glu<br>5745     5750     5755 | 17342 |
| ttg cag cag tgc gac acg gac gac gac gtg gcc atg tgc ttc atc aag<br>Leu Gln Gln Cys Asp Thr Asp Asp Asp Val Ala Met Cys Phe Ile Lys<br>5760     5765     5770 | 17390 |
| aac cag gcg gcc ttt gag cag tac ctg gag ttc ctg gtg ggg cgt gtg<br>Asn Gln Ala Ala Phe Glu Gln Tyr Leu Glu Phe Leu Val Gly Arg Val<br>5775     5780     5785 | 17438 |
| cag gct gag tcg gtg gtc gtc agc acg gcc atc cag gag ttc tac aag<br>Gln Ala Glu Ser Val Val Val Ser Thr Ala Ile Gln Glu Phe Tyr Lys<br>5790     5795     5800     5805 | 17486 |
| aaa tac gcg gag gag gcc ctg ttg gca ggg gac ccc tct cag ccc ccg | 17534 |

|  |  |
|---|---|
| Lys Tyr Ala Glu Glu Ala Leu Leu Ala Gly Asp Pro Ser Gln Pro Pro<br>           5810                        5815                    5820 |  |
| cca cca cct ctg cag cac tac ctg gag cag cca gtg gag cgg gtg cag<br>Pro Pro Pro Leu Gln His Tyr Leu Glu Gln Pro Val Glu Arg Val Gln<br>           5825                       5830                    5835 | 17582 |
| cgc tac cag gcc ttg ctg aag gag ttg atc cgc aac aag gcg cgg aac<br>Arg Tyr Gln Ala Leu Leu Lys Glu Leu Ile Arg Asn Lys Ala Arg Asn<br>           5840                       5845                    5850 | 17630 |
| aga cag aac tgc gcg ctg ctg gag cag gcc tat gcc gtg gtg tct gcc<br>Arg Gln Asn Cys Ala Leu Leu Glu Gln Ala Tyr Ala Val Val Ser Ala<br>           5855                       5860                    5865 | 17678 |
| ctg cca cag cgc gct gag aac aag ctg cac gtg tcc ctc atg gag aac<br>Leu Pro Gln Arg Ala Glu Asn Lys Leu His Val Ser Leu Met Glu Asn<br>5870                    5875                    5880                    5885 | 17726 |
| tac cca ggc acc ctg gag gcc ctg ggc gag ccc atc cgc cag ggc cac<br>Tyr Pro Gly Thr Leu Glu Ala Leu Gly Glu Pro Ile Arg Gln Gly His<br>           5890                       5895                    5900 | 17774 |
| ttc atc gtg tgg gag ggt gca ccg ggg gcc cgc atg ccc tgg aag ggc<br>Phe Ile Val Trp Glu Gly Ala Pro Gly Ala Arg Met Pro Trp Lys Gly<br>           5905                       5910                    5915 | 17822 |
| cac aac cgt cac gtg ttc ctc ttc cgc aac cac ctg gta atc tgc aag<br>His Asn Arg His Val Phe Leu Phe Arg Asn His Leu Val Ile Cys Lys<br>           5920                       5925                    5930 | 17870 |
| ccc cgg cga gac tcc cgc acc gat acc gtc agc tac gtg ttc cgg aac<br>Pro Arg Arg Asp Ser Arg Thr Asp Thr Val Ser Tyr Val Phe Arg Asn<br>           5935                       5940                    5945 | 17918 |
| atg atg aag ctg agc agc atc gac ctg aac gac cag gtg gag ggg gat<br>Met Met Lys Leu Ser Ser Ile Asp Leu Asn Asp Gln Val Glu Gly Asp<br>5950                    5955                    5960                    5965 | 17966 |
| gac cgc gcc ttc gag gtg tgg cag gag cgg gag gac tcg gtg cgc aag<br>Asp Arg Ala Phe Glu Val Trp Gln Glu Arg Glu Asp Ser Val Arg Lys<br>           5970                       5975                    5980 | 18014 |
| tac ctg ctg cag gca cgg aca gcc att atc aag agc tcg tgg gtg aag<br>Tyr Leu Leu Gln Ala Arg Thr Ala Ile Ile Lys Ser Ser Trp Val Lys<br>           5985                       5990                    5995 | 18062 |
| gag atc tgt ggc atc cag cag cgt ctg gcc ctg cct gtg tgg cgg ccc<br>Glu Ile Cys Gly Ile Gln Gln Arg Leu Ala Leu Pro Val Trp Arg Pro<br>           6000                       6005                    6010 | 18110 |
| ccg gac ttt gaa gag gag ctg gcc gac tgc aca gcc gag ctg ggt gag<br>Pro Asp Phe Glu Glu Glu Leu Ala Asp Cys Thr Ala Glu Leu Gly Glu<br>           6015                       6020                    6025 | 18158 |
| aca gtc aag ctg gcc tgc cgc gtg acg ggc aca ccc aag cct gtc atc<br>Thr Val Lys Leu Ala Cys Arg Val Thr Gly Thr Pro Lys Pro Val Ile<br>6030                    6035                    6040                    6045 | 18206 |
| agc tgg tac aaa gat ggg aaa gca gtg cag gtg gac ccc cac cac atc<br>Ser Trp Tyr Lys Asp Gly Lys Ala Val Gln Val Asp Pro His His Ile<br>           6050                       6055                    6060 | 18254 |
| ctc att gaa gac cct gat ggc tcg tgt gca ctc atc ctg gac agc ctg<br>Leu Ile Glu Asp Pro Asp Gly Ser Cys Ala Leu Ile Leu Asp Ser Leu<br>           6065                       6070                    6075 | 18302 |
| acc ggt gtg gac tct ggc cag tac atg tgc ttc gcg gcc agc gcc gct<br>Thr Gly Val Asp Ser Gly Gln Tyr Met Cys Phe Ala Ala Ser Ala Ala<br>           6080                       6085                    6090 | 18350 |
| ggc aac tgc agt acc ctg ggc aag atc ctg gtg caa gtc cca cca cgg<br>Gly Asn Cys Ser Thr Leu Gly Lys Ile Leu Val Gln Val Pro Pro Arg<br>           6095                       6100                    6105 | 18398 |
| ttc gtg aac aag gtc cgg gcc tca ccc ttt gtg gag gga gag gac gcc<br>Phe Val Asn Lys Val Arg Ala Ser Pro Phe Val Glu Gly Glu Asp Ala<br>6110                    6115                    6120                    6125 | 18446 |

```
                                             -continued cag ttc acc tgc acc atc gaa ggc gcc ccg tac ccg cag atc agg tgg    18494
Gln Phe Thr Cys Thr Ile Glu Gly Ala Pro Tyr Pro Gln Ile Arg Trp
        6130                6135                6140 tac aag gac ggg gcc ctg ctg acc act ggc aac aag ttc cag aca ctg    18542
Tyr Lys Asp Gly Ala Leu Leu Thr Thr Gly Asn Lys Phe Gln Thr Leu
        6145                6150                6155 agt gag cct cgc agc ggc ctg cta gtg ctg gtg atc cgg gcg gcc agc    18590
Ser Glu Pro Arg Ser Gly Leu Leu Val Leu Val Ile Arg Ala Ala Ser
        6160                6165                6170 aag gag gac ctg ggg ctc tac gag tgt gag ctg gtg aac cgg ctg ggc    18638
Lys Glu Asp Leu Gly Leu Tyr Glu Cys Glu Leu Val Asn Arg Leu Gly
        6175                6180                6185 tcc gcg cgg gct agt gcg gag ctg cgc att cag agc ccc atg ctg cag    18686
Ser Ala Arg Ala Ser Ala Glu Leu Arg Ile Gln Ser Pro Met Leu Gln
6190                6195                6200                6205 gcc cag gag cag tgt cac agg gag cag ctc gtg gct gca gtg gaa gac    18734
Ala Gln Glu Gln Cys His Arg Glu Gln Leu Val Ala Ala Val Glu Asp
                6210                6215                6220 acc acc ctg gag cga gcg gac cag gag gtc aca tct gtc ctg aag aga    18782
Thr Thr Leu Glu Arg Ala Asp Gln Glu Val Thr Ser Val Leu Lys Arg
        6225                6230                6235 ctg ctg ggc ccc aag gcg cca ggc ccc tcc aca ggg gac ctc act ggc    18830
Leu Leu Gly Pro Lys Ala Pro Gly Pro Ser Thr Gly Asp Leu Thr Gly
        6240                6245                6250 cct ggc ccc tgc ccc agg ggg gca ccc gca ctc cag gaa acc ggc tcc    18878
Pro Gly Pro Cys Pro Arg Gly Ala Pro Ala Leu Gln Glu Thr Gly Ser
        6255                6260                6265 cag ccc cca gtc acc gga act tcg gag gca cct gcc gtg ccc ccg agg    18926
Gln Pro Pro Val Thr Gly Thr Ser Glu Ala Pro Ala Val Pro Pro Arg
6270                6275                6280                6285 gtg cca cag ccc ctc ctc cac gaa ggc cca gag cag gag ccg gag gcc    18974
Val Pro Gln Pro Leu Leu His Glu Gly Pro Glu Gln Glu Pro Glu Ala
                6290                6295                6300 att gcc aga gcc cag gaa tgg act gtg ccc att cgg atg gag ggt gca    19022
Ile Ala Arg Ala Gln Glu Trp Thr Val Pro Ile Arg Met Glu Gly Ala
        6305                6310                6315 gcc tgg ccc ggg gca ggc aca ggg gag ctg ctc tgg gac gtc cac agc    19070
Ala Trp Pro Gly Ala Gly Thr Gly Glu Leu Leu Trp Asp Val His Ser
        6320                6325                6330 cac gtg gtc aga gag acc aca cag agg acc tac aca tac cag gcc atc    19118
His Val Val Arg Glu Thr Thr Gln Arg Thr Tyr Thr Tyr Gln Ala Ile
        6335                6340                6345 gac acg cac acc gca cgg ccc cca tcc atg cag gta acc atc gag gat    19166
Asp Thr His Thr Ala Arg Pro Pro Ser Met Gln Val Thr Ile Glu Asp
6350                6355                6360                6365 gtg cag gca cag aca ggc gga acg gcc caa ttc gag gct atc att gag    19214
Val Gln Ala Gln Thr Gly Gly Thr Ala Gln Phe Glu Ala Ile Ile Glu
        6370                6375                6380 ggc gac cca cag ccc tcg gtg acc tgg tac aag gac agc gtc cag ctg    19262
Gly Asp Pro Gln Pro Ser Val Thr Trp Tyr Lys Asp Ser Val Gln Leu
        6385                6390                6395 gtg gac agc acc cgg ctt agc cag cag caa gaa ggc acc aca tac tcc    19310
Val Asp Ser Thr Arg Leu Ser Gln Gln Gln Glu Gly Thr Thr Tyr Ser
        6400                6405                6410 ctg gtg ctg agg cat gtg gcc tcg aag gat gcc ggc gtt tac acc tgc    19358
Leu Val Leu Arg His Val Ala Ser Lys Asp Ala Gly Val Tyr Thr Cys
        6415                6420                6425 ctg gcc caa aac act ggt ggc cag gtg ctc tgc aag gca gag ctg ctg    19406
Leu Ala Gln Asn Thr Gly Gly Gln Val Leu Cys Lys Ala Glu Leu Leu
6430                6435                6440                6445
```

```
gtg ctt ggg ggg gac aat gag ccg gac tca gag aag caa agc cac cgg      19454
Val Leu Gly Gly Asp Asn Glu Pro Asp Ser Glu Lys Gln Ser His Arg
            6450                6455                6460 agg aag ctg cac tcc ttc tat gag gtc aag gag gag att gga agg ggc      19502
Arg Lys Leu His Ser Phe Tyr Glu Val Lys Glu Glu Ile Gly Arg Gly
            6465                6470                6475 gtg ttt ggc ttc gta aaa aga gtg cag cac aaa gga aac aag atc ttg      19550
Val Phe Gly Phe Val Lys Arg Val Gln His Lys Gly Asn Lys Ile Leu
            6480                6485                6490 tgc gct gcc aag ttc atc ccc cta cgg agc aga act cgg gcc cag gca      19598
Cys Ala Ala Lys Phe Ile Pro Leu Arg Ser Arg Thr Arg Ala Gln Ala
            6495                6500                6505 tac agg gag cga gac atc ctg gcc gcg ctg agc cac ccg ctg gtc acg      19646
Tyr Arg Glu Arg Asp Ile Leu Ala Ala Leu Ser His Pro Leu Val Thr
6510                6515                6520                6525 ggg ctg ctg gac cag ttt gag acc cgc aag acc ctc atc ctc atc ctg      19694
Gly Leu Leu Asp Gln Phe Glu Thr Arg Lys Thr Leu Ile Leu Ile Leu
            6530                6535                6540 gag ctg tgc tca tcc gag gag ctg ctg gac cgc ctg tac agg aag ggc      19742
Glu Leu Cys Ser Ser Glu Glu Leu Leu Asp Arg Leu Tyr Arg Lys Gly
            6545                6550                6555 gtg gtg acg gag gcc gag gtc aag gtc tac atc cag cag ctg gtg gag      19790
Val Val Thr Glu Ala Glu Val Lys Val Tyr Ile Gln Gln Leu Val Glu
            6560                6565                6570 ggg ctg cac tac ctg cac agc cat ggc gtt ctc cac ctg gac ata aag      19838
Gly Leu His Tyr Leu His Ser His Gly Val Leu His Leu Asp Ile Lys
            6575                6580                6585 ccc tct aac atc ctg atg gtg cat cct gcc cgg gaa gac att aaa atc      19886
Pro Ser Asn Ile Leu Met Val His Pro Ala Arg Glu Asp Ile Lys Ile
6590                6595                6600                6605 tgc gac ttt ggc ttt gcc cag aac atc acc cca gca gag ctg cag ttc      19934
Cys Asp Phe Gly Phe Ala Gln Asn Ile Thr Pro Ala Glu Leu Gln Phe
            6610                6615                6620 agc cag tac ggc tcc cct gag ttc gtc tcc ccc gag atc atc cag cag      19982
Ser Gln Tyr Gly Ser Pro Glu Phe Val Ser Pro Glu Ile Ile Gln Gln
            6625                6630                6635 aac cct gtg agc gaa gcc tcc gac att tgg gcc atg ggt gtc atc tcc      20030
Asn Pro Val Ser Glu Ala Ser Asp Ile Trp Ala Met Gly Val Ile Ser
            6640                6645                6650 tac ctc agc ctg acc tgc tca tcc cca ttt gcc ggc gag agt gac cgt      20078
Tyr Leu Ser Leu Thr Cys Ser Ser Pro Phe Ala Gly Glu Ser Asp Arg
            6655                6660                6665 gcc acc ctc ctg aac gtc ctg gag ggg cgc gtg tca tgg agc agc ccc      20126
Ala Thr Leu Leu Asn Val Leu Glu Gly Arg Val Ser Trp Ser Ser Pro
6670                6675                6680                6685 atg gct gcc cac ctc agc gaa gac gcc aaa gac ttc atc aag gct acg      20174
Met Ala Ala His Leu Ser Glu Asp Ala Lys Asp Phe Ile Lys Ala Thr
            6690                6695                6700 ctg cag aga gcc cct cag gcc cgg cct agt gcg gcc cag tgc ctc tcc      20222
Leu Gln Arg Ala Pro Gln Ala Arg Pro Ser Ala Ala Gln Cys Leu Ser
            6705                6710                6715 cac ccc tgg ttc ctg aaa tcc atg cct gcg gag gag gcc cac ttc atc      20270
His Pro Trp Phe Leu Lys Ser Met Pro Ala Glu Glu Ala His Phe Ile
            6720                6725                6730 aac acc aag cag ctc aag ttc ctc ctg gcc cga agt cgc tgg cag cgt      20318
Asn Thr Lys Gln Leu Lys Phe Leu Leu Ala Arg Ser Arg Trp Gln Arg
            6735                6740                6745 tcc ctg atg agc tac aag tcc atc ctg gtg atg cgc tcc atc cct gag      20366
Ser Leu Met Ser Tyr Lys Ser Ile Leu Val Met Arg Ser Ile Pro Glu
```

-continued

```
      6750              6755              6760              6765
ctg ctg cgg ggc cca ccc gac agc ccc tcc ctc ggc gta gcc cgg cac      20414
Leu Leu Arg Gly Pro Pro Asp Ser Pro Ser Leu Gly Val Ala Arg His
                 6770              6775              6780 ctc tgc agg gac act ggt ggc tcc tcc agt tcc tcc tcc tcc tct gac      20462
Leu Cys Arg Asp Thr Gly Gly Ser Ser Ser Ser Ser Ser Ser Ser Asp
                 6785              6790              6795 aac gag ctc gcc cca ttt gcc cgg gct aag tca ctg cca ccc tcc ccg      20510
Asn Glu Leu Ala Pro Phe Ala Arg Ala Lys Ser Leu Pro Pro Ser Pro
                 6800              6805              6810 gtg aca cac tca cca ctg ctg cac ccc cgg ggc ttc ctg cgg ccc tcg      20558
Val Thr His Ser Pro Leu Leu His Pro Arg Gly Phe Leu Arg Pro Ser
                 6815              6820              6825 gcc agc ctg cct gag gaa gcc gag gcc agt gag cgc tcc acc gag gcc      20606
Ala Ser Leu Pro Glu Glu Ala Glu Ala Ser Glu Arg Ser Thr Glu Ala
6830              6835              6840              6845 cca gct ccg cct gca tct ccc gag ggt gcc ggg cca ccg gcc gcc cag      20654
Pro Ala Pro Pro Ala Ser Pro Glu Gly Ala Gly Pro Pro Ala Ala Gln
                 6850              6855              6860 ggc tgc gtg ccc cgg cac agc gtc atc cgc agc ctg ttc tac cac cag      20702
Gly Cys Val Pro Arg His Ser Val Ile Arg Ser Leu Phe Tyr His Gln
                 6865              6870              6875 gcg ggt gag agc cct gag cac ggg gcc ctg gcc ccg ggg agc agg cgg      20750
Ala Gly Glu Ser Pro Glu His Gly Ala Leu Ala Pro Gly Ser Arg Arg
                 6880              6885              6890 cac ccg gcc cgg cgg cgg cac ctg ctg aag ggc ggg tac att gcg ggg      20798
His Pro Ala Arg Arg Arg His Leu Leu Lys Gly Gly Tyr Ile Ala Gly
                 6895              6900              6905 gcg ctg cca ggc ctg cgc gag cca ctg atg gag cac cgc gtg ctg gag      20846
Ala Leu Pro Gly Leu Arg Glu Pro Leu Met Glu His Arg Val Leu Glu
6910              6915              6920              6925 gag gag gcc gcc agg gag gag cag gcc acc ctc ctg gcc aaa gcc ccc      20894
Glu Glu Ala Ala Arg Glu Glu Gln Ala Thr Leu Leu Ala Lys Ala Pro
                 6930              6935              6940 tca ttc gag act gcc ctc cgg ctg cct gcc tct ggc acc cac ttg gcc      20942
Ser Phe Glu Thr Ala Leu Arg Leu Pro Ala Ser Gly Thr His Leu Ala
                 6945              6950              6955 cct ggc cac agc cac tcc ctg gaa cat gac tct ccg agc acc ccc cgc      20990
Pro Gly His Ser His Ser Leu Glu His Asp Ser Pro Ser Thr Pro Arg
                 6960              6965              6970 ccc tcc tcg gag gcc tgc ggt gag gca cag cga ctg cct tca gcc ccc      21038
Pro Ser Ser Glu Ala Cys Gly Glu Ala Gln Arg Leu Pro Ser Ala Pro
                 6975              6980              6985 tcc ggg ggg gcc cct atc agg gac atg ggg cac cct cag ggc tcc aag      21086
Ser Gly Gly Ala Pro Ile Arg Asp Met Gly His Pro Gln Gly Ser Lys
6990              6995              7000              7005 cag ctt cca tcc act ggt ggc cac cca ggc act gct cag cca gag agg      21134
Gln Leu Pro Ser Thr Gly Gly His Pro Gly Thr Ala Gln Pro Glu Arg
                 7010              7015              7020 cca tcc ccg gac agc cct tgg ggg cag cca gcc cct ttc tgc cac ccc      21182
Pro Ser Pro Asp Ser Pro Trp Gly Gln Pro Ala Pro Phe Cys His Pro
                 7025              7030              7035 aag cag ggt tct gcc ccc cag gag ggc tgc agc ccc cac cca gca gtt      21230
Lys Gln Gly Ser Ala Pro Gln Glu Gly Cys Ser Pro His Pro Ala Val
                 7040              7045              7050 gcc cca tgc cct cct ggc tcc ttc cct cca gga tct tgc aaa gag gcc      21278
Ala Pro Cys Pro Pro Gly Ser Phe Pro Pro Gly Ser Cys Lys Glu Ala
                 7055              7060              7065 ccc tta gta ccc tca agc ccc ttc ttg gga cag ccc cag gca ccc cct      21326
```

```
Pro Leu Val Pro Ser Ser Pro Phe Leu Gly Gln Pro Gln Ala Pro Pro
7070            7075                7080            7085 gcc cct gcc aaa gca agc ccc cca ttg gac tct aag atg ggg cct gga    21374
Ala Pro Ala Lys Ala Ser Pro Pro Leu Asp Ser Lys Met Gly Pro Gly
                7090            7095            7100 gac atc tct ctt cct ggg agg cca aaa ccc ggc ccc tgc agt tcc cca    21422
Asp Ile Ser Leu Pro Gly Arg Pro Lys Pro Gly Pro Cys Ser Ser Pro
            7105            7110            7115 ggg tca gcc tcc cag gcg agc tct tcc caa gtg agc tcc ctc agg gtg    21470
Gly Ser Ala Ser Gln Ala Ser Ser Ser Gln Val Ser Ser Leu Arg Val
        7120            7125            7130 ggc tcc tcc cag gtg ggc aca gag cct ggc ccc tcc ctg gat gcg gag    21518
Gly Ser Ser Gln Val Gly Thr Glu Pro Gly Pro Ser Leu Asp Ala Glu
    7135            7140            7145 ggc tgg acc cag gag gct gag gat ctg tcc gac tcc aca ccc acc ttg    21566
Gly Trp Thr Gln Glu Ala Glu Asp Leu Ser Asp Ser Thr Pro Thr Leu
7150            7155            7160            7165 cag cgg cct cag gaa cag gcg acc atg cgc aag ttc tcc ctg ggt ggt    21614
Gln Arg Pro Gln Glu Gln Ala Thr Met Arg Lys Phe Ser Leu Gly Gly
            7170            7175            7180 cgc ggg ggc tac gca ggc gtg gct ggc tat ggc acc ttt gcc ttt ggt    21662
Arg Gly Gly Tyr Ala Gly Val Ala Gly Tyr Gly Thr Phe Ala Phe Gly
        7185            7190            7195 gga gat gca ggg ggc atg ctg ggg cag ggg ccc atg tgg gcc agg ata    21710
Gly Asp Ala Gly Gly Met Leu Gly Gln Gly Pro Met Trp Ala Arg Ile
    7200            7205            7210 gcc tgg gct gtg tcc cag tcg gag gag gag gag cag gag gag gcc agg    21758
Ala Trp Ala Val Ser Gln Ser Glu Glu Glu Gln Glu Glu Ala Arg
7215            7220            7225 gct gag tcc cag tcg gag gag cag cag gag gcc agg gct gag agc cca    21806
Ala Glu Ser Gln Ser Glu Glu Gln Gln Glu Ala Arg Ala Glu Ser Pro
7230            7235            7240            7245 ctg ccc cag gtc agt gca agg cct gtg cct gag gtc ggc agg gct ccc    21854
Leu Pro Gln Val Ser Ala Arg Pro Val Pro Glu Val Gly Arg Ala Pro
            7250            7255            7260 acc agg agc tct cca gag ccc acc cca tgg gag gac atc ggg cag gtc    21902
Thr Arg Ser Ser Pro Glu Pro Thr Pro Trp Glu Asp Ile Gly Gln Val
        7265            7270            7275 tcc ctg gtg cag atc cgg gac ctg tca ggt gat gcg gag gcg gcc gac    21950
Ser Leu Val Gln Ile Arg Asp Leu Ser Gly Asp Ala Glu Ala Ala Asp
    7280            7285            7290 aca ata tcc ctg gac att tcc gag gtg gac ccc gcc tac ctc aac ctc    21998
Thr Ile Ser Leu Asp Ile Ser Glu Val Asp Pro Ala Tyr Leu Asn Leu
    7295            7300            7305 tca gac ctg tac gat atc aag tac ctc cca ttc gag ttt atg atc ttc    22046
Ser Asp Leu Tyr Asp Ile Lys Tyr Leu Pro Phe Glu Phe Met Ile Phe
7310            7315            7320            7325 agg aaa gtc ccc aag tcc gct cag cca gag ccg ccc tcc ccc atg gct    22094
Arg Lys Val Pro Lys Ser Ala Gln Pro Glu Pro Pro Ser Pro Met Ala
            7330            7335            7340 gag gag gag ctg gcc gag ttc ccg gag ccc acg tgg ccc tgg cca ggt    22142
Glu Glu Glu Leu Ala Glu Phe Pro Glu Pro Thr Trp Pro Trp Pro Gly
        7345            7350            7355 gaa ctg ggc ccc cac gca ggc ctg gag atc aca gag gag tca gag gat    22190
Glu Leu Gly Pro His Ala Gly Leu Glu Ile Thr Glu Glu Ser Glu Asp
    7360            7365            7370 gtg gac gcg ctg ctg gca gag gct gcc gtg ggc agg aag cgc aag tgg    22238
Val Asp Ala Leu Leu Ala Glu Ala Ala Val Gly Arg Lys Arg Lys Trp
    7375            7380            7385
```

```
tcc tcg ccg tca cgc agc ctc ttc cac ttc cct ggg agg cac ctg ccg    22286
Ser Ser Pro Ser Arg Ser Leu Phe His Phe Pro Gly Arg His Leu Pro
7390             7395             7400             7405 ctg gat gag cct gca gag ctg ggg ctg cgt gag aga gtg aag gcc tcc    22334
Leu Asp Glu Pro Ala Glu Leu Gly Leu Arg Glu Arg Val Lys Ala Ser
        7410             7415             7420 gtg gag cac atc tcc cgg atc ctg aag ggc agg ccg gaa ggt ctg gag    22382
Val Glu His Ile Ser Arg Ile Leu Lys Gly Arg Pro Glu Gly Leu Glu
            7425             7430             7435 aag gag ggg ccc ccc agg aag aag cca ggc ctt gct tcc ttc cgg ctc    22430
Lys Glu Gly Pro Pro Arg Lys Lys Pro Gly Leu Ala Ser Phe Arg Leu
                7440             7445             7450 tca ggt ctg aag agc tgg gac cga gcg ccg aca ttc cta agg gag ctc    22478
Ser Gly Leu Lys Ser Trp Asp Arg Ala Pro Thr Phe Leu Arg Glu Leu
    7455             7460             7465 tca gat gag act gtg gtc ctg ggc cag tca gtg aca ctg gcc tgc cag    22526
Ser Asp Glu Thr Val Val Leu Gly Gln Ser Val Thr Leu Ala Cys Gln
7470             7475             7480             7485 gtg tca gcc cag cca gct gcc cag gcc acc tgg agc aaa gac gga gcc    22574
Val Ser Ala Gln Pro Ala Ala Gln Ala Thr Trp Ser Lys Asp Gly Ala
        7490             7495             7500 ccc ctg gag agc agc agc cgt gtc ctc atc tct gcc acc ctc aag aac    22622
Pro Leu Glu Ser Ser Ser Arg Val Leu Ile Ser Ala Thr Leu Lys Asn
            7505             7510             7515 ttc cag ctt ctg acc atc ctg gtg gtg gtg gct gag gac ctg ggt gtg    22670
Phe Gln Leu Leu Thr Ile Leu Val Val Val Ala Glu Asp Leu Gly Val
                7520             7525             7530 tac acc tgc agc gtg agc aat gcg ctg ggg aca gtg acc acc acg ggc    22718
Tyr Thr Cys Ser Val Ser Asn Ala Leu Gly Thr Val Thr Thr Thr Gly
    7535             7540             7545 gtc ctc cgg aag gca gag cgc ccc tca tct tcg cca tgc ccg gat atc    22766
Val Leu Arg Lys Ala Glu Arg Pro Ser Ser Ser Pro Cys Pro Asp Ile
7550             7555             7560             7565 ggg gag gtg tac gcg gat ggg gtg ctg ctg gtc tgg aag ccc gtg gaa    22814
Gly Glu Val Tyr Ala Asp Gly Val Leu Leu Val Trp Lys Pro Val Glu
        7570             7575             7580 tcc tac ggc cct gtg acc tac att gtg cag tgc agc cta gaa ggc ggc    22862
Ser Tyr Gly Pro Val Thr Tyr Ile Val Gln Cys Ser Leu Glu Gly Gly
            7585             7590             7595 agc tgg acc aca ctg gcc tcc gac atc ttt gac tgc tgc tac ctg acc    22910
Ser Trp Thr Thr Leu Ala Ser Asp Ile Phe Asp Cys Cys Tyr Leu Thr
                7600             7605             7610 agc aag ctc tcc cgg ggt ggc acc tac acc ttc cgc acg gca tgt gtc    22958
Ser Lys Leu Ser Arg Gly Gly Thr Tyr Thr Phe Arg Thr Ala Cys Val
    7615             7620             7625 agc aag gca gga atg ggt ccc tac agc agc ccc tcg gag caa gtc ctc    23006
Ser Lys Ala Gly Met Gly Pro Tyr Ser Ser Pro Ser Glu Gln Val Leu
7630             7635             7640             7645 ctg gga ggg ccc agc cac ctg gcc tct gag gag gag agc cag ggg cgg    23054
Leu Gly Gly Pro Ser His Leu Ala Ser Glu Glu Glu Ser Gln Gly Arg
        7650             7655             7660 tca gcc caa ccc ctg ccc agc aca aag acc ttc gca ttc cag aca cag    23102
Ser Ala Gln Pro Leu Pro Ser Thr Lys Thr Phe Ala Phe Gln Thr Gln
            7665             7670             7675 atc cag agg ggc cgc ttc agc gtg gtg cgg caa tgc tgg gag aag gcc    23150
Ile Gln Arg Gly Arg Phe Ser Val Val Arg Gln Cys Trp Glu Lys Ala
                7680             7685             7690 agc ggg cgg gcg ctg gcc gcc aag atc atc ccc tac cac ccc aag gac    23198
Ser Gly Arg Ala Leu Ala Ala Lys Ile Ile Pro Tyr His Pro Lys Asp
    7695             7700             7705
```

|     |     |     |     |     |     |     |     |     |     |     |     |     |     |     |     |     |
|---|---|---|---|---|---|---|---|---|---|---|---|---|---|---|---|---|
| aag | aca | gca | gtg | ctg | cgc | gaa | tac | gag | gcc | ctc | aag | ggc | ctg | cgc | cac | 23246 |
| Lys | Thr | Ala | Val | Leu | Arg | Glu | Tyr | Glu | Ala | Leu | Lys | Gly | Leu | Arg | His | |
| 7710 | | | | 7715 | | | | | 7720 | | | | | 7725 | | |
| ccg | cac | ctg | gcc | cag | ctg | cac | gca | gcc | tac | ctc | agc | ccc | cgg | cac | ctg | 23294 |
| Pro | His | Leu | Ala | Gln | Leu | His | Ala | Ala | Tyr | Leu | Ser | Pro | Arg | His | Leu | |
| | | | | 7730 | | | | | 7735 | | | | | 7740 | | |
| gtg | ctc | atc | ttg | gag | ctg | tgc | tct | ggg | ccc | gag | ctg | ctc | ccc | tgc | ctg | 23342 |
| Val | Leu | Ile | Leu | Glu | Leu | Cys | Ser | Gly | Pro | Glu | Leu | Leu | Pro | Cys | Leu | |
| | | | | 7745 | | | | | 7750 | | | | | 7755 | | |
| gcc | gag | agg | gcc | tcc | tac | tca | gaa | tcc | gag | gtg | aag | gac | tac | ctg | tgg | 23390 |
| Ala | Glu | Arg | Ala | Ser | Tyr | Ser | Glu | Ser | Glu | Val | Lys | Asp | Tyr | Leu | Trp | |
| | | | | 7760 | | | | | 7765 | | | | | 7770 | | |
| cag | atg | ttg | agt | gcc | acc | cag | tac | ctg | cac | aac | cag | cac | atc | ctg | cac | 23438 |
| Gln | Met | Leu | Ser | Ala | Thr | Gln | Tyr | Leu | His | Asn | Gln | His | Ile | Leu | His | |
| | | | | 7775 | | | | | 7780 | | | | | 7785 | | |
| ctg | gac | ctg | agg | tcc | gag | aac | atg | atc | atc | acc | gaa | tac | aac | ctg | ctc | 23486 |
| Leu | Asp | Leu | Arg | Ser | Glu | Asn | Met | Ile | Ile | Thr | Glu | Tyr | Asn | Leu | Leu | |
| 7790 | | | | | 7795 | | | | | 7800 | | | | | 7805 | |
| aag | gtc | gtg | gac | ctg | ggc | aat | gca | cag | agc | ctc | agc | cag | gag | aag | gtg | 23534 |
| Lys | Val | Val | Asp | Leu | Gly | Asn | Ala | Gln | Ser | Leu | Ser | Gln | Glu | Lys | Val | |
| | | | | 7810 | | | | | 7815 | | | | | 7820 | | |
| ctg | ccc | tca | gac | aag | ttc | aag | gac | tac | cta | gag | acc | atg | gct | cca | gag | 23582 |
| Leu | Pro | Ser | Asp | Lys | Phe | Lys | Asp | Tyr | Leu | Glu | Thr | Met | Ala | Pro | Glu | |
| | | | | 7825 | | | | | 7830 | | | | | 7835 | | |
| ctc | ctg | gag | ggc | cag | ggg | gct | gtt | cca | cag | aca | gac | atc | tgg | gcc | atc | 23630 |
| Leu | Leu | Glu | Gly | Gln | Gly | Ala | Val | Pro | Gln | Thr | Asp | Ile | Trp | Ala | Ile | |
| | | | | 7840 | | | | | 7845 | | | | | 7850 | | |
| ggt | gtg | aca | gcc | ttc | atc | atg | ctg | agc | gcc | gag | tac | ccg | gtg | agc | agc | 23678 |
| Gly | Val | Thr | Ala | Phe | Ile | Met | Leu | Ser | Ala | Glu | Tyr | Pro | Val | Ser | Ser | |
| | | | | 7855 | | | | | 7860 | | | | | 7865 | | |
| gag | ggt | gca | cgc | gac | ctg | cag | aga | gga | ctg | cgc | aag | ggg | ctg | gtc | cgg | 23726 |
| Glu | Gly | Ala | Arg | Asp | Leu | Gln | Arg | Gly | Leu | Arg | Lys | Gly | Leu | Val | Arg | |
| 7870 | | | | | 7875 | | | | | 7880 | | | | | 7885 | |
| ctg | agc | cgc | tgc | tac | gcg | ggg | ctg | tcc | ggg | ggc | gcc | gtg | gcc | ttc | ctg | 23774 |
| Leu | Ser | Arg | Cys | Tyr | Ala | Gly | Leu | Ser | Gly | Gly | Ala | Val | Ala | Phe | Leu | |
| | | | | 7890 | | | | | 7895 | | | | | 7900 | | |
| cgc | agc | act | ctg | tgc | gcc | cag | ccc | tgg | ggc | cgg | ccc | tgc | gcg | tcc | agc | 23822 |
| Arg | Ser | Thr | Leu | Cys | Ala | Gln | Pro | Trp | Gly | Arg | Pro | Cys | Ala | Ser | Ser | |
| | | | | 7905 | | | | | 7910 | | | | | 7915 | | |
| tgc | ctg | cag | tgc | ccg | tgg | cta | aca | gag | gag | ggc | ccg | gcc | tgt | tcg | cgg | 23870 |
| Cys | Leu | Gln | Cys | Pro | Trp | Leu | Thr | Glu | Glu | Gly | Pro | Ala | Cys | Ser | Arg | |
| | | | | 7920 | | | | | 7925 | | | | | 7930 | | |
| ccc | gcg | ccc | gtg | acc | ttc | cct | acc | gcg | cgg | ctg | cgc | gtc | ttc | gtg | cgc | 23918 |
| Pro | Ala | Pro | Val | Thr | Phe | Pro | Thr | Ala | Arg | Leu | Arg | Val | Phe | Val | Arg | |
| | | | | 7935 | | | | | 7940 | | | | | 7945 | | |
| aat | cgc | gag | aag | aga | cgc | gcg | ctg | ctg | tac | aag | agg | cac | aac | ctg | gcc | 23966 |
| Asn | Arg | Glu | Lys | Arg | Arg | Ala | Leu | Leu | Tyr | Lys | Arg | His | Asn | Leu | Ala | |
| 7950 | | | | | 7955 | | | | | 7960 | | | | | 7965 | |
| cag | gtg | cgc | tga | gggtcgcccc | | ggccacaccc | | ttggtctccc | | cgctgggggt | | | | | | 24018 |
| Gln | Val | Arg | * | | | | | | | | | | | | | | cgctgcagac gcgccaataa aaacgcccag ccgggcgaga aaaaaaaaaa aaaaaaaaaa 24078 aaaaaaaaaa aaaaaaaaag gcggccgcta aaaaagtcta ga 24120

```
<210> SEQ ID NO 5
<211> LENGTH: 7968
<212> TYPE: PRT
<213> ORGANISM: Homo sapiens

<400> SEQUENCE: 5
```

-continued

```
Met Asp Gln Pro Gln Phe Ser Gly Ala Pro Arg Phe Leu Thr Arg Pro
  1               5                  10                  15

Lys Ala Phe Val Val Ser Val Gly Lys Asp Ala Thr Leu Ser Cys Gln
             20                  25                  30

Ile Val Gly Asn Pro Thr Pro Gln Val Ser Trp Glu Lys Asp Gln Gln
         35                  40                  45

Pro Val Thr Ala Gly Ala Arg Phe Arg Leu Ala Gln Asp Gly Asp Leu
     50                  55                  60

Tyr Arg Leu Thr Ile Leu Asp Leu Ala Leu Gly Asp Ser Gly Gln Tyr
 65                  70                  75                  80

Val Cys Arg Ala Arg Asn Ala Ile Gly Glu Ala Phe Ala Ala Val Gly
                 85                  90                  95

Leu Gln Val Asp Ala Glu Ala Ala Cys Ala Glu Gln Ala Pro His Phe
            100                 105                 110

Leu Leu Arg Pro Thr Ser Ile Arg Val Arg Glu Gly Ser Glu Ala Thr
            115                 120                 125

Phe Arg Cys Arg Val Gly Gly Ser Pro Arg Pro Ala Val Ser Trp Ser
130                 135                 140

Lys Asp Gly Arg Arg Leu Gly Glu Pro Asp Gly Pro Arg Val Arg Val
145                 150                 155                 160

Glu Glu Leu Gly Glu Ala Ser Ala Leu Arg Ile Arg Ala Ala Arg Pro
                165                 170                 175

Arg Asp Gly Gly Thr Tyr Glu Val Arg Ala Glu Asn Pro Leu Gly Ala
            180                 185                 190

Ala Ser Ala Ala Ala Leu Val Val Asp Ser Asp Ala Ala Asp Thr
            195                 200                 205

Ala Ser Arg Pro Gly Thr Ser Thr Ala Ala Leu Leu Ala His Leu Gln
210                 215                 220

Arg Arg Arg Glu Ala Met Arg Ala Glu Gly Ala Pro Ala Ser Pro Pro
225                 230                 235                 240

Ser Thr Gly Thr Arg Thr Cys Thr Val Thr Glu Gly Lys His Ala Arg
                245                 250                 255

Leu Ser Cys Tyr Val Thr Gly Glu Pro Lys Pro Glu Thr Val Trp Lys
            260                 265                 270

Lys Asp Gly Gln Leu Val Thr Glu Gly Arg Arg His Val Val Tyr Glu
            275                 280                 285

Asp Ala Gln Glu Asn Phe Val Leu Lys Ile Leu Phe Cys Lys Gln Ser
290                 295                 300

Asp Arg Gly Leu Tyr Thr Cys Thr Ala Ser Asn Leu Val Gly Gln Thr
305                 310                 315                 320

Tyr Ser Ser Val Leu Val Val Arg Glu Pro Ala Val Pro Phe Lys
                325                 330                 335

Lys Arg Leu Gln Asp Leu Glu Val Arg Glu Lys Glu Ser Ala Thr Phe
            340                 345                 350

Leu Cys Glu Val Pro Gln Pro Ser Thr Glu Ala Ala Trp Phe Lys Glu
            355                 360                 365

Glu Thr Arg Leu Trp Ala Ser Ala Lys Tyr Gly Ile Glu Glu Glu Gly
370                 375                 380

Thr Glu Arg Arg Leu Thr Val Arg Asn Val Ser Ala Asp Asp Ala
385                 390                 395                 400

Val Tyr Ile Cys Glu Thr Pro Glu Gly Ser Arg Thr Val Ala Glu Leu
                405                 410                 415
```

-continued

```
Ala Val Gln Gly Asn Leu Leu Arg Lys Leu Pro Arg Lys Thr Ala Val
                420                 425                 430
Arg Val Gly Asp Thr Ala Met Phe Cys Val Glu Leu Ala Val Pro Val
            435                 440                 445
Gly Pro Val His Trp Leu Arg Asn Gln Glu Val Val Ala Gly Gly
        450                 455                 460
Arg Val Ala Ile Ser Ala Glu Gly Thr Arg His Thr Leu Thr Ile Ser
465                 470                 475                 480
Gln Cys Cys Leu Glu Asp Val Gly Gln Val Ala Phe Met Ala Gly Asp
                485                 490                 495
Cys Gln Thr Ser Thr Arg Phe Cys Val Ser Ala Pro Arg Lys Pro Pro
            500                 505                 510
Leu Gln Pro Pro Val Asp Pro Val Val Lys Ala Arg Met Glu Ser Ser
        515                 520                 525
Val Ile Leu Ser Trp Ser Pro Pro His Gly Glu Arg Pro Val Thr
530                 535                 540
Ile Asp Gly Tyr Leu Val Glu Lys Lys Lys Leu Gly Thr Tyr Thr Trp
545                 550                 555                 560
Ile Arg Cys His Glu Ala Glu Trp Val Ala Thr Pro Glu Leu Thr Val
                565                 570                 575
Ala Asp Val Ala Glu Glu Gly Asn Phe Gln Phe Arg Val Ser Ala Leu
            580                 585                 590
Asn Ser Phe Gly Gln Ser Pro Tyr Leu Glu Phe Pro Gly Thr Val His
        595                 600                 605
Leu Ala Pro Lys Leu Ala Val Arg Thr Pro Leu Lys Ala Val Gln Ala
        610                 615                 620
Val Glu Gly Gly Glu Val Thr Phe Ser Val Asp Leu Thr Val Ala Ser
625                 630                 635                 640
Ala Gly Glu Trp Phe Leu Asp Gly Gln Ala Leu Lys Ala Ser Ser Val
                645                 650                 655
Tyr Glu Ile His Cys Asp Arg Thr Arg His Thr Leu Thr Ile Arg Glu
                660                 665                 670
Val Pro Ala Ser Leu His Gly Ala Gln Leu Lys Phe Val Ala Asn Gly
            675                 680                 685
Ile Glu Ser Ser Ile Arg Met Glu Val Arg Ala Ala Pro Gly Leu Thr
        690                 695                 700
Ala Asn Lys Pro Pro Ala Ala Ala Arg Glu Val Leu Ala Arg Leu
705                 710                 715                 720
His Glu Glu Ala Gln Leu Leu Ala Glu Leu Ser Asp Gln Ala Ala Ala
                725                 730                 735
Val Thr Trp Leu Lys Asp Gly Arg Thr Leu Ser Pro Gly Pro Lys Tyr
            740                 745                 750
Glu Val Gln Ala Ser Ala Gly Arg Arg Val Leu Leu Val Arg Asp Val
        755                 760                 765
Ala Arg Asp Asp Ala Gly Leu Tyr Glu Cys Val Ser Arg Gly Gly Arg
        770                 775                 780
Ile Ala Tyr Gln Leu Ser Val Gln Gly Leu Ala Arg Phe Leu His Lys
785                 790                 795                 800
Asp Met Ala Gly Ser Cys Val Asp Ala Val Ala Gly Pro Ala Gln
                805                 810                 815
Phe Glu Cys Glu Thr Ser Glu Ala His Val His Val His Trp Tyr Lys
            820                 825                 830
Asp Gly Met Glu Leu Gly His Ser Gly Glu Arg Phe Leu Gln Glu Asp
```

-continued

```
                835                 840                 845
Val Gly Thr Arg His Arg Leu Val Ala Ala Thr Val Thr Arg Gln Asp
850                 855                 860
Glu Gly Thr Tyr Ser Cys Arg Val Gly Glu Asp Ser Val Asp Phe Arg
865                 870                 875                 880
Leu Arg Val Ser Glu Pro Lys Val Val Phe Ala Lys Glu Gln Leu Ala
                885                 890                 895
Arg Arg Lys Leu Gln Ala Glu Ala Gly Ala Ser Ala Thr Leu Ser Cys
                900                 905                 910
Glu Val Ala Gln Ala Gln Thr Glu Val Thr Trp Tyr Lys Asp Gly Lys
                915                 920                 925
Lys Leu Ser Ser Ser Lys Val Cys Met Glu Ala Thr Gly Cys Thr
                930                 935                 940
Arg Arg Leu Val Val Gln Gln Ala Gly Gln Ala Asp Ala Gly Glu Tyr
945                 950                 955                 960
Ser Cys Glu Ala Gly Gly Gln Arg Leu Ser Phe His Leu Asp Val Lys
                965                 970                 975
Glu Pro Lys Val Val Phe Ala Lys Asp Gln Val Ala His Ser Glu Val
                980                 985                 990
Gln Ala Glu Ala Gly Ala Asn Ala Thr Leu Ser Cys Glu Val Ala Gln
                995                 1000                1005
Ala Gln Ala Glu Val Met Trp Tyr Lys Asp Gly Lys Lys Leu Ser Ser
                1010                1015                1020
Ser Leu Lys Val His Val Glu Ala Lys Gly Cys Arg Arg Leu Val
1025                1030                1035                1040
Val Gln Gln Ala Gly Lys Thr Asp Ala Gly Asp Tyr Ser Cys Glu Ala
                1045                1050                1055
Arg Gly Gln Arg Val Ser Phe Arg Leu His Ile Thr Glu Pro Lys Met
                1060                1065                1070
Met Phe Ala Lys Glu Gln Ser Val His Asn Glu Val Gln Ala Glu Ala
                1075                1080                1085
Gly Ala Ser Ala Met Leu Ser Cys Glu Val Ala Gln Ala Gln Thr Glu
                1090                1095                1100
Val Thr Trp Tyr Lys Asp Gly Lys Lys Leu Ser Ser Ser Lys Val
1105                1110                1115                1120
Gly Met Glu Val Lys Gly Cys Thr Arg Arg Leu Val Leu Pro Gln Ala
                1125                1130                1135
Gly Lys Ala Asp Ala Gly Glu Tyr Ser Cys Glu Ala Gly Gly Gln Arg
                1140                1145                1150
Val Ser Phe His Leu His Ile Thr Glu Pro Lys Gly Val Phe Ala Lys
                1155                1160                1165
Glu Gln Ser Val His Asn Glu Val Gln Ala Glu Ala Gly Thr Thr Ala
                1170                1175                1180
Met Leu Ser Cys Glu Val Ala Gln Pro Gln Thr Glu Val Thr Trp Tyr
1185                1190                1195                1200
Lys Asp Gly Lys Lys Leu Ser Ser Ser Lys Val Arg Met Glu Val
                1205                1210                1215
Lys Gly Cys Thr Arg Arg Leu Val Val Gln Gln Val Gly Lys Ala Asp
                1220                1225                1230
Ala Gly Glu Tyr Ser Cys Glu Ala Gly Gly Gln Arg Val Ser Phe Gln
                1235                1240                1245
Leu His Ile Thr Glu Pro Lys Ala Val Phe Ala Lys Glu Gln Leu Val
                1250                1255                1260
```

```
His Asn Glu Val Arg Thr Glu Ala Gly Ala Ser Ala Thr Leu Ser Cys
1265                 1270                1275                1280

Glu Val Ala Gln Ala Gln Thr Glu Val Thr Trp Tyr Lys Asp Gly Lys
            1285                1290                1295

Lys Leu Ser Ser Ser Ser Lys Val Arg Ile Glu Ala Ala Gly Cys Met
            1300                1305                1310

Arg Gln Leu Val Val Gln Ala Gly Gln Ala Asp Ala Gly Glu Tyr
            1315                1320                1325

Thr Cys Glu Ala Gly Gly Gln Arg Leu Ser Phe His Leu Asp Val Ser
1330                 1335                1340

Glu Pro Lys Ala Val Phe Ala Lys Glu Gln Leu Ala His Arg Lys Val
1345                 1350                1355                1360

Gln Ala Glu Ala Gly Ala Ile Ala Thr Leu Ser Cys Glu Val Ala Gln
            1365                1370                1375

Ala Gln Thr Glu Val Thr Trp Tyr Lys Asp Gly Lys Lys Leu Ser Ser
            1380                1385                1390

Ser Ser Lys Val Arg Met Glu Ala Val Gly Cys Thr Arg Arg Leu Val
            1395                1400                1405

Val Gln Gln Ala Cys Gln Ala Asp Thr Gly Glu Tyr Ser Cys Glu Ala
        1410                1415                1420

Gly Gly Gln Arg Leu Ser Phe Ser Leu Asp Val Ala Glu Pro Lys Val
1425                 1430                1435                1440

Val Phe Ala Lys Glu Gln Pro Val His Arg Glu Val Gln Ala Gln Ala
            1445                1450                1455

Gly Ala Ser Thr Thr Leu Ser Cys Glu Val Ala Gln Ala Gln Thr Glu
            1460                1465                1470

Val Met Trp Tyr Lys Asp Gly Lys Lys Leu Ser Phe Ser Ser Lys Val
            1475                1480                1485

Arg Met Glu Ala Val Gly Cys Thr Arg Arg Leu Val Val Gln Gln Ala
            1490                1495                1500

Gly Gln Ala Asp Ala Gly Glu Tyr Ser Cys Glu Ala Gly Ser Gln Arg
1505                 1510                1515                1520

Leu Ser Phe His Leu His Val Ala Glu Pro Lys Ala Val Phe Ala Lys
            1525                1530                1535

Glu Gln Pro Ala Ser Arg Glu Val Gln Ala Glu Ala Gly Thr Ser Ala
            1540                1545                1550

Thr Leu Ser Cys Glu Val Ala Gln Ala Gln Thr Glu Val Thr Trp Tyr
            1555                1560                1565

Lys Asp Gly Lys Lys Leu Ser Ser Ser Ser Lys Val Arg Met Glu Ala
1570                 1575                1580

Val Gly Cys Thr Arg Arg Leu Val Val Gln Glu Ala Gly Gln Ala Asp
1585                 1590                1595                1600

Ala Gly Glu Tyr Ser Cys Lys Ala Gly Asp Gln Arg Leu Ser Phe His
            1605                1610                1615

Leu His Val Ala Glu Pro Lys Val Val Phe Ala Lys Glu Gln Pro Ala
            1620                1625                1630

His Arg Glu Val Gln Ala Glu Ala Gly Ala Ser Ala Thr Leu Ser Cys
            1635                1640                1645

Glu Val Ala Gln Ala Gln Thr Glu Val Thr Trp Tyr Lys Asp Gly Lys
1650                 1655                1660

Lys Leu Ser Ser Ser Ser Lys Val Arg Val Glu Ala Val Gly Cys Thr
1665                 1670                1675                1680
```

-continued

Arg Arg Leu Val Val Gln Gln Ala Gly Gln Ala Asp Ala Gly Glu Tyr
            1685                1690                1695

Ser Cys Glu Ala Gly Gly Gln Arg Leu Ser Phe Arg Leu His Val Ala
            1700                1705                1710

Glu Leu Glu Pro Gln Ile Ser Glu Arg Pro Cys Arg Arg Glu Pro Leu
            1715                1720                1725

Val Val Lys Glu His Glu Asp Ile Ile Leu Thr Ala Thr Leu Ala Thr
            1730                1735                1740

Pro Ser Ala Ala Thr Val Thr Trp Leu Lys Asp Gly Val Glu Ile Arg
1745                1750                1755                1760

Arg Ser Lys Arg His Glu Thr Ala Ser Gln Gly Asp Thr His Thr Leu
            1765                1770                1775

Thr Val His Gly Ala Gln Val Leu Asp Ser Ala Ile Tyr Ser Cys Arg
            1780                1785                1790

Val Gly Ala Glu Gly Gln Asp Phe Pro Val Gln Val Glu Glu Val Ala
            1795                1800                1805

Ala Lys Phe Cys Arg Leu Leu Glu Pro Val Cys Gly Glu Leu Gly Gly
            1810                1815                1820

Thr Val Thr Leu Ala Cys Glu Leu Ser Pro Ala Cys Ala Glu Val Val
1825                1830                1835                1840

Trp Arg Cys Gly Asn Thr Gln Pro Arg Val Gly Lys Arg Phe Gln Met
            1845                1850                1855

Val Ala Glu Gly Pro Val Arg Ser Leu Thr Val Leu Gly Leu Arg Ala
            1860                1865                1870

Glu Asp Ala Gly Glu Tyr Val Cys Glu Ser Arg Asp Asp His Thr Ser
            1875                1880                1885

Ala Gln Leu Thr Val Ser Val Pro Arg Val Val Lys Phe Met Ser Gly
            1890                1895                1900

Leu Ser Thr Val Val Ala Glu Glu Gly Gly Glu Ala Thr Phe Gln Cys
1905                1910                1915                1920

Val Val Ser Pro Ser Asp Val Ala Val Val Trp Phe Arg Asp Gly Ala
            1925                1930                1935

Leu Leu Gln Pro Ser Glu Lys Phe Ala Ile Ser Gln Ser Gly Ala Ser
            1940                1945                1950

His Ser Leu Thr Ile Ser Asp Leu Val Leu Glu Asp Ala Gly Gln Ile
            1955                1960                1965

Thr Val Glu Ala Glu Gly Ala Ser Ser Ser Ala Ala Leu Arg Val Arg
            1970                1975                1980

Glu Ala Pro Val Leu Phe Lys Lys Lys Leu Glu Pro Gln Thr Val Glu
1985                1990                1995                2000

Glu Arg Ser Ser Val Thr Leu Glu Val Glu Leu Thr Arg Pro Trp Pro
            2005                2010                2015

Glu Leu Arg Trp Thr Arg Asn Ala Thr Ala Leu Ala Pro Gly Lys Asn
            2020                2025                2030

Val Glu Ile His Ala Glu Gly Ala Arg His Arg Leu Val Leu His Asn
            2035                2040                2045

Val Gly Phe Ala Asp Arg Gly Phe Phe Gly Cys Glu Thr Pro Asp Asp
            2050                2055                2060

Lys Thr Gln Ala Lys Leu Thr Val Glu Met Arg Gln Val Arg Leu Val
2065                2070                2075                2080

Arg Gly Leu Gln Ala Val Glu Ala Arg Glu Gln Gly Thr Ala Thr Met
            2085                2090                2095

Glu Val Gln Leu Ser His Ala Asp Val Asp Gly Ser Trp Thr Arg Asp

-continued

```
                2100                2105                2110
Gly Leu Arg Phe Gln Gln Gly Pro Thr Cys His Leu Ala Val Arg Gly
            2115                2120                2125
Pro Met His Thr Leu Thr Leu Ser Gly Leu Arg Pro Glu Asp Ser Gly
            2130                2135                2140
Leu Met Val Phe Lys Ala Glu Gly Val His Thr Ser Ala Arg Leu Val
2145                2150                2155                2160
Val Thr Glu Leu Pro Val Ser Phe Ser Arg Pro Leu Gln Asp Val Val
            2165                2170                2175
Thr Thr Glu Lys Glu Lys Val Thr Leu Glu Cys Glu Leu Ser Arg Pro
            2180                2185                2190
Asn Val Asp Val Arg Trp Leu Lys Asp Gly Val Glu Leu Arg Ala Gly
            2195                2200                2205
Lys Thr Met Ala Ile Ala Ala Gln Gly Ala Cys Arg Ser Leu Thr Ile
            2210                2215                2220
Tyr Arg Cys Glu Phe Ala Asp Gln Gly Val Tyr Val Cys Asp Ala His
2225                2230                2235                2240
Asp Ala Gln Ser Ser Ala Ser Val Lys Val Gln Gly Arg Thr Tyr Thr
            2245                2250                2255
Leu Ile Tyr Arg Arg Val Leu Ala Glu Asp Ala Gly Glu Ile Gln Phe
            2260                2265                2270
Val Ala Glu Asn Ala Glu Ser Arg Ala Gln Leu Arg Val Lys Glu Leu
            2275                2280                2285
Pro Val Thr Leu Val Arg Pro Leu Arg Asp Lys Ile Ala Met Glu Lys
            2290                2295                2300
His Arg Gly Val Leu Glu Cys Gln Val Ser Arg Ala Ser Ala Gln Val
2305                2310                2315                2320
Arg Trp Phe Lys Gly Ser Gln Glu Leu Gln Pro Gly Pro Lys Tyr Glu
            2325                2330                2335
Leu Val Ser Asp Gly Leu Tyr Arg Lys Leu Ile Ile Ser Asp Val His
            2340                2345                2350
Ala Glu Asp Glu Asp Thr Tyr Thr Cys Asp Ala Gly Asp Val Lys Thr
            2355                2360                2365
Ser Ala Gln Phe Phe Val Glu Glu Gln Ser Ile Thr Ile Val Arg Gly
            2370                2375                2380
Leu Gln Asp Val Thr Val Met Glu Pro Ala Pro Ala Trp Phe Glu Cys
2385                2390                2395                2400
Glu Thr Ser Ile Pro Ser Val Arg Pro Pro Lys Trp Leu Leu Gly Lys
            2405                2410                2415
Thr Val Leu Gln Ala Gly Gly Asn Val Gly Leu Glu Gln Glu Gly Thr
            2420                2425                2430
Val His Arg Leu Met Leu Arg Arg Thr Cys Ser Thr Met Thr Gly Pro
            2435                2440                2445
Val His Phe Thr Val Gly Lys Ser Arg Ser Ser Ala Arg Leu Val Val
            2450                2455                2460
Ser Asp Ile Pro Val Val Leu Thr Arg Pro Leu Glu Pro Lys Thr Gly
2465                2470                2475                2480
Arg Glu Leu Gln Ser Val Val Leu Ser Cys Asp Phe Arg Pro Ala Pro
            2485                2490                2495
Lys Ala Val Gln Trp Tyr Lys Asp Asp Thr Pro Leu Ser Pro Ser Glu
            2500                2505                2510
Lys Phe Lys Met Ser Leu Glu Gly Gln Met Ala Glu Leu Arg Ile Leu
            2515                2520                2525
```

```
Arg Leu Met Pro Ala Asp Ala Gly Val Tyr Arg Cys Gln Ala Gly Ser
    2530                2535                2540

Ala His Ser Ser Thr Glu Val Thr Val Glu Ala Arg Glu Val Thr Val
2545                2550                2555                2560

Thr Gly Pro Leu Gln Asp Ala Glu Ala Thr Glu Glu Gly Trp Ala Ser
                2565                2570                2575

Phe Ser Cys Glu Leu Ser His Glu Asp Glu Val Glu Trp Ser Leu
            2580                2585                2590

Asn Gly Met Pro Leu Tyr Asn Asp Ser Phe His Glu Ile Ser His Lys
                2595                2600                2605

Gly Arg Arg His Thr Leu Val Leu Lys Ser Ile Gln Arg Ala Asp Ala
    2610                2615                2620

Gly Ile Val Arg Ala Ser Ser Leu Lys Val Ser Thr Ser Ala Arg Leu
2625                2630                2635                2640

Glu Val Arg Val Lys Pro Val Val Phe Leu Lys Ala Leu Asp Asp Leu
                2645                2650                2655

Ser Ala Glu Glu Arg Gly Thr Leu Ala Leu Gln Cys Glu Val Ser Asp
            2660                2665                2670

Pro Glu Ala His Val Val Trp Arg Lys Asp Gly Val Gln Leu Gly Pro
        2675                2680                2685

Ser Asp Lys Tyr Asp Phe Leu His Thr Ala Gly Thr Arg Gly Leu Val
    2690                2695                2700

Val His Asp Val Ser Pro Glu Asp Ala Gly Leu Tyr Thr Cys His Val
2705                2710                2715                2720

Gly Ser Glu Glu Thr Arg Ala Arg Val Arg Val His Asp Leu His Val
                2725                2730                2735

Gly Ile Thr Lys Arg Leu Lys Thr Met Glu Val Leu Glu Gly Glu Ser
                2740                2745                2750

Cys Ser Phe Glu Cys Val Leu Ser His Glu Ser Ala Ser Asp Pro Ala
            2755                2760                2765

Met Trp Thr Val Gly Gly Lys Thr Val Gly Ser Ser Ser Arg Phe Gln
    2770                2775                2780

Ala Thr Arg Gln Gly Arg Lys Tyr Ile Leu Val Val Arg Glu Ala Ala
2785                2790                2795                2800

Pro Ser Asp Ala Gly Glu Val Val Phe Ser Val Arg Gly Leu Thr Ser
                2805                2810                2815

Lys Ala Ser Leu Ile Val Arg Glu Arg Pro Ala Ala Ile Ile Lys Pro
            2820                2825                2830

Leu Glu Asp Gln Trp Val Ala Pro Gly Glu Asp Val Glu Leu Arg Cys
        2835                2840                2845

Glu Leu Ser Arg Ala Gly Thr Pro Val His Trp Leu Lys Asp Arg Lys
    2850                2855                2860

Ala Ile Arg Lys Ser Gln Lys Tyr Asp Val Val Cys Glu Gly Thr Met
2865                2870                2875                2880

Ala Met Leu Val Ile Arg Gly Ala Ser Leu Lys Asp Ala Gly Glu Tyr
                2885                2890                2895

Thr Cys Glu Val Glu Ala Ser Lys Ser Thr Ala Ser Leu His Val Glu
            2900                2905                2910

Glu Lys Ala Asn Cys Phe Thr Glu Glu Leu Thr Asn Leu Gln Val Glu
        2915                2920                2925

Glu Lys Gly Thr Ala Val Phe Thr Cys Lys Thr Glu His Pro Ala Ala
    2930                2935                2940
```

-continued

```
Thr Val Thr Trp Arg Lys Gly Leu Leu Glu Leu Arg Ala Ser Gly Lys
2945                2950                2955                2960

His Gln Pro Ser Gln Glu Gly Leu Thr Leu Arg Leu Thr Ile Ser Ala
                2965                2970                2975

Leu Glu Lys Ala Asp Ser Asp Thr Tyr Thr Cys Asp Ile Gly Gln Ala
            2980                2985                2990

Gln Ser Arg Ala Gln Leu Leu Val Gln Gly Arg Arg Val His Ile Ile
        2995                3000                3005

Glu Asp Leu Glu Asp Val Asp Val Gln Glu Gly Ser Ser Ala Thr Phe
    3010                3015                3020

Arg Cys Arg Ile Ser Pro Ala Asn Tyr Glu Pro Val His Trp Phe Leu
3025                3030                3035                3040

Asp Lys Thr Pro Leu His Ala Asn Glu Leu Asn Glu Ile Asp Ala Gln
                3045                3050                3055

Pro Gly Gly Tyr His Val Leu Thr Leu Arg Gln Leu Ala Leu Lys Asp
            3060                3065                3070

Ser Gly Thr Ile Tyr Phe Glu Ala Gly Asp Gln Arg Ala Ser Ala Ala
        3075                3080                3085

Leu Arg Val Thr Glu Lys Pro Ser Val Phe Ser Arg Glu Leu Thr Asp
    3090                3095                3100

Ala Thr Ile Thr Glu Gly Glu Asp Leu Thr Leu Val Cys Glu Thr Ser
3105                3110                3115                3120

Thr Cys Asp Ile Pro Met Cys Trp Thr Lys Asp Gly Lys Thr Leu Arg
                3125                3130                3135

Gly Ser Ala Arg Cys Gln Leu Ser His Glu Gly His Arg Ala Gln Leu
            3140                3145                3150

Leu Ile Thr Gly Ala Thr Leu Gln Asp Ser Gly Arg Tyr Lys Cys Glu
        3155                3160                3165

Ala Gly Gly Ala Cys Ser Ser Ser Ile Val Arg Val His Ala Arg Pro
    3170                3175                3180

Val Arg Phe Gln Glu Ala Leu Lys Asp Leu Glu Val Leu Glu Gly Gly
3185                3190                3195                3200

Ala Ala Thr Leu Arg Cys Val Leu Ser Ser Val Ala Ala Pro Val Lys
                3205                3210                3215

Trp Cys Tyr Gly Asn Asn Val Leu Arg Pro Gly Asp Lys Tyr Ser Leu
            3220                3225                3230

Arg Gln Glu Gly Ala Met Leu Glu Leu Val Val Arg Asn Leu Arg Pro
        3235                3240                3245

Gln Asp Ser Gly Arg Tyr Ser Cys Ser Phe Gly Asp Gln Thr Thr Ser
    3250                3255                3260

Ala Thr Leu Thr Val Thr Ala Leu Pro Ala Gln Phe Ile Gly Lys Leu
3265                3270                3275                3280

Arg Asn Lys Glu Ala Thr Glu Gly Ala Thr Ala Thr Leu Arg Cys Glu
                3285                3290                3295

Leu Ser Lys Thr Ala Pro Val Glu Trp Arg Lys Gly Ser Glu Thr Leu
            3300                3305                3310

Arg Asp Gly Asp Arg Tyr Cys Leu Arg Gln Asp Gly Ala Met Cys Glu
        3315                3320                3325

Leu Gln Ile Arg Gly Leu Ala Met Val Asp Ala Ala Glu Tyr Ser Cys
    3330                3335                3340

Val Cys Gly Glu Glu Arg Thr Ser Ala Ser Leu Thr Ile Arg Pro Met
3345                3350                3355                3360

Pro Ala His Phe Ile Gly Arg Leu Arg His Gln Glu Ser Ile Glu Gly
```

-continued

```
                3365                3370                3375
Ala Thr Ala Thr Leu Arg Cys Glu Leu Ser Lys Ala Ala Pro Val Glu
            3380                3385                3390
Trp Arg Lys Gly Arg Glu Ser Leu Arg Asp Gly Asp Arg His Ser Leu
            3395                3400            3405
Arg Gln Asp Gly Ala Val Cys Glu Leu Gln Ile Cys Gly Leu Ala Val
            3410                3415            3420
Ala Asp Ala Gly Glu Tyr Ser Cys Val Cys Gly Glu Arg Thr Ser
3425            3430                3435                3440
Ala Thr Leu Thr Val Lys Ala Leu Pro Ala Lys Phe Thr Glu Gly Leu
            3445                3450                3455
Arg Asn Glu Glu Ala Val Glu Gly Ala Thr Ala Met Leu Trp Cys Glu
            3460                3465            3470
Leu Ser Lys Val Ala Pro Val Glu Trp Arg Lys Gly Pro Glu Asn Leu
            3475                3480            3485
Arg Asp Gly Asp Arg Tyr Ile Leu Arg Gln Glu Gly Thr Arg Cys Glu
            3490                3495                3500
Leu Gln Ile Cys Gly Leu Ala Met Ala Asp Ala Gly Glu Tyr Leu Cys
3505            3510                3515                3520
Val Cys Gly Gln Glu Arg Thr Ser Ala Thr Leu Thr Ile Arg Ala Leu
            3525                3530                3535
Pro Ala Arg Phe Ile Glu Asp Val Lys Asn Gln Glu Ala Arg Glu Gly
            3540                3545                3550
Ala Thr Ala Val Leu Gln Cys Glu Leu Asn Ser Ala Ala Pro Val Glu
            3555                3560                3565
Trp Arg Lys Gly Ser Glu Thr Leu Arg Asp Gly Asp Arg Tyr Ser Leu
            3570                3575                3580
Arg Gln Asp Gly Thr Lys Cys Glu Leu Gln Ile Arg Gly Leu Ala Met
3585            3590                3595                3600
Ala Asp Thr Gly Glu Tyr Ser Cys Val Cys Gly Gln Glu Arg Thr Ser
            3605                3610                3615
Ala Met Leu Thr Val Arg Ala Leu Pro Ile Lys Phe Thr Glu Gly Leu
            3620                3625                3630
Arg Asn Glu Glu Ala Thr Glu Gly Ala Thr Ala Val Leu Arg Cys Glu
            3635                3640                3645
Leu Ser Lys Met Ala Pro Val Glu Trp Trp Lys Gly His Glu Thr Leu
            3650                3655                3660
Arg Asp Gly Asp Arg His Ser Leu Arg Gln Asp Gly Ala Arg Cys Glu
3665            3670                3675                3680
Leu Gln Ile Arg Gly Leu Val Ala Glu Asp Ala Gly Glu Tyr Leu Cys
            3685                3690                3695
Met Cys Gly Lys Glu Arg Thr Ser Ala Met Leu Thr Val Arg Ala Met
            3700                3705                3710
Pro Ser Lys Phe Ile Glu Gly Leu Arg Asn Glu Glu Ala Thr Glu Gly
            3715                3720                3725
Asp Thr Ala Thr Leu Trp Cys Glu Leu Ser Lys Ala Ala Pro Val Glu
            3730                3735                3740
Trp Arg Lys Gly His Glu Thr Leu Arg Asp Gly Asp Arg His Ser Leu
3745            3750                3755                3760
Arg Gln Asp Gly Ser Arg Cys Glu Leu Gln Ile Arg Gly Leu Ala Val
            3765                3770                3775
Val Asp Ala Gly Glu Tyr Ser Cys Val Cys Gly Gln Glu Arg Thr Ser
            3780                3785                3790
```

-continued

```
Ala Thr Leu Thr Val Arg Ala Leu Pro Ala Arg Phe Ile Glu Asp Val
        3795                3800                3805

Lys Asn Gln Glu Ala Arg Glu Gly Ala Thr Ala Val Leu Gln Cys Glu
    3810                3815                3820

Leu Ser Lys Ala Ala Pro Val Glu Trp Arg Lys Gly Ser Glu Thr Leu
3825                3830                3835                3840

Arg Gly Gly Asp Arg Tyr Ser Leu Arg Gln Asp Gly Thr Arg Cys Glu
            3845                3850                3855

Leu Gln Ile His Gly Leu Ser Val Ala Asp Thr Gly Glu Tyr Ser Cys
        3860                3865                3870

Val Cys Gly Gln Glu Arg Thr Ser Ala Thr Leu Thr Val Arg Ala Pro
    3875                3880                3885

Gln Pro Val Phe Arg Glu Pro Leu Gln Ser Leu Gln Ala Glu Glu Gly
    3890                3895                3900

Ser Thr Ala Thr Leu Gln Cys Glu Leu Ser Glu Pro Thr Ala Thr Val
3905                3910                3915                3920

Val Trp Ser Lys Gly Gly Leu Gln Leu Gln Ala Asn Gly Arg Arg Glu
            3925                3930                3935

Pro Arg Leu Gln Gly Cys Thr Ala Glu Leu Val Leu Gln Asp Leu Gln
            3940                3945                3950

Arg Glu Asp Thr Gly Glu Tyr Thr Cys Thr Cys Gly Ser Gln Ala Thr
        3955                3960                3965

Ser Ala Thr Leu Thr Val Thr Ala Ala Pro Val Arg Phe Leu Arg Glu
    3970                3975                3980

Leu Gln His Gln Glu Val Asp Glu Gly Gly Thr Ala His Leu Cys Cys
3985                3990                3995                4000

Glu Leu Ser Arg Ala Gly Ala Ser Val Glu Trp Arg Lys Gly Ser Leu
            4005                4010                4015

Gln Leu Phe Pro Cys Ala Lys Tyr Gln Met Val Gln Asp Gly Ala Ala
        4020                4025                4030

Ala Glu Leu Leu Val Arg Gly Val Glu Gln Glu Asp Ala Gly Asp Tyr
        4035                4040                4045

Thr Cys Asp Thr Gly His Thr Gln Ser Met Ala Ser Leu Ser Val Arg
    4050                4055                4060

Val Pro Arg Pro Lys Phe Lys Thr Arg Leu Gln Ser Leu Glu Gln Glu
4065                4070                4075                4080

Thr Gly Asp Ile Ala Arg Leu Cys Cys Gln Leu Ser Asp Ala Glu Ser
            4085                4090                4095

Gly Ala Val Val Gln Trp Leu Lys Glu Gly Val Glu Leu His Ala Gly
            4100                4105                4110

Pro Lys Tyr Glu Met Arg Ser Gln Gly Ala Thr Arg Glu Leu Leu Ile
    4115                4120                4125

His Gln Leu Glu Ala Lys Asp Thr Gly Glu Tyr Ala Cys Val Thr Gly
    4130                4135                4140

Gly Gln Lys Thr Ala Ala Ser Leu Arg Val Thr Glu Pro Glu Val Thr
4145                4150                4155                4160

Ile Val Arg Gly Leu Val Asp Ala Glu Val Thr Ala Asp Glu Asp Val
            4165                4170                4175

Glu Phe Ser Cys Glu Val Ser Arg Ala Gly Ala Thr Gly Val Gln Trp
        4180                4185                4190

Cys Leu Gln Gly Leu Pro Leu Gln Ser Asn Glu Val Thr Glu Val Ala
        4195                4200                4205
```

```
Val Arg Asp Gly Arg Ile His Thr Leu Arg Leu Lys Gly Val Thr Pro
    4210                4215                4220

Glu Asp Ala Gly Thr Val Ser Phe His Leu Gly Asn His Ala Ser Ser
4225                4230                4235                4240

Ala Gln Leu Thr Val Arg Ala Pro Glu Val Thr Ile Leu Glu Pro Leu
                4245                4250                4255

Gln Asp Val Gln Leu Ser Glu Gly Gln Asp Ala Ser Phe Gln Cys Arg
                4260                4265                4270

Leu Ser Arg Ala Ser Gly Gln Glu Ala Arg Trp Ala Leu Gly Gly Val
            4275                4280                4285

Pro Leu Gln Ala Asn Glu Met Asn Asp Ile Thr Val Glu Gln Gly Thr
        4290                4295                4300

Leu His Leu Leu Thr Leu His Lys Val Thr Leu Glu Asp Ala Gly Thr
4305                4310                4315                4320

Val Ser Phe His Val Gly Thr Cys Ser Ser Glu Ala Gln Leu Lys Val
                4325                4330                4335

Thr Ala Lys Asn Thr Val Val Arg Gly Leu Glu Asn Val Glu Ala Leu
                4340                4345                4350

Glu Gly Gly Glu Ala Leu Phe Glu Cys Gln Leu Ser Gln Pro Glu Val
            4355                4360                4365

Ala Ala His Thr Trp Leu Leu Asp Asp Glu Pro Val Arg Thr Ser Glu
        4370                4375                4380

Asn Ala Glu Val Val Phe Phe Glu Asn Gly Leu Arg His Leu Leu Leu
4385                4390                4395                4400

Leu Lys Asn Leu Arg Pro Gln Asp Ser Cys Arg Val Thr Phe Leu Ala
                4405                4410                4415

Gly Asp Met Val Thr Ser Ala Phe Leu Thr Val Arg Gly Trp Arg Leu
            4420                4425                4430

Glu Ile Leu Glu Pro Leu Lys Asn Ala Ala Val Arg Ala Gly Ala Gln
        4435                4440                4445

Ala Arg Phe Thr Cys Thr Leu Ser Glu Ala Val Pro Val Gly Glu Ala
        4450                4455                4460

Ser Trp Tyr Ile Asn Gly Ala Ala Val Gln Pro Asp Asp Ser Asp Trp
4465                4470                4475                4480

Thr Val Thr Ala Asp Gly Ser His Gln Ala Leu Leu Leu Arg Ser Ala
                4485                4490                4495

Gln Pro His His Ala Gly Glu Val Thr Phe Ala Cys Arg Asp Ala Val
                4500                4505                4510

Ala Ser Ala Arg Leu Thr Val Leu Gly Leu Pro Asp Pro Pro Glu Asp
            4515                4520                4525

Ala Glu Val Val Ala His Ser Ser His Thr Val Thr Leu Ser Trp Ala
        4530                4535                4540

Ala Pro Met Ser Asp Gly Gly Gly Leu Cys Gly Tyr Arg Val Glu
4545                4550                4555                4560

Val Lys Glu Gly Ala Thr Gly Gln Trp Arg Leu Cys His Glu Leu Val
                4565                4570                4575

Pro Gly Pro Glu Cys Val Val Asp Gly Leu Ala Pro Gly Glu Thr Tyr
            4580                4585                4590

Arg Phe Arg Val Ala Ala Val Gly Pro Val Gly Ala Gly Glu Pro Val
            4595                4600                4605

His Leu Pro Gln Thr Val Arg Leu Ala Glu Pro Pro Lys Pro Val Pro
        4610                4615                4620

Pro Gln Pro Ser Ala Pro Glu Ser Arg Gln Val Ala Ala Gly Glu Asp
```

```
                4625                4630                4635                4640
Val Ser Leu Glu Leu Glu Val Ala Glu Ala Gly Glu Val Ile Trp
                        4645                4650                4655
His Lys Gly Met Glu Arg Ile Gln Pro Gly Gly Arg Phe Glu Val Val
            4660                4665                4670
Ser Gln Gly Arg Gln Gln Met Leu Val Ile Lys Gly Phe Thr Ala Glu
        4675                4680                4685
Asp Gln Gly Glu Tyr His Cys Gly Leu Ala Gln Gly Ser Ile Cys Pro
    4690                4695                4700
Ala Ala Ala Thr Phe Gln Val Ala Leu Ser Pro Ala Ser Val Asp Glu
4705                4710                4715                4720
Ala Pro Gln Pro Ser Leu Pro Pro Glu Ala Ala Gln Glu Gly Asp Leu
                4725                4730                4735
His Leu Leu Trp Glu Ala Leu Ala Arg Lys Arg Arg Met Ser Arg Glu
                    4740                4745                4750
Pro Thr Leu Asp Ser Ile Ser Glu Leu Pro Glu Glu Asp Gly Arg Ser
                4755                4760                4765
Gln Arg Leu Pro Gln Glu Ala Glu Val Ala Pro Asp Leu Ser Glu
    4770                4775                4780
Gly Tyr Ser Thr Ala Asp Glu Leu Ala Arg Thr Gly Asp Ala Asp Leu
4785                4790                4795                4800
Ser His Thr Ser Ser Asp Asp Glu Ser Arg Ala Gly Thr Pro Ser Leu
                    4805                4810                4815
Val Thr Tyr Leu Lys Lys Ala Gly Arg Pro Gly Thr Ser Pro Leu Ala
            4820                4825                4830
Ser Lys Val Gly Ala Pro Ala Ala Pro Ser Val Lys Pro Gln Gln Gln
        4835                4840                4845
Gln Glu Pro Leu Ala Ala Val Arg Pro Pro Leu Gly Asp Leu Ser Thr
4850                4855                4860
Lys Asp Leu Gly Asp Pro Ser Met Asp Lys Ala Ala Val Lys Ile Gln
4865                4870                4875                4880
Ala Ala Phe Lys Gly Tyr Lys Val Arg Lys Glu Met Lys Gln Gln Glu
                    4885                4890                4895
Gly Pro Met Phe Ser His Thr Phe Gly Asp Thr Glu Ala Gln Val Gly
                4900                4905                4910
Asp Ala Leu Arg Leu Glu Cys Val Val Ala Ser Lys Ala Asp Val Arg
            4915                4920                4925
Ala Arg Trp Leu Lys Asp Gly Val Glu Leu Thr Asp Gly Arg His His
            4930                4935                4940
His Ile Asp Gln Leu Gly Asp Gly Thr Cys Ser Leu Leu Ile Ala Gly
4945                4950                4955                4960
Leu Asp Arg Ala Asp Ala Gly Cys Tyr Thr Cys Gln Val Ser Asn Lys
                    4965                4970                4975
Phe Gly Gln Val Thr His Ser Ala Cys Val Val Val Ser Gly Ser Glu
                4980                4985                4990
Ser Glu Ala Glu Ser Ser Ser Gly Gly Glu Leu Asp Asp Ala Phe Arg
        4995                5000                5005
Arg Ala Ala Arg Arg Leu His Arg Leu Phe Arg Thr Lys Ser Pro Ala
    5010                5015                5020
Glu Val Ser Asp Glu Glu Leu Phe Leu Ser Ala Asp Glu Gly Pro Ala
5025                5030                5035                5040
Glu Pro Glu Glu Pro Ala Asp Trp Gln Thr Tyr Arg Glu Asp Glu His
                    5045                5050                5055
```

```
Phe Ile Cys Ile Arg Phe Glu Ala Leu Thr Glu Ala Arg Gln Ala Val
        5060                5065                5070

Thr Arg Phe Gln Glu Met Phe Ala Thr Leu Gly Ile Gly Val Glu Ile
        5075                5080                5085

Lys Leu Val Glu Gln Gly Pro Arg Arg Val Glu Met Cys Ile Ser Lys
        5090                5095                5100

Glu Thr Pro Ala Pro Val Val Pro Pro Glu Pro Leu Pro Ser Leu Leu
5105                5110                5115                5120

Thr Ser Asp Ala Ala Pro Val Phe Leu Thr Glu Leu Gln Asn Gln Glu
            5125                5130                5135

Val Gln Asp Gly Tyr Pro Val Ser Phe Asp Cys Val Val Thr Gly Gln
            5140                5145                5150

Pro Met Pro Ser Val Arg Trp Phe Lys Asp Gly Lys Leu Leu Glu Glu
            5155                5160                5165

Asp Asp His Tyr Met Ile Asn Glu Asp Gln Gln Gly Gly His Gln Leu
        5170                5175                5180

Ile Ile Thr Ala Val Val Pro Ala Asp Met Gly Val Tyr Arg Cys Leu
5185                5190                5195                5200

Ala Glu Asn Ser Met Gly Val Ser Ser Thr Lys Ala Glu Leu Arg Val
            5205                5210                5215

Asp Leu Thr Ser Thr Asp Tyr Asp Thr Ala Ala Asp Ala Thr Glu Ser
            5220                5225                5230

Ser Ser Tyr Phe Ser Ala Gln Gly Tyr Leu Ser Ser Arg Glu Gln Glu
            5235                5240                5245

Gly Thr Glu Ser Thr Thr Asp Glu Gly Gln Leu Pro Gln Val Val Glu
        5250                5255                5260

Glu Leu Arg Asp Leu Gln Val Ala Pro Gly Thr Arg Leu Ala Lys Phe
5265                5270                5275                5280

Gln Leu Lys Val Lys Gly Tyr Pro Ala Pro Arg Leu Tyr Trp Phe Lys
            5285                5290                5295

Asp Gly Gln Pro Leu Thr Ala Ser Ala His Ile Arg Met Thr Gly Lys
            5300                5305                5310

Lys Ile Leu His Thr Leu Glu Ile Ile Ser Val Thr Arg Glu Asp Ser
            5315                5320                5325

Gly Gln Tyr Ala Ala Tyr Ile Ser Asn Ala Met Gly Ala Ala Tyr Ser
            5330                5335                5340

Ser Ala Arg Leu Leu Val Arg Gly Pro Asp Glu Pro Glu Glu Lys Pro
5345                5350                5355                5360

Ala Ser Asp Val His Glu Gln Leu Val Pro Pro Arg Met Leu Glu Arg
            5365                5370                5375

Phe Thr Pro Lys Lys Val Lys Lys Gly Ser Ser Ile Thr Phe Ser Val
            5380                5385                5390

Lys Val Glu Gly Arg Pro Val Pro Thr Val His Trp Leu Arg Glu Glu
            5395                5400                5405

Ala Glu Arg Gly Val Leu Trp Ile Gly Pro Asp Thr Pro Gly Tyr Thr
        5410                5415                5420

Val Ala Ser Ser Ala Gln Gln His Ser Leu Val Leu Leu Asp Val Gly
5425                5430                5435                5440

Arg Gln His Gln Gly Thr Tyr Thr Cys Ile Ala Ser Asn Ala Ala Gly
            5445                5450                5455

Gln Ala Leu Cys Ser Ala Ser Leu His Val Ser Gly Leu Pro Lys Val
            5460                5465                5470
```

```
Glu Glu Gln Glu Lys Val Lys Glu Ala Leu Ile Ser Thr Phe Leu Gln
        5475                5480                5485
Gly Thr Thr Gln Ala Ile Ser Ala Gln Gly Leu Glu Thr Ala Ser Phe
    5490                5495                5500
Ala Asp Leu Gly Gly Gln Arg Lys Glu Pro Leu Ala Ala Lys Glu
5505                5510                5515                5520
Ala Leu Gly His Leu Ser Leu Ala Glu Val Gly Thr Glu Phe Leu
                5525                5530                5535
Gln Lys Leu Thr Ser Gln Ile Thr Glu Met Val Ser Ala Lys Ile Thr
            5540                5545                5550
Gln Ala Lys Leu Gln Val Pro Gly Gly Asp Ser Asp Glu Asp Ser Lys
            5555                5560                5565
Thr Pro Ser Ala Ser Pro Arg His Gly Arg Ser Arg Pro Ser Ser Ser
        5570                5575                5580
Ile Gln Glu Ser Ser Ser Glu Ser Glu Asp Gly Asp Ala Arg Gly Glu
5585                5590                5595                5600
Ile Phe Asp Ile Tyr Val Val Thr Ala Asp Tyr Leu Pro Leu Gly Ala
                5605                5610                5615
Glu Gln Asp Ala Ile Thr Leu Arg Glu Gly Gln Tyr Val Glu Val Leu
            5620                5625                5630
Asp Ala Ala His Pro Leu Arg Trp Leu Val Arg Thr Lys Pro Thr Lys
            5635                5640                5645
Ser Ser Pro Ser Arg Gln Gly Trp Val Ser Pro Ala Tyr Leu Asp Arg
        5650                5655                5660
Arg Leu Lys Leu Ser Pro Glu Trp Gly Ala Ala Glu Ala Pro Glu Phe
5665                5670                5675                5680
Pro Gly Glu Ala Val Ser Glu Asp Glu Tyr Lys Ala Arg Leu Ser Ser
                5685                5690                5695
Val Ile Gln Glu Leu Leu Ser Ser Glu Gln Ala Phe Val Glu Glu Leu
            5700                5705                5710
Gln Phe Leu Gln Ser His His Leu Gln His Leu Glu Arg Cys Pro His
            5715                5720                5725
Val Pro Ile Ala Val Ala Gly Gln Lys Ala Val Ile Phe Arg Asn Val
        5730                5735                5740
Arg Asp Ile Gly Arg Phe His Ser Ser Phe Leu Gln Glu Leu Gln Gln
5745                5750                5755                5760
Cys Asp Thr Asp Asp Asp Val Ala Met Cys Phe Ile Lys Asn Gln Ala
                5765                5770                5775
Ala Phe Glu Gln Tyr Leu Glu Phe Leu Val Gly Arg Val Gln Ala Glu
            5780                5785                5790
Ser Val Val Val Ser Thr Ala Ile Gln Glu Phe Tyr Lys Lys Tyr Ala
        5795                5800                5805
Glu Glu Ala Leu Leu Ala Gly Asp Pro Ser Gln Pro Pro Pro Pro
            5810                5815                5820
Leu Gln His Tyr Leu Glu Gln Pro Val Glu Arg Val Gln Arg Tyr Gln
5825                5830                5835                5840
Ala Leu Leu Lys Glu Leu Ile Arg Asn Lys Ala Arg Asn Arg Gln Asn
                5845                5850                5855
Cys Ala Leu Leu Glu Gln Ala Tyr Ala Val Val Ser Ala Leu Pro Gln
            5860                5865                5870
Arg Ala Glu Asn Lys Leu His Val Ser Leu Met Glu Asn Tyr Pro Gly
        5875                5880                5885
Thr Leu Glu Ala Leu Gly Glu Pro Ile Arg Gln Gly His Phe Ile Val
```

```
                  5890                5895                5900
Trp Glu Gly Ala Pro Gly Ala Arg Met Pro Trp Lys Gly His Asn Arg
5905                5910                5915                5920

His Val Phe Leu Phe Arg Asn His Leu Val Ile Cys Lys Pro Arg Arg
                  5925                5930                5935

Asp Ser Arg Thr Asp Thr Val Ser Tyr Val Phe Arg Asn Met Met Lys
                  5940                5945                5950

Leu Ser Ser Ile Asp Leu Asn Asp Gln Val Glu Gly Asp Asp Arg Ala
                  5955                5960                5965

Phe Glu Val Trp Gln Glu Arg Glu Asp Ser Val Arg Lys Tyr Leu Leu
                  5970                5975                5980

Gln Ala Arg Thr Ala Ile Ile Lys Ser Ser Trp Val Lys Glu Ile Cys
5985                5990                5995                6000

Gly Ile Gln Gln Arg Leu Ala Leu Pro Val Trp Arg Pro Asp Phe
                  6005                6010                6015

Glu Glu Glu Leu Ala Asp Cys Thr Ala Glu Leu Gly Glu Thr Val Lys
                  6020                6025                6030

Leu Ala Cys Arg Val Thr Gly Thr Pro Lys Pro Val Ile Ser Trp Tyr
                  6035                6040                6045

Lys Asp Gly Lys Ala Val Gln Val Asp Pro His His Ile Leu Ile Glu
6050                6055                6060

Asp Pro Asp Gly Ser Cys Ala Leu Ile Leu Asp Ser Leu Thr Gly Val
6065                6070                6075                6080

Asp Ser Gly Gln Tyr Met Cys Phe Ala Ala Ser Ala Ala Gly Asn Cys
                  6085                6090                6095

Ser Thr Leu Gly Lys Ile Leu Val Gln Val Pro Pro Arg Phe Val Asn
                  6100                6105                6110

Lys Val Arg Ala Ser Pro Phe Val Glu Gly Glu Asp Ala Gln Phe Thr
                  6115                6120                6125

Cys Thr Ile Glu Gly Ala Pro Tyr Pro Gln Ile Arg Trp Tyr Lys Asp
                  6130                6135                6140

Gly Ala Leu Leu Thr Thr Gly Asn Lys Phe Gln Thr Leu Ser Glu Pro
6145                6150                6155                6160

Arg Ser Gly Leu Leu Val Leu Val Ile Arg Ala Ala Ser Lys Glu Asp
                  6165                6170                6175

Leu Gly Leu Tyr Glu Cys Glu Leu Val Asn Arg Leu Gly Ser Ala Arg
                  6180                6185                6190

Ala Ser Ala Glu Leu Arg Ile Gln Ser Pro Met Leu Gln Ala Gln Glu
                  6195                6200                6205

Gln Cys His Arg Glu Gln Leu Val Ala Ala Val Glu Asp Thr Thr Leu
                  6210                6215                6220

Glu Arg Ala Asp Gln Glu Val Thr Ser Val Leu Lys Arg Leu Leu Gly
6225                6230                6235                6240

Pro Lys Ala Pro Gly Pro Ser Thr Gly Asp Leu Thr Gly Pro Gly Pro
                  6245                6250                6255

Cys Pro Arg Gly Ala Pro Ala Leu Gln Glu Thr Gly Ser Gln Pro Pro
                  6260                6265                6270

Val Thr Gly Thr Ser Glu Ala Pro Ala Val Pro Pro Arg Val Pro Gln
                  6275                6280                6285

Pro Leu Leu His Glu Gly Pro Glu Gln Glu Pro Glu Ala Ile Ala Arg
                  6290                6295                6300

Ala Gln Glu Trp Thr Val Pro Ile Arg Met Glu Gly Ala Ala Trp Pro
6305                6310                6315                6320
```

-continued

Gly Ala Gly Thr Gly Glu Leu Leu Trp Asp Val His Ser His Val Val
                6325                6330                6335

Arg Glu Thr Thr Gln Arg Thr Tyr Thr Tyr Gln Ala Ile Asp Thr His
                6340                6345                6350

Thr Ala Arg Pro Pro Ser Met Gln Val Thr Ile Glu Asp Val Gln Ala
                6355                6360                6365

Gln Thr Gly Gly Thr Ala Gln Phe Glu Ala Ile Ile Glu Gly Asp Pro
                6370                6375                6380

Gln Pro Ser Val Thr Trp Tyr Lys Asp Ser Val Gln Leu Val Asp Ser
6385                6390                6395                6400

Thr Arg Leu Ser Gln Gln Gln Glu Gly Thr Thr Tyr Ser Leu Val Leu
                6405                6410                6415

Arg His Val Ala Ser Lys Asp Ala Gly Val Tyr Thr Cys Leu Ala Gln
                6420                6425                6430

Asn Thr Gly Gly Gln Val Leu Cys Lys Ala Glu Leu Leu Val Leu Gly
                6435                6440                6445

Gly Asp Asn Glu Pro Asp Ser Glu Lys Gln Ser His Arg Arg Lys Leu
6450                6455                6460

His Ser Phe Tyr Glu Val Lys Glu Glu Ile Gly Arg Gly Val Phe Gly
6465                6470                6475                6480

Phe Val Lys Arg Val Gln His Lys Gly Asn Lys Ile Leu Cys Ala Ala
                6485                6490                6495

Lys Phe Ile Pro Leu Arg Ser Arg Thr Arg Ala Gln Ala Tyr Arg Glu
                6500                6505                6510

Arg Asp Ile Leu Ala Ala Leu Ser His Pro Leu Val Thr Gly Leu Leu
                6515                6520                6525

Asp Gln Phe Glu Thr Arg Lys Thr Leu Ile Leu Ile Leu Glu Leu Cys
                6530                6535                6540

Ser Ser Glu Glu Leu Leu Asp Arg Leu Tyr Arg Lys Gly Val Val Thr
6545                6550                6555                6560

Glu Ala Glu Val Lys Val Tyr Ile Gln Gln Leu Val Glu Gly Leu His
                6565                6570                6575

Tyr Leu His Ser His Gly Val Leu His Leu Asp Ile Lys Pro Ser Asn
                6580                6585                6590

Ile Leu Met Val His Pro Ala Arg Glu Asp Ile Lys Ile Cys Asp Phe
                6595                6600                6605

Gly Phe Ala Gln Asn Ile Thr Pro Ala Glu Leu Gln Phe Ser Gln Tyr
                6610                6615                6620

Gly Ser Pro Glu Phe Val Ser Pro Glu Ile Ile Gln Gln Asn Pro Val
6625                6630                6635                6640

Ser Glu Ala Ser Asp Ile Trp Ala Met Gly Val Ile Ser Tyr Leu Ser
                6645                6650                6655

Leu Thr Cys Ser Ser Pro Phe Ala Gly Glu Ser Asp Arg Ala Thr Leu
                6660                6665                6670

Leu Asn Val Leu Glu Gly Arg Val Ser Trp Ser Ser Pro Met Ala Ala
                6675                6680                6685

His Leu Ser Glu Asp Ala Lys Asp Phe Ile Lys Ala Thr Leu Gln Arg
                6690                6695                6700

Ala Pro Gln Ala Arg Pro Ser Ala Ala Gln Cys Leu Ser His Pro Trp
6705                6710                6715                6720

Phe Leu Lys Ser Met Pro Ala Glu Glu Ala His Phe Ile Asn Thr Lys
                6725                6730                6735

-continued

```
Gln Leu Lys Phe Leu Leu Ala Arg Ser Arg Trp Gln Arg Ser Leu Met
            6740                6745                6750

Ser Tyr Lys Ser Ile Leu Val Met Arg Ser Ile Pro Glu Leu Leu Arg
        6755                6760            6765

Gly Pro Pro Asp Ser Pro Ser Leu Gly Val Ala Arg His Leu Cys Arg
    6770            6775                6780

Asp Thr Gly Gly Ser Ser Ser Ser Ser Ser Ser Asp Asn Glu Leu
6785        6790                6795                6800

Ala Pro Phe Ala Arg Ala Lys Ser Leu Pro Pro Ser Pro Val Thr His
            6805                6810                6815

Ser Pro Leu Leu His Pro Arg Gly Phe Leu Arg Pro Ser Ala Ser Leu
        6820                6825                6830

Pro Glu Glu Ala Glu Ala Ser Glu Arg Ser Thr Glu Ala Pro Ala Pro
        6835                6840                6845

Pro Ala Ser Pro Glu Gly Ala Gly Pro Pro Ala Ala Gln Gly Cys Val
        6850                6855                6860

Pro Arg His Ser Val Ile Arg Ser Leu Phe Tyr His Gln Ala Gly Glu
6865            6870                6875                6880

Ser Pro Glu His Gly Ala Leu Ala Pro Gly Ser Arg Arg His Pro Ala
        6885                6890                6895

Arg Arg Arg His Leu Leu Lys Gly Gly Tyr Ile Ala Gly Ala Leu Pro
        6900                6905                6910

Gly Leu Arg Glu Pro Leu Met Glu His Arg Val Leu Glu Glu Glu Ala
        6915                6920                6925

Ala Arg Glu Glu Gln Ala Thr Leu Leu Ala Lys Ala Pro Ser Phe Glu
        6930                6935                6940

Thr Ala Leu Arg Leu Pro Ala Ser Gly Thr His Leu Ala Pro Gly His
6945            6950                6955                6960

Ser His Ser Leu Glu His Asp Ser Pro Ser Thr Pro Arg Pro Ser Ser
                6965                6970                6975

Glu Ala Cys Gly Glu Ala Gln Arg Leu Pro Ser Ala Pro Ser Gly Gly
            6980                6985                6990

Ala Pro Ile Arg Asp Met Gly His Pro Gln Gly Ser Lys Gln Leu Pro
        6995                7000                7005

Ser Thr Gly Gly His Pro Gly Thr Ala Gln Pro Glu Arg Pro Ser Pro
    7010            7015                7020

Asp Ser Pro Trp Gly Gln Pro Ala Pro Phe Cys His Pro Lys Gln Gly
7025            7030                7035                7040

Ser Ala Pro Gln Glu Gly Cys Ser Pro His Pro Ala Val Ala Pro Cys
            7045                7050                7055

Pro Pro Gly Ser Phe Pro Pro Gly Ser Cys Lys Glu Ala Pro Leu Val
        7060                7065                7070

Pro Ser Ser Pro Phe Leu Gly Gln Pro Gln Ala Pro Ala Pro Ala
        7075                7080                7085

Lys Ala Ser Pro Pro Leu Asp Ser Lys Met Gly Pro Gly Asp Ile Ser
        7090                7095                7100

Leu Pro Gly Arg Pro Lys Pro Gly Pro Cys Ser Ser Pro Gly Ser Ala
7105            7110                7115                7120

Ser Gln Ala Ser Ser Ser Gln Val Ser Ser Leu Arg Val Gly Ser Ser
                7125                7130                7135

Gln Val Gly Thr Glu Pro Gly Pro Ser Leu Asp Ala Glu Gly Trp Thr
            7140                7145                7150

Gln Glu Ala Glu Asp Leu Ser Asp Ser Thr Pro Thr Leu Gln Arg Pro
```

-continued

```
                7155                7160                7165
Gln Glu Gln Ala Thr Met Arg Lys Phe Ser Leu Gly Gly Arg Gly Gly
    7170                7175                7180
Tyr Ala Gly Val Ala Gly Tyr Gly Thr Phe Ala Phe Gly Gly Asp Ala
7185                7190                7195                7200
Gly Gly Met Leu Gly Gln Gly Pro Met Trp Ala Arg Ile Ala Trp Ala
                7205                7210                7215
Val Ser Gln Ser Glu Glu Glu Gln Glu Ala Arg Ala Glu Ser
        7220                7225                7230
Gln Ser Glu Glu Gln Gln Glu Ala Arg Ala Glu Ser Pro Leu Pro Gln
        7235                7240                7245
Val Ser Ala Arg Pro Val Pro Glu Val Gly Arg Ala Pro Thr Arg Ser
    7250                7255                7260
Ser Pro Glu Pro Thr Pro Trp Glu Asp Ile Gly Gln Val Ser Leu Val
7265                7270                7275                7280
Gln Ile Arg Asp Leu Ser Gly Asp Ala Glu Ala Ala Asp Thr Ile Ser
                7285                7290                7295
Leu Asp Ile Ser Glu Val Asp Pro Ala Tyr Leu Asn Leu Ser Asp Leu
            7300                7305                7310
Tyr Asp Ile Lys Tyr Leu Pro Phe Glu Phe Met Ile Phe Arg Lys Val
        7315                7320                7325
Pro Lys Ser Ala Gln Pro Glu Pro Pro Ser Pro Met Ala Glu Glu Glu
    7330                7335                7340
Leu Ala Glu Phe Pro Glu Pro Thr Trp Pro Trp Pro Gly Glu Leu Gly
7345                7350                7355                7360
Pro His Ala Gly Leu Glu Ile Thr Glu Glu Ser Glu Asp Val Asp Ala
                7365                7370                7375
Leu Leu Ala Glu Ala Ala Val Gly Arg Lys Arg Lys Trp Ser Ser Pro
            7380                7385                7390
Ser Arg Ser Leu Phe His Phe Pro Gly Arg His Leu Pro Leu Asp Glu
        7395                7400                7405
Pro Ala Glu Leu Gly Leu Arg Glu Arg Val Lys Ala Ser Val Glu His
    7410                7415                7420
Ile Ser Arg Ile Leu Lys Gly Arg Pro Glu Gly Leu Glu Lys Glu Gly
7425                7430                7435                7440
Pro Pro Arg Lys Lys Pro Gly Leu Ala Ser Phe Arg Leu Ser Gly Leu
                7445                7450                7455
Lys Ser Trp Asp Arg Ala Pro Thr Phe Leu Arg Glu Leu Ser Asp Glu
            7460                7465                7470
Thr Val Val Leu Gly Gln Ser Val Thr Leu Ala Cys Gln Val Ser Ala
        7475                7480                7485
Gln Pro Ala Ala Gln Ala Thr Trp Ser Lys Asp Gly Ala Pro Leu Glu
    7490                7495                7500
Ser Ser Ser Arg Val Leu Ile Ser Ala Thr Leu Lys Asn Phe Gln Leu
7505                7510                7515                7520
Leu Thr Ile Leu Val Val Ala Glu Asp Leu Gly Val Tyr Thr Cys
                7525                7530                7535
Ser Val Ser Asn Ala Leu Gly Thr Val Thr Thr Gly Val Leu Arg
            7540                7545                7550
Lys Ala Glu Arg Pro Ser Ser Ser Pro Cys Pro Asp Ile Gly Glu Val
        7555                7560                7565
Tyr Ala Asp Gly Val Leu Leu Val Trp Lys Pro Val Glu Ser Tyr Gly
    7570                7575                7580
```

Pro Val Thr Tyr Ile Val Gln Cys Ser Leu Glu Gly Gly Ser Trp Thr
7585                7590                7595                7600

Thr Leu Ala Ser Asp Ile Phe Asp Cys Tyr Leu Thr Ser Lys Leu
            7605                7610                7615

Ser Arg Gly Gly Thr Tyr Thr Phe Arg Thr Ala Cys Val Ser Lys Ala
            7620                7625                7630

Gly Met Gly Pro Tyr Ser Ser Pro Ser Glu Gln Val Leu Leu Gly Gly
            7635                7640                7645

Pro Ser His Leu Ala Ser Glu Glu Ser Gln Gly Arg Ser Ala Gln
            7650                7655                7660

Pro Leu Pro Ser Thr Lys Thr Phe Ala Phe Gln Thr Gln Ile Gln Arg
7665                7670                7675                7680

Gly Arg Phe Ser Val Val Arg Gln Cys Trp Glu Lys Ala Ser Gly Arg
            7685                7690                7695

Ala Leu Ala Ala Lys Ile Ile Pro Tyr His Pro Lys Asp Lys Thr Ala
            7700                7705                7710

Val Leu Arg Glu Tyr Glu Ala Leu Lys Gly Leu Arg His Pro His Leu
            7715                7720                7725

Ala Gln Leu His Ala Ala Tyr Leu Ser Pro Arg His Leu Val Leu Ile
            7730                7735                7740

Leu Glu Leu Cys Ser Gly Pro Glu Leu Leu Pro Cys Leu Ala Glu Arg
7745                7750                7755                7760

Ala Ser Tyr Ser Glu Ser Glu Val Lys Asp Tyr Leu Trp Gln Met Leu
            7765                7770                7775

Ser Ala Thr Gln Tyr Leu His Asn Gln His Ile Leu His Leu Asp Leu
            7780                7785                7790

Arg Ser Glu Asn Met Ile Ile Thr Glu Tyr Asn Leu Leu Lys Val Val
            7795                7800                7805

Asp Leu Gly Asn Ala Gln Ser Leu Ser Gln Glu Lys Val Leu Pro Ser
            7810                7815                7820

Asp Lys Phe Lys Asp Tyr Leu Glu Thr Met Ala Pro Glu Leu Leu Glu
7825                7830                7835                7840

Gly Gln Gly Ala Val Pro Gln Thr Asp Ile Trp Ala Ile Gly Val Thr
            7845                7850                7855

Ala Phe Ile Met Leu Ser Ala Glu Tyr Pro Val Ser Ser Glu Gly Ala
            7860                7865                7870

Arg Asp Leu Gln Arg Gly Leu Arg Lys Gly Leu Val Arg Leu Ser Arg
            7875                7880                7885

Cys Tyr Ala Gly Leu Ser Gly Gly Ala Val Ala Phe Leu Arg Ser Thr
            7890                7895                7900

Leu Cys Ala Gln Pro Trp Gly Arg Pro Cys Ala Ser Ser Cys Leu Gln
7905                7910                7915                7920

Cys Pro Trp Leu Thr Glu Glu Gly Pro Ala Cys Ser Arg Pro Ala Pro
            7925                7930                7935

Val Thr Phe Pro Thr Ala Arg Leu Arg Val Phe Val Arg Asn Arg Glu
            7940                7945                7950

Lys Arg Arg Ala Leu Leu Tyr Lys Arg His Asn Leu Ala Gln Val Arg
            7955                7960                7965

<210> SEQ ID NO 6
<211> LENGTH: 23907
<212> TYPE: DNA
<213> ORGANISM: Homo sapiens

<400> SEQUENCE: 6

```
atggatcagc cacagttcag cggggcgccc cgctttctca cccggcccaa ggccttcgtg      60
gtgtcggtgg gcaaggacgc caccctcagc tgccagatcg tgggtaatcc cacgccacag     120
gtgagctggg agaaggacca gcagccggtg acggccggcg cgcgcttccg tctggcccag     180
gacggcgacc tctaccgcct cactatcctg gacctggcgc tgggcgacag tgggcaatac     240
gtgtgccgcc cgcgcaatgc cataggcgag gccttcgctg ccgtgggcct gcaggtggac     300
gcggaggccg cgtgcgccga gcaggcgccg cacttcctgc tgcggcccac gtccatccgc     360
gtgcgcgagg gctcagaggc caccttccgc tgccgcgtgg tggctcccc gaggccggca      420
gtgagctggt ccaaggacgg gcggcgcctg ggtgagcccg acggccccg cgtgcgcgtg      480
gaggagctcg gcgaggcaag tgcgctgcgc attcgggcgg cgcggccgcg cgacggcggc     540
acttacgagg tccgcgccga gaacccgctg gccgctgcca gcgccgccgc ggcgctagtg     600
gtggactcgg acgccgcgga cacggccagc cggcccggga cctccacggc cgcgctcctg     660
gcgcacctgc agcggcggcg cgaggctatg cgcgccgagg cgcccccgc ctcaccgccc      720
agcaccggca cgcgcacctg cacggtgact gaaggcaagc acgcgcgcct cagctgctac     780
gtgaccggcg agcccaagcc cgagacggtg tggaagaagg acggccagct ggtgaccgag     840
ggccggcgcc acgtggtgta cgaggacgcg caggagaact tcgtgctcaa gatcctcttc     900
tgcaagcagt cggaccgcgg cctctacacc tgcacggcgt ccaacctcgt gggccagacc     960
tacagctctg tgctggtcgt agtgcgcgag cccgcggttc ccttcaaaaa gcggctgcaa    1020
gatctggagg tgcgggagaa ggagtcggct acgttcctat gtgaggtgcc ccagccgtcc    1080
actgaggccg cgtggttcaa ggaggagacg cggttgtggg cgagcgccaa gtacggcatc    1140
gaggaggagg gcaccgagcg ccgcctgacc gtgcgcaatg tctcggccga cgacgacgcg    1200
gtgtacatct gcgagacgcc agagggcagc cgcacggtgg cggagctcgc agtccaagga    1260
aacctcctcc gaaagctccc tcggaagacg gcggtgcgcg tgggcgacac ggctatgttt    1320
tgcgtggagc tggcggtccc ggtgggcccc gtccactggc tgcggaacca ggaggaagtg    1380
gtggcggggg gccgcgtggc catctccgcg gagggcacgc gccacacact gaccatctcc    1440
cagtgctgcc tggaggatgt gggccaggtg gcctttatgg ctggcgactg ccagacgtcc    1500
acccggttct gcgtgtcggc ccccaggaag cctcccctgc aaccccctgt ggatcctgtg    1560
gtaaaggcca ggatggagag ttccgtgatt ctcagctggt ccccaccacc ccatggggaa    1620
cgccctgtca ctatcgacgg ctacctggta gagaagaaga agcttggcac ctacacctgg    1680
atcaggtgcc acgaggctga atgggtggct acacctgagc tgaccgtggc tgatgtggcg    1740
gaggagggga acttccagtt ccgagtgtcc gctctcaaca gctttggtca gagtccctac    1800
ctcgagttcc cggggactgt ccacctggcc cccaagctgg ccgtgaggac accgctgaag    1860
gcggtgcagg cggtagaggg tggcgaggtc actttctccg tggacctcac ggtggcctca    1920
gcgggtgagt ggttcctgga tgggcaggcc ctgaaggcca gcagtgtgta tgagatccac    1980
tgtgatcgca cccggcacac gctcaccatc cgggaggtgc ccgccagcct gcacggggcg    2040
cagctgaagt tcgtggccaa cggcattgag agcagcatcc ggatggaggt ccgggcggcc    2100
ccagggctga ctgccaacaa gccgccagcc gcagctgccc gggaggtgct ggctcggctg    2160
cacgaggagg cgcagctgct ggctgagctg tcagatcagg ctgcggctgt gacgtggctg    2220
aaggatggtc gcacactgtc cccaggcccc aagtatgagg tgcaggcatc ggccgggcgg    2280
cgggtgctcc ttgtgcgaga tgtggcccgg gacgatgcag gcctctacga gtgcgtcagc    2340
```

-continued

```
cgcgggggcc gcatcgccta ccagctctcc gtgcaaggcc tcgcgcgctt tctgcacaag    2400
gacatggcgg gcagctgtgt ggatgccgtg gctgggggcc cggcgcagtt tgagtgtgag    2460
acctccgaag cccacgtcca cgtgcactgg tacaaggatg gcatggagct gggccactcc    2520
ggtgagcgct tcttgcagga ggatgtgggg acgcggcacc ggctggtggc agccacagtc    2580
accaggcagg atgaaggcac ctactcctgc cgcgtgggcg aggactctgt ggacttccgg    2640
ctccgcgtct ctgagcccaa ggtggtgttt gctaaggagc agctggcacg caggaagctg    2700
caggcagagg caggagccag tgccacactg agctgcgagg tgcccaggc ccagacggag     2760 gtgacgtggt acaaggatgg gaagaagctg agctccagct cgaaagtgtg catggaggcc    2820
acaggctgca cgcgcaggct ggttgtgcag caggcaggcc aggcggatgc cggggagtat    2880
agctgcgagg ctgggggcca gcggctctcc ttccatctgg atgtcaaaga gcccaaggtg    2940
gtgtttgcca aggaccaggt ggcacacagt gaggtgcagg ctgaggcagg ggccaatgcc    3000
acgctgagct gcgaggtggc ccaggcccag gcggaggtga tgtggtacaa agatgggaag    3060
aagctgagct ccagcttgaa agtgcatgta gaggccaaag gctgcagacg gaggctggtg    3120
gtgcagcagg caggcaagac ggatgccggg gactacagct cgaggccag gggccagagg    3180 gtctccttcc gcctgcacat cacagagccc aagatgatgt ttgcaaagga gcagtcagtg    3240
cataatgagg tgcaggctga ggcggggcc agtgccatgc tgagctgtga ggtggcccag    3300
gcccagacgg aggtgacgtg gtacaaggat gggaagaagc tgagctccag ctcaaaagtg    3360
ggcatggagg tcaaagggtg cacacggagg ctggtgctgc acaggcgggc aaagcagat    3420 gctgggagt acagctgtga ggctgggggc cagagagtct ccttccacct gcacatcaca    3480
gagcccaagg gggtgtttgc gaaggagcag tcagtgcata tgaggtgca ggctgaggcg    3540 gggaccactg ccatgctgag ctgtgaggtg gcccagcccc agacggaggt gacgtggtac    3600
aaggacggga gaagctgag ctccagctca aaagtacgca tggaggtcaa gggctgcaca    3660
cgaaggctgg tagtgcagca ggtgggcaaa gcagatgctg gggagtacag ctgcgaggct    3720
gggggccaga gagtctcctt tcaactgcac atcacagagc ccaaggcagt gtttgccaag    3780
gagcagttgg tgcataatga ggtgcggact gaggcagggg ccagtgccac actgagctgt    3840
gaggtggccc aggcccagac agaggtgacg tggtacaagg atgggaagaa gctgagctcc    3900
agttcgaaag tgcgcataga ggctgcgggc tgcatgcggc agctggtggt gcagcaggca    3960
ggccaggcag atgctgggga gtacacctgt gaggctgggg ccagcggct ctccttccac    4020 ctggatgttt cagagcccaa ggcggtgttt gcaaaggagc agctggcaca caggaaggtg    4080
caggccgagg cggggccat tgccacgctg agctgcgagg tggcccaggc ccagacagag    4140
gtgacgtggt acaaggacgg gaagaagctg agctccagct cgaaagttcg aatggaggct    4200
gtgggctgca cacggaggct ggtggtgcag caggcatgcc aggcggacac cggggagtat    4260
agctgcgagg ccggggcca gcggctctcc ttcagcctgg acgtggcaga gcccaaggtg    4320
gtgtttgcca aggagcagcc agtgcacagg gaggtgcagg cccaggcggg ggccagcacc    4380
acactcagct gcgaggtggc tcaggcccag acggaggtga tgtggtacaa ggacgggaag    4440
aagctgagct tcagctcgaa agtgcgcatg gaggctgtgg gctgcacacg gaggctggtg    4500
gtgcagcagg cgggccaggc ggacgccggg gagtacagct cgaggcggg gagccagcgg    4560 ctctccttcc acctgcacgt ggcagagccc aaggcggtgt ttgccaagga gcagccagcg    4620
agcagggagg tgcaggctga ggcggggacc agtgccacgc tgagctgcga ggtggcccag    4680
```

-continued

| | |
|---|---|
| gcccagacag aggtgacgtg gtacaaggac gggaagaaac tgagctccag ctcgaaagtg | 4740 |
| cgaatggagg ccgtgggctg cacacggagg ctggtggtgc aggaggcagg ccaggcggac | 4800 |
| gccggggagt acagctgcaa ggccggggat cagcggctgt ccttccacct gcacgtggca | 4860 |
| gagcccaagg tggtgtttgc caaggagcag ccagcacaca gggaggtgca ggctgaggcg | 4920 |
| ggggccagtg ccacgctgag ctgcgaggtg gcccaggccc agacagaggt gacgtggtac | 4980 |
| aaggatggga agaagctgag ttccagctcg aaagtgcgcg tggaggccgt gggctgcaca | 5040 |
| cggaggctgg tggtgcagca ggcgggccag gcggatgctg gggagtacag ctgtgaggcg | 5100 |
| gggggccaac ggctgtcctt ccgcctgcac gtggcagagc tggagcccca aatttcagag | 5160 |
| agaccctgcc gcagggagcc tctggtggtc aaggagcatg aagacatcat cctgaccgcc | 5220 |
| acactggcca caccctctgc ggccacggtg acctggctca aggatggtgt ggagattcgc | 5280 |
| cgcagcaagc ggcatgagac agccagccag ggggacaccc acaccctgac cgtgcatggc | 5340 |
| gcccaggttc tggacagcgc catctacagc tgccgtgtgg gcgcagaggg gcaggacttc | 5400 |
| ccagtgcagg tggaagaggt ggccgccaag ttctgccggc tgctggagcc tgtgtgcggc | 5460 |
| gagctgggtg gcacggtgac actggcctgc gagctaagcc cagcgtgtgc agaggtggtg | 5520 |
| tggcgctgcg gcaacacgca gcctcgggtg ggcaagcgct tccagatggt ggccgagggg | 5580 |
| cccgtgcgct cactcactgt gttggggctg cgcgcagagg acgcagggga gtacgtgtgt | 5640 |
| gagagccgtg atgaccacac cagtgcgcag ctcaccgtca gtgtgccccg agtggtgaag | 5700 |
| tttatgtctg ggctgagcac cgtggtcgca gaggagggcg cgcaggccac cttccagtgc | 5760 |
| gtggtgtccc ccagtgatgt ggcagtcgtg tggttccggg acggtgccct gcttcagccc | 5820 |
| agcgagaagt tgccatatc acagagtggc gccagccaca gcctgaccat ctcagacctg | 5880 |
| gtgctggagg acgcgggcca gatcaccgtg gaggctgagg gcgcctcatc ctctgctgcc | 5940 |
| ctgagggtcc gagaggcgcc tgtgctgttc aaaaagaagc tggagccgca gacggtggag | 6000 |
| gagcggagct cggtgaccct ggaggtggag ctgacgcggc cgtggccgga gctgaggtgg | 6060 |
| acacggaacg cgacgccct ggcgccggga aagaacgtgg agatccacgc cgagggcgcc | 6120 |
| cgccaccgcc tggttctgca caacgtaggt tttgccgacc gtggcttctt tggctgcgag | 6180 |
| acgccggatg acaagacaca ggccaaactc accgtggaga tgcgccaggt acggctcgta | 6240 |
| cggggcctgc aggcagtgga ggcacgggag cagggcacgg ctaccatgga ggtgcagctg | 6300 |
| tcgcatgcgg acgtgatgg cagctggact cgtgacggtc tgcggttcca gcaggggccc | 6360 |
| acgtgccacc tggctgtgcg ggcccccatg cacaccctca cactctcggg gctgcggcca | 6420 |
| gaggatagtg gccttatggt cttcaaggcc gaaggagtgc acacgtcggc gcggctcgtg | 6480 |
| gtcaccgagc ttcccgtgag cttcagccgc ccgctgcagg acgtggtgac cactgagaag | 6540 |
| gagaaggtta ccctggagtg cgagctgtcg cgtcctaatg tggatgtgcg ctggctgaag | 6600 |
| gacggtgtgg agctgcgggc aggcaagacg atggccatcg cagcccaggg cgcctgcagg | 6660 |
| agcctcacca tttaccggtg cgagttcgcg gatcagggag tgtatgtgtg tgatgcccat | 6720 |
| gatgcccaga gctctgcctc cgtgaaggta caaggaagga catacactct catctaccgg | 6780 |
| agagtcctgg cggaagatgc aggagagatc caatttgtag ccgaaaatgc agaatcgcga | 6840 |
| gcccagctcc gagtgaagga gctgccagtg accctcgtgc gcccgctgcg ggacaagatt | 6900 |
| gccatggaga agcaccgcgg tgtgctggag tgtcaggtgt cccgggccag cgcccaggtg | 6960 |
| cggtggttca aggcagtcca ggagctgcag cccgggccca gtacgagct ggtcagtgat | 7020 |
| ggcctctacc gcaagctgat catcagtgat gtccacgcag aggacgagga cacctacacc | 7080 |

-continued

```
tgtgacgccg gtgatgtcaa gaccagtgca cagttcttcg tggaagagca atccatcacc    7140
attgtgcggg gtctgcagga cgtgacagtg atggagcccg ctcctgcctg gtttgagtgt    7200
gagacctcca tcccctcagt gcggccacct aagtggctcc tggggaagac ggtgttgcag    7260
gctgggggga acgtgggcct ggagcaggag ggcacggtgc accggctgat gctgcggcgg    7320
acctgctcca ccatgaccgg gcccgtgcac ttcaccgttg gcaagtcgcg ctcctctgcc    7380
cgcctggtgg tctcagacat ccccgtagtc ctcacacggc cgttggagcc aagacaggg    7440
cgtgagctgc agtcagtggt cctgtcctgc gacttccggc cagccccaa ggctgtgcag    7500
tggtacaagg atgacacgcc cctgtctccc tctgagaagt ttaagatgag cctggagggt    7560
cagatggctg agctgcgcat cctccggctc atgcctgctg atgctggtgt ctaccggtgc    7620
caggcgggca gtgcccacag cagcactgag gtcactgtgg aagcgcggga ggtgacagtg    7680
acagggccgc tacaggatgc agaggccacg gaggagggct gggccagctt ctcctgtgag    7740
ctgtcccacg aggatgagga ggtcgagtgg tcgctcaacg ggatgcccct gtacaacgac    7800
agcttccatg agatctcaca caaggggccg cgccacacgc tggtactgaa gagcatccag    7860
cgggctgatg cgggcatagt acgcgcctcc tccctgaagg tgtcgacctc tgcccgcctg    7920
gaggtccgag tgaagccggt ggtgttcctg aaggcgctgg atgacctgtc cgcagaggag    7980
cgcggcaccc tggccctgca gtgtgaagtc tctgaccccg aggcccatgt ggtgtggcgc    8040
aaagatggcg tgcagctggg ccccagtgac aagtatgact tcctgcacac ggcgggcacg    8100
cgggggctcg tggtgcatga cgtgagccct gaagacgccg gcctgtacac ctgccacgtg    8160
ggctccgagg agacccgggc ccgggtccgc gtgcacgatc tgcacgtggg catcaccaag    8220
aggctgaaga caatggaggt gctggaaggg gaaagctgca gctttgagtg cgtcctgtcc    8280
cacgagagtg ccagcgaccc ggccatgtgg acagtcggtg ggaagacagt gggcagctcc    8340
agccgcttcc aggccacacg tcagggccga aaatacatcc tggtggtccg ggaggctgca    8400
ccaagtgatg ccggggaggt ggtcttctct gtgcggggcc tcacctccaa ggcctcactc    8460
attgtcagag agaggccggc cgccatcatc aagcccctgg aagaccagtg ggtggcgcca    8520
ggggaggacg tggagctgcg ctgtgagctg tcacgggcgg gaacgcccgt gcactggctg    8580
aaggacagga aggccatccg caagagccag aagtatgatg tggtctgcga gggcacgatg    8640
gccatgctgg tcatccgcgg ggcctcgctc aaggacgcgg gcgagtacac gtgtgaggtg    8700
gaggcttcca agagcacagc cagcctccat gtggaagaaa aagcaaactg cttcacagag    8760
gagctgacca atctgcaggt ggaggagaaa ggcacagctg tgttcacgtg caagacggag    8820
caccccgcgg ccacagtgac ctggcgcaag ggcctcttgg agctacgggc ctcagggaag    8880
caccagccca gccaggaggg cctgacccto cggctcacca tcagtgccct ggagaaggca    8940
gacagcgaca cctataccto cgacattggc caggcccagt cccgggccca gctcctagtg    9000
caaggccgga gagtgcacat catcgaggac ctggaggatg tggatgtgca ggagggctcc    9060
tcggccacct tccgttgccg gatctccccg gccaactacg agcctgtgca ctggttcctg    9120
gacaagacac ccctgcatgc caacgagctc aatgagatcg atgcccagcc cggggggctac    9180
cacgtgctga ccctgcggca gctggcgctc aaggactcgg gcaccatcta ctttgaggcg    9240
ggtgaccagc gggcctcggc cgcccctgcgg gtcactgaga agccaagcgt cttctcccgg    9300
gagctcacag atgccaccat cacagagggt gaggacttga ccctggtgtg cgagaccagc    9360
acctgcgaca ttcctatgtg ctggaccaag gatgggaaga ccctgcgggg gtctgcccgg    9420
```

```
tgccagctga gccatgaggg ccaccgggcc cagctgctca tcactggggc caccctgcag    9480
gacagtggac gctacaagtg tgaggctggg ggcgcctgca gcagctccat tgtcaggtg     9540 catgcgcggc cagtgcggtt ccaggaggcc ctgaaggacc tggaggtgct ggagggtggt    9600
gctgccacac tgcgctgtgt gctgtcatct gtggctgcgc ccgtgaagtg gtgctatgga    9660
aacaacgtcc tgaggccagg tgacaaatac agcctacgcc aggagggtgc catgctggag    9720
ctggtggtcc ggaacctccg gccgcaggac agcgggcggt actcatgctc cttcgggac     9780 cagactactt ctgccaccct cacagtgact gccctgcctg cccagttcat cgggaaactg    9840
agaaacaagg aggccacaga aggggccacg gccacgctgc ggtgtgagct gagcaagaca    9900
gcccctgtgg agtggagaaa ggggtccgag accctcagag atggggacag atactgtctg    9960
aggcaggacg gggccatgtg tgagctgcag atccgtggcc tggccatggt ggatgccgcg    10020
gagtactcgt gtgtgtgtgg agaggagagg acctcagcct cactcaccat caggcccatg    10080
cctgcccact tcataggaag actgagacac caagagagca tagaaggggc cacagccacg    10140
ctgcggtgtg agctgagcaa ggcggccccc gtggagtgga ggaaggggcg tgagagcctc    10200
agagatgggg acagacatag cctgaggcag acgggggctg tgtgcgagct gcagatctgt    10260
ggcctggctg tggcagatgc tggggagtac tcctgtgtgt gtgggggagga gaggacctct   10320 gccactctca ccgtgaaggc cctgccagcc aagttcacag agggtctgag gaatgaagag    10380
gccgtggaag gggccacagc catgttgtgg tgtgaactga gcaaggtggc ccctgtggag    10440
tggaggaagg ggcccgagaa cctcagagat ggggacagat acatcctgag gcaggagggg    10500
accaggtgtg agctgcagat ctgtggcctg gccatggcgg acgccgggga gtacttgtgt    10560
gtgtgcgggc aggagaggac ctcagccacg ctcaccatca gggctctgcc tgccaggttc    10620
atagaagatg tgaaaaacca ggaggccaga gaaggggcca cggctgtgct gcagtgtgag    10680
ctgaacagtg cagcccctgt ggagtggaga aagggtctg  agaccctcag agatggggac    10740
agatacagcc tgaggcagga cgggactaaa tgtgagctgc agattcgtgg cctggccatg    10800
gcagacactg gggagtactc gtgcgtgtgc gggcaggaga ggacctcggc tatgctcacc    10860
gtcagggctc tacccatcaa gttcacagag gtctgagga  acgaagaggc cacagaaggg    10920
gcaacagccg tgctgcggtg tgagctgagc aagatggccc ccgtggagtg gtggaagggg    10980
catgagaccc tcagagatgg agacagacac agcctgaggc aggacgggc  caggtgtgag    11040 ctgcagatcc gcggcctcgt ggcagaggac gctggggagt acctgtgcat gtgcgggaag    11100
gagaggacct cagccatgct caccgtcagg gccatgcctt ccaagttcat agagggtctg    11160
aggaatgaag aggccacaga aggggacacg ccacgctgt ggtgtgagct gagcaaggcg    11220
gcaccggtgg agtggaggaa ggggcatgag accctcagag atggggacag acacagcctg    11280
aggcaggacg gtccaggtgt gagctgcag  atccgtggcc tggctgtggt ggatgccggg    11340
gagtactcgt gtgtgcgg   gcaggagagg acctcagcca cactcactgt cagggccctg    11400
cctgccagat tcatagaaga tgtgaaaaac caggaggcca gaagggggc  cacggccgtg    11460 ctgcaatgtg agctgagcaa ggcggccccc gtggagtgga ggaaggggtc tgagaccctc    11520
agagtggggg acagatacag cctgaggcag gatgggacca gatgtgagct gcagattcat    11580
ggcctgtctg tggcagacac tggggagtac tcgtgtgtgt gcgggcagga gaggacctcg    11640
gccacactca ccgtcagggc cccacagcca gtgttccggg agccgctgca gagtctgcag    11700
gcggaggagg ctccacggc  cacccctcag tgtgagctgt ctgagcccac tgctacagtg    11760
gtctggagca agggtggcct gcagctgcag gccaatgggc gccgggagcc acggcttcag    11820
```

```
ggctgcaccg cggagctggt gttacaggac ctacaacgtg aagacactgg cgaatacact   11880
tgcacctgtg gctcccaggc caccagtgcc accctcactg tcacagctgc gcctgtgcgg   11940
ttcctccgag agctgcagca ccaggaggtg gatgagggag gcaccgcaca cttatgctgc   12000
gagctgagcc gggcgggtgc gagcgtggag tggcgcaagg gctccctaca gctcttccct   12060
tgtgccaagt accagatggt gcaggatggt gcagctgcag agctgctggt acgcggagtg   12120
gagcaggagg atgcgggtga ctacacgtgt gacacgggcc acacgcagag catggccagc   12180
ctctctgtcc gtgtccccag gcccaagttc aagacccggc ttcagagtct ggagcaggag   12240
acaggtgaca tagcccggct gtgctgtcag ctgagtgatg cagagtcggg ggccgtggtg   12300
caatggctca aggagggcgt ggagctgcat gcgggcccca agtacgagat gcggagccag   12360
ggggccacgc gggagctgct gatccaccaa ctggaggcca aggacacggg cgagtatgcc   12420
tgtgtgacag gcggcagaa aaccgctgcc tccctcaggg tcacagagcc tgaggtgacc   12480
attgtacggg gctggttga tgcggaggtg acggccgatg aggatgttga gttcagctgt   12540
gaggtgtcca gggctggagc cacaggcgtg cagtggtgcc tacagggcct gccactgcaa   12600
agcaatgagg tgacagaggt ggctgtgcgg gatggccgca tccacaccct gcggctgaag   12660
ggcgtgacgc ccgaggacgc tggcactgtc tccttccatt tgggaaacca tgcttcctct   12720
gcccagctca ccgtcagagc tcctgagtg accatcctgg agccctgca ggacgtgcag   12780 ctcagtgagg gccaggatgc cagcttccag tgccggctat ccagagcttc aggccaggag   12840
gcccgctggg ctttaggagg ggtgcccctg caggccaacg agatgaatga catcactgtg   12900
gagcagggca cactccacct gctcaccctg cacaaggtga cccttgagga tgctggaact   12960
gtcagtttcc acgtgggcac gtgtagctct gaggcccagc tgaaagtcac agccaagaac   13020
acggtggtgc gggggctgga gaatgtggag gcgctggagg gcggcgaggc gctgttcgag   13080
tgccagctgt cccagcccga ggtggccgcc cacacctggc tgctgacga cgaacccgtg   13140 cgcacctcgg agaacgccga ggtggtcttc ttcgagaacg gcctgcgcca cctgctgctg   13200
ctcaaaaact gcggccaca agacagctgc cgggtgacct tcctggctgg ggatatggtg   13260
acgtccgcat tcctcacggt ccgaggctgg cgcctggaga tcctggagcc tctgaaaaac   13320
gcggcggtcc gggccggcgc acaggcacgc ttcacctgca cgctcagcga ggcggtgccc   13380
gtgggagagg cgtcctggta catcaatggc gcggcagtgc agccggatga cagcgactgg   13440
actgtcaccg ccgacggcag tcaccaagcc tactgctgc gcagcgccca gccccaccac   13500
gccggggagg tcaccttcgc ttgccgcgac gccgtggcct ctgcacggct caccgtgctg   13560
ggcctccctg atccccagaa ggatgctgag gtggtggctc acagcagcca cactgtgaca   13620
ctgtcttggg cagctcccat gagtgatgga ggcggtggtc tctgtggcta ccgcgtggag   13680
gtgaaggagg gggccacagg ccagtggcgg ctgtgccacg agctggtgcc tggacccgag   13740
tgtgtggtgg atggcctggc ccccggggag acctaccgct tccgtgtggc agctgtgggc   13800
cctgtgggtg ctggggaacc ggttcacctg ccccagacag tgcggcttgc agagccaccg   13860
aagcctgtgc ctccccagcc ctcagcccct gagagccggc aggtggcagc tggtgaagat   13920
gtctctctgg agcttgaggt ggtggctgag gctggtgagg tcatctggca aagggaatg   13980 gagcgcatcc agcccggtgg gcggttcgag gtggtctccc agggtcggca acagatgctg   14040
gtgatcaagg gcttcacggc agaagaccag ggcgagtacc actgtggcct ggctcagggc   14100
tccatctgcc ctgcggctgc caccttccag gtggcactga gcccagcctc tgtggatgag   14160
```

-continued

```
gccccctcagc  ccagcttgcc  ccccgaggca  gcccaggagg  gtgacctgca  cctactgtgg    14220
gaggccctgg   ctcggaaacg  tcgcatgagc  cgtgagccca  cgctggactc  cattagcgag    14280
ctgccagagg   aggacggccg  ctcgcagcgc  ctgccacagg  aggcagagga  ggtggcacct    14340
gatctctctg   aaggctactc  cacggccgat  gagctggccc  gcactggaga  tgctgacctc    14400
tcacacacca   gctctgatga  tgagtcccgg  gcaggcaccc  cttccctggt  cacctacctc    14460
aagaaggctg   ggaggccagg  cacctcacca  ctggccagca  aggttggggc  cccagcagcc    14520
ccctctgtga   agccacagca  gcagcaggag  ccactggctg  ctgtgcgccc  accactggga    14580
gacctgagca   ccaaagacct  gggtgatccc  tcaatggaca  aggcagctgt  gaagatccag    14640
gctgcccttta  agggctacaa  ggtccggaag  gagatgaagc  agcaggaagg  gcccatgttc    14700
tcccacacat   ttggggacac  cgaggcacag  gtggggatg   ccctgcggct  ggagtgtgtc    14760
gtggccagca   aggcagatgt  gcgagcccgc  tggctgaagg  atggtgtgga  gctgaccgat    14820
gggcggcacc   atcacatcga  ccagcttggg  gatggcacct  gctctctgct  gatcgctggc    14880
ctggaccgtg   ctgatgctgg  ctgctacacc  tgtcaggtga  gcaacaagtt  tggccaggtg    14940
acccacagtg   cctgtgtggt  ggtcagtggg  tcagagagtg  aagccgagag  ctcctctggg    15000
ggtgagctgg   acgatgcctt  ccgccgggct  gcccgtcggc  tgcaccggct  cttccgcacc    15060
aaaagtccgg   ctgaagtttc  agatgaggag  ctcttcctga  gtgcagacga  gggccctgca    15120
gagccagagg   agcccgcgga  ctggcagaca  taccgcgaag  atgagcattt  catctgcatc    15180
cgttttgagg   cgctcactga  ggcccgccag  gcggtaactc  gcttccagga  gatgtttgcc    15240
acactgggca   ttggggtgga  gatcaagctg  gtggaacagg  ggcctcggag  ggtagagatg    15300
tgcatcagca   aagagactcc  tgcccctgtg  gtgcctccag  agccattgcc  cagcctactg    15360
acttctgacg   ctgccccagt  gttcctgact  gagttgcaga  accaagaagt  gcaggatggg    15420
tatcctgtga   gctttgactg  cgtggtgaca  ggtcagccca  tgccagtgt   gcgctggttc    15480
aaggatggga   agttgttgga  ggaggatgat  cactacatga  ttaatgaaga  ccaacagggt    15540
ggccatcagc   tcatcatcac  agccgtggtg  ccagcagaca  tgggcgtcta  ccgctgcctg    15600
gccgagaaca   gcatgggtgt  ctcctccacc  aaggctgagc  tccgtgtgga  cttgacaagc    15660
acagactatg   acactgcagc  agatgccacg  gagtcctcat  cctacttcag  tgcccaaggc    15720
tacctgtcca   gccgggagca  ggagggaaca  gagtccacca  ctgatgaggg  ccagctgccc    15780
caggtggtgg   aggagctgag  agacctccag  gtggcccctg  gcacacgcct  ggccaagttc    15840
cagctcaagg   tgaaaggcta  ccctgctccc  agattatact  ggttcaaaga  tggccagccc    15900
ctgaccgcat   ctgcccacat  ccgcatgact  ggcaagaaga  tcctgcacac  cctggagatc    15960
atctccgtca   cccgggagga  ctctggccag  tatgcagcct  atatcagcaa  tgccatgggt    16020
gctgcctact   cgtctgcccg  gctgctggtt  cgaggccctg  atgagccaga  agagaagcct    16080
gcatcagatg   tgcatgagca  gctggtgccg  ccccgaatgc  tggagaggtt  cacccccaag    16140
aaagtgaaga   aaggctccag  catcaccttc  tctgtgaagg  tagaaggacg  cccggtgccc    16200
accgtgcact   ggctcaggga  ggaggctgag  agaggcgtgc  tgtggattgg  ccctgacaca    16260
ccgggctaca   ccgtggccag  ctctgcgcag  cagcacagcc  tggtcctgct  ggacgtgggc    16320
cggcagcacc   agggcaccta  cacatgcatt  gccagcaacg  ctgccggcca  ggccctctgc    16380
tccgccagcc   tgcacgtctc  gggcctgcct  aaggtggagg  agcaggagaa  agtgaaggaa    16440
gcgctgattt   ccactttcct  gcaggggacc  acacaagcca  tctcagcaca  ggggttgaa    16500
actgcgagtt   ttgctgacct  tggtgggcag  aggaaagaag  agcctctggc  tgccaaggag    16560
```

-continued

```
gccctcggcc acctgtccct cgctgaggtg ggcacagagg agttcctgca gaaactgacc    16620
tcccagatca ctgagatggt atcggccaag atcacgcagg ccaagctgca ggtgcccgga    16680
ggtgacagtg atgaggactc caagacacca tctgcatccc cccgccatgg ccgatcacgg    16740
ccatcctcca gcatccagga gtcttcctca gagtcagagg acggcgatgc ccgaggcgag    16800
atctttgaca tctacgtggt caccgctgac tacctgcccc taggggctga gcaggatgcc    16860
atcacgctgc gggaaggcca gtatgtggag gtcctggatg cagcccaccc actgcgctgg    16920
cttgtccgca ccaagcccac caagtccagc ccctcacggc agggctgggt gtcaccagcc    16980
tacctggaca ggaggctcaa gctgtcacct gagtgggggg ccgctgaggc ccctgagttc    17040
cctggggagg ctgtgtctga agacgaatac aaggcaaggc tgagctctgt gatccaggag    17100
ctgctgagtt ctgagcaggc cttcgtggag gagctgcagt cctgcagag ccaccacctg    17160
cagcacctgg agcgctgccc ccacgtgccc atagccgtgg ccggccagaa ggcagtcatc    17220
ttccgcaatg tgcgggacat cggccgcttc cacagcagct cctgcagga gttgcagcag    17280
tgcgacacgg acgacgacgt ggccatgtgc ttcatcaaga accaggcggc ctttgagcag    17340
tacctggagt tcctggtggg gcgtgtgcag gctgagtcgg tggtcgtcag cacggccatc    17400
caggagttct acaagaaata cgcggaggag gccctgttgg caggggaccc ctctcagccc    17460
ccgccaccac ctctgcagca ctacctggag cagccagtgg agcgggtgca gcgctaccag    17520
gccttgctga aggagttgat ccgcaacaag gcgcggaaca gacagaactg cgcgctgctg    17580
gagcaggcct atgccgtggt gtctgccctg ccacagcgcg ctgagaacaa gctgcacgtg    17640
tccctcatgg agaactaccc aggcaccctg gaggccctgg gcgagcccat ccgccagggc    17700
cacttcatcg tgtgggaggg tgcaccgggg gcccgcatgc cctggaaggg ccacaaccgt    17760
cacgtgttcc tcttccgcaa ccacctggta atctgcaagc cccggcgaga ctcccgcacc    17820
gataccgtca gctacgtgtt ccggaacatg atgaagctga gcagcatcga cctgaacgac    17880
caggtggagg gggatgaccg cgccttcgag gtgtggcagg agcgggagga ctcggtgcgc    17940
aagtacctgc tgcaggcacg gacagccatt atcaagagct cgtgggtgaa ggagatctgt    18000
ggcatccagc agcgtctggc cctgcctgtg tggcggcccc cggactttga agaggagctg    18060
gccgactgca cagccgagct gggtgagaca gtcaagctgg cctgccgcgt gacgggcaca    18120
cccaagcctg tcatcagctg gtacaaagat gggaaagcag tgcaggtgga cccccaccac    18180
atcctcattg aagaccctga tggctcgtgt gcactcatcc tggacagcct gaccggtgtg    18240
gactctggcc agtacatgtg cttcgcggcc agcgccgctg gcaactgcag taccctgggc    18300
aagatcctgg tgcaagtccc accacggttc gtgaacaagg tccgggcctc acccttttgtg    18360
gagggagagg acgcccagtt cacctgcacc atcgaaggcg cccccgtaccc gcagatcagg    18420
tggtacaagg acgggccct gctgaccact ggcaacaagt tccagacact gagtgagcct    18480
cgcagcggcc tgctagtgct ggtgatccgg gcggccagca aggaggacct ggggctctac    18540
gagtgtgagc tggtgaaccg gctgggctcc gcgcgggcta gtgcggagct gcgcattcag    18600
agccccatgc tgcaggccca ggagcagtgt cacagggagc agctcgtggc tgcagtggaa    18660
gacaccaccc tggagcgagc ggaccaggag gtcacatctg tcctgaagag actgctgggc    18720
cccaaggcgc caggcccctc cacaggggac ctcactggcc ctggccctg ccccaggggg    18780
gcacccgcac tccaggaaac cggctcccag ccccagtcca ccggaacttc ggaggcacct    18840
gccgtgcccc cgagggtgcc acagcccctc ctccacgaag gcccagagca ggagccggag    18900
```

```
gccattgcca gagcccagga atggactgtg cccattcgga tggagggtgc agcctggccc    18960
ggggcaggca caggggagct gctctgggac gtccacagcc acgtggtcag agagaccaca    19020
cagaggacct acacatacca ggccatcgac acgcacaccg cacggccccc atccatgcag    19080
gtaaccatcg aggatgtgca ggcacagaca ggcggaacgg cccaattcga ggctatcatt    19140
gagggcgacc cacagccctc ggtgacctgg tacaaggaca gcgtccagct ggtggacagc    19200
acccggctta gccagcagca agaaggcacc acatactccc tggtgctgag gcatgtggcc    19260
tcgaaggatg ccggcgttta cacctgcctg gcccaaaaca ctggtggcca ggtgctctgc    19320
aaggcagagc tgctggtgct tgggggggac aatgagccgg actcagagaa gcaaagccac    19380
cggaggaagc tgcactcctt ctatgaggtc aaggaggaga ttggaagggg cgtgtttggc    19440
ttcgtaaaaa gagtgcagca caaaggaaac aagatcttgt gcgctgccaa gttcatcccc    19500
ctacggagca gaactcgggc ccaggcatac agggagcgag acatcctggc cgcgctgagc    19560
cacccgctgg tcacgggct gctggaccag tttgagaccc gcaagaccct catcctcatc    19620
ctggagctgt gctcatccga ggagctgctg accgcctgt acaggaaggg cgtggtgacg    19680
gaggccgagg tcaaggtcta catccagcag ctggtggagg ggctgcacta cctgcacagc    19740
catggcgttc tccacctgga cataaagccc tctaacatcc tgatggtgca tcctgcccgg    19800
gaagacatta aaatctgcga cttttggcttt gcccagaaca tcaccccagc agagctgcag    19860
ttcagccagt acggctcccc tgagttcgtc tcccccgaga tcatccagca gaaccctgtg    19920
agcgaagcct ccgacatttg ggccatgggt gtcatctcct acctcagcct gacctgctca    19980
tccccatttg ccggcgagag tgaccgtgcc accctcctga acgtcctgga ggggcgcgtg    20040
tcatggagca gccccatggc tgcccacctc agcgaagacg ccaaagactt catcaaggct    20100
acgctgcaga gagcccctca ggcccggcct agtgcggccc agtgcctctc ccacccctgg    20160
ttcctgaaat ccatgcctgc ggaggaggcc cacttcatca acaccaagca gctcaagttc    20220
ctcctggccc gaagtcgctg gcagcgttcc ctgatgagct acaagtccat cctggtgatg    20280
cgctccatcc ctgagctgct gcggggccca cccgacagcc cctccctcgg cgtagcccgg    20340
cacctctgca gggacactgg tggctcctcc agttcctcct cctcctctga caacgagctc    20400
gccccatttg cccgggctaa gtcactgcca ccctccccgg tgacacactc accactgctg    20460
caccccgggg gcttcctgcg gccctcggcc agcctgcctg aggaagccga ggccagtgag    20520
cgctccaccg aggccccagc tccgcctgca tctcccgagg gtgccgggcc accggccgcc    20580
cagggctgcg tgccccggca cagcgtcatc cgcagcctgt tctaccacca ggcgggtgag    20640
agccctgagc acggggccct ggccccgggg agcaggcggc acccggcccg gcggcggcac    20700
ctgctgaagg gcgggtacat tgcggggcg ctgccaggcc tgcgcgagcc actgatggag    20760
caccgcgtgc tggaggagga ggccgccagg gaggagcagg ccaccctcct ggccaaagcc    20820
ccctcattcg agactgccct ccggctgcct gcctctggca cccacttggc ccctggccac    20880
agccactccc tggaacatga ctctccgagc accccccgcc cctcctcgga ggcctgcggt    20940
gaggcacagc gactgccttc agcccctcc gggggggccc ctatcaggga catggggcac    21000
cctcagggct ccaagcagct tccatccact ggtggccacc caggcactgc tcagccagag    21060
aggccatccc cggacagccc ttgggggcag ccagccccctt tctgccaccc caagcagggt    21120
tctgcccccc aggagggctg cagccccac ccagcagttg cccatgccc tcctggctcc    21180 ttccctccag gatcttgcaa agaggccccc ttagtaccct caagcccctt cttgggacag    21240
ccccaggcac cccctgcccc tgccaaagca agccccccat tggactctaa gatggggcct    21300
```

```
ggagacatct ctcttcctgg gaggccaaaa cccggcccct gcagttcccc agggtcagcc    21360
tcccaggcga gctcttccca agtgagctcc ctcaggtgg  gctcctccca ggtgggcaca    21420
gagcctggcc cctccctgga tgcggagggc tggacccagg aggctgagga tctgtccgac    21480
tccacaccca ccttgcagcg gcctcaggaa caggcgacca tgcgcaagtt ctccctgggt    21540
ggtcgcgggg gctacgcagg cgtggctggc tatggcacct ttgcctttgg tggagatgca    21600
gggggcatgc tggggcaggg gcccatgtgg gccaggatag cctgggctgt gtcccagtcg    21660
gaggaggagg agcaggagga ggccagggct gagtcccagt cggaggagca gcaggaggcc    21720
agggctgaga gcccactgcc ccaggtcagt gcaaggcctg tgcctgaggt cggcagggct    21780
cccaccagga gctctccaga gcccacccca tgggaggaca tcgggcaggt ctccctggtg    21840
cagatccggg acctgtcagg tgatgcggag gcggccgaca caatatccct ggacatttcc    21900
gaggtggacc ccgcctacct caacctctca gacctgtacg atatcaagta cctcccattc    21960
gagtttatga tcttcaggaa agtccccaag tccgctcagc cagagccgcc ctcccccatg    22020
gctgaggagg agctggccga gttcccggag cccacgtggc cctggccagg tgaactgggc    22080
ccccacgcag gcctggagat cacagaggag tcagaggatg tggacgcgct gctggcagag    22140
gctgccgtgg gcaggaagcg caagtggtcc tcgccgtcac gcagcctctt ccacttccct    22200
gggaggcacc tgccgctgga tgagcctgca gagctggggc tgcgtgagag agtgaaggcc    22260
tccgtggagc acatctcccg gatcctgaag ggcaggccgg aagtctggga aaggaggggg    22320 cccccccagga agaagccagg ccttgcttcc ttccggctct caggtctgaa gagctgggac    22380
cgagcgccga cattcctaag ggagctctca gatgagactg tggtcctggg ccagtcagtg    22440
acactggcct gccaggtgtc agcccagcca gctgcccagg ccacctggag caaagacgga    22500
gcccccctgg agagcagcag ccgtgtcctc atctctgcca ccctcaagaa cttccagctt    22560
ctgaccatcc tggtggtggt ggctgaggac ctgggtgtgt acacctgcag cgtgagcaat    22620
gcgctgggga cagtgaccac cacgggcgtc ctccggaagg cagagcgccc ctcatcttcg    22680
ccatgcccga tatcggggga ggtgtacgcg gatggggtgc tgctggtctg aagcccgtg     22740 gaatcctacg gcctgtgac  ctacattgtg cagtgcagcc tagaaggcgg cagctggacc    22800
acactggcct ccgacatctt tgactgctgc tacctgacca gcaagctctc ccggggtggc    22860
acctacacct tccgcacggc atgtgtcagc aaggcaggaa tgggtcccta cagcagcccc    22920
tcggagcaag tcctcctggg agggcccagc cacctggcct ctgaggagga gagccagggg    22980
cggtcagccc aaccctgcc  cagcacaaag accttcgcat tccagacaca gatccagagg    23040
ggccgcttca gcgtggtgcg gcaatgctgg gagaaggcca gcgggcgggc gctgccgcc     23100 aagatcatcc cctaccaccc caaggacaag acagcagtgc tgcgcgaata cgaggccctc    23160
aagggcctgc gccacccgca cctggcccag ctgcacgcag cctacctcag cccccggcac    23220
ctggtgctca tcttggagct gtgctctggg cccgagctgc tcccctgcct ggccgagagg    23280
gcctcctact cagaatccga ggtgaaggac tacctgtggc agatgttgag tgccaccag     23340 tacctgcaca accagcacat cctgcacctg gacctgaggt ccgagaacat gatcatcacc    23400
gaatacaacc tgctcaaggt cgtggacctg ggcaatgcac agagcctcag ccaggagaag    23460
gtgctgccct cagacaagtt caaggactac ctagagacca tggctccaga gctcctggag    23520 ggccagggg  ctgttccaca gacagacatc tgggccatcg gtgtgacagc cttcatcatg    23580
ctgagcgccg agtacccggt gagcagcgag ggtgcacgcg acctgcagag aggactgcgc    23640
```

-continued

```
aaggggctgg tccggctgag ccgctgctac gcggggctgt ccgggggcgc cgtggccttc    23700
ctgcgcagca ctctgtgcgc ccagcccctgg ggccggcccct gcgcgtccag ctgcctgcag    23760
tgcccgtggc taacagagga gggcccggcc tgttcgcggc ccgcgcccgt gaccttccct    23820
accgcgcggc tgcgcgtctt cgtgcgcaat cgcgagaaga gacgcgcgct gctgtacaag    23880
aggcacaacc tggcccaggt gcgctga                                        23907
```

<210> SEQ ID NO 7
<211> LENGTH: 17
<212> TYPE: PRT
<213> ORGANISM: Artificial Sequence
<220> FEATURE:
<221> NAME/KEY: VARIANT
<222> LOCATION: 1
<223> OTHER INFORMATION: The L at position 1 can be I or V.
<221> NAME/KEY: VARIANT
<222> LOCATION: 3
<223> OTHER INFORMATION: The amino acid at position 3 can be any amino
      acid except P.
<221> NAME/KEY: VARIANT
<222> LOCATION: 5
<223> OTHER INFORMATION: The amino acid at position 5 can be any amino
      acid except P.
<221> NAME/KEY: VARIANT
<222> LOCATION: (6)...(0)
<223> OTHER INFORMATION: The F at position 6 can be Y, W, M, G, S, T, N,
      or H.
<221> NAME/KEY: VARIANT
<222> LOCATION: 7
<223> OTHER INFORMATION: The S at position 7 can be G or A.
<221> NAME/KEY: VARIANT
<222> LOCATION: 8
<223> OTHER INFORMATION: The amino acid at position 8 can be any amino
      acid except P or W.
<221> NAME/KEY: VARIANT
<222> LOCATION: (9)...(9)
<223> OTHER INFORMATION: The L at position 9 can be I, V, C, A, or T.
<221> NAME/KEY: VARIANT
<222> LOCATION: (10)...(10)
<223> OTHER INFORMATION: The amino acd at position 10 can be any amino
      acid except P or D.
<221> NAME/KEY: VARIANT
<222> LOCATION: (11)...(11)
<223> OTHER INFORMATION: The amino acid at position 11 can be any amino
      acid.
<221> NAME/KEY: VARIANT
<222> LOCATION: (12)...(12)
<223> OTHER INFORMATION: The G at position 12 can be S, T, A,
      C, L, I, V, M, F, or Y.
<221> NAME/KEY: VARIANT
<222> LOCATION: (13)...(13)
<223> OTHER INFORMATION: The amino acid at position 13 can be any amino
      acid and as few as 5, up to 18.
<221> NAME/KEY: VARIANT
<222> LOCATION: (14)...(14)
<223> OTHER INFORMATION: The L at position 14 can be I, V, M, F, Y,
      W, C, S, T, A, or R.
<221> NAME/KEY: VARIANT
<222> LOCATION: (15)...(15)
<223> OTHER INFORMATION: The A at position 15 can be I, V, or P.
<221> NAME/KEY: VARIANT
<222> LOCATION: (16)...(16)
<223> OTHER INFORMATION: The L at position 16 can be I, V, M, F, A, G,
      C, K, or R.

<400> SEQUENCE: 7

Leu Gly Xaa Gly Xaa Phe Ser Xaa Leu Xaa Xaa Gly Xaa Leu Ala Leu
 1               5                  10                  15

Lys

<210> SEQ ID NO 8
<211> LENGTH: 12

```
<212> TYPE: PRT
<213> ORGANISM: Artificial Sequence
<220> FEATURE:
<221> NAME/KEY: VARIANT
<222> LOCATION: 1
<223> OTHER INFORMATION: The L at position 1 can be I, V, M, F, Y,
      or C.
<221> NAME/KEY: VARIANT
<222> LOCATION: 2
<223> OTHER INFORMATION: The amino acid at position 2 can be any amino
      acid.
<221> NAME/KEY: VARIANT
<222> LOCATION: 3
<223> OTHER INFORMATION: The H at position 3 can be Y.
<221> NAME/KEY: VARIANT
<222> LOCATION: 4
<223> OTHER INFORMATION: The amino acid at position 4 can be any amino
      acid.
<221> NAME/KEY: VARIANT
<222> LOCATION: 6
<223> OTHER INFORMATION: The L at position 6 can be I, V, M, F, or Y.
<221> NAME/KEY: VARIANT
<222> LOCATION: 8
<223> OTHER INFORMATION: The amino acid at position 8 can be any 2
      amino acids.
<221> NAME/KEY: VARIANT
<222> LOCATION: (10)...(12)
<223> OTHER INFORMATION: The amino acid at positions 10, 11, and 12 can
      be any three amino acids selected from the group of  L, I, V, M, F,
      Y, C, and T.

<400> SEQUENCE: 8

Leu Xaa His Xaa Asp Leu Lys Xaa Asn Xaa Xaa Xaa
 1               5                  10

<210> SEQ ID NO 9
<211> LENGTH: 13
<212> TYPE: PRT
<213> ORGANISM: Artificial Sequence
<220> FEATURE:
<221> NAME/KEY: VARIANT
<222> LOCATION: 1
<223> OTHER INFORMATION: The L at position 1 can be I, V, M, F, Y,
      or C.
<221> NAME/KEY: VARIANT
<222> LOCATION: 2
<223> OTHER INFORMATION: The amino acid at position 2 can be any amino
      acid.
<221> NAME/KEY: VARIANT
<222> LOCATION: 3
<223> OTHER INFORMATION: The H at position 3 can be Y.
<221> NAME/KEY: VARIANT
<222> LOCATION: 4
<223> OTHER INFORMATION: The amino acid at position 4 can be any amino
      acid.
<221> NAME/KEY: VARIANT
<222> LOCATION: 6
<223> OTHER INFORMATION: The L at position 6 can be I, V, M, F, or
      Y.
<221> NAME/KEY: VARIANT
<222> LOCATION: 7
<223> OTHER INFORMATION: The R at position 7 can be S, T, A, or C.
<221> NAME/KEY: VARIANT
<222> LOCATION: (8)...(9)
<223> OTHER INFORMATION: The amino acid at positions 8 and 9 can be any 2
      amino acids.
<221> NAME/KEY: VARIANT
<222> LOCATION: (10)...(12)
<223> OTHER INFORMATION: The amino acid at positions 10, 11, and 12 can
      be any 3 amino acids selected from  L, I, V, M, F, Y, and C.

<400> SEQUENCE: 9

Leu Xaa His Xaa Asp Leu Arg Xaa Xaa Asn Xaa Xaa Xaa
 1               5                  10
```

59079 AND 12599, PROTEIN KINASE FAMILY MEMBERS AND USES THEREFOR

CROSS REFERENCE TO RELATED APPLICATION

This application claims the benefit of U.S. Provisional Application No. 60/269,201, filed Feb. 15, 2001, the contents of which are incorporated herein by this reference.

BACKGROUND OF THE INVENTION

Phosphate tightly associated with a molecule, e.g., a protein, has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated molecules, e.g., proteins, implies the existence of one or more kinases, e.g., protein kinases, capable of phosphorylating various molecules, e.g., amino acid residues on proteins, and also of phosphatases, e.g., protein phosphatases, capable of hydrolyzing various phosphorylated molecules, e.g., phosphorylated amino acid residues on proteins.

Protein kinases play critical roles in the regulation of biochemical and morphological changes associated with cellular growth and division (D'Urso et al. (1990) *Science* 250:786–791; Birchmeier et al. (1993) *Bioessays* 15:185–189). For example, these kinases have been shown to participate in the transmission of signals from growth-factor receptors (Sturgill et al. (1988) *Nature* 344:715–718; Gomez et al. (1991) *Nature* 353:170–173), control of entry of cells into mitosis (Nurse (1990) *Nature* 344:503–508; Maller (1991) *Curr. Opin. Cell Biol.* 3:269–275), and regulation of actin bundling (Husain-Chishti et al. (1988) *Nature* 334:718–721). Protein kinases serve as growth factor receptors and signal transducers and have been implicated in cellular transformation and malignancy (Hunter et al. (1992) *Cell* 70:375–387; Posada et al. (1992) *Mol. Biol. Cell* 3:583–592; Hunter et al. (1994) *Cell* 79:573–582). Alterations in kinase genes and their products can lead to deregulated cell proliferation, a hallmark of cancer. Modulation of these genes and their regulatory activities may permit the control of tumor cell proliferation and invasion.

Protein kinases can be divided into different groups based on either amino acid sequence similarity or specificity for either serine/threonine or tyrosine residues. A small number of dual-specificity kinases have also been described. Within the broad classification, kinases can be further subdivided into families whose members share a higher degree of catalytic domain amino acid sequence identity and also have similar biochemical properties. Most protein kinase family members also share structural features outside the kinase catalytic domain that reflect their particular cellular roles. These include regulatory domains that control kinase activity or interaction with other proteins (Hanks et al. (1988) *Science* 241:42–52).

Extracellular signal-regulated kinases/mitogen-activated protein kinases (ERKs\MAPKs) and cyclin-directed kinases (Cdks) represent two large families of serine-threonine kinases (see Songyang et al. (1996) *Mol. Cell. Biol.* 16: 6486–6493). Both types of kinases function in cell growth, cell division, and cell differentiation in response to extracellular stimuli. The ERK\MAPK family members are critical participants in intracellular signaling pathways. Upstream activators as well as the ERK\MAPK components are phosphorylated following contact of cells with growth factors or hormones or in response to cellular stressors, for example, heat, ultraviolet light, and inflammatory cytokines. These kinases transport messages that have been relayed from the plasma membrane to the cytoplasm by upstream kinases into the nucleus where they phosphorylate transcription factors and effect gene transcription modulation (Karin et al. (1995) *Curr. Biol.* 5: 747–757). Substrates of the ERK\MAPK family include c-fos, c-jun, APF2, and ETS family members Elk1, Sap1a, and c-Ets-1 (cited in Brott et al. (1998) *Proc. Natl. Acad. Sci. USA* 95: 963–968).

Signal-transduction pathways that employ members of the ERK/MAPK family of serine/threonine kinases are widely conserved among eukaryotes. The multiplicity of these pathways allows the cell to respond to divergent extracellular stimuli by initiating a broad array of responses ranging from cell growth to apoptosis. ERK/MAPK pathways are comprised of a three-tiered core-signaling module wherein ERK/MAPKs are regulated by MAPK/ERK kinases (MEKs), and MEKs, in turn, are regulated by MAPK kinase kinases (MAPKKKs). Mammalian stress-activated ERK/MAPK pathways have been implicated in numerous important physiological functions, including cell growth and proliferation, inflammatory responses, and apoptosis. For example, activation of the ERK1,2 signaling pathway by a mitogenic growth factor, a tumor promoter, or by transformation suppresses decorin gene expression in fibroblasts, which in turn may promote proliferation and migration of normal and malignant cells (Laine et al. (2000) *Biochem. J.* 349: 19–25).

Cdks regulate transitions between successive stages of the cell cycle. The activity of these molecules is controlled by phosphorylation events and by association with cyclin. Cdk activity is negatively regulated by the association of small inhibitory molecules (Dynlacht (1997) *Nature* 389:148–152). Cdk targets include various transcriptional activators such as p110Rb, p107, and transcription factors, such as p53, E2F, and RNA polymerase II, as well as various cytoskeletal proteins and cytoplasmic signaling proteins (cited in Brott et al. (1998) *Proc. Natl. Acad. Sci. USA* 95: 963–968).

Protein kinases play critical roles in cellular growth, particularly in the transduction of signals for cell proliferation, differentiation, and apoptosis. Therefore, novel protein kinase polynucleotides and proteins are useful for modulating cellular growth, differentiation, and/or development.

SUMMARY OF THE INVENTION

The present invention is based, in part, on the discovery of novel human protein kinase family members, referred to herein as "59079" and "12599". The nucleotide sequence of a cDNA encoding 59079 is shown in SEQ ID NO: 1, and the amino acid sequence of a 59079 polypeptide is shown in SEQ ID NO:2. In addition, the nucleotide sequence of the coding region is depicted in SEQ ID NO:3. The nucleotide sequence of a cDNA encoding 12599 is shown in SEQ ID NO:4, and the amino acid sequence of a 12599 polypeptide is shown in SEQ ID NO:5. In addition, the nucleotide sequence of the coding region is depicted in SEQ ID NO:6.

Accordingly, in one aspect, the invention features nucleic acid molecules which encode a 59079 protein or polypeptide or a 12599 protein or polypeptide, e.g., a biologically active portion of the 59079 or 12599 protein. In a preferred embodiment the isolated nucleic acid molecule encodes a polypeptide having the amino acid sequence of SEQ ID NO:2 or 5. In other embodiments, the invention provides isolated 59079 and 12599 nucleic acid molecules having the nucleotide sequence shown in SEQ ID NOs: 1, 3, 4, or 6. In still other embodiments, the invention provides nucleic acid molecules that are substantially identical (e.g., naturally occurring allelic variants) to the nucleotide sequence shown in SEQ ID NOs: 1, 3, 4, or 6. In other embodiments, the invention provides a nucleic acid molecule which hybridizes under stringent hybridization conditions to a nucleic acid molecule comprising the nucleotide sequence of SEQ ID NO: 1, 3, 4, or 6, wherein the nucleic acid encodes a full length 59079 or 12599 protein, or a biologically active fragment thereof.

In a related aspect, the invention further provides nucleic acid constructs which include a 59079 or 12599 nucleic acid molecule described herein. In certain embodiments, the nucleic acid molecules of the invention are operatively linked to native or heterologous regulatory sequences. Also included are vectors and host cells containing the 59079 or 12599 nucleic acid molecules of the invention, e.g., vectors and host cells suitable for producing 59079 or 12599 polypeptides.

In another related aspect, the invention provides nucleic acid fragments suitable as primers or hybridization probes for the detection of 59079- or 12599-encoding nucleic acids.

In still another related aspect, isolated nucleic acid molecules that are antisense to a 59079- or 12599-encoding nucleic acid molecule are provided.

In another aspect, the invention features 59079 and 12599 polypeptides, and biologically active or antigenic fragments thereof, that are useful, e.g., as reagents or targets in assays applicable to treatment and diagnosis of 59079- or 12599-mediated or -related disorders. In another embodiment, the invention provides 59079 polypeptides having a 59079 activity and 12599 polypeptides having a 12599 activity. Preferred polypeptides are 59079 and 12599 proteins including at least one protein kinase catalytic domain, and, preferably, having a 59079 or 12599 activity, e.g., a 59079 or 12599 activity as described herein.

In other embodiments, the invention provides 59079 and 12599 polypeptides, e.g., a 59079 or 12599 polypeptide having the amino acid sequence shown in SEQ ID NO:2 or 5; an amino acid sequence that is substantially identical to the amino acid sequence shown in SEQ ID NO:2 or 5; or an amino acid sequence encoded by a nucleic acid molecule having a nucleotide sequence which hybridizes under stringent hybridization conditions to a nucleic acid molecule comprising the nucleotide sequence of SEQ ID NOs: 1, 3, 4, or 6, wherein the nucleic acid encodes a full length 59079 or 12599 protein, or a biologically active fragment thereof.

In a related aspect, the invention further provides nucleic acid constructs which include a 59079 or 12599 nucleic acid molecule described herein.

In a related aspect, the invention provides 59079 and 12599 polypeptides, or fragments thereof, operatively linked to non-59079 or non-12599 polypeptides to form fusion proteins.

In another aspect, the invention features antibodies, and antigen-binding fragments thereof, that react with, or more preferably, specifically or selectively bind 59079 or 12599 polypeptides.

In another aspect, the invention provides methods of screening for compounds that modulate the expression or activity of the 59079 polypeptides or nucleic acids or the 12599 polypeptides or nucleic acids.

In still another aspect, the invention provides a process for modulating 59079 polypeptide or nucleic acid expression or activity, e.g., using the compounds identified in the screens. In certain embodiments, the methods involve treatment of conditions or disorders related to aberrant activity or expression of the 59079 or 12599 polypeptides or nucleic acids, such as conditions involving aberrant or deficient 59079 or 12599 protein or nucleic acid expression or activity. In a preferred embodiment, the disorder characterized by aberrant 59079 or 12599 protein activity or nucleic acid expression is a nervous system disorder, a cardiovascular disorder, a sugar or fatty acid metabolism disorder, an inflammatory or immune disorder, a musculoskeletal disorder, or a disorder involving aberrant cellular proliferation, differentiation, or migration.

The invention also provides assays for determining the activity of or the presence or absence of 59079 or 12599 polypeptides or nucleic acid molecules in a biological sample, including for disease diagnosis.

In a further aspect, the invention provides assays for determining the presence or absence of a genetic alteration in a 59079 or 12599 polypeptide or nucleic acid molecule, including for disease diagnosis.

Other features and advantages of the invention will be apparent from the following detailed description and from the claims.

DETAILED DESCRIPTION OF THE INVENTION

The human 59079 nucleic acid sequence (SEQ ID NO:1), which is approximately 8106 nucleotides long including untranslated regions, contains a predicted methionine-initiated coding sequence of about 7893 nucleotides, including the termination codon (shown as the nucleotides of SEQ ID NO:1 indicated as coding, and the sequence shown in SEQ ID NO:3). The coding sequence encodes a 2631 amino acid protein (SEQ ID NO:2).

The human 12599 nucleic acid sequence (SEQ ID NO:4), which is approximately 24,120 nucleotides long including untranslated regions, contains a predicted methionine-initiated coding sequence of about 23,907 nucleotides, including the termination codon (shown as the nucleotides of SEQ ID NO:4 indicated as coding, and the sequence shown in SEQ ID NO:6). The coding sequence encodes a 7968 amino acid protein (SEQ ID NO:5).

To determine whether a polypeptide or protein of interest has a conserved sequence or domain common to members of a protein family, the amino acid sequence of the protein can be searched against a database of profile hidden Markov models (profile HMMs), which uses statistical descriptions of a sequence family's consensus (e.g., HMMER, version 2.1.1) and PFAM, a collection of multiple sequence alignments and hidden Markov models covering many common protein domains (e.g., PFAM, version 5.5) using the default parameters (http://www.sanger.ac.uk/Software/Pfam/HMM_search). For example, the hmmsf program, which is available as part of the HMMER package of search programs, is a family specific default program for MIL-PAT0063 and a score of 15 is the default threshold score for determining a hit. Alternatively, the threshold score for determining a hit can be lowered (e.g., to 8 bits). A description of the PFAM database can be found in Sonhammer et al., (1997) *Proteins* 28(3):405–420 and a detailed description of HMMs can be found, for example, in Gribskov et al., (1990) *Meth. Enzymol.* 183:146–159; Gribskov et al., (1987) *Proc. Natl. Acad. Sci. USA* 84:4355–4358; Krogh et al., (1994) *J. Mol. Biol.* 235:1501–1531; and Stultz et al., (1993) *Protein Sci.* 2:305–314, the contents of which are incorporated herein by reference. See also, for example, http://hmmer.wustl.edu/. For general information regarding PFAM identifiers, PS prefix and PF prefix domain identification numbers, refer to Sonnhammer et al. (1997) *Protein* 28:405–420 and http://pfam.wustl.edu/. See also, for example, http://www.expasy.ch/prosite and http://smart.embl-heidelberg.de/.

Using such search tools, the 59079 and 12599 protein sequences were found to contain significant structural characteristics in common with members of the protein kinase family of molecules. Some of these structural characteristics include, for example, a protein kinase catalytic domain (e.g., PFAM Accession No. PF00069), a pleckstrin homology domain consensus sequence (e.g., PFAM Accession No. PF00169), a fibronectin type III domain (e.g., PFAM Accession No. PF00041), a RhoGEF domain (e.g., PFAM Accession No. PF00621), and a IQ calmodulin-binding motif (e.g., PFAM Accession No. PF00612).

As used herein, the term "protein kinase" includes a protein or polypeptide which is capable of modulating its own phosphorylation state or the phosphorylation state of another molecule, e.g., protein or polypeptide. Protein kinases can have a specificity for (i.e., a specificity to phosphorylate) serine/threonine residues, tyrosine residues, or both serine/threonine and tyrosine residues, e.g., the dual specificity kinases.

The term "family" when referring to the protein and nucleic acid molecules of the invention is intended to mean two or more proteins or nucleic acid molecules having a common structural domain or signature sequence and having sufficient amino acid or nucleotide sequence homology as defined herein. Such family members can be naturally or non-naturally occurring and can be from either the same or different species. For example, a family can contain a first protein of human origin, as well as other distinct proteins of human origin, or alternatively, can contain homologues of non-human origin, e.g., rat or mouse proteins. Members of a family can also have common functional characteristics.

With regard to common structural characteristics described above, the protein kinases of the present invention include a protein kinase catalytic core or domain and can include at least one of the following signature sequences or motifs within the catalytic core: a protein kinase ATP-binding region signature sequence, a serine/threonine protein kinase active site signature sequence, and a tyrosine kinase active site signature sequence (see Hanks et al. (1988) *Science* 241:42–52).

As used herein, a "protein kinase catalytic core or domain" includes a consensus sequence, e.g., PFAM Accession No. PF00069, that includes the catalytic domain of the enzyme. The catalytic domain can be characterized by the presence of an ATP binding signature sequence (e.g., Prosite Accession No. PS00107) and/or a serine/threonine or tyrosine kinase active-site signature sequence (e.g., Prosite Accession No. PS00108 or Prosite Accession No. PS00109). The protein kinase catalytic domain of the present invention preferably includes a catalytic domain of about 150–400 amino acid residues in length, preferably about 200–300 amino acid residues in length, or more preferably about 225–300 amino acid residues in length, which includes at least one of the signature sequences or motifs described herein.

Accordingly, protein kinase polypeptides having at least 50–60% homology, preferably about 60–70%, more preferably about 70–80%, or about 80–90% homology with a protein kinase catalytic domain of 59079 or 12599 are within the scope of the invention.

The protein kinase ATP-binding region signature sequence is located in the N-terminal extremity of the catalytic domain and typically includes a glycine-rich stretch of residues in the vicinity of a lysine residue. A consensus sequence (Prosite Accession No. PS00107; SEQ ID NO:7) for this region is [LIV]-G-{P}-G-{P}-[FYWMGSTNH]-[SGA]-{PW}-[LIVCAT]-{PD}-x-[GSTACLIVMFY]-x(5,18)-[LIVMFYWCSTAR]-[AIVP]-[LIV MFAGCKR]-K. In the above consensus sequence pattern, lysine (K) binds ATP.

In this and the following consensus sequence patterns, each element in the pattern is separated by a dash (–); square brackets, [ ], indicate the particular residues that are accepted at that position; ornate brackets,{ }, indicate the residues that are not accepted at that position; x indicates any residue is accepted at that position; repetition of a particular element is indicated by following the element with a numerical value or a numerical range enclosed in parentheses (i.e., above, x(5,18) indicates anywhere from 5 to 18 residues are present in the element, and any amino acid residue is accepted at each of these 5 to 18 residue positions); and the standard IUPAC one-letter code for the amino acids is used.

Analysis of the 59079 polypeptide for sequence patterns in the Prosite database showed a match to a protein kinase ATP binding region signature pattern of Prosite Accession No. PS00107 at about amino acids 1136 to 1159 and at about amino acid residues 2340 to 2363 of SEQ ID NO:2. The lysine residue at position 1145, 1150, 1153, 1159, 2354, and/or 2363 of SEQ ID NO:2 can be involved in ATP binding. Each of these protein kinase ATP-binding region signature sequences lies within a protein kinase catalytic domain identified in a PFAM search against the HMM database (HMMER2.1.1); the first, in the protein kinase catalytic domain spanning amino acid residues 1130 to 1383; the second, in the protein kinase catalytic domain from amino acid residues 2334 to 2586 of SEQ ID NO:2.

Analysis of the 12599 polypeptide for sequence patterns in the Prosite database showed a match to a protein kinase ATP binding region signature pattern of Prosite Accession No. PS00107 at about amino acids 6474 to 6497 of SEQ ID NO:5. The lysine residue at position 6483, 6488, 6491, and/or 6497 of SEQ ID NO:5 can be involved in ATP binding. This protein kinase ATP binding region signature pattern lies within a protein kinase catalytic domain identified in a PFAM search against the HMM database (HMMER2.1.1) and located from amino acid residues 6468 to 6721 of SEQ ID NO:5.

Another region, located in the central part of the catalytic core or domain, contains a conserved aspartic acid residue, which is important for the catalytic activity of the enzyme (Knighton et al. (1991) *Science* 253:407–414). Two active-site signature sequences have been described for this region: one specific for serine/threonine kinases and one for tyrosine kinases. In both signature sequences aspartic acid (D) is conserved and is an active site residue. A consensus sequence for the serine/threonine kinases (Prosite Accession No. PS00108; SEQ ID NO:8) is [LIVMFYC]-x-[HY]-x-D-[LIVMFY]-K-x(2)-N-[LIVMFYCT](3). A consensus sequence for the tyrosine kinases (Prosite Accession No. PS00109; SEQ ID NO:9) is [LIVMFYC]-x-[HY]-x-D-[LIVMFY]-[RSTAC]-x(2)-N-[LIVMFYC](3).

Analysis of the 59079 polypeptide for sequence patterns in the Prosite database showed a match of amino acid residues 1245 to 1257 of SEQ ID NO:2 to the serine/threonine kinase active-site signature sequence of Prosite Accession No. PS00108. The aspartic acid residue (D) at position 1249 of SEQ ID NO:2 is an active site residue. This serine/threonine kinase active-site signature sequence lies within the protein kinase catalytic domain spanning amino acid residues 1130 to 1383 of SEQ ID NO:2.

Analysis of the 12599 polypeptide for sequence patterns in the Prosite database showed a match of amino acid residues 6583 to 6595 of SEQ ID NO:5 to the serine/threonine kinase active-site signature sequence of Prosite Accession No. PS00108. The aspartic acid residue (D) at position 6587 of SEQ ID NO:5 is an active site residue. This serine/threonine kinase active-site signature sequence lies within the protein kinase catalytic domain spanning amino acid residues 6468 to 6721 of SEQ ID NO:2.

Analysis of the 59079 polypeptide for other sequence patterns in the Prosite database showed a match of amino acid residues 2449 to 2461 of SEQ ID NO:2 to the tyrosine protein kinase active site signature sequence of Prosite Accession No. PS00109. The aspartic acid residue (D) at position 2453 of SEQ ID NO:2 is an active site residue. This tyrosine protein kinase active site signature sequence lies within the protein kinase catalytic domain spanning amino acid residues 2334 to 2586 of SEQ ID NO:2.

Analysis of the 12599 polypeptide for other sequence patterns in the Prosite database showed a match of amino acid residues 7787 to 7799 of SEQ ID NO:5 to the tyrosine protein kinase active site signature sequence of Prosite Accession No. PS00109. The aspartic acid residue (D) at position 7791 of SEQ ID NO:5 is an active site residue. This tyrosine protein kinase active site signature sequence lies within the protein kinase catalytic domain spanning amino acid residues 7672 to 7924 of SEQ ID NO:5.

As used herein, a "pleckstrin homology domain" is a domain that is characterized by the matrix profile described by PFAM Accession No. PF00169 or Prosite Accession No. PS50003. The pleckstrin homology domain is a domain of about 100 amino acid residues that can occur in protein kinases, e.g., serine/threonine protein kinases belonging to the Akt/Rac family, the beta-adrenergic receptor kinase family, the trypanosomal NrkA family, and the mu isoform of protein kinase C, and tyrosine protein kinases, e.g., belonging to the Btk/Itk/Tec subfmaily. This domain is likely involved in binding phosphorylated serine/threonine residues. The presence of a pleckstrin homology domain was identified in 59079 at about amino acid residues 558 to 666 of SEQ ID NO:2 and in 12599 at about amino acid residues 5896 to 6004 of SEQ ID NO:5.

The sequence analyses of the 59079 and 12599 proteins demonstrate that the 59079 and 12599 proteins can act as serine/threonine or tyrosine protein kinases, and can also include a pleckstrin homology domain. Based on the above-described sequence similarities, the 59079 and 12599 molecules of the present invention have similar biological or functional activities as protein kinase family members.

As used interchangeably herein, he terms, a "59079- and/or 12599-mediated activity", "biological activity of 59079 and/or 12599" or "functional activity of 59079 and/or 12599", refer to an activity exerted by a 59079 or 12599 protein, polypeptide or nucleic acid molecule on, e.g., a 59079- or 12599-responsive cell or tissue, or on a 59079 or 12599 substrate, ligand, or target molecule, e.g., a protein substrate or target molecule, as determined in vivo, in vitro, or in situ according to standard techniques.

In one embodiment, a 59079 or 12599 activity is a direct activity, such as an association with a 59079 or 12599 ligand, binding partner, or target molecule. As used interchangeably herein, a "ligand", "binding partner", or "target molecule" is a molecule with which a 59079 or 12599 protein binds or interacts in nature, such that a 59079- or 12599-mediated function is achieved. A 59079 or 12599 target molecule can be a 59079 or a 12599 protein or polypeptide of the present invention or a non-59079 or non-12599 protein molecule. In one embodiment, a 59079 or non-12599 protein molecule. In one embodiment, a 59079 or 12599 target molecule can be a non-59079 or a non-12599 protein molecule. In an exemplary embodiment, a 59079 or 12599 target molecule is a 59079 ligand, e.g., a protein kinase ligand, e.g., serine, threonine, or tyrosine containing polypeptide.

Protein kinases play a role in signalling pathways associated with cellular growth. For example, protein kinases are involved in the regulation of signal transmission from cellular receptors, e.g., growth-factor receptors; entry of cells into mitosis; and the regulation of cytoskeleton function, e.g., actin bundling. Thus, the 59079 and 12599 molecules of the present invention can be involved in: 1) the regulation of transmission of signals from cellular receptors, e.g., cell growth factor receptors; 2) the modulation of the entry of cells, e.g., precursor cells, into mitosis; 3) the modulation of cellular differentiation; 4) the modulation of cell death; and 5) the regulation of cytoskeleton function, e.g., actin bundling. These kinases can function in these biological activities because of their ability to phosphorylate themselves or other substrate molecules.

Substrates of tyrosine protein kinases are generally characterized by a lysine or an arginine seven residues to the N-terminal side of the phosphorylated tyrosine. An acidic residue (aspartic acid or glutatmic acid) is often found at either three or four residues to the N-terminal side of the tyrosine (see Patschinsky et al. (1982) *Proc. Natl. Acad. Sci. U.S.A.* 79:973–977; Hunter T. (1982) *J. Biol. Chem.* 257:4843–4848; Cooper et al. (1984) *J. Biol. Chem.* 259:7835–7841).

A 59079 or 12599 activity can also be an indirect activity, such as an activity mediated by interaction of the 59079 or 12599 protein with a 59079 or 12599 target molecule such that the target molecule modulates a downstream cellular activity, e.g., a cellular signaling activity modulated indirectly by an interaction of the 59079 or 12599 protein with a 59079 or 12599 target molecule.

The 59079 and 12599 molecules of the invention can modulate the activities of cells in tissues where they are expressed. For example, 59079 and 12599 mRNA are expressed in normal heart and upregulated in diseased heart. Accordingly, the 59079 and 12599 molecules of the invention can act as therapeutic or diagnostic agents for cardiovascular disorders.

Cardiovascular disorders include, but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, disorders involving cardiac transplantation, and congestive heart failure.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi's sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Blood platelet disorders include, but are not limited to, thrombocytopenia due to a reduced number of megakaryocytes in the bone marrow, for example, as a result of chemotherapy; invasive disorders, such as leukemia, idiopathic or drug- or toxin-induced aplasia of the marrow, or rare hereditary amegakaryocytic thrombocytopenias; ineffective thrombopoiesis, for example, as a result of megaloblastic anemia, alcohol toxicity, vitamin B12 or folate deficiency, myelodysplastic disorders, or rare hereditary disorders (e.g., Wiskott-Aldrich syndrome and May-hegglin anomaly); a reduction in platelet distribution, for example, as a result of cirrhosis, a splenic invasive disease (e.g., Gaucher's disease), or myelofibrosis with extramedullary myeloid metaplasia; increased platelet destruction, for example, as a result of removal of IgG-coated platelets by the mononuclear phagocytic system (e.g., idiopathic thrombocytopenic purpura (ITP), secondary immune thrombocytopenia (e.g., systemic lupus erythematosus, lymphoma, or chronic lymphocytic leukemia), drug-related immune thrombocytopenias (e.g., as with quinidine, aspirin, and heparin), post-transfusion purpura, and neonatal thrombocytopenia as a result of maternal platelet autoantibodies or maternal platelet alloantibodies). Also included are thrombocytopenia secondary to intravascular clotting and thrombin induced damage to platelets as a result of, for example, obstetric complications, metastatic tumors, severe gram-negative bacteremia, thrombotic thrombocytopenic purpura, or severe illness. Also included is dilutional thrombocytopenia, for example, due to massive hemorrhage. Blood platelet disorders also include, but are not limited to, essential thrombocytosis and thrombocytosis associated with, for example, splenectomy, acute or chronic inflammatory diseases, hemolytic anemia, carcinoma, Hodgkin's disease, lymphoproliferative disorders, and malignant lymphomas.

As the 59079 and 12599 molecules of the present invention share structural features with protein kinases and can modulate protein kinase-mediated activities, the 59079 and 12599 compositions of the invention (e.g., nucleic acids, polypeptides, proteins, antibodies, and modulators of 59079 or 12599 gene expression or biological activity) are useful for developing novel diagnostic and therapeutic agents for protein kinase associated disorders. As used herein, a "protein kinase associated disorder" includes a disorder, disease, or condition which is caused by, characterized by, or associated with a misregulation (e.g., an aberrant downregulation or upregulation) of a protein kinase mediated activity. Protein kinase associated disorders can result in, e.g., upregulated or downregulated, cell growth and/or proliferation.

Protein kinase associated disorders can detrimentally affect cellular functions such as cellular proliferation, growth, differentiation, and cellular regulation of homeostasis, e.g., glucose homeostasis; inter- or intracellular communication; tissue function, such as cardiac function or musculoskeletal function; systemic responses in an organism, such as nervous system responses, hormonal responses (e.g., insulin response), or immune responses; and protection of cells from toxic compounds (e.g., carcinogens, toxins, mutagens, and toxic byproducts of metabolic activity, e.g., reactive oxygen species). Accordingly, the 59079 molecules of the invention, as protein kinases, can mediate various protein kinase associated disorders, including cellular proliferative and/or differentiative disorders, hormonal disorders, immune and inflammatory disorders, neurological disorders, cardiovascular disorders, blood vessel disorders, and platelet disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the term "cancer" (also used interchangeably with the terms, "hyperproliferative" and "neoplastic") refers to cells having the capacity for autonomous growth, i.e., an abnormal state or condition characterized by rapidly proliferating cell growth. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genitourinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

The 59079 molecules of the invention can be used to monitor, treat and/or diagnose a variety of proliferative disorders. Such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Typically, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L., (1991) *Crit. Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Protein kinase associated disorders can include hormonal disorders, such as conditions or diseases in which the production and/or regulation of hormones in an organism is aberrant. Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

Protein kinase associated disorders also include immune and inflammatory disorders, such as autoimmune disorders or immune deficiency disorders, e.g., congenital X-linked infantile hypogammaglobulinemia, transient hypogammaglobulinemia, common variable immunodeficiency, selective IgA deficiency, chronic mucocutaneous candidiasis, or severe combined immunodeficiency. Other examples of disorders include autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, inflammatory bowel disease (e.g., Crohn's disease and ulcerative colitis), aphthous ulcer, iritis, conjunctivitis, keratoconjunctivitis, respiratory inflammation (e.g., asthma, allergic asthma, and chronic obstructive pulmonary disease), cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Additional protein kinase associated disorders are neurological disorders. Such neurological disorders include, for example, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, *Herpes simplex* virus Type 1, *Herpes simplex* virus Type 2, *Varicella-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer's disease and Pick's disease, degenerative diseases of basal ganglia and brain stem, including Parkinsonism, idiopathic Parkinson's disease (paralysis agitans), progressive supranuclear palsy, corticobasal degenration, multiple system atrophy, including striatonigral degenration, Shy-Drager syndrome, and olivopontocerebellar atrophy, and Huntington's disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

The 59079 and 12599 proteins, fragments thereof, and derivatives and other variants of the sequences in SEQ ID NO:2 and SEQ ID NO:5 are collectively referred to as "polypeptides or proteins of the invention" or "59079 and/or 12599 polypeptides or proteins". Nucleic acid molecules encoding such polypeptides or proteins are collectively referred to as "nucleic acids of the invention" or "59079 and/or 12599 nucleic acids."

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in *Current Protocols in Molecular Biology*, John Wiley & Sons, N.Y. (1989), 6.3.1–6.3.6. Aqueous and nonaqueous methods are described in that reference and either can be used. A preferred, example of stringent hybridization conditions are hybridization in 6×sodium chloride/sodium citrate (SSC) at about 45° C., followed by one or more washes in 0.2×SSC, 0.1% SDS at 50° C. Another example of stringent hybridization conditions are hybridization in 6×SSC at about 45° C., followed by one or more washes in 0.2×SSC, 0.1% SDS at 55° C. A further example of stringent hybridization conditions are hybridization in 6×SSC at about 45° C., followed by one or more washes in 0.2×SSC, 0.1% SDS at 60° C. Preferably, stringent hybridization conditions are hybridization in 6×SSC at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M sodium phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NOs: 1, 3, 4, or 6, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 59079 or 12599 protein, preferably a mammalian 59079 or 12599 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means a preparation of 59079 or 12599 protein having less than about 30%, 20%, 10% and more preferably 5% (by dry weight), of non-59079 or non-12599 protein (also referred to herein as a "contaminating protein"), or of chemical precursors or non-59079 or non-12599 chemicals. When the 59079 or 12599 protein, or biologically active portion thereof, is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 59079 (e.g., the sequence of SEQ ID NO: 1 or 3) or 12599 (e.g., the sequence of SEQ ID NO:4 or 6) without abolishing or more preferably, without substantially altering a biological activity, whereas an "essential" amino acid residue results in such a change. For example, amino acid residues that are conserved among the polypeptides of the present invention, e.g., those present in the protein kinasedomain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 59079 or 12599 protein is preferably replaced with another amino acid residue from the same side chain family. Alternatively, in another embodiment, mutations can be introduced randomly along all or part of a 59079 or 12599 coding sequence, such as by saturation mutagenesis, and the resultant mutants can be screened for 59079 or 12599 biological activity to identify mutants that retain activity. Following mutagenesis of SEQ ID NOs:1, 3, 4, or 6, the encoded protein can be expressed recombinantly and the activity of the protein can be determined.

As used herein, a "biologically active portion" of a 59079 or 12599 protein includes a fragment of a 59079 or 12599 protein which participates in an interaction between a 59079 molecule and a non-59079 molecule or in an interaction between a 12599 molecule and a non-12599 molecule. Biologically active portions of a 59079 or 12599 protein include peptides comprising amino acid sequences sufficiently identical to or derived from the amino acid sequence of the 59079 protein, e.g., the amino acid sequence shown in SEQ ID NO:2, or the amino acid sequence of the 12599 protein, e.g., the amino acid sequence shown in SEQ ID NO:5 which include less amino acids than the full length 59079 or 12599 proteins, and exhibit at least one activity of a 59079 or 12599 protein. Typically, biologically active portions comprise a domain or motif with at least one activity of the 59079 or 12599 protein, including, e.g., the ability to as a protein kinase or activate a protein kinase activity.

A biologically active portion of a 59079 or 12599 protein can be a polypeptide which is, for example, 10, 25, 50, 100, 200, or more, amino acids in length. Biologically active portions of a 59079 or 12599 protein can be used as targets for developing agents which modulate a 59079- or 12599-mediated activity as described herein.

Calculations of homology or sequence identity (the terms are used interchangeably herein) between sequences are performed as follows:

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 59079 amino acid sequence of SEQ ID NO:2, at least 789, preferably at least 1052, more preferably at least 1315, even more preferably at least 1578, and even more preferably at least 1841, 2104, 2367, or 2630 amino acid residues of the two sequences are aligned; and when aligning a second sequence to the 12599 amino acid sequence of SEQ ID NO:5, at least 2391, preferably at least 3187, more preferably at least 3984, even more preferably at least 4781, and even more preferably at least 5578, 6374, 7171, or 7968 amino acid residues of the two sequences are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444–453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length as weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS*, 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to 59079 nucleic acid molecules of the invention. BLAST protein searches can be performed with the XBLAST program, score=50, wordlength=3 to obtain amino acid sequences homologous to 59079 protein molecules of the invention. To obtain gapped alignments for comparison purposes, Gapped BLAST can be utilized as described in Altschul et al., (1997) Nucleic Acids Res. 25:3389–3402. When utilizing BLAST and Gapped BLAST programs, the default parameters of the respective programs (e.g., XBLAST and NBLAST) can be used. See http://www.ncbi.nlm.nih.gov.

Particular 59079 and 12599 polypeptides of the present invention have an amino acid sequence sufficiently identical or substantially identical to the amino acid sequence of SEQ ID NO:2 or SEQ ID NO:5. The term "sufficiently identical" or "substantially identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%, 91%, 92%, 93%, 94%, 95%, 96%, 97%, 98% or 99% identity are defined herein as sufficiently or substantially identical.

"Misexpression or aberrant expression", as used herein, refers to a non-wild type pattern of gene expression, at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 59079 or 12599 polypeptide described herein, e.g., a full length 59079 or 12599 protein or a fragment thereof, e.g., a biologically active portion of a 59079 or 12599 protein. Also included is a nucleic acid fragment suitable for use as a hybridization probe, which can be used, e.g., to identify a nucleic acid molecule encoding a polypeptide of the invention, 59079 or 12599 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO: 1, or a portion or fragment thereof. In one embodiment, the nucleic acid molecule includes sequences encoding the human 59079 protein (i.e., "the coding region", from nucleotides 72 to 7964 of SEQ ID NO:1, including the termination codon, shown as in SEQ ID NO:3), as well as untranslated (e.g., noncoding) sequences, e.g., 5' untranslated sequence (i.e., nucleotides 1 to 71 of SEQ ID NO:1) and/or 3' untranslated sequence (i.e., nucleotides 7965 to 8106 of SEQ ID NO:1). Alternatively, the nucleic acid molecule can include only the coding region of SEQ ID NO: 1 (e.g., nucleotides 1 to 7893 of SEQ ID NO:3) and, e.g., no flanking sequences which normally accompany the subject sequence. In another embodiment, the nucleic acid molecule encodes a sequence corresponding to the mature protein of SEQ ID NO:2. In yet another embodiment, the nucleic acid molecule encodes a sequence corresponding to a fragment of the protein from about amino acids 1130 to 1383 or from about amino acids 2334 to 2586 of SEQ ID NO:2.

In another embodiment, an isolated nucleic acid molecule of the invention includes the nucleotide sequence shown in SEQ ID NO:4, or a portion or fragment thereof. In one embodiment, the nucleic acid molecule includes sequences encoding the human 59079 protein (i.e., "the coding region", from nucleotides 72 to 23,978 of SEQ ID NO:4, including the termination codon, shown as in SEQ ID NO:3), as well as untranslated (e.g., noncoding) sequences, e.g., 5' untranslated sequence (i.e., nucleotides 1 to 71 of SEQ ID NO:4) and/or 3' untranslated sequence (i.e., nucleotides 23,979 to 24,120 of SEQ ID NO:4). Alternatively, the nucleic acid molecule can include only the coding region of SEQ ID NO:4 (e.g., nucleotides 1 to 23,907 of SEQ ID NO:6) and, e.g., no flanking sequences which normally accompany the subject sequence. In another embodiment, the nucleic acid molecule encodes a sequence corresponding to the mature protein of SEQ ID NO:5. In yet another embodiment, the nucleic acid molecule encodes a sequence corresponding to a fragment of the protein from about amino acids 6468 to 6721 or from about amino acids 7672 to 7924 of SEQ ID NO:5.

In another embodiment, an isolated nucleic acid molecule of the invention includes a nucleic acid molecule which is a complement of the nucleotide sequence shown in SEQ ID NOs: 1, 3, 4, or 6, or a portion or fragment thereof. In other embodiments, the nucleic acid molecule of the invention is sufficiently complementary to the nucleotide sequence shown in SEQ ID NOs: 1, 3, 4, or 6 such that it can hybridize to the nucleotide sequence shown in SEQ ID NO: 1 or 3, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more, homologous to the entire length of the nucleotide sequence shown in SEQ ID NOs: 1, 3, 4, or 6, or a portion or fragment thereof, preferably of the same length, of any of these nucleotide sequences.

59079 Nucleic Acid Fragments

A nucleic acid molecule of the invention can include only a portion or fragment of the nucleic acid sequence of SEQ ID NO: 1, 3, 4, or 6. For example, such a nucleic acid molecule can include a fragment which can be used as a probe or primer or a fragment encoding a portion of a 59079 or 12599 protein, e.g., an immunogenic or biologically active portion of a 59079 or 12599 protein. A fragment or portion can comprise those nucleotides of SEQ ID NO: 1 or 4 which encode a protein kinase catalytic domain of human 59079 or 12599. The nucleotide sequences determined from the cloning of the 59079 gene allows for the generation of probes and primers designed for use in identifying and/or cloning other 59079 family members, e.g., 12599, or fragments thereof, as well as 59079 homologues, or fragments thereof, from other species.

In another embodiment, a nucleic acid includes a nucleotide sequence that includes part, or all, of the coding region and extends into either (or both) the 5' or 3' noncoding or untranslated region. Other embodiments include a fragment which includes a nucleotide sequence encoding an amino acid fragment described herein. Nucleic acid fragments can encode a specific domain or site described herein or fragments thereof, particularly fragments thereof which are at least 75 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 59079 nucleic acid fragment can include a sequence corresponding to a protein kinase catalytic domain.

59079 and 12599 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NOs: 1, 3, 4, or 6, or of a naturally occurring allelic variant or mutant of SEQ ID NOs: 1, 3, 4, or 6.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes a protein kinase catalytic domain (e.g., the nucleotides encoding amino acid residues 1130 to 1383 or 2334 to 2586 of SEQ ID NO:2, and the nucleotides encoding amino acid residues 6468 to 6721 or 7672 to 7924 of SEQ ID NO:5) or a pleckstrin homology domain (e.g., the nucleotides encoding amino acid residues 558 to 666 of SEQ ID NO:2, or the nucleotides encoding amino acid residues 5896 to 6004 of SE ID NO:5), or a fragment thereof.

In another embodiment, a set of primers is provided, e.g., primers suitable for use in a PCR, which can be used to amplify a selected region of a 59079 orml2599 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: protein kinase catalytic domain from about amino acids 1130 to 1383 or 2334 to 2586 of SEQ ID NO:2, or from about amino acids 6468 to 6721 or 7672 to 7924 of SEQ ID NO:5, and a pleckstrin homology domain from about amino acids 558 to 666 of SEQ ID NO:2, or from about amino acids 5896 to 6004 of SEQ ID NO:5.

A nucleic acid fragment can encode an epitope bearing region of a polypeptide described herein.

A nucleic acid fragment encoding a "biologically active portion of a 59079 or a 12599 polypeptide" can be prepared by isolating a portion of the nucleotide sequence of SEQ ID NO:1, 3, 4, or 6 which encodes a polypeptide having a 59079 or 12599 biological activity (e.g., any of the biological activities of the 59079 and 12599 proteins described herein), expressing the encoded portion of the 59079 or 12599 protein (e.g., by recombinant expression in vitro) and assessing the activity of the encoded portion of the 59079 or 12599 protein. For example, a nucleic acid fragment encoding a biologically active portion of 59079 or 12599 includes a protein kinase catalytic domain, e.g., amino acid residues from about 1130 to 1383 or 2334 to 2586 of SEQ ID NO:2, or amino acid residues from about 6468 to 6721 or 7672 to 7924 of SEQ ID NO:5. A nucleic acid fragment encoding a biologically active portion of a 59079 or 12599 polypeptide, may comprise a nucleotide sequence which is greater than 700 or more nucleotides in length.

In preferred embodiments, a nucleic acid includes a nucleotide sequence which is about 300, 400, 500, 600, 700, 800, 900, 1000, 1100, 1200, 1300, 2000, 3000, 4000, 5000, 5500, 6000, 6500, 7000, 12,000, 15,000, 18,000, 20,000, 21,000, 22, 000, 23,000, 24,000, or more, nucleotides in length and hybridizes under stringent hybridization conditions to a nucleic acid molecule of SEQ ID NO: 1, 3, 4, or 6, or a complement thereof.

59079 and 12599 Nucleic Acid Variants

The invention further encompasses nucleic acid molecules that differ from the nucleotide sequence shown in SEQ ID NOs: 1, 3, 4, or 6. Such differences can be due to degeneracy of the genetic code and result in a nucleic acid which encodes the same 59079 proteins as those encoded by the nucleotide sequence disclosed herein. In another embodiment, an isolated nucleic acid molecule of the invention has a nucleotide sequence encoding a protein having an amino acid sequence which differs, by at least 1, but less than 10, 50, 75, 100, 200, 400, or 500 amino acid residues shown in SEQ ID NO:2, or by at least 1, but less than 100, 200, 300, 400, 500, 700, 1000, 1200, or 1500 amino acid residues shown in SEQ ID NO:5. If alignment is needed for this comparison, the sequences should be aligned for maximum homology. "Looped" out sequences from deletions or insertions, or mismatches, are considered differences.

Nucleic acids of the inventor can be chosen for having codons which are preferred or non-preferred for a particular expression system. For example, the nucleic acid can be one in which at least one codon, preferably at least 10% or 20% of the codons, has been altered such that the sequence is optimized for expression in bacterial (e.g., E. coli), yeast, human, insect, or nonhuman mammalian (e.g., CHO) cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO: 1, 3, 4, or 6, e.g., as follows: by at least one but less than 10, 20, 30, or 40 nucleotides; at least one, but less than 1%, 5%, 10% or 20%, of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more, identical to the nucleotide sequence shown in SEQ ID NO:2, or a fragment of this sequence. Such nucleic acid molecules can readily be identified as being able to hybridize under stringent conditions to the nucleotide sequence shown in SEQ ID NO:2 or 5, or a fragment of the sequence. Nucleic acid molecules corresponding to orthologs, homologs, and allelic variants of the 59079 and 12599 cDNAs of the invention can further be isolated by mapping to the same chromosome or locus as the 59079 or 12599 genes.

Preferred variants include those that are correlated with at least one of the following 59079 and 12599 biological activities: (1) the ability to act as a protein kinase; (2) the ability to activate a protein kinase activity; (3) the ability to regulate transmission of signals from cellular receptors, e.g., cell growth factor receptors; (4) the ability to modulate the entry of cells, e.g., precursor cells, into mitosis; (5) the ability to modulate cellular differentiation; (6) the ability to modulate cell death; and (7) the ability to regulate cytoskeleton function, e.g., actin bundling.

Allelic variants of 59079 and 12599, e.g., human 59079 and human 12599, include both functional and non-functional proteins. Functional allelic variants are naturally occurring amino acid sequence variants of the 59079 or 12599 proteins within a population that maintain at least one of the 59079 or 12599 biological activities described herein.

Functional allelic variants will typically contain only conservative substitution of one or more amino acids of SEQ ID NO:2 or 5, or substitution, deletion or insertion of non-critical residues in non-critical regions of the protein. Non-functional allelic variants are naturally occurring amino acid sequence variants of the 59079 or 12599, e.g., human 59079, protein within a population that do not have any of the 59079 biological activities described herein. Non-functional allelic variants can typically contain a non-conservative substitution, a deletion, or insertion, or premature truncation of the amino acid sequence of SEQ ID NO:2 or 5, or a substitution, insertion, or deletion in critical residues or critical regions of the protein.

Moreover, nucleic acid molecules encoding other 59079 and 12599 family members, and, thus, which have a nucleotide sequence which differs from the 59079 sequences of SEQ ID NOs: 1, 3, 4, or 6 are intended to be within the scope of the invention.

Antisense Nucleic Acid Molecules, Ribozymes and Modified 59079 Nucleic Acid Molecules In another aspect, the invention features, an isolated nucleic acid molecule which is antisense to 59079 or 12599. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 59079 or 12599 coding strand, or to only a portion thereof (e.g., the coding region of human 59079 corresponding to SEQ ID NO:3, or the coding region of human 12599 corresponding to SEQ ID NO:5). In another embodiment, the antisense nucleic acid molecule is antisense to a "noncoding region" of the coding strand of a nucleotide sequence encoding 59079 or 12599 (e.g., the 5' and 3' untranslated regions).

An antisense nucleic acid can be designed such that it is complementary to the entire coding region of 59079 or 12599 mRNA, but more preferably is an oligonucleotide which is antisense to only a portion of the coding or noncoding region of 59079 or 12599 mRNA. For example, the antisense oligonucleotide can be complementary to the region surrounding the translation start site of 59079 or 12599 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 59079 or 12599 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. A ribozyme having specificity for a 59079- or 12599-encoding nucleic acid can include one or more sequences complementary to the nucleotide sequence of a 59079 or 12599 cDNA disclosed herein (i.e., SEQ ID NOs: 1, 3, 4, or 6), and a sequence having known catalytic sequence responsible for mRNA cleavage (see U.S. Pat. No. 5,093,246 or Haselhoff and Gerlach (1988) *Nature* 334:585–591). For example, a derivative of a *Tetrahymena* L-19 IVS RNA can be constructed in which the nucleotide sequence of the active site is complementary to the nucleotide sequence to be cleaved in a 59079-encoding mRNA. See, e.g., Cech et al. U.S. Pat. No. 4,987,071; and Cech et al. U.S. Pat. No. 5,116,742. Alternatively, 59079 mRNA can be used to select a catalytic RNA having a specific ribonuclease activity from a pool of RNA molecules. See, e.g., Bartel, D. and Szostak, J. W. (1993) *Science* 261:1411–1418.

59079 and 12599 gene expression can be inhibited by targeting nucleotide sequences complementary to the regulatory region of 59079 or 12599 (e.g., the 59079 or 12599 promoter and/or enhancers) to form triple helical structures that prevent transcription of the 59079 gene in target cells. See generally, Helene, C. (1991) *Anticancer Drug Des.* 6:569–84; Helene, C. i (1992) *Ann. N.Y. Acad. Sci.* 660:27–36; and Maher, L. J. (1992) *Bioassays* 14:807–15. The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or calorimetric.

A 59079 or 12599 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4: 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of 59079 and 12599 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 59079 and 12599 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958–976) or intercalating agents. (see, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 59079 or 12599 nucleic acid of the invention, two complementary regions one having a fluorophore and one a quencher such that the molecular beacon is useful for quantitating the presence of the 59079 or 12599 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 59079 Polypeptides

In another aspect, the invention features, isolated 59079 and 12599 proteins, or a fragment, e.g., a biologically active portion, for use as immunogens or antigens to raise or test (or more generally to bind) anti-59079 and anti-12599 antibodies. 59079 and 12599 proteins can be isolated from cells or tissue sources using standard protein purification techniques. 59079 and 12599 proteins, or fragments thereof, can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 59079 and a 12599 polypeptide each has one or more of the following characteristics:

the ability to act as a protein kinase, activate a protein kinase activity, act as a substrate for a protein kinase or perform any of the 59079 or 12599 biological activities described herein;

a molecular weight, e.g., a deduced molecular weight, amino acid composition or other physical characteristic of the polypeptide of SEQ ID NO:2 or 5;

an overall sequence similarity of at least 50%, preferably at least 60%, more preferably at least 70, 80, 90, 95%, 96%, 97%, or 98%, with a polypeptide of SEQ ID NO:2 or 5; and a protein kinase catalytic domain which preferably has an overall sequence similarity of about 70%, 80%, 90% or 95% with amino acid residues 1130 to 1383 or 2334 to 2586 of SEQ ID NO:2 or amino acid residues 6468 to 6721 or 7672 to 7924 of SEQ ID NO:5; and In a preferred embodiment, the 59079 and 12599 proteins, or a fragment thereof, differs from the corresponding sequence in SEQ ID NO:2 or 5. In one embodiment it differs by at least one, but by less than 15, 10 or 5, amino acid residues. In another it differs from the corresponding sequence in SEQ ID NO:2 or 5 by at least one residue, but less than 20%, 15%, 10% or 5%, of the residues in it differ from the corresponding sequence in SEQ ID NO:2 or 5. (If this comparison requires alignment the sequences should be aligned for maximum homology. "Looped" out sequences from deletions or insertions, or mismatches, are considered differences.) The differences are, preferably, differences or changes at a nonessential residue or a conservative substitution. In a preferred embodiment the differences are not in the protein kinase catalytic domain. In another preferred embodiment one or more differences are in the protein kinase catalytic domain.

Other embodiments include a protein that contain one or more changes in amino acid sequence, e.g., a change in an amino acid residue which is not essential for activity. Such 59079 and 12599 proteins differ in amino acid sequence from SEQ ID NO:2 and 5, yet retain biological activity.

In one embodiment, the protein includes an amino acid sequence at least about 50%, 55%, 60%, 65%, 70%, 75%, 80%, 85%, 90%, 95%, 98%, or more, homologous to SEQ ID NO:2 or 5.

A 59079 protein or fragment is provided which varies from the sequences of SEQ ID NO.2 in regions defined by amino acids from about 1 to 1129, 1384 to 2333, or 2587 to 2630 by at least one, but by less than 50, 15, 10 or 5, amino acid residues in the protein or fragment, but which does not differ from SEQ ID NO.2 in a region defined by amino acids about 1130 to 1383 or 2334 to 2586. A 12599 protein or fragment is provided which varies from the sequence of SEQ ID NO:5 in regions defined by amino acids from about 1 to 6467, 6722 to 7671, or 7925 to 7968 by least one, but by less than 50, 15, 10, or 5, amino acid residues in the protein or fragment, but which does not differ from SEQ ID NO:5 in a region defind by amino acids at about 6468 to 6721 or 7672 to 7924 of SEQ ID NO:5. (If this comparison requires alignment the sequences should be aligned for maximum homology. "Looped" out sequences from deletions or insertions, or mismatches, are considered differences.) In some embodiments the difference is at a non essential residue or is a conservative substitution, while in others the difference is at an essential residue or is a non conservative substitution.

In one embodiment, a biologically active portion of a 59079 or 12599 protein includes a protein kinase catalytic domain. Moreover, other biologically active portions, in which other regions of the protein are deleted, can be prepared by recombinant techniques and evaluated for one or more of the functional activities of a native 59079 or 12599 protein.

In a preferred embodiment, the 59079 protein has an amino acid sequence shown in SEQ ID NO:2. In other embodiments, the 59079 protein is substantially identical to SEQ ID NO:2. In yet another embodiment, the 59079 protein is substantially identical to SEQ ID NO:2 and retains the functional activity of the protein of SEQ ID NO:2, as described herein.

In a preferred embodiment, the 12599 protein has an amino acid sequence shown in SEQ ID NO:5. In other embodiments, the 12599 protein is substantially identical to SEQ ID NO:5. In yet another embodiment, the 12599 protein is substantially identical to SEQ ID NO:5 and retains the functional activity of the protein of SEQ ID NO:5, as described herein.

59079 and 12599 Chimeric or Fusion Proteins

In another aspect, the invention provides 59079 and 12599 chimeric or fusion proteins. As used herein, a 59079 or 12599 "chimeric protein" or "fusion protein" includes a 59079 or 12599 polypeptide linked to a non-59079 or non-12599 polypeptide. A "non-59079 polypeptide" or a "non-12599 polypeptide" refers to a polypeptide having an amino acid sequence corresponding to a protein which is not substantially homologous to the 59079 or 12599 protein, e.g., a protein which is different from the 59079 or 12599 protein and which is derived from the same or a different organism. The 59079 or 12599 polypeptide of the fusion protein can correspond to all or a portion, e.g., a fragment, described herein of a 59079 or 12599 amino acid sequence. In a preferred embodiment, a 59079 fusion protein includes at least one (or two) biologically active portion of a 59079 protein. In another preferred embodiment, a 12599 fusion protein includes at least one (or two) biologically active portion of a 12599 protein. The non-59079 and non-12599 polypeptides can be fused to the N-terminus or C-terminus of the 59079 or 12599 polypeptide.

The fusion protein can include a moiety which has a high affinity for a ligand. For example, the fusion protein can be a GST-59079 or -12599 fusion protein in which the 59079 or 12599 sequences are fused to the C-terminus of the GST sequences. Such fusion proteins can facilitate the purification of recombinant 59079 or 12599. Alternatively, the fusion protein can be a 59079 or 12599 protein containing a heterologous signal sequence at its N-terminus. In certain host cells (e.g., mammalian host cells), expression and/or secretion of 59079 or 12599 can be increased through use of a heterologous signal sequence.

Fusion proteins can include all or a part of a serum protein, e.g., a portion of an immunoglobulin (e.g., IgG, IgA, or IgE), e.g., an Fc region and/or the hinge C1 and C2 sequences of an immunoglobulin or human serum albumin.

The 59079 and 12599 fusion proteins of the invention can be incorporated into pharmaceutical compositions and administered to a subject in vivo. The 59079 or 12599 fusion proteins can be used to affect the bioavailability of a 59079 or 12599 substrate. 59079 and 12599 fusion proteins can be used therapeutically for the treatment of disorders caused by, for example, (i) aberrant modification or mutation of a gene encoding a 59079 or 12599 protein; (ii) mis-regulation of the 59079 or 12599 gene; and (iii) aberrant post-translational modification of a 59079 or 12599 protein.

Moreover, the 59079 and 12599 fusion proteins of the invention can be used as immunogens to produce anti-59079 or anti-12599 antibodies in a subject, to purify 59079 or 12599 ligands and in screening assays to identify molecules which inhibit the interaction of 59079 with a 59079 substrate or the interaction of 12599 with a 12599 substrate.

Expression vectors are commercially available that already encode a fusion moiety (e.g., a GST polypeptide). A 59079-encoding nucleic acid can be cloned into such an expression vector such that the fusion moiety is linked in-frame to the 59079 protein.

Variants of 59079 and 12599 Proteins

In another aspect, the invention also features a variant of a 59079 and 12599 polypeptide, e.g., which functions as an agonist (mimetics) or as an antagonist. Variants of the 59079 and 12599 proteins can be generated by mutagenesis, e.g., discrete point mutation, the insertion or deletion of sequences or the truncation of a 59079 or 12599 protein. An agonist of the 59079 or 12599 proteins can retain substantially the same, or a subset, of the biological activities of the naturally occurring form of a 59079 or 12599 protein. An antagonist of a 59079 or 12599 protein can inhibit one or more of the activities of the naturally occurring form of the 59079 or 12599 protein by, for example, competitively modulating a 59079- or 12599-mediated activity of a 59079 or 12599 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 59079 or 12599 protein.

Variants of a 59079 or 12599 protein can be identified by screening combinatorial libraries of mutants, e.g., truncation mutants, of a 59079 or 12599 protein for agonist or antagonist activity.

Libraries of fragments, e.g., N terminal, C terminal, or internal fragments, of a 59079 protein coding sequence can be used to generate a variegated population of fragments for screening and subsequent selection of variants of a 59079 or 12599 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 59079 and 12599 variants (Arkin and Yourvan (1992) *Proc. Natl. Acad. Sci. USA* 89:7811–7815; Delgrave et al. (1993) *Protein Engineering* 6:327–331).

Cell based assays can be exploited to analyze a variegated 59079 library. For example, a library of expression vectors can be transfected into a cell line, e.g., an endothelial cell line, which ordinarily responds to 59079 or 12599 in a particular 59079 or 12599 substrate-dependent manner. The transfected cells are then contacted with 59079 or 12599 and the effect of expression of the mutant on signaling by the 59079 or 12599 substrate can be detected, e.g., by monitoring intracellular calcium, IP3, or diacylglycerol concentration, phosphorylation profile of intracellular proteins, or the activity of an 59079- or 12599-regulated transcription factor. Plasmid DNA can then be recovered from the cells which score for inhibition, or alternatively, potentiation of signaling by the HST-1 substrate, and the individual clones further characterized.

In another aspect, the invention features a method of making a 59079 or 12599 polypeptide, e.g., a peptide having a non-wild type activity, e.g., an antagonist, agonist, or super agonist of a naturally occurring 59079 or 12599 polypeptide, e.g., a naturally occurring 59079 or 12599 polypeptide. The method includes: altering the sequence of a 59079 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 59079 or 12599 polypeptide a biological activity of a naturally occurring 59079 or 12599 polypeptide. The method includes: altering the sequence, e.g., by substitution or deletion of one or more residues, of a 59079 or 12599 polypeptide, e.g., altering the sequence of a non-conserved region, or a domain or residue described herein, and testing the altered polypeptide for the desired activity.

Anti-59079 and Andti-12599 Antibodies

In another aspect, the invention provides an anti-59079 and anti-12599 antibodies. The term "antibody" as used herein refers to an immunoglobulin molecule and immunologically active portions of immunoglobulin molecules, i.e., molecules that contain an antigen binding site which specifically binds (immunoreacts with) an antigen, such as a 59079 or 12599 molecule. Examples of immunologically active portions of immunoglobulin molecules include scFV and dcFV fragments, Fab and F(ab')$_2$ fragments which can be generated by treating the antibody with an enzyme such as papain or pepsin, respectively.

The antibody can be a polyclonal, monoclonal, recombinant, e.g., a chimeric, humanized, fully human, non-human (e.g., murine, rat, rabbit, or goat), or single chain antibody. In a preferred embodiment it has effector function and can fix complement. The antibody can be coupled to a toxin or imaging agent.

The term "monoclonal antibody" or "monoclonal antibody composition", as used herein, refers to a population of antibody molecules that contain only one species of an antigen binding site capable of immunoreacting with a particular epitope of 59079 or 12599. A monoclonal antibody composition thus typically displays a single binding affinity for a particular 59079 or 12599 protein with which it immunoreacts.

Polyclonal anti-59079 and anti-12599 antibodies can be prepared as described above by immunizing a suitable subject with a 59079 or 12599 immunogen. The specific antibody titer in the immunized subject can be monitored over time by standard techniques, such as with an enzyme linked immunosorbent assay (ELISA) using immobilized 59079 or 12599. If desired, the antibody molecules directed against 59079 or 12599 can be isolated from the mammal (e.g., from the blood) and further purified by well known techniques, such as protein A chromatography to obtain the IgG fraction. At an appropriate time after immunization, e.g., when the anti-59079 or anti-12599 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a 59079 immunogen as described above, and the culture supernatants of the resulting hybridoma cells are screened to identify a hybridoma producing a monoclonal antibody that binds 59079.

Any of the many well known protocols used for fusing lymphocytes and immortalized cell lines can be applied for the purpose of generating an anti-59079 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind 59079, e.g., using a standard ELISA assay.

Alternative to preparing monoclonal antibody-secreting hybridomas, a monoclonal anti-59079 or anti-12599 antibody can be identified and isolated by screening a recombinant combinatorial immunoglobulin library (e.g., an antibody phage display library) with 59079 or 12599 to thereby isolate immunoglobulin library members that bind 59079 or 12599. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, chimeric, humanized, and completely human antibodies are also within the scope of the invention. Chimeric, humanized, but most preferably, completely human antibodies are desirable for applications which include repeated administration, e.g., therapeutic treatment of human patients, and some diagnostic applications.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

A full-length 59079 or 12599 protein, or an antigenic peptide fragment of 59079 or 12599, can be used as an immunogen or can be used to identify anti-59079 or anti-12599 antibodies made with other immunogens, e.g., cells, membrane preparations, and the like. The antigenic peptides of 59079 should include at least 8 amino acid residues of the amino acid sequence shown in SEQ ID NO:2 and encompass an epitope of 59079, respectively. The antigenic peptides of 12599 should include at least 8 amino acid esidues of the amino acid sequence shown in SEQ ID NO:5 and encompass an epitope of 12599, respectively. Preferably, the antigenic peptide includes at least 10 amino acid residues, more preferably at least 15 amino acid residues, even more preferably at least 20 amino acid residues, and most preferably at least 30 amino acid residues.

Fragments of 59079 which include, e.g., residues 1130 to 1383 or 2334 to 2586 of SEQ ID NO:2, can be used as immunogens to make an antibody against the protein kinase catalytic domain of the 59079 protein.

Fragments of 12599 which include, e.g., residues 6468 to 6721 or 7672 to 7924 of SEQ ID NO:5, can be used as immunogens to make an antibody against the protein kinase catalytic domain of the 12599 protein.

Antibodies reactive with, or specific or selective for, any of these regions, or other regions or domains described herein are provided.

In an alternative embodiment, the antibody fails to bind to an Fc receptor, e.g., it is a type which does not support Fc receptor binding or has been modified, e.g., by deletion or other mutation, such that is does not have a functional Fc receptor binding region.

Preferred epitopes encompassed by the antigenic peptide are regions of 59079 and 12599 which are located on the surface of the protein, e.g., hydrophilic regions, as well as regions with high antigenicity. For example, an Emini surface probability analysis of the human 59079 and 12599 protein sequences can be used to identify the regions that have a particularly high probability of being localized to the surface of the 59079 or 12599 protein, and are thus likely to constitute surface residues useful for targeting antibody production.

In a preferred embodiment the antibody binds an epitope on any domain or region on 59079 proteins described herein.

In another preferred embodiment, the antibody binds an epitope on any domain or region on 12599 proteins described herein.

The anti-59079 or anti-12599 antibody can be a single chain antibody. A single-chain antibody (scFV) may be engineered as described, for example, in Colcher, D. et al., (1999) *Ann. NY Acad. Sci.* 880: 263–80; and Reiter, Y., *Clin. Cancer Res.* 1996 Feb;2(2):245–52. The single chain antibody can be dimerized or multimerized to generate multivalent antibodies having specificities for different epitopes of the same target 59079 protein.

Anti-59079 and anti-12599 antibodies (e.g., monoclonal antibodies) can be used to isolate 59079 or 12599, respectively, by standard techniques, such as affinity chromatography or immunoprecipitation. Moreover, an anti-59079 or anti-12599 antibody can be used to detect 59079 or 12599 protein, respectively, (e.g., in a cellular lysate or cell supernatant) in order to evaluate the abundance and pattern of expression of the protein. Anti-59079 and anti-12599 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 59079 or 12599 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 59079 and 12599 proteins, mutant forms of 59079 and 12599 proteins, fusion proteins, and the like).

The recombinant expression vectors of the invention can be designed for expression of 59079 or 12599 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, and enterokinase. Typical fusion expression vectors include pGEX (Pharmacia Biotech, Inc; Smith, D. B. and Johnson, K. S. (1988) *Gene* 67:31–40), pMAL (New England Biolabs, Beverly Mass.) and pRIT5 (Pharmacia, Piscataway N.J.) which fuse glutathione S-transferase (GST), maltose E binding protein, or protein A, respectively, to the target recombinant protein.

Purified fusion proteins can be used in 59079 or 12599 activity assays, (e.g., direct assays or competitive assays described in detail below), or to generate antibodies specific for 59079 or 12599 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119–128). Another strategy is to alter the nucleic acid sequence of the nucleic acid to be inserted into an expression vector so that the individual codons for each amino acid are those preferentially utilized in *E. coli* (Wada et al., (1992)

Nucleic Acids Res. 20:2111–2118). Such alteration of nucleic acid sequences of the invention can be carried out by standard DNA synthesis techniques.

The 59079 and 12599 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., (1986) Antisense RNA as a molecular tool for genetic analysis, Reviews—Trends in Genetics 1:1.

Another aspect the invention provides a host cell which includes a nucleic acid molecule described herein, e.g., a 59079 or 12599 nucleic acid molecule within a recombinant expression vector or a 59079 or 12599 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 59079 or 12599 protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 59079 or 12599 protein. Accordingly, the invention further provides methods for producing a 59079 or 12599 protein using the host cells of the invention. In one embodiment, the method includes culturing the host cell of the invention (into which a recombinant expression vector encoding a 59079 or 12599 protein has been introduced) in a suitable medium such that a 59079 or 12599 protein is produced. In another embodiment, the method further includes isolating a 59079 or 12599 protein from the medium or the host cell.

In another aspect, the invention features a cell or a purified preparation of cells which includes a 59079 or 12599 transgene, or which otherwise misexpresses 59079 or 12599. The cell preparation can consist of human or non-human cells, e.g., rodent cells, e.g., mouse or rat cells, rabbit cells, or pig cells. In preferred embodiments, the cell, or cells, include a 59079 or 12599 transgene, e.g., a heterologous form of 59079 or 12599, e.g., a gene derived from humans (in the case of a non-human cell). The 59079 or 12599 transgene can be misexpressed, e.g., overexpressed or underexpressed. In other preferred embodiments, the cell, or cells, includes a gene which misexpresses an endogenous 59079 or 12599, e.g., a gene, the expression of which is disrupted, e.g., a knockout. Such cells can serve as a model for studying disorders which are related to mutated or mis-expressed 59079 or 12599 alleles or for use in drug screening.

In another aspect, the invention features, a human cell, e.g., a hematopoietic stem cell, transformed with nucleic acid which encodes a subject 59079 or 12599 polypeptide.

Also provided are cells, preferably human cells, e.g., human hematopoietic or fibroblast cells, in which an endogenous 59079 or 12599 gene is under the control of a regulatory sequence that does not normally control the expression of the endogenous 59079 or 12599 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 59079 or 12599 gene. For example, an endogenous 59079 or 12599 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Transgenic Animals

The invention provides non-human transgenic animals. Such animals are useful for studying the function and/or activity of a 59079 or a 12599 protein and for identifying and/or evaluating modulators of 59079 or 12599 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 59079 or 12599 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 59079 or 12599 protein to particular cells. A transgenic founder animal can be identified based upon the presence of a 59079 or 12599 transgene in its genome and/or expression of 59079 or 12599 mRNA in tissues or cells of the animals. A transgenic founder animal can then be used to breed additional animals carrying the transgene. Moreover, transgenic animals carrying a transgene encoding a 59079 or 12599 protein can further be bred to other transgenic animals carrying other transgenes.

59079 and 12599 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 59079 or 12599 protein (e.g., via a recombinant expression vector in a host cell in gene therapy applications), to detect a 59079 or 12599 mRNA (e.g., in a biological sample) or a genetic alteration in a 59079 or 12599 gene, and to modulate 59079 or 12599 activity, as described further below. The 59079 and 12599 proteins can be used to treat disorders characterized by insufficient or excessive production of a 59079 or 12599 substrate or production of 59079 or 12599 inhibitors. In addition, the 59079 and 12599 proteins can be used to screen for naturally occurring 59079 or 12599 substrates, to screen for drugs or compounds which modulate 59079 or 12599 activity, as well as to treat disorders characterized by insufficient or excessive production of 59079 or 12599 protein or production of 59079 or 12599 protein forms which have decreased, aberrant or unwanted activity compared to 59079 or 12599 wild type protein. Moreover, the anti-59079 and anti-12599 antibodies of the invention can be used to detect and isolate 59079 or 12599 proteins, regulate the bioavailability of 59079 or 12599 proteins, and modulate 59079 or 12599 activity.

A method of evaluating a compound for the ability to interact with, e.g., bind, a subject 59079 or 12599 polypeptide is provided. The method includes: contacting the compound with the subject 59079 or 12599 polypeptide; and evaluating ability of the compound to interact with, e.g., to bind or form a complex with the subject 59079 or 12599 polypeptide. This method can be performed in vitro, e.g., in a cell free system, or in vivo, e.g., in a two-hybrid interaction trap assay. This method can be used to identify naturally occurring molecules which interact with subject 59079 or 12599 polypeptide. It can also be used to find natural or synthetic inhibitors of subject 59079 or 12599 polypeptide. Screening methods are discussed in more detail below.

Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to 59079 or 12599 proteins, have a stimulatory or inhibitory effect on, for example, 59079 or 12599 expression or 59079 or 12599 activity, or have a stimulatory or inhibitory effect on, for example, the expression or activity of a 59079 or 12599 substrate. Compounds thus identified can be used to modulate the activity of target gene products (e.g., 59079 and 12599 genes) in a therapeutic protocol, to elaborate the biological function of the target gene product, or to identify compounds that disrupt normal target gene interactions.

In one embodiment, the invention provides assays for screening candidate or test compounds which are substrates of a 59079 or 12599 protein or polypeptide or a biologically active portion thereof. In another embodiment, the invention provides assays for screening candidate or test compounds which bind to or modulate the activity of a 59079 or 12599 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223,409), spores (Ladner U.S. Pat. No. '409), plasmids (Cull et al. (1992) *Proc. Natl. Acad Sci USA* 89:1865–1869)

or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

In another embodiment, an assay is a cell-based assay comprising contacting a cell expressing a 59079 or 12599 target molecule (e.g., a 59079 or 12599 phosphorylation substrate) with a test compound and determining the ability of the test compound to modulate (e.g., stimulate or inhibit) the activity of the 59079 or 12599 target molecule. Determining the ability of the test compound to modulate the activity of a 59079 or 12599 target molecule can be accomplished, for example, by determining the ability of the 59079 or 12599 protein to bind to or interact with the 59079 or 12599 target molelcule, or by determining the ability of the 59079 or 12599 protein to phosphorylate the 59079 or 12599 target molecule.

The ability of the 59079 or 12599 protein to phosphorylate a substrate or target molecule can be determined by, for example, an in vitro kinase assay. Briefly, a substrate or target molecule, e.g., an immunoprecipitated substrate or target molecule from a cell line expressing such a molecule, can be incubated with the 59079 or 12599 protein and radioactive ATP, e.g., $[\gamma\text{-}^{32}p]$ ATP, in a buffer containing $MgCl_2$ and $MnCl_2$, e.g., 10 mM $MgCl_2$ and 5 mM $MnCl_2$. Following the incubation, the immunoprecipitated substrate/target molecule can be separated by SDS-polyacrylamide gel electrophoresis under reducing conditions, transferred to a membrane, e.g., a PVDF membrane, and autoradiographed. The appearance of detectable bands on the autoradiograph indicates that the 59079 or 12599 substrate or target molecule has been phosphorylated. Phosphoamino acid analysis of the phosphorylated substrate or target molecule can also be performed in order to determine which residues on the 59079 or 12599 substrate or target molecule are phosphorylated and isolated by SDS polyacrylamidge gel electrophoresis. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards.

The ability of the test compound to modulate 59079 or 12599 binding to a compound, e.g., a 59079 or 12599 substrate, or to bind to 59079 or 12599 can also be evaluated. This can be accomplished, for example, by coupling the compound, e.g., the substrate, with a radioisotope or enzymatic label such that binding of the compound, e.g., the substrate, to 59079 or 12599 can be determined by detecting the labeled compound, e.g., substrate, in a complex. Alternatively, 59079 or 12599 could be coupled with a radioisotope or enzymatic label to monitor the ability of a test compound to modulate 59079 or 12599 binding to a 59079 or 12599 substrate in a complex. For example, compounds (e.g., 59079 or 12599 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 59079 or 12599 substrate) to interact with 59079, with or without the labeling of any of the interactants, can be evaluated. For example, a microphysiometer can be used to detect the interaction of a compound with 59079 or 12599 without the labeling of either the compound or the 59079 or 12599. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 59079 or between a compound and 12599.

In yet another embodiment, a cell-free assay is provided in which a 59079 or a 12599 protein, or biologically active portion thereof, is contacted with a test compound and the ability of the test compound to bind to the 59079 or 12599 protein, or biologically active portion thereof, is evaluated. Preferred biologically active portions of the 59079 and 12599 proteins to be used in assays of the present invention include fragments which participate in interactions with non-59079 or non-12599 molecules, e.g., fragments with high surface probability scores.

Soluble and/or membrane-bound forms of isolated proteins (e.g., 59079 and 12599 proteins, or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$3-[(3-cholamidopropyl)dimethylarninio]-1-propane sulfonate (CHAPS), 3-[(3-cholamidopropyl)dimethylamminio]-2-hydroxy-1-propane sulfonate (CHAPSO), or N-dodecyl=N, N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 59079 and 12599 protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize 59079 or 12599, an anti-59079 or anti-12599 antibody, or a 59079 or 12599 target molecule to facilitate separation of complexed from uncomplexed forms of one or both of the proteins, as well as to accommodate automation of the assay. Binding of a test compound to a 59079 or 12599 protein, or interaction of a 59079 or 12599 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/59079 fusion proteins or glutathione-S-transferase/12599 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 59079 or 12599 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 59079 or 12599 binding or activity determined using standard techniques.

Other techniques for immobilizing either a 59079 or 12599 protein or a target molecule on matrices include using conjugation of biotin and streptavidin. Biotinylated 59079 or 12599 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 59079 or 12599 protein or target molecules but which do not interfere with binding of the 59079 or 12599 protein to its target molecule. Such antibodies can be derivatized to the wells of the plate, and unbound target or 59079 or 12599 protein trapped in the wells by antibody conjugation. Methods for detecting such complexes, in addition to those described above for the GST-immobilized complexes, include immunodetection of complexes using antibodies reactive with the 59079 or 12599 protein or target molecule, as well as enzyme-linked assays which rely on detecting an enzymatic activity associated with the 59079 or 12599 protein or target molecule.

Alternatively, cell-free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284–7); chromatography (gel filtration chromatography, ion-exchange chromatography); electrophoresis (see, e.g., Ausubel, F. et al., eds. *Current Protocols in Molecular Biology* 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141–8; Hage, D. S., and Tweed, S. A. (1997) *J Chromatogr B Biomed Sci Appl*. 699:499–525). Further, fluorescence energy transfer may also be conveniently utilized, as described herein, to detect binding without further purification of the complex from solution.

In a preferred embodiment, the assay includes contacting the 59079 or 12599 protein, or biologically active portion thereof, with a known compound which binds 59079 or 12599 to form an assay mixture, contacting the assay mixture with a test compound, and determining the ability of the test compound to interact with a 59079 or 12599 protein, wherein determining the ability of the test compound to interact with a 59079 protein includes determining the ability of the test compound to preferentially bind to 59079 or 12599, or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to, molecules such as antibodies, peptides, and small molecules. The preferred target genes/ products for use in this embodiment are the 59079 and 12599 genes herein identified. In an alternative embodiment, the invention provides methods for determining the ability of the test compound to modulate the activity of a 59079 or 12599 protein through modulation of the activity of a downstream effector of a 59079 or 12599 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 59079 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 59079 or 12599 ("59079-binding proteins" or "59079-bps", "12599-binding proteins" or "12599-bps") and are involved in 59079 or 12599 activity. Such 59079-bps and 12599-bps can be activators or inhibitors of signals by the 59079 or 12599 proteins or 59079 or 12599 targets as, for example, downstream elements of a 59079- or 12599-mediated signaling pathway.

The two-hybrid system is based on the modular nature of most transcription factors, which consist of separable DNA-binding and activation domains. Briefly, the assay utilizes two different DNA constructs. In one construct, the gene that codes for a 59079 or 12599 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 59079 or 12599 protein can be the fused to the activator domain.) If the "bait" and the "prey" proteins are able to interact, in vivo, forming a 59079-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 59079 protein.

In another embodiment, modulators of 59079 or 12599 expression are identified. For example, a cell or cell free mixture is contacted with a candidate compound and the expression of 59079 or 12599 mRNA or protein evaluated relative to the level of expression of 59079 or 12599 mRNA or protein in the absence of the candidate compound. When expression of 59079 or 12599 mRNA or protein is greater in the presence of the candidate compound than in its absence, the candidate compound is identified as a stimulator of 59079 or 12599 mRNA or protein expression. Alternatively, when expression of 59079 or 12599 mRNA or protein is less (statistically significantly less) in the presence of the candidate compound than in its absence, the candidate compound is identified as an inhibitor of 59079 or 12599 mRNA or protein expression. The level of 59079 or 12599 mRNA or protein expression can be determined by methods described herein for detecting 59079 or 12599 mRNA or protein.

In another aspect, the invention pertains to a combination of two or more of the assays described herein. For example, a modulating agent can be identified using a cell-based or a cell free assay, and the ability of the agent to modulate the activity of a 59079 or 12599 protein can be confirmed in vivo in an animal model.

This invention further pertains to novel agents identified by the above-described screening assays. Accordingly, it is within the scope of this invention to further use an agent identified as described herein (e.g., a 59079 or 12599 modulating agent, an anti-sense 59079 or 12599 nucleic acid molecule, a 59079- or 12599-specific antibody, or a 59079- or 12599-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 59079 and 12599 with a disease; (ii) identify an individual from a minute biological sample (tissue typing); and (iii) aid in forensic identification of a biological sample. These applications are described in the subsections below.

Chromosome Mapping

The 59079 and 12599 nucleotide sequences or portions thereof can be used to map the location of the 59079 and 12599 genes on a chromosome. This process is called chromosome mapping. Chromosome mapping is useful in correlating the 59079 and 12599 sequences with genes associated with disease.

Briefly, 59079 and 12599 genes can be mapped to chromosomes by preparing PCR primers (preferably 15–25 bp in length) from the 59079 or 12599 nucleotide sequences. These primers can then be used for PCR screening of somatic cell hybrids containing individual human chromosomes. Only those hybrids containing the human gene corresponding to the 59079 or 12599 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919–924).

Other mapping strategies e.g., in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries can be used to map 59079 or 12599 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., *Human Chromosomes: A Manual of Basic Techniques* ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the 59079 or 12599 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 59079 and 12599 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 59079 and 12599 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 and SEQ ID NO:4 can provide positive individual identification with a panel of perhaps 10 to 1,000 primers which each yield a noncoding amplified sequence of 100 bases. If predicted coding sequences, such as those in SEQ ID NO:3 and 5 are used, a more appropriate number of primers for positive individual identification would be 500–2,000.

If a panel of reagents from 59079 or 12599 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 59079 and 12599 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 or 4 (e.g., fragments derived from the noncoding regions of SEQ ID NO:1 or 4 having a length of at least 20 bases, preferably at least 30 bases) are particularly appropriate for this use.

The 59079 and 12599 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 59079 or 12599 probes can be used to identify tissue by species and/or by organ type.

In a similar fashion, these reagents, e.g., 59079 and 12599 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 59079.

Such disorders include, e.g., a disorder associated with the misexpression of 59079 or 12599 gene.

The method includes one or more of the following:

detecting, in a tissue of the subject, the presence or absence of a mutation which affects the expression of the 59079 or 12599 gene, or detecting the presence or absence of a mutation in a region which controls the expression of the gene, e.g., a mutation in the 5' control region;

detecting, in a tissue of the subject, the presence or absence of a mutation which alters the structure of the 59079 or 12599 gene;

detecting, in a tissue of the subject, the misexpression of the 59079 or 12599 gene, at the mRNA level, e.g., detecting a non-wild type level of a mRNA; or detecting, in a tissue of the subject, the misexpression of the gene, at the protein level, e.g., detecting a non-wild type level of a 59079 or 12599 polypeptide.

In preferred embodiments the method includes: ascertaining the existence of at least one of: a deletion of one or more nucleotides from the 59079 or 12599 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO: 1 or 4, or naturally occurring mutants thereof or 5' or 3' flanking sequences naturally associated with the 59079 or 12599 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 59079 or 12599 gene; the presence of a non-wild type splicing pattern of a messenger RNA transcript of the gene; or a non-wild type level of 59079 or 12599.

Methods of the invention can be used prenatally or to determine if a subject's offspring will be at risk for a disorder.

In preferred embodiments the method includes determining the structure of a 59079 gene, an abnormal structure being indicative of risk for the disorder.

In preferred embodiments the method includes contacting a sample from the subject with an antibody to the 59079 protein or a nucleic acid, which hybridizes specifically with the gene. There and other embodiments are discussed below.

Diagnostic and Prognostic Assays

The presence, level, or absence of 59079 or 12599 protein or nucleic acid in a biological sample can be evaluated by obtaining a biological sample from a test subject and contacting the biological sample with a compound or an agent capable of detecting 59079 or 12599 protein or nucleic acid (e.g., mRNA, genomic DNA) that encodes 59079 or 12599 protein such that the presence of 59079 or 12599 protein or nucleic acid is detected in the biological sample. The term "biological sample" includes tissues, cells and biological fluids isolated from a subject, as well as tissues, cells and fluids present within a subject. A preferred biological sample is serum. The level of expression of the 59079 or 12599 gene can be measured in a number of ways, including, but not limited to: measuring the mRNA encoded by the 59079 or 12599 genes; measuring the amount of protein encoded by the 59079 or 12599 genes; or measuring the activity of the protein encoded by the 59079 or 12599 genes.

The level of mRNA corresponding to the 59079 or 12599 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 59079 or 12599 nucleic acid, such as the nucleic acid of SEQ ID NO:1 or 4, or a portion thereof, such as an oligonucleotide of at least 7, 15, 30, 50, 100, 250 or 500 nucleotides in length and sufficient to specifically hybridize under stringent conditions to 59079 or 12599 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 59079 or 12599 genes.

The level of mRNA in a sample that is encoded by 59079 or 12599 can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189–193), self sustained sequence replication (Guatelli et al., (1990) Proc. Natl. Acad. Sci. USA 87:1874–1878), transcriptional amplification system (Kwoh et al., (1989), Proc. Natl. Acad. Sci. USA 86:1173–1177), Q-Beta Replicase (Lizardi et al., (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 59079 or 12599 gene being analyzed.

In another embodiment, the methods further contacting a control sample with a compound or agent capable of detecting 59079 or 12599 mRNA, or genomic DNA, and comparing the presence of 59079 or 12599 mRNA or genomic DNA in the control sample with the presence of 59079 or 12599 mRNA or genomic DNA in the test sample.

A variety of methods can be used to determine the level of protein encoded by 59079 or 12599. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 59079 or 12599 protein in a biological sample in vitro, as well as in vivo. In vitro techniques for detection of 59079 or 12599 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 59079 or 12599 protein include introducing into a subject a labeled anti-59079 or anti-12599 antibody. For example, the antibody can be labeled with a radioactive marker whose presence and location in a subject can be detected by standard imaging techniques.

In another embodiment, the methods further include contacting the control sample with a compound or agent capable of detecting 59079 or 12599 protein, and comparing the presence of 59079 or 12599 protein in the control sample with the presence of 59079 or 12599 protein in the test sample.

The invention also includes kits for detecting the presence of 59079 or 12599 in a biological sample. For example, the kit can include a compound or agent capable of detecting 59079 or 12599 protein or mRNA in a biological sample; and a standard. The compound or agent can be packaged in a suitable container. The kit can further comprise instructions for using the kit to detect 59079 or 12599 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention, or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 59079 or 12599 expression or activity. As used interchangeably herein, the terms "unwanted" and "undesirable" include an unwanted phenomenon involved in a biological response such as pain or deregulated cell proliferation.

In one embodiment, a disease or disorder associated with aberrant or unwanted 59079 or 12599 expression or activity is identified. A test sample is obtained from a subject and 59079 or 12599 protein or nucleic acid (e.g., mRNA or genomic DNA) is evaluated, wherein the level, e.g., the presence or absence, of 59079 or 12599 protein or nucleic acid is diagnostic for a subject having or at risk of developing a disease or disorder associated with aberrant or unwanted 59079 or 12599 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 59079 or 12599 expression or activity. For example, such methods can be used to determine whether a subject can be effectively treated with an agent for a cellular proliferative and/or differentiative disorder, a hormonal disorder, an immune or inflammatory disorder, a neurological disorder, a cardiovascular disorder, a blood vessel disorder, or a platelet disorder.

The methods of the invention can also be used to detect genetic alterations in a 59079 or 12599 gene, thereby determining if a subject with the altered gene is at risk for a disorder characterized by misregulation in 59079 or 12599 protein activity or nucleic acid expression, such as a cellular proliferative and/or differentiative disorder, a hormonal disorder, an immune or inflammatory disorder, a neurological disorder, a cardiovascular disorder, a blood vessel disorder, or a platelet disorder. In preferred embodiments, the methods include detecting, in a sample from the subject, the presence or absence of a genetic alteration characterized by at least one of an alteration affecting the integrity of a gene encoding a 59079 or 12599 protein, or the misexpression of the 59079 or 12599gene. For example, such genetic alterations can be detected by ascertaining the existence of at least one of: (1) a deletion of one or more nucleotides from a 59079 or 12599 gene; (2) an addition of one or more nucleotides to a 59079 or 12599 gene; (3) a substitution of one or more nucleotides of a 59079 or 12599 gene, (4) a chromosomal rearrangement of a 59079 or 12599 gene; (5) an alteration in the level of a messenger RNA transcript of a 59079 or 12599 gene; (6) aberrant modification of a 59079 or 12599 gene, such as of the methylation pattern of the genomic DNA; (7) the presence of a non-wild type splicing pattern of a messenger RNA transcript of a 59079 or 12599 gene; (8) a non-wild type level of a 59079 or 12599 protein; (9) allelic loss of a 59079 or 12599 gene; and (10) inappropriate post-translational modification of a 59079 or 12599 protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 59079 or 12599 gene. This method can include the steps of collecting a sample of cells from a subject, isolating nucleic acid (e.g., genomic, mRNA or both) from the sample, contacting the nucleic acid sample with one or more primers which specifically hybridize to a 59079 or 12599 gene under conditions such that hybridization and amplification of the 59079 or 12599 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 59079 or 12599 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel ectrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 59079 and 12599 can be identified by hybridizing a sample and control nucleic acids, e.g., DNA or RNA, two dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 59079 or 12599 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 59079 and 12599 genes and detect mutations by comparing the sequence of the sample 59079 or 12599 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 59079 or 12599 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol*. 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 59079 or 12599 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 59079 and 12599 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144;

and Hayashi (1992) *Genet. Anal. Tech. Appl.* 9:73–79). Single-stranded DNA fragments of sample and control 59079 and 12599 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230).

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989)*Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 59079 gene.

Use of 59079 Molecules as Surrogate Markers

The 59079 and 12599 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 59079 or 12599 molecules of the invention may be detected, and may be correlated with one or more biological states in vivo. For example, the 59079 and 12599 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 59079 and 12599 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 59079 marker) transcription or expression, the amplified marker may be in a quantity which is more readily detectable than the drug itself. Also, the marker may be more easily detected due to the nature of the marker itself; for example, using the methods described herein, anti-59079 and anti-12599 antibodies may be employed in an immune-based detection system for a 59079 or 12599 protein marker, or 59079- or 12599-specific radiolabeled probes may be used to detect a 59079 or 12599 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect*. 90: 229–238; Schentag (1999) *Am. J. Health-Syst. Pharm*. 56 Suppl. 3: S21–S24; and Nicolau (1999) *Am. J. Health-Syst. Pharm*. 56 Suppl. 3: S16–S20.

The 59079 and 12599 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 59079 and 12599 protein or RNA) for specific tumor markers in a subject, a drug or course of treatment may be selected that is optimized for the treatment of the specific tumor likely to be present in the subject. Similarly, the presence or absence of a specific sequence mutation in 59079 or 12599 DNA may correlate 59079 or 12599 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-59079 and anti-12599 antibodies and small molecule modulators of 59079 and 12599 molecules (also referred to herein as "active compounds") of the invention can be incorporated into pharmaceutical compositions. Such compositions typically include the nucleic acid molecule, protein, or antibody and a pharmaceutically acceptable carrier. As used herein, a "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermnal, subcutaneous, oral (e.g., inhalation), trans dermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates of phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (Palo Alto Calif.) and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e.,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or undesirable 59079 or 12599 expression or activity. With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and commercially available. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 59079 or 12599 molecules of the present invention or 59079 or 12599 modulators according to that individual's drug response genotype. Pharmacogenomics allows a clinician or physician to target prophylactic or therapeutic treatments to patients who will most benefit from the treatment and to identify patients who will experience toxic drug-related side effects.

"Treatment", as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, palliate, improve or affect the disease, the symptoms of disease or the predisposition toward disease. A therapeutic agent includes, but is not limited to, small molecules, peptides, antibodies, ribozymes and antisense oligonucleotides.

In one aspect, the invention provides a method for preventing in a subject, a disease or condition associated with an aberrant or undesirable 59079 or 12599 expression or activity, by administering to the subject a 59079 or 12599 molecule or an agent which modulates 59079 or 12599 expression or at least one 59079 or 12599 activity. Subjects at risk for a disease which is caused or contributed to by aberrant or undesirable 59079 or 12599 expression or activity can be identified by, for example, any or a combination of diagnostic or prognostic assays as described herein. Administration of a prophylactic agent can occur prior to the manifestation of symptoms characteristic of the 59079 or 12599 aberrance, such that a disease or disorder is prevented or, alternatively, delayed in its progression. Depending on the type of 59079 or 12599 aberrance, for example, a 59079 or 12599 molecule (e.g., a 59079 or 12599 nucleic acid molecule or a 59079 or 12599 protein or polypeptide, or a fragment thereof, as described herein), or 59079 or 12599 agonist or 59079 or 12599 antagonist agent can be used for treating the subject. The appropriate agent can be determined based on screening assays described herein.

It is possible that some 59079 and 12599 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 59079 and 12599 disorders can be brought about by techniques that serve to inhibit the expression or activity of 59079 or 12599 target gene products. For example, compounds, e.g., an agent identified using an assays described above, that proves to exhibit negative modulatory activity, can be used in accordance with the invention to prevent and/or ameliorate symptoms of 59079 or 12599 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by undesirable 59079 or 12599 expression is through the use of aptamer molecules specific for 59079 or 12599 protein. Aptamers are nucleic acid molecules having a tertiary structure which permits them to specifically bind to protein ligands (see, e.g., Osborne, et al., Curr. Opin. Chem. Biol. 1997, 1:5–9; and Patel, D. J., Curr. Opin. Chem. Biol. 1997 June; 1:32–46). Since nucleic acid molecules may in many cases be more conveniently introduced into target cells than therapeutic protein molecules may be, aptamers offer a method by which 59079 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 59079 or 12599 disorders. For a description of antibodies, see the Antibody section above.

In circumstances wherein injection of an animal or a human subject with a 59079 or 12599 protein or epitope for stimulating antibody production is harmful to the subject, it is possible to generate an immune response against 59079 or 12599 through the use of anti-idiotypic antibodies (see, for example, Herlyn, D., Ann. Med. 1999; 31:66–78; and Bhattacharya-Chatterjee, M., and Foon, K. A. (1998) Cancer Treat. Res. 94:51–68). If an anti-idiotypic antibody is introduced into a mammal or human subject, it should stimulate the production of anti-anti-idiotypic antibodies, which should be specific to the 59079 or 12599 protein. Vaccines directed to a disease characterized by 59079 or 12599 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al., (1993, Proc. Natl. Acad. Sci. USA 90:7889–7893).

The identified compounds that inhibit target gene expression, synthesis and/or activity can be administered to a patient at therapeutically effective doses to prevent, treat or ameliorate 59079 and 12599 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another measurement which can be used to determine the effective dose for an individual is to directly assay levels of "free" and "bound" compound in the serum of the test subject. Such assays may utilize antibody mimics and/or "biosensors" that have been created through molecular imprinting techniques. The compound which is able to modulate 59079 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique is found in Ansell, R. J. et al., (1996) Current Opinion in Biotechnology 7:89–94 and in Shea, K. J., (1994) Trends in Polymer Science 2:166–173. Such "imprinted" affinity matrixes are amenable to ligand-binding assays, whereby the immobilized monoclonal antibody component is replaced by an appropriately imprinted matrix. An example of the use of such matrices in this way can be seen in Vlatakis, G. et al., (1993) Nature 361:645–647. Through the use of isotope-labeling, the "free" concentration of compound which modulates the expression or activity of 59079 can be readily monitored and used in calculations of $IC_{50}$.

Such "imprinted" affinity matrices can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al., (1995) Analytical Chemistry 67:2142–2144.

Another aspect of the invention pertains to methods of modulating 59079 expression or activity for therapeutic purposes. Accordingly, in an exemplary embodiment, the modulatory method of the invention involves contacting a cell with a 59079 molecule (e.g., a 59079 or 12599 nucleic acid molecule or 59079 or 12599 protein or polypeptide, or a fragment thereof, as described herein) or an agent that modulates one or more of the activities of the 59079 or 12599 protein activity associated with the cell. An agent that modulates 59079 or 12599 protein activity can be an agent as described herein, such as a nucleic acid or a protein, a naturally-occurring target molecule of a 59079 or 12599 protein (e.g., a 59079 or 12599 substrate, ligand, or receptor), an anti-59079 or anti-12599 antibody, a 59079 or 12599 agonist or antagonist, a peptidomimetic of a 59079 or 12599 agonist or antagonist, or other small molecule.

In one embodiment, the agent stimulates one or more 59079 or 12599 activities. Examples of such stimulatory agents include active 59079 and 12599 proteins and nucleic acid molecules encoding a 59079 or 12599 protein or polypeptide, or a fragment thereof. In another embodiment, the agent inhibits one or more 59079 or 12599 activities. Examples of such inhibitory agents include antisense 59079 and 12599 nucleic acid molecules, anti-59079 and anti-12599 antibodies, and 59079 and 12599 inhibitors. These modulatory methods can be performed in vitro (e.g., by culturing the cell with the agent) or, alternatively, in vivo (e.g., by administering the agent to a subject), or in situ. As such, the present invention provides methods of treating an individual afflicted with a disease or disorder characterized by aberrant or unwanted expression or activity of a 59079 or 12599 protein or nucleic acid molecule. In one embodiment, the method involves administering an agent (e.g., an agent identified by a screening assay described herein), or combination of agents that modulates (e.g., upregulates or downregulates) 59079 or 12599 expression or activity. In another embodiment, the method involves administering a 59079 or 12599 protein or nucleic acid molecule as therapy to compensate for reduced, aberrant, or undesirable 59079 or 12599 expression or activity.

Stimulation of 59079 or 12599 expression or activity is desirable in situations in which 59079 or 12599 expression or activity is abnormally downregulated and/or in which increased 59079 or 12599 expression or activity is likely to have a beneficial effect. Likewise, inhibition of 59079 or 12599 expression or activity is desirable in situations in which 59079 or 12599 expression or activity is abnormally upregulated and/or in which decreased 59079 or 12599 expression or activity is likely to have a beneficial effect.

The 59079 and 12599 molecules can act as novel diagnostic targets and therapeutic agents for controlling one or more of cellular proliferative and/or differentiative disorders, hormonal disorders, immune and inflammatory disorders, neurological disorders, cardiovascular disorders, blood vessel disorders, and platelet disorders, as described above, as well as disorders associated with bone metabolism, hepatic disorders, viral diseases, and pain and metabolic or pain disorders.

Aberrant expression and/or activity of 59079 or 12599 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 59079 or 12599 molecules effects in bone cells, e.g. osteoclasts and osteoblasts, that may in turn result in bone formation and degeneration. For example, 59079 or 12599 molecules may support different activities of bone resorbing osteoclasts such as the stimulation of differentiation of monocytes and mononuclear phagocytes into osteoclasts. Accordingly, 59079 and 12599 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Hepatic disorders which can be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolsim, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 59079 and 12599 molecules may play an important role in the etiology of certain viral diseases, including but not limited to, Hepatitis B, Hepatitis C and Herpes Simplex Virus (HSV). Modulators of 59079activity can be used to control viral diseases. The modulators can be used in the treatment and/or diagnosis of viral infected tissue or virus-associated tissue fibrosis, especially liver and liver fibrosis. Also, 59079 modulators can be used in the treatment and/or diagnosis of virus-associated carcinomas, especially hepatocellular cancers.

Additionally, 59079 and 12599 may play an important role in the regulation of metabolism or pain disorders. Diseases of metabolic imbalance include, but are not limited to, obesity, anorexia nervosa, bullemia, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L., (1987) *Pain,* N.Y.:McGraw-Hill); pain associated with muscoloskeletal disorders, e.g., joint pain; tooth pain; headaches; pain associated with surgery; pain related to irritable bowel syndrome; and chest pain.

Pharmacogenomics

The 59079 and 12599 molecules of the present invention, as well as agents, and modulators which have a stimulatory or inhibitory effect on a 59079 or 12599 activity (e.g., 59079 or 12599 gene expression) as identified by a screening assay described herein can be administered to individuals to treat (prophylactically or therapeutically) 59079 and 12599 associated disorders (e.g., cellular proliferative and/or differentiative disorders, hormonal disorders, immune and inflammatory disorders, neurological disorders, cardiovascular disorders, blood vessel disorders, and platelet disorders) associated with aberrant or undesirable 59079 or 12599 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 59079 or 12599 molecule or 59079 or 12599 modulator as well as tailoring the dosage and/or therapeutic regimen of treatment with a 59079 or 12599 molecule or 59079 or 12599 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983–985 and Linder, M. W. et al. (1997) *Clin. Chem.* 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 59079 or 12599 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 59079 or 12599 molecule or 59079 or 12599 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 59079 or 12599 molecule or 59079 or 12599 modulator, such as a modulator identified by one of the exemplary screening assays described herein.

The present invention further provides methods for identifying new agents, or combinations, that are based on identifying agents that modulate the activity of one or more of the gene products encoded by one or more of the 59079 and 12599 genes of the present invention, wherein these products may be associated with resistance of the cells to a therapeutic agent. Specifically, the activity of the proteins encoded by the 59079 and 12599 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 59079 or 12599 protein can be applied in clinical trials. For example, the effectiveness of an agent determined by a screening assay as described herein to increase 59079 or 12599 gene expression or protein levels, or upregulate 59079 or 12599 activity, can be monitored in clinical trials of subjects exhibiting decreased 59079 or 12599 gene expression or protein levels, or downregulated 59079 or 12599 activity. Alternatively, the effectiveness of an agent determined by a screening assay to decrease 59079 or 12599 gene expression or protein levels, or downregulate 59079 or 12599 activity, can be monitored in clinical trials of subjects exhibiting increased 59079 or 12599 gene expression or protein levels, or upregulated 59079 or 12599 activity. In such clinical trials, the expression or activity of a 59079 or 12599 gene, and preferably, other genes that have been implicated in, for example, a protein kinase associated disorder can be used as a "read out" or markers of the phenotype of a particular cell.

Other Embodiments

In another aspect, the invention features a method of analyzing a plurality of capture probes. The method is useful, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence, wherein the capture probes are from a cell or subject which expresses 59079 or 12599 or from a cell or subject in which a 59079- or 12599-mediated response has been elicited; contacting the array with a 59079 nucleic acid (preferably purified), a 59079 or 12599 polypeptide (preferably purified), or an anti-59079 or anti-12599 antibody, and thereby evaluating the plurality of capture probes. Binding, e.g., in the case of a nucleic acid, hybridization with a capture probe at an address of the plurality, is detected, e.g., by a signal generated from a label attached to the 59079 or 12599 nucleic acid, polypeptide, or antibody.

The capture probes can be a set of nucleic acids from a selected sample, e.g., a sample of nucleic acids derived from a control or non-stimulated tissue or cell.

The method can include contacting the 59079 or 12599 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 59079 or 12599. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features, a method of analyzing 59079 or 12599, e.g., analyzing structure, function, or relatedness to other nucleic acid or amino acid sequences. The method includes: providing a 59079 or 12599 nucleic acid or amino acid sequence; comparing the 59079 or 12599 sequence with one or more preferably a plurality of sequences from a collection of sequences, e.g., a nucleic acid or protein sequence database; to thereby analyze 59079 or 12599.

The method can include evaluating the sequence identity between a 59079 or 12599 sequence and a database sequence. The method can be performed by accessing the database at a second site, e.g., over the internet. Preferred databases include GenBank™ and SwissProt.

In another aspect, the invention features, a set of oligonucleotides, useful, e.g., for identifying SNP's, or identifying specific alleles of 59079 or 12599. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

The sequence of a 59079 or 12599 molecule is provided in a variety of mediums to facilitate use thereof. A sequence can be provided as a manufacture, other than an isolated nucleic acid or amino acid molecule, which contains a 59079 or 12599 molecule. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form.

A 59079 or 12599 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as compact disc and CD-ROM; electrical storage media such as RAM, ROM, EPROM, EEPROM, and the like; and general hard disks and hybrids of these categories such as magnetic/optical storage media. The medium is adapted or configured for having thereon 59079 sequence information of the present invention.

As used herein, the term "electronic apparatus" is intended to include any suitable computing or processing apparatus of other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as personal digital assistants (PDAs), cellular phones, pagers, and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 59079 or 12599 sequence information.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif.

The present invention therefore provides a medium for holding instructions for performing a method for determining whether a subject has a protein kinase associated disease or disorder or a pre-disposition to a protein kinase associated disease or disorder, wherein the method comprises the steps of determining 59079 or 12599 sequence information associated with the subject and based on the 59079 or 12599 sequence information, determining whether the subject has a protein kinase associated disease or disorder and/or recommending a particular treatment for the disease, disorder, or pre-disease condition.

The present invention further provides in an electronic system and/or in a network, a method for determining whether a subject has a protein kinase associated disease or disorder or a pre-disposition to a disease associated with 59079 or 12599, wherein the method comprises the steps of determining 59079 or 12599 sequence information associated with the subject, and based on the 59079 or 12599 sequence information, determining whether the subject has a protein kinase associated disease or disorder or a pre-disposition to a protein kinase associated disease or disorder, and/or recommending a particular treatment for the disease, disorder, or pre-disease condition. The method may further comprise the step of receiving phenotypic information associated with the subject and/or acquiring from a network phenotypic information associated with the subject.

The present invention also provides in a network, a method for determining whether a subject has a protein kinase associated disease or disorder or a pre-disposition to a protein kinase associated disease or disorder, said method comprising the steps of receiving 59079 or 12599 sequence information from the subject and/or information related thereto, receiving phenotypic information associated with the subject, acquiring information from the network corresponding to 59079 or 12599 and/or corresponding to a protein kinase associated disease or disorder, and based on one or more of the phenotypic information, the 59079 or 12599 information (e.g., sequence information and/or information related thereto), and the acquired information, determining whether the subject has a protein kinase associated disease or disorder or a pre-disposition to a protein kinase associated disease or disorder. The method may further comprise the step of recommending a particular treatment for the disease, disorder, or pre-disease condition.

The present invention also provides a business method for determining whether a subject has a protein kinase associated disease or disorder or a pre-disposition to a protein kinase associated disease or disorder, said method comprising the steps of receiving information related to 59079 (e.g., sequence information and/or information related thereto), receiving phenotypic information associated with the subject, acquiring information from the network related to 59079 or 12599 and/or related to a protein kinase associated disease or disorder, and based on one or more of the phenotypic information, the 59079 or 12599 information, and the acquired information, determining whether the subject has a protein kinase associated disease or disorder or a pre-disposition to a protein kinase associated disease or disorder. The method may further comprise the step of recommending a particular treatment for the disease, disorder, or pre-disease condition.

The invention also includes an array comprising a 59079 or 12599 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, which can include 59079 and/or 12599. This allows a profile to be developed showing a battery of genes specifically expressed in one or more tissues.

In addition to such qualitative information, the invention allows the quantitation of gene expression. Thus, not only tissue specificity, but also the level of expression of a battery of genes in the tissue if ascertainable. Thus, genes can be grouped on the basis of their tissue expression per se and level of expression in that tissue. This is useful, for example, in ascertaining the relationship of gene expression in that tissue. Thus, one tissue can be perturbed and the effect on gene expression in a second tissue can be determined. In this context, the effect of one cell type on another cell type in response to a biological stimulus can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a protein kinase associated disease or disorder, progression of protein kinase associated disease or disorder, and processes, such a cellular transformation associated with the protein kinase associated disease or disorder.

The array is also useful for ascertaining the effect of the expression of a gene on the expression of other genes in the same cell or in different cells (e.g., ascertaining the effect of 59079 or 12599 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including 59079) that could serve as a molecular target for diagnosis or therapeutic intervention.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention.

Examples of such software include, but are not limited to, MacPattern (EMBL), BLASTN and BLASTX (NCBI).

Thus, the invention features a method of making a computer readable record of a sequence of a 59079 or 12599 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 59079 or 12599 sequence, or record, in computer readable form; comparing a second sequence to the 59079 or 12599 sequence; thereby analyzing a sequence. Comparison can include comparing to sequences for sequence identity or determining if one sequence is included within the other, e.g., determining if the 59079 or 12599 sequence includes a sequence being compared. In a preferred embodiment the 59079 or second sequence is stored on a first computer, e.g., at a first site and the comparison is performed, read, or recorded on a second computer, e.g., at a second site. For example, the 59079 or 12599 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

This invention is further illustrated by the following exemplification, which should not be construed as limiting.

Exemplification
59079 Gene Expression Analysis

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using β-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPT™ Choice System following the manufacturer's instructions (GibcoBRL). A negative control of RNA without reverse transcriptase was mock reverse transcribed for each RNA sample.

Human 59079 expression was measured by TaqMan® quantitative PCR (Perkin Elmer Applied Biosystems) in cDNA prepared from a variety of normal and diseased (e.g., cancerous) human tissues or cell lines.

Probes were designed by PrimerExpress software (PE Biosystems) based on the sequence of the human 59079 gene. Each human 59079 gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target gene. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human 59079 gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human 59079 gene is normalized by subtracting the Ct value of the γ-2 microglobulin gene to obtain a $_\Delta Ct$ value using the following formula: $_\Delta Ct = Ct_{human\ 59914\ and\ 59921} - Ct_{\beta-2\ microglobulin}$. Expression is then calibrated against a cDNA sample showing a comparatively low level of expression of the human 59079 gene. The $_\Delta Ct$ value for the calibrator sample is then subtracted from $_\Delta Ct$ for each tissue sample according to the following formula: $_{\Delta\Delta}Ct = {_\Delta Ct}_{sample} - {_\Delta Ct}_{calibrator}$. Relative expression is then calculated using the arithmetic formula given by $2^{-\Delta\Delta Ct}$. Expression of the target human 59079 gene in each of the tissues tested is then graphically represented as discussed in more detail below.

The results indicate significant 59079 expression in normal heart and upregulated expression in diseased heart. Significant expression was also seen in skeletal muscle.

The contents of all references, patents and published patent applications cited throughout this application are incorporated herein by reference.

Equivalents

Those skilled in the art will recognize, or be able to ascertain using no more than routine experimentation, many equivalents to the specific embodiments of the invention described herein.

What is claimed is:

1. An isolated nucleic acid molecule selected from the group consisting of:
   a. a nucleic acid molecule comprising a nucleotide sequence which is at least 95% identical to the nucleotide sequence of SEQ ID NO:4 or SEQ ID NO:6, wherein the nucleic acid encodes a polypeptide having kinase activity; and
   b. a nucleic acid molecule which encodes a polypeptide comprising the amino acid sequence of SEQ ID NO:5.

2. The isolated nucleic acid molecule of claim 1, which is selected from the group consisting of:
   a. a nucleic acid comprising the nucleotide sequence of SEQ ID NO:4 or SEQ ID NO:6; and
   b. a nucleic acid molecule which encodes a polypeptide comprising the amino acid sequence of SEQ ID NO:5.

3. The nucleic acid molecule of claim 1 further comprising vector nucleic acid sequences.

4. The nucleic acid molecule of claim 1 further comprising nucleic acid sequences encoding a heterologous polypeptide.

5. A host cell which contains the nucleic acid molecule of claim 1.

6. The host cell of claim 5 which is a mammalian host cell.

7. A non-human mammalian host cell containing the nucleic acid molecule of claim 1.

8. A method for producing a polypeptide selected from the group consisting of:
   a. a polypeptide comprising the amino acid sequence of SEQ ID NO:5; and
   a polypeptide comprising the amino acid sequence of SEQ ID NO:5, wherein the polypeptide is encoded by a nucleic acid molecule comprising a nucleotide sequence which is at least 95% identical to the nucleotide sequence of SEQ ID NO:4 or SEQ ID NO:6, wherein the polypeptide has kinase activity;
   comprising culturing the host cell of claim 5 under conditions in which the nucleic acid molecule is expressed.

9. A kit comprising the nucleic acid molecule of claim 1 and instructions for use.

* * * * *

UNITED STATES PATENT AND TRADEMARK OFFICE
CERTIFICATE OF CORRECTION

| | | |
|---|---|---|
| PATENT NO. | : 7,001,753 B2 | Page 1 of 1 |
| APPLICATION NO. | : 10/077130 | |
| DATED | : February 21, 2006 | |
| INVENTOR(S) | : Rosana Kapeller-Libermann | |

It is certified that error appears in the above-identified patent and that said Letters Patent is hereby corrected as shown below:

<u>Title page,</u>
Item [75], Inventors, delete "Susan L. Acton, Lexington, MA (US).".

Signed and Sealed this

Twenty-seventh Day of June, 2006

JON W. DUDAS
*Director of the United States Patent and Trademark Office*